(12) United States Patent
Kamb et al.

(10) Patent No.: US 12,195,513 B2
(45) Date of Patent: *Jan. 14, 2025

(54) LILRB1-BASED CHIMERIC ANTIGEN RECEPTOR

(71) Applicant: A2 Biotherapeutics, Inc., Agoura Hills, CA (US)

(72) Inventors: Carl Alexander Kamb, Westlake Village, CA (US); Agnes E. Hamburger, Newbury Park, CA (US); Breanna Diandreth, Agoura Hills, CA (US); Mark E. Daris, Newbury Park, CA (US); Kiran Deshmukh, Culver City, CA (US)

(73) Assignee: A2 Biotherapeutics, Inc., Agoura Hills, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 17/589,093

(22) Filed: Jan. 31, 2022

(65) Prior Publication Data

US 2022/0153807 A1 May 19, 2022

Related U.S. Application Data

(60) Division of application No. 17/230,637, filed on Apr. 14, 2021, now Pat. No. 11,254,726, which is a continuation of application No. PCT/US2020/064607, filed on Dec. 11, 2020.

(60) Provisional application No. 63/085,969, filed on Sep. 30, 2020, provisional application No. 62/946,888, filed on Dec. 11, 2019.

(51) Int. Cl.
| | |
|---|---|
| *C07K 14/705* | (2006.01) |
| *A61K 35/17* | (2015.01) |
| *A61K 39/00* | (2006.01) |
| *A61P 35/00* | (2006.01) |
| *C07K 14/725* | (2006.01) |
| *C07K 16/28* | (2006.01) |
| *C07K 16/30* | (2006.01) |

(52) U.S. Cl.
CPC ........ *C07K 14/70503* (2013.01); *A61K 35/17* (2013.01); *A61P 35/00* (2018.01); *C07K 14/7051* (2013.01); *C07K 14/70521* (2013.01); *C07K 14/70578* (2013.01); *C07K 16/2803* (2013.01); *C07K 16/2833* (2013.01); *C07K 16/3069* (2013.01); *A61K 2039/505* (2013.01); *C07K 2317/622* (2013.01); *C07K 2317/76* (2013.01); *C07K 2317/92* (2013.01); *C07K 2319/03* (2013.01)

(58) Field of Classification Search
CPC ........ C07K 14/70503; C07K 2317/622; C07K 2319/03; C07K 2319/00; C07K 14/7051; C12N 5/0636
See application file for complete search history.

(56) References Cited

U.S. PATENT DOCUMENTS

| | | | |
|---|---|---|---|
| 5,350,674 A | 9/1994 | Boenisch et al. | |
| 5,585,362 A | 12/1996 | Wilson et al. | |
| 5,858,358 A | 1/1999 | June et al. | |
| 5,883,223 A | 3/1999 | Gray | |
| 6,326,193 B1 | 12/2001 | Liu et al. | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 9,745,368 B2 | 8/2017 | Milone et al. | |
| 10,040,846 B2 | 8/2018 | Frigault et al. | |
| 10,172,885 B2 | 1/2019 | Pule et al. | |
| 10,172,886 B2 | 1/2019 | Pule et al. | |
| 11,254,726 B2 | 2/2022 | Kamb et al. | |
| 11,267,901 B2 | 3/2022 | Fedorov et al. | |
| 2004/0043401 A1* | 3/2004 | Sadelain | C07K 14/70521 435/325 |
| 2004/0101519 A1 | 5/2004 | June et al. | |

(Continued)

FOREIGN PATENT DOCUMENTS

| | | |
|---|---|---|
| CN | 106574272 A | 4/2017 |
| EP | 3632461 A1 | 4/2020 |

(Continued)

OTHER PUBLICATIONS

Alignment A (Year: 2024).*
Alignment B (Year: 2024).*
Alignment C (Year: 2024).*
Wallrapp. Loss of the Y Chromosome is a Frequent Chromosomal Imbalance in Pancreatic Cancer and Allows Differentiation to Chronic Pancreatitis.Int. J. Cancer: 91, 340-344 (2001) (Year: 2001).*
Brown et al. The LILR family: modulators of innate and adaptive immune pathways in health and disease. Tissue Antigens 2004: 64: 215-225 (Year: 2004).*

(Continued)

*Primary Examiner* — Amy E Juedes
*Assistant Examiner* — Brian Hartnett
(74) *Attorney, Agent, or Firm* — Mintz Levin Cohn Ferris Glovsky and Popeo, P.C.; James Whittle; Edmund Koundakjian

(57) ABSTRACT

Provided are chimeric antigen receptors having the hinge, transmembrane region, and/or intracellular domain of LILRB1, or functional fragments or variants thereof. Also provided herein are cells comprising the LILRB1 based receptors, and methods of making and using same.

18 Claims, 48 Drawing Sheets

Specification includes a Sequence Listing.

(56) References Cited

U.S. PATENT DOCUMENTS

| | | |
|---|---|---|
| 2006/0034810 A1 | 2/2006 | Riley et al. |
| 2006/0121005 A1 | 6/2006 | Berenson et al. |
| 2015/0376296 A1 | 12/2015 | Fedorov et al. |
| 2016/0289293 A1 | 10/2016 | Pule et al. |
| 2016/0289294 A1 | 10/2016 | Pule et al. |
| 2017/0296623 A1 | 10/2017 | Juillerat et al. |
| 2018/0044399 A1 | 2/2018 | Rajpal et al. |
| 2018/0251558 A1* | 9/2018 | Maute ............... A61K 38/1774 |
| 2018/0346541 A1 | 12/2018 | Wong et al. |
| 2019/0023761 A1 | 1/2019 | Pule et al. |
| 2019/0169289 A1 | 6/2019 | Young et al. |
| 2019/0248869 A1 | 8/2019 | Gross et al. |
| 2019/0290691 A1 | 9/2019 | Jackel et al. |
| 2019/0359678 A1 | 11/2019 | O'Donoghue et al. |
| 2020/0016203 A1 | 1/2020 | Pule et al. |
| 2020/0016204 A1 | 1/2020 | Pule et al. |
| 2020/0188434 A1 | 6/2020 | Cordoba et al. |
| 2020/0199550 A1 | 6/2020 | Cordoba et al. |
| 2020/0261499 A1 | 8/2020 | Gross et al. |
| 2020/0316120 A1 | 10/2020 | Gross et al. |
| 2021/0206826 A1 | 7/2021 | Lim et al. |
| 2021/0230247 A1 | 7/2021 | Kamb et al. |
| 2021/0230251 A1 | 7/2021 | Gross et al. |
| 2022/0162287 A1 | 5/2022 | Kamb et al. |
| 2022/0289818 A1 | 9/2022 | Kamb et al. |
| 2023/0029341 A1 | 1/2023 | Kamb et al. |

FOREIGN PATENT DOCUMENTS

| | | | |
|---|---|---|---|
| EP | 3634990 A1 | 4/2020 | |
| EP | 3688155 A1 | 8/2020 | |
| WO | WO-0129058 A1 | 4/2001 | |
| WO | WO-0196584 A2 | 12/2001 | |
| WO | WO-2014145252 A2 | 9/2014 | |
| WO | WO-2015017214 A1 | 2/2015 | |
| WO | WO-2015075468 A1 * | 5/2015 | ............. A61K 35/17 |
| WO | WO-2015120096 A2 | 8/2015 | |
| WO | WO-2015142314 A1 | 9/2015 | |
| WO | WO-2016075612 A1 | 5/2016 | |
| WO | WO-2016097231 A2 * | 6/2016 | ............. A61K 35/17 |
| WO | WO-2016126608 A1 | 8/2016 | |
| WO | WO-2016138034 A1 | 9/2016 | |
| WO | WO-2016142532 A1 | 9/2016 | |
| WO | WO-2016160622 A2 | 10/2016 | |
| WO | WO-2017011804 A1 | 1/2017 | |
| WO | WO-2017079705 A1 | 5/2017 | |
| WO | WO-2017087723 A1 | 5/2017 | |
| WO | WO-2017091905 A1 | 6/2017 | |
| WO | WO-2017156484 A1 | 9/2017 | |
| WO | WO-2018061012 A1 | 4/2018 | |
| WO | WO-2018144535 A1 | 8/2018 | |
| WO | WO-2018148454 A1 | 8/2018 | |
| WO | 2018191748 A1 | 10/2018 | |
| WO | 2018211246 A1 | 11/2018 | |
| WO | WO-2018211244 A1 | 11/2018 | |
| WO | WO-2018211245 A1 | 11/2018 | |
| WO | WO-2019056099 A1 | 3/2019 | |
| WO | WO-2019068007 A1 * | 4/2019 | ............. A61K 35/00 |
| WO | WO-2019090215 A2 | 5/2019 | |
| WO | 2019192972 A1 | 10/2019 | |
| WO | WO-2019241549 A1 | 12/2019 | |
| WO | WO-2020065406 A2 | 4/2020 | |
| WO | WO-2020070290 A1 | 4/2020 | |
| WO | 2021035093 A1 | 2/2021 | |
| WO | WO-2021030149 A1 | 2/2021 | |
| WO | WO-2021030153 A2 | 2/2021 | |
| WO | WO-2021030182 A1 | 2/2021 | |
| WO | WO-2021096868 A1 | 5/2021 | |
| WO | WO-2021119489 A1 | 6/2021 | |
| WO | WO-2021222576 A1 | 11/2021 | |
| WO | 2022115472 A1 | 6/2022 | |

OTHER PUBLICATIONS

Vignard. Adoptive Transfer of Tumor-Reactive Melan-A-Specific CTL Clones in Melanoma Patients Is Followed by Increased Frequencies of Additional Melan-A-Specific T Cells. J Immunol (2005) 175 (7): 4797-4805. (Year: 2005).*

(2022) Sequence Alignments, Wikipedia, 18 pages.

(Jan. 30, 2023) TCGA AML Gene Expression Suite—LILRB1, https://leylab.shinyapps.io/TCGA_AML_Web_App, 1 page.

(Jan. 30, 2023) The Human Protein Atlas—LILRB1, https://www.proteinatlas.org/ENSG00000104972-LILRB1, 2 pages.

Abdallah et al. (Sep. 14, 2021) "Leukocyte Immunoglobulin-like Receptors in Regulating the Immune Response in Infectious Diseases: A Window of Opportunity to Pathogen Persistence and a Sound Target in Therapeutics", Frontiers in Immunology, 12:717998 (16 pages).

Alcover et al. (Apr. 26, 2018) "Cell Biology of T Cell Receptor Expression and Regulation", Annual Review of Immunology, 36:103-125.

Barkal et al. (Nov. 27, 2017) "Engagement of MHC Class I by the Inhibitory Receptor LILRB1 Suppresses Macrophages and is a Target of Cancer Immunotherapy", Nature Immunology, 19(1):76-84 (25 pages).

Brown et al. (Sep. 2004) "The LILR Family: Modulators of Innate and Adaptive Immune Pathways in Health and Disease", Tissue Antigens, Available online at: <https://onlinelibrary.wiley.com/doi/10.1111/j.0001-2815.2004.00290.x>, 64(3):215-225.

Cadena-Mota et al. (Dec. 2018) "Effect of Cytomegalovirus Infection and Leukocyte Immunoglobulin Like Receptor B1 Polymorphisms on Receptor Expression in Peripheral Blood Mononuclear Cells", Medical Microbiology and Immunology, 62(12):755-762.

Campoli et al. (Oct. 6, 2008) "HLA Antigen Changes in Malignant Cells: Epigenetic Mechanisms and Biologic Significance", Oncogene, 27(45):5869-5885.

Chandran et al. (2019) "T Cell Receptor-Based Cancer Immunotherapy: Emerging Efficacy and Pathways of Resistance", Immunological Reviews, 290(1):127-147.

Chang et al. (Mar. 2002) "Tolerization of Dendritic Cells by T(S) Cells: The Crucial Role of Inhibitory Receptors ILT3 and ILT4", Nature Immunology, 3(3):237-243.

Chen et al. (Aug. 2020) "Antagonistic Anti-LILRB1 Monoclonal Antibody Regulates Antitumor Functions of Natural Killer Cells", The Journal for ImmunoTherapy of Cancer, 8(2):e000515.

Chen et al. (Mar. 21, 2012) "Structural and Functional Distinctiveness of HLA-A2 Allelic Variants", Immunologic Research, 53:182-190.

Dechavanne et al. (Oct. 26, 2021) "LILRB1 and LILRB2 Expression in Peripheral Blood Immune Cells at 18 and 24 Months of Age in Infants Born from Mothers with Placental Malaria", BioRxiv, 37 pages.

Diandreth et al. (2022) "The Tmod Cellular Logic Gate as a Solution for Tumor-Selective Immunotherapy", Clinical Immunology, 241:109030.

Fan et al. (Mar. 24, 2022) "Analysis of the Expression and Prognosis for Leukocyte Immunoglobulin-Like Receptor Subfamily B in Human Liver Cancer", World Journal of Surgical Oncology, 20(1):92 (15 pages).

Guedan et al. (Dec. 31, 2018) "Engineering and Design of Chimeric Antigen Receptors", Molecular Therapy Methods and Clinical Development, eCollection Mar. 15, 2019, Available online at: <https://pubmed.ncbi.nlm.nih.gov/30666307/>, 12:145-156.

Harrer et al. (May 2018) "Chimeric Antigen Receptors in Different Cell Types: New Vehicles Join the Race", Human Gene Therapy, 29(5):547-558.

Hudecek et al. (Feb. 2015) "The Non-Signaling Extracellular Spacer Domain of Chimeric Antigen Receptors is Decisive for in Vivo Antitumor Activity", Cancer Immunology Research, 3(2): 125-135.

Jayaraman et al. (2020) "CAR-T Design: Elements and their Synergistic Function", EBioMedicine, 58:102931.

Jose et al. (Feb. 2000) "Triggering the TCR Complex Causes the Downregulation of Nonengaged Receptors by a Signal Transduction-Dependent Mechanism", Immunity, Available online at: <https://pubmed.nobi.nim.nih.gov/10714682/>, 12(2):161-170.

(56) References Cited

OTHER PUBLICATIONS

Katz et al. (2015) "Phase I Hepatic Immunotherapy for Metastases Study of Intra-Arterial Chimeric Antigen Receptor-Modified T-cell Therapy for CEA+ Liver Metastases", Clinical Cancer Research, 21(14):3149-3159.
Kim et al. (Aug. 15, 2019) "LILRB1 Blockade Enhances Bispecific T Cell Engager Antibody-Induced Tumor Cell Killing by Effector CD8+ T Cells", Journal of Immunology, 203(4):1076-1087.
Liu et al. (Mar. 15, 2016) "A Chimeric Switch-Receptor Targeting PD1 Augments the Efficacy of Second-Generation Car T Cells in Advanced Solid Tumors", Cancer Research, 76(6):1578-1590.
Lv et al. (2019) "Mesothelin as a Biomarker for Targeted Therapy", Biomarker Research, 7:18 pages.
Meyaard, Linde (Apr. 2008) "The inhibitory Collagen Receptor LAIR-1 (CD305)", Journal of Leukocyte Biology, 83(4):799-803.
Mock et al. (2022) "HLA-A?02-Gated Safety Switch for Cancer Therapy has Exquisite Specificity for its Allelic Target Antigen", Molecular Therapy-Oncolytics, 27:157-166.
Natali et al. (Sep. 1, 1989) "Selective Changes in Expression of HLA Class I Polymorphic Determinants in Human Solid Tumors", Proceedings of the National Academy of Sciences of the United States of America, 86 (17):6719-6723.
Norell et al. (Jun. 15, 2006) "Frequent Loss of HLA-A2 Expression in Metastasizing Ovarian Carcinomas Associated with Genomic Haplotype Loss and HLA-A2-Restricted HER-2/neu-Specific Immunity", Cancer Research, 66(12):6387-6394.
Rafiq et al. (2016) "Engineering Armored T Cell Receptor-Mimic (TCRm) Chimeric Antigen Receptor (CAR) T Cells Specific for the Intracellular Protein Wilms Tumor 1 (WT1) for Treatment of Hematologic and Solid Malignancies", Molecular Therapy, 24(1):S156.
Romo et al. (Aug. 4, 2011) "Association of Atherosclerosis with Expression of the LILRB1 Receptor By Human NK and T-Cells Supports the Infectious Burden Hypothesis", Arteriosclerosis, Thrombosis, and Vascular Biology, 31 (10):2314-2321.
Rosen et al. (Aug. 15, 2004) "A Structural Basis for the Association of DAP12 with Mouse, but not Human, NKG2D", Journal of Immunology, 173(4):2470-2478.
Zhao et al. (Nov. 2019) "The MHC Class I-LILRB1 Signalling Axis as a Promising Target in Cancer Therapy", Scandinavian Journal of Immunology, 90(5):e12804 (11 pages).
Sandberg et al. (2022) "A Carcinoembryonic Antigen-specific Cell Therapy Selectively Targets Tumor Cells with HLA Loss of Heterozygosity in Vitro and in Vivo", Science Translational Medicine, 14(634):eabm0306.
Saverino et al. (Oct. 1, 2000) "The CD85/LIR-1/ILT2 Inhibitory Receptor Is Expressed by All Human T Lymphocytes and Down-Regulates Their Functions", Journal of Immunology, 165(7):3742-3755.
Sergeeva et al. (Nov. 16, 2008) "Direct Visualization of PR1/HLA-A2 on the Membrane of HLAA2+ CD13+CD33+ Myeloid Leukemia Blasts by a Novel Monoclonal Antibody", Blood, 112(11):2545 (2 pages).
Skuljec et al. (Sep. 12, 2017) "Chimeric Antigen Receptor-Redirected Regulatory T Cells Suppress Experimental Allergic Airway Inflammation, a Model of Asthma", Frontiers in Immunology, Article 1125, 8:12 pages.
Staub et al. (May 2004) "Systematic Identification of Immunoreceptor Tyrosine-Based Inhibitory Motifs in the Human Proteome", Cellular Signalling, 16(4):435-456.
Stein et al. (May 1994) "The Cytoplasmic Domain of CD28 is Both Necessary and Sufficient for Costimulation of Interleukin-2 Secretion and Association with Phosphatidylinositol 3'-kinase.", Molecular and Cellular Biology, 14(5):3392-3402.
Tokatlian et al. (2022) "Mesothelin-Specific CAR-T Cell Therapy That Incorporates an HLA-Gated Safety Mechanism Selectively Kills Tumor Cells", Journal for Immunotherapy of Cancer, 10(1):e003826.
Tutusaus et al. (Nov. 8, 2021) "LILRB1: A Novel Diagnostic B-Cell Marker to Distinguish Neoplastic B Lymphoblasts from Hematogones", American Journal of Clinical Pathology, 156(6):941-949.
Wang et al. (2017) "New Development in CAR-T Cell Therapy", Journal of Hematology and Oncology, 10(1):53.
Young et al. (Mar. 15, 2008) "The Inhibitory Receptor LILRB1 Modulates the Differentiation and Regulatory Potential of Human Dendritic Cells", Blood, 111(6):3090-3096.
Zeltsman et al. (2017) "CAR T-Cell Therapy for Lung Cancer and Malignant Pleural Mesothelioma", Translational Research, 187:1-10.
Zhang et al. (Aug. 2000) "Roles of the SHP-1 Tyrosine Phosphatase in the Negative Regulation of Cell Signalling", Seminars in Immunology, 12(4):361-378.
Abecasis et al. "A map of human genome variation from population-scale sequencing." Nature—1000 Genomes Project Consortium. 467.7319 (2010): 1061-1073.
Abeyweera, Thushara P., Ernesto Merino, and Morgan Huse. "Inhibitory signaling blocks activating receptor clustering and induces cytoskeletal retraction in natural killer cells." Journal of Cell Biology 192.4 (2011):675-690.
Altschul, S. et al., "Basic local alignment search tool", J Mol Biol (1990); 215(3):403-410.
Altschul et al., "Gapped BLAST and PSI-BLAST: a new generation of protein database search programs," Nucleic Acids Res. 25:3389-3402 (1997).
Auton et al. "A global reference for human genetic variation." Nature—1000 Genomes Project Consortium. 526.7571 (2015): 68-74.
Badran et al., "Identification of three NFAT binding motifs in the 5'-upstream region of the human CD3y gene that differentially bind NFATc1, NFATc2, and NF-KB p50," J. Biological Chemistry vol. 277: 47136-47148 (2002).
Barrett, Michael T., et al. "Evolution of neoplastic cell lineages in Barrett oesophagus." Nature genetics 22.1 (1999): 106-109.
Basilion et al., "Selective Killing of Cancer Cells Based on Loss of Heterozygosity and Normal Variation in the Human Genome: A New Paradigm for Anticancer Drug Therapy," Mol Pharmacal. 56(2):359-369 (1999).
Bausch-Fluck, Damaris, et al. "A mass spectrometric-derived cell surface protein atlas." PloS one 10.4 (2015) 1-22.
Bayle, J. Henri, et al. "Rapamycin analogs with differential binding specificity permit orthogonal control of protein activity." Chemistry & biology 13.1 (2006): 99-107.
Bellon et al., "Mutational Analysis of Immunoreceptor Tyrosine-Based Inhibition Motifs of the Ig-Like Transcript 2 (CD85j) Leukocyte Receptor," J Immunol 2002; 168:3351-3359.
Bergbold, Nina, and Marius K. Lemberg. "Emerging role of rhomboid family proteins in mammalian biology and disease." Biochimica et Biophysica Acta (BBA)—Biomembranes 1828.12 (2013): 2840-2848.
Beroukhim et al., "The landscape of somatic copy-number alteration across human cancers," Nature 463(7283):899-905 (2010).
Binstadt et al., "Sequential involvement of Lck and SHP-1 with MHC-recognizing receptors on NK cells inhibits FcR-initiated tyrosine kinase activation, " Immunity Dec. 1996;5(6):629-638.
Blankenstein, Thomas, et al. "Targeting cancer-specific mutations by T cell receptor gene therapy." Current opinion in immunology 33 (2015): 112-119.
Boczkowski, D et al., Induction of tumor immunity and cytotoxic T lymphocyte responses using dendritic cells transfected with messenger RNA amplified from tumor cells. Cancer Res. Feb. 15, 2000;60(4):1028-34.
Burrell, Rebecca A., et al. "The causes and consequences of genetic heterogeneity in cancer evolution." Nature 501.7467 (2013): 338-345.
Caescu, Cristina I., Grace R. Jeschke, and Benjamin E. Turk. "Active-site determinants of substrate recognition by the metalloproteinases TACE and ADAM10." Biochemical Journal 424.1 (2009): 79-88.
Carney, W. P., et al. "Monoclonal antibody specific for an activated RAS protein." Proceedings of the National Academy of Sciences 83.19 (1986): 7485-7489.
Cerami, Ethan, et al. "The cBio cancer genomics portal: an open platform for exploring multidimensional cancer genomics data." Cancer Discov. 2(5) (2012): 401-404.

(56) References Cited

OTHER PUBLICATIONS

Chao, Ginger, et al. "Isolating and engineering human antibodies using yeast surface display." Nature protocols 1.2 (2006): 755-768.
Chess, Andrew. "Mechanisms and consequences of widespread random monoallelic expression." Nature Reviews Genetics 13.6 (2012): 421-428.
Chicaybam et al. (2014) "Construction and validation of an activating and inhibitory chimeric antigen receptor (CAR) system," Cancer Research. vol. 74, Issue 19, Abstract 2797, 4 pages.
Chicaybam et al. (2015) "Construction and validation of an activating and inhibitory chimeric antigen receptor (CAR) system." Cancer Research. vol. 75, Issue 15, Abstract 3156, 4 pages.
Cordoba, et al. "The large ectodomains of CD45 and CD148 regulate their segregation from and inhibition of ligated T-cell receptor." Blood 121.21 (2013): 4295-4302.
Da Cunha, J.P. C., et al. "Bioinformatics construction of the human cell surfaceome." Proceedings of the National Academy of Sciences 106.39 (2009): 16752-16757.
Devilee, Peter, Anne-Marie Cleton-Jansen, and Gees J. Cornelisse. "Ever since Knudson." Trends in genetics 17.10 (2001): 569-573.
Dotti, Gianpietro, et al. "Design and development of therapies using chimeric antigen receptor-expressing T cells." Immunological reviews 257.1 (2014): 107-126.
Ebsen, Henriette, et al. "Differential surface expression of ADAM10 and ADAM17 on human T lymphocytes and tumor cells." PloS one 8.10 (2013) e76853, 1-16.
Ellis et al., "Frequencies of HLA-A2 alleles in five U.S. population groups," Human Immunology 61:334-340 (2000).
Eriksson, Mikael, et al. "Inhibitory receptors alter natural killer cell interactions with target cells yet allow simultaneous killing of susceptible targets." The Journal of experimental medicine 190.7 (1999): 1005-1012.
European Search Report corresponding to European Patent Application No. 17855171.9, dated Mar. 26, 2020, 8 pages.
Federov, V.D. et al. (2013). "PD-1- and CTLA-4-Based inhibitory chimeric antigen receptors (iCARs) divert off-target immunotherapy responses," Science Translational Medicine 5(215), 215ra172, 14 total pages.
Feenstra, M., et al. "HLA class I expression and chromosomal deletions at 6p and 15q in head and neck squamous cell carcinomas." Tissue antigens 54.3 (1999): 235-245.
Gao, Jianjiong, et al. "Integrative analysis of complex cancer genomics and clinical profiles using the cBioPortal." Sci. Signal. 6.269 (2013): 1-34.
Garland, R. J., et al. "The use of Teflon cell culture bags to expand functionally active CD8+ cytotoxic T lymphocytes." Journal of Immunological Methods (1999); 227.1: 53-63.
Gill, Saar, and Carl H. June. "Going viral: chimeric antigen receptor T-cell therapy for hematological malignancies." Immunological reviews 263.1 (2015): 68-89.
Gordon, Wendy R., et al. "Mechanical allostery: evidence for a force requirement in the proteolytic activation of Notch." Developmental cell 33.6 (2015): 729-736.
Graef, Isabella A., et al. "Proximity and orientation underlie signaling by the non-receptor tyrosine kinase ZAP70." The EMBO journal 16.18 (1997): 5618-5628.
Gross et al. (2016) "Therapeutic Potential of T Cell Chimeric Antigen Receptors (CARs) in Cancer Treatment: Counteracting Off-Tumor Toxicities for Safe CART Cell Therapy," Annu. Rev. Pharmacol. Toxicol. 56:59-83.
Gross, Gideon, Tova Waks, and Zelig Eshhar. "Expression of immunoglobulin-T-cell receptor chimeric molecules as functional receptors with antibody-type specificity." Proceedings of the National Academy of Sciences 86.24 (1989): 10024-10028.
GTEx Consortium. "The Genotype-Tissue Expression (GTEx) pilot analysis: multitissue gene regulation in humans." Science 348.6235 (2015): 648-660.
Gustafson et al., "Immune Checkpoint Function of CD85j in CD8 T Cell Differentiation and Aging," Frontiers in Immunology 8:692, pp. 1-12 (2017).

Haanen, John B.A.G., et al. "Selective expansion of cross-reactive CD8+ memory T cells by viral variants." Journal of Experimental Medicine (1999); 190.9: 1319-1328.
Haapasalo, Annakaisa, and Kovacs, Dora M. "The many substrates of presenilin/γ-secretase." Journal of Alzheimer's disease 25.1 (2011): 3-28.
Hamburger et al., "Engineered T cells directed at tumors with defined allelic loss", Molecular Immunology, Pergamon GB 128:298-310 (2020).
Hanes, Jozef, and Andreas Pluckthun. "In vitro selection and evolution of functional proteins by using ribosome display." Proceedings of the National Academy of Sciences 94.10 (1997): 4937-4942.
Heemskerk, Bianca, Pia Kvistborg, and Ton NM Schumacher. "The cancer antigenome." The EMBO journal 32.2 (2013): 194-203.
Hemming, Matthew L., et al. "Identification of β-secretase (BACE1) substrates using quantitative proteomics." PloS one 4.12 (2009) e8477, 1-14.
Hilton and Parham, "Direct Binding to Antigen-coated Beads Refines the Specificity and Cross-reactivity of Four Monoclonal Antibodies That Recognize Polymorphic Epitopes of Hla Class I Molecules," Tissue Antigens 81:212-220 (2013).
Huse, Morgan, S. Catherine Milanoski, and Thushara P. Abeyweera. "Building tolerance by dismantling synapses: inhibitory receptor signaling in natural killer cells." Immunological reviews 251.1 (2013): 143-153.
Hwang et al., "Targeting Loss of Heterozygosity for Cancer-specific Immunotherapy," PNAS 118(12), pp. 1-10 (2021).
International Search Report with Written Opinion corresponding to International Patent Application No. PCT/IL17/51102, dated Jan. 14, 2018, 8 pages.
Irles, et al. "CD45 ectodomain controls interaction with GEMs and Lek activity for optimal TCR signaling," Nature Immunology 4:189-197 (2003).
Jimenez, Pilar, et al. "Chromosome loss is the most frequent mechanism contributing to HLA haplotype loss in human tumors." International journal of cancer 83.1 (1999): 91-97.
Karlin et al. "Applications and statistics for multiple high-scoring segments in molecular sequences." Proceedings of National Academy of Sciences 90:5873-5877 (1993).
Karlin, Samuel, and Altschul, Stephen F. "Methods for assessing the statistical significance of molecular sequence features by using general scoring schemes." Proceedings of the National Academy of Sciences (1990); 87.6: 2264-2268.
Klebanoff, Christopher A., Steven A. Rosenberg, and Nicholas P. Restifo. "Prospects for gene-engineered T cell immunotherapy for solid cancers." Nature medicine 22.1 (2016): 26-36.
Kloss, Christopher C., et al. "Combinatorial antigen recognition with balanced signaling promotes selective tumor eradication by engineered T cells." Nature biotechnology 31.1 (2013): 71-75.
Knudson, Alfred G. "Mutation and cancer: statistical study of retinoblastoma." Proceedings of the National Academy of Sciences 68.4 (1971): 820-823.
Lanitis, Evripidis, et al. "Chimeric antigen receptor T Cells with dissociated signaling domains exhibit focused antitumor activity with reduced potential for toxicity in vivo." Cancer immunology research 1.1 (2013): 43-53.
Lawrence et al. (2014) "Discovery and saturation analysis of cancer genes across 21 tumour types," Nature. 505:495-501.
Lawrence, Michael S., et al. "Mutational heterogeneity in cancer and the search for new cancer-associated genes." Nature 499.7457 (2013): 214-218.
Lee, Andria, et al. "Distribution analysis of nonsynonymous polymorphisms within the G-protein-coupled receptor gene family." Genomics 81.3 (2003): 245-248.
Lek, Monkol, et al. "Analysis of protein-coding genetic variation in 60,706 humans." Nature 536.7616 (2016): 285-291.
Lengauer, Christoph, Kenneth W. Kinzler, and Bert Vogelstein. "Genetic instabilities in human cancers." Nature 396.6712 (1998): 643-649.
Leung et al., "Sensitive and adaptable pharmacological control of CART cells through extracellular receptor dimerization," JCI Insight 4(11):e124430, 19 pages (2019).

(56) References Cited

OTHER PUBLICATIONS

Li et al., "LILRB4 ITIMs mediate the T cell suppression and infiltration of acute myeloid leukemia cells", Cellular & Molecular Immunology, Chinese Society of Immunology CH 17(3):272-282 (2019).
Li, Hongsheng, et al. "A preliminary study of the relationship between breast cancer metastasis and loss of heterozygosity by using exome sequencing." Scientific reports 4 (2014): 5460 1-6.
Liberles, Stephen D., et al. "Inducible gene expression and protein translocation using nontoxic ligands identified by a mammalian three-hybrid screen." Proceedings of the National Academy of Sciences 94.15 (1997): 7825-7830.
Lindblad-Toh, Kerstin, et al. "Loss-of-heterozygosity analysis of small-cell lung carcinomas using single-nucleotide polymorphism arrays." Nature biotechnology 18.9 (2000): 1001-1005.
Lo, Ken C., et al. "Comprehensive analysis of loss of heterozygosity events in glioblastoma using the 1DOK SNP mapping arrays and comparison with copy number abnormalities defined by BAC array comparative genomic hybridization." Genes, Chromosomes and Cancer 47.3 (2008): 221-237.
Long, Eric O., et al. "Controlling natural killer cell responses: integration of signals for activation and inhibition." Annual review of immunology 31 (2013): 227-258.
Macdonald et al, "Alloantigen-specific Regulatory T Cells Generated With a Chimeric Antigen Receptor," J. Clin. Invest. 126:1413-1424 (2016).
Maleno, Isabel, et al. "Distribution of HLA class I altered phenotypes in colorectal carcinomas: high frequency of HLA haplotype loss associated with loss of heterozygosity in chromosome region 6p21." Immunogenetics 56.4 (2004): 244-253.
Maleno, Isabel, et al. "Frequent loss of heterozygosity in the 132-microglobulin region of chromosome 15 in primary human tumors." Immunogenetics 63.2 (2011): 65-71.
Maleno, Isabel, et al. "LOH at 6p21. 3 region and HLA class altered phenotypes in bladder carcinomas." Immunogenetics 58.7 (2006): 503-510.
Maleno, Isabel, et al. "Multiple mechanisms generate HLA class I altered phenotypes in laryngeal carcinomas: high frequency of HLA haplotype loss associated with loss of heterozygosity in chromosome region 6p21." Cancer Immunology, Immunotherapy 51.7 (2002): 389-396.
McEvoy et al., Frequency and genetic basis of MHC, beta-2-microglobulin and MEMO-1 loss of heterozygosity in sporadic breast cancer. Tissue Antigens, 60:235-243 (2002).
McGranahan, Nicholas, et al. "Cancer chromosomal instability: therapeutic and diagnostic challenges." EMBO reports 13.6 (2012): 528-538.
Medintz et al. (2000) "Loss of heterozygosity assay for molecular detection of cancer using energy-transfer primers and capillary array electrophoresis," Genome research. 10(8):1211-1218.
Morgan et al., "Case report of a serious adverse event following the administration of T cells transduced with a chimeric antigen receptor recognizing ERBB2," Molecular Therapy 18(4): 843-851 (2010).
Morsut, Leonardo, et al. "Engineering customized cell sensing and response behaviors using synthetic notch receptors." Cell 164.4 (2016): 780-791.
Ng, Pauline C., and Steven Henikoff. "SIFT: Predicting amino acid changes that affect protein function." Nucleic acids research 31.13 (2003): 3812-3814.
Nirschl, Christopher J., and Charles G. Drake. "Molecular pathways: coexpression of immune checkpoint molecules: signaling pathways and implications for cancer immunotherapy." Clinical cancer research 19.18 (2013): 4917-4924.
Ohgaki, Hiroko, et al. "Genetic pathways to glioblastoma: a population-based study." Cancer research 64.19 (2004): 6892-6899.
O'Keefe, Christine, Michael A. McDevitt, and Jaroslaw P. Maciejewski. "Copy neutral loss of heterozygosity: a novel chromosomal lesion in myeloid malignancies." Blood, The Journal of the American Society of Hematology 115.14 (2010): 2731-2739.
Overwijk, Willem W., et al. "Mining the mutanome: developing highly personalized Immunotherapies based on mutational analysis of tumors." Journal for immunotherapy of cancer 1.1 (2013):11, 4 pages.
Patel et al. (2014) "Cancer CARtography: charting out a new approach to cancer immunotherapy," Immunotherapy. 6(6):675-678.
Rana, Brinda K., Tetsuo Shiina, and Paul A. Insel. "Genetic variations and polymorphisms of G protein-coupled receptors: functional and therapeutic implications." Annual review of pharmacology and toxicology 41.1 (2001): 593-624.
Rawson, Robert B. "The site-2 protease." Biochimica et Biophysica Acta (BBA)—Biomembranes 1828.12 (2013): 2801-2807.
Rosenberg, Steven A., and Nicholas P. Restifo. "Adoptive cell transfer as personalized immunotherapy for human cancer." Science 348.6230 (2015): 62-68.
Rosenberg, Steven A. "Finding suitable targets is the major obstacle to cancer gene therapy." Cancer gene therapy 21.2 (2014): 45-47.
Roybal et al. (2016) "Precision Tumor Recognition by T Cells with Combinatorial Antigen-Sensing Circuits," Cell. 164:770-779.
Sathirapongsasuti, Jarupon Fah, et al. "Exome sequencing-based copy-number variation and loss of heterozygosity detection: ExomeCNV." Bioinformatics 27.19 (2011): 2648-2654.
Savage, Peter A. "Tumor antigenicity revealed." Trends in immunology 35.2 (2014): 47-48.
Savova, Virginia, et al. "Genes with monoallelic expression contribute disproportionately to genetic diversity in humans." Nature genetics 48.3 (2016): 231-237.
Sayos et al., "Recruitment of C-terminal Src kinase by the leukocyte inhibitory receptor CD85j," Biochem Biophys Res Commun. Nov. 12, 2004;324(2):640-647.
Schumacher, Ton N., and Robert D. Schreiber. "Neoantigens in cancer immunotherapy." Science 348.6230 (2015): 69-74.
Sela-Culang, Inbal, et al. "PEASE: predicting B-cell epitopes utilizing antibody sequence." Bioinformatics 31.8 (2015): 1313-1315.
Sela-Culang, Inbal, Yanay Ofran, and Bjoern Peters. "Antibody specific epitope prediction-emergence of a new paradigm." Current opinion in virology 11 (2015): 98-102.
Skora, Andrew D., et al. "Generation of MANAbodies specific to HLA-restricted epitopes encoded by somatically mutated genes." Proceedings of the National Academy of Sciences 112.32 (2015): 9967-9972.
Stark, Mitchell, and Nicholas Hayward. "Genome-wide loss of heterozygosity and copy number analysis in melanoma using high-density single-nucleotide polymorphism arrays." Cancer research 67.6 (2007): 2632-2642.
Stark, Susan E., and Andrew J. Caton. "Antibodies that are specific for a single amino acid interchange in a protein epitope use structurally distinct variable regions." The Journal of experimental medicine 174.3 (1991): 613-624.
Sun et al., "Construction and evaluation of a novel humanized HER2-specific chimeric receptor," Breast Cancer Research 16:R61, pp. 1-10 (2014).
Ten Berge, I. J. M., et al. "Selective expansion of a peripheral blood CD8+ memory T cell subset expressing both granzyme B and I-selectin during primary viral infection in renal allograft recipients." Transplantation Proceedings (1998); 30(8): 3975-3977.
Teo, Shu Mei, et al. "Statistical challenges associated with detecting copy number variations with next-generation sequencing." Bioinformatics 28.21 (2012): 2711-2718.
Thul, Peter J., et al. "A subcellular map of the human proteome." Science 356.6340 (2017): eaal3321, 1-14.
Treanor, Bebhinn, et al. "Microclusters of inhibitory killer immunoglobulin-like receptor signaling at natural killer cell immunological synapses." The Journal of cell biology 174.1 (2006): 153-161.
Uhlen, Mathias, et al. "Tissue-based map of the human proteome." Science 347.6220 (2015): 1260419-1-1260419-11.
Ui-Tei et al., "Sensitive assay of RNA interference in *Drosophila* and Chinese hamster cultured cells using firefly luciferase gene as target," FEBS Letters 479:79-82 (2000).
Van Buuren, Marit M., Jorg JA Calis, and Ton NM Schumacher. "High sensitivity of cancer exome-based CD8 T cell neo-antigen identification." Oncoimmunology 3.5 (2014): e28836, 1-7.

(56) References Cited

OTHER PUBLICATIONS

Vogelstein, Bert, et al. "Allelotype of colorectal carcinomas." Science 244.4901 (1989): 207-211.

Vogelstein, Bert, et al. "Cancer genome landscapes." Science 339.6127 (2013): 1546-1558.

Voss, Matthias, Bernd Schroder, and Regina Fluhrer. "Mechanism, specificity, and physiology of signal peptide peptidase (SPP) and SPP-like proteases." Biochimica Et Biophysica Acta (BBA)—Biomembranes 1828.12 (2013): 2828-2839.

Vyas, Yatin M., et al. "Spatial organization of signal transduction molecules in the NK cell immune synapses during MHC class I-regulated noncytolytic and cytolytic interactions." The Journal of immunology 167.8 (2001): 4358-4367.

Walseng et al., A TCR-based Chimeric Antigen Receptor, Scientific Reports 7, Article No. 10713,10 pages (2017).

Wang, Zhigang C., et al. "Loss of heterozygosity and its correlation with expression profiles in subclasses of invasive breast cancers." Cancer research 64.1 (2004): 64-71.

Wilkie, Scott, et al. "Dual targeting of ErbB2 and MUC1 in breast cancer using chimeric antigen receptors engineered to provide complementary signaling." Journal of clinical immunology 32.5 (2012): 1059-1070.

Wu, Chia-Yung, et al. "Remote control of therapeutic T cells through a small molecule-gated chimeric receptor." Science 350.6258 (2015): aab4077 1-21.

Yeung, Jacky T., et al. "LOH in the HLA class I region at 6p21 is associated with shorter survival in newly diagnosed adult glioblastoma." Clinical Cancer Research 19.7 (2013): 1816-1826.

Badri et al. (2016) "Optimization of Radiation Dosing Schedules for Proneural Glioblastoma", J Math Biol., 72(5):1301-1336.

Baylot et al. (2017) "TCTP Has a Crucial Role in the Different Stages of Prostate Cancer Malignant Progression", Results Probl Cell Differ., 64:255-261.

Brunner et al. (1999) "Cytotoxic T Cells: Double-barreled Shot Guns", Nature Medicine, 5(1):20-20.

Mariuzza et al. (1987) "The Structural Basis of Antigen-Antibody Recognition", Annual Review of Biophysics and Biophysical Chemistry, 16:139-159.

* cited by examiner

FIG. 2A

| Ligand binding domain (LBDα) | Hinge | TM | Intracellular signaling domain (ICD) |

| Ligand binding domain (LBDβ) | Hinge | TM | Intracellular signaling domain (ICD) |

FIG. 2B

| Ligand binding domain (LBDα) | Hinge | TM | Intracellular signaling domain (ICD) |

| Ligand binding domain (LBDβ) |

| blocker | hinge | length |
|---|---|---|
| mPA2.1_scFv LIR1 iTIM | LIR1 | 64 |
| PA2.1_scFv LIR1 trHTICD | LIR1 trunc | 32 |
| PA2.1_scFv LIR1 2x sH TICD | 2x LIR1 short | 85 |
| PA2.1_scFv sAGSPVTN_H LIR1 TICD | sAGSPVTN | 67 |
| PA2.1_scFv lAGSPVTN_H LIR1 TICD | lAGSPVTN | 75 |

| | |
|---|---|
| mPA2.1_scFv LIR1 iTIM | SSYGSQSSKPYLLTHPSDPLELVVSGPSGGPSSPTTGPTSTSGPEDQPLTPTGSDPQSGLGRHLGVVIGIL (SEQ ID NO: 115) |
| PA2.1_scFv LIR1 trHTICD | SSTTGPTSTSGPEDQPLTPTGSDPQSGLGRHLGVVIGIL (SEQ ID NO: 116) |
| PA2.1_scFv sAGSPVTN_H LIR1 TICD | SSAGSGGSGGSGGSPVPSTPPTPSPSTPPTPSPSGGSGNSSGSGGSPVPSTPPTPSPSTPPTPSPSASVVIGIL (SEQ ID NO: 117) |
| PA2.1_scFv lAGSPVTN_H LIR1 TICD | SSAGSGGSGGSGGSPVPSTPPTNSSSTPPTPSPSPVPSTPPTNSSSTPPTPSPSPVPSTPPTNSSSTPPTPSPSASVVIGIL (SEQ ID NO: 118) |
| PA2.1_scFv LIR1 2x sH TICD | SSVVSGPSGGPSSPTTGPTSTSGPEDQPLTPTGSDPQSGLGRHVVSGPSGGPSSPTTGPTSTSGPEDQPLTPTGSDPQSGLGRHLGVVIGIL (SEQ ID NO: 119) |

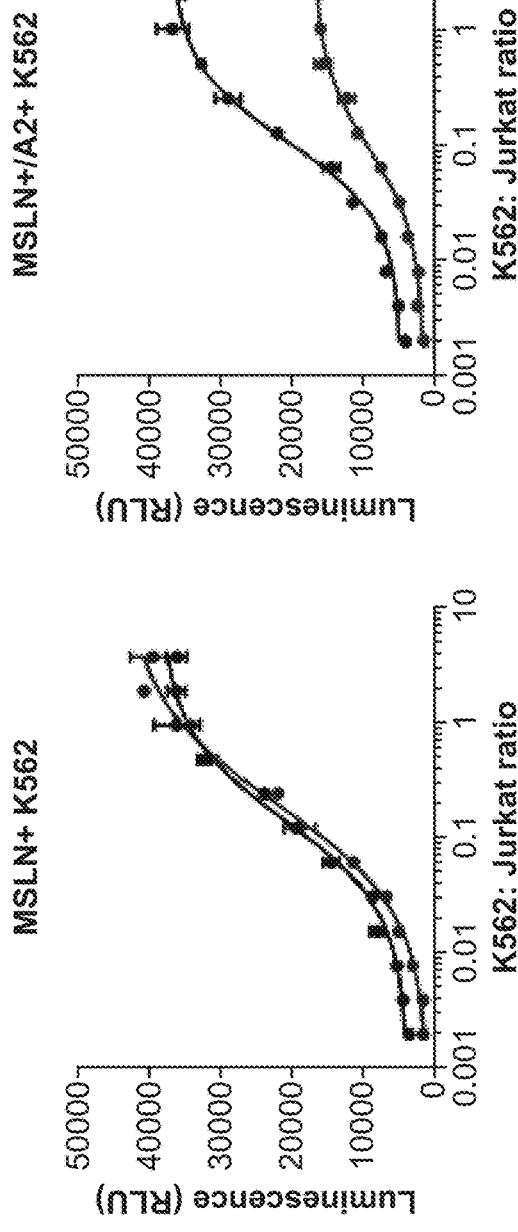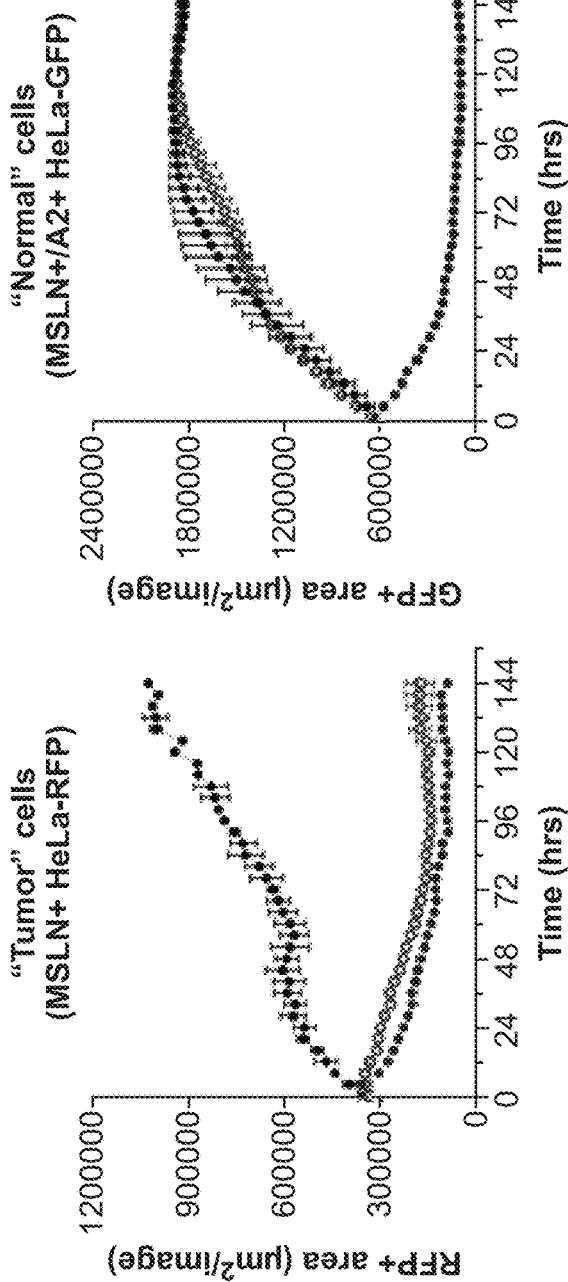
FIG. 22A
FIG. 22B

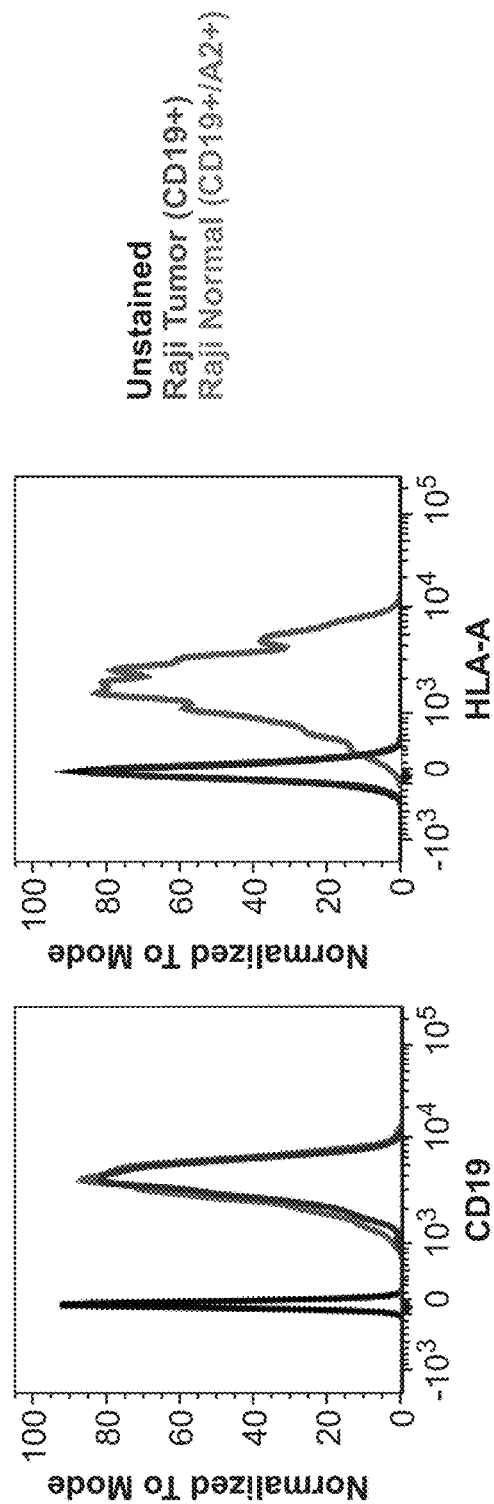
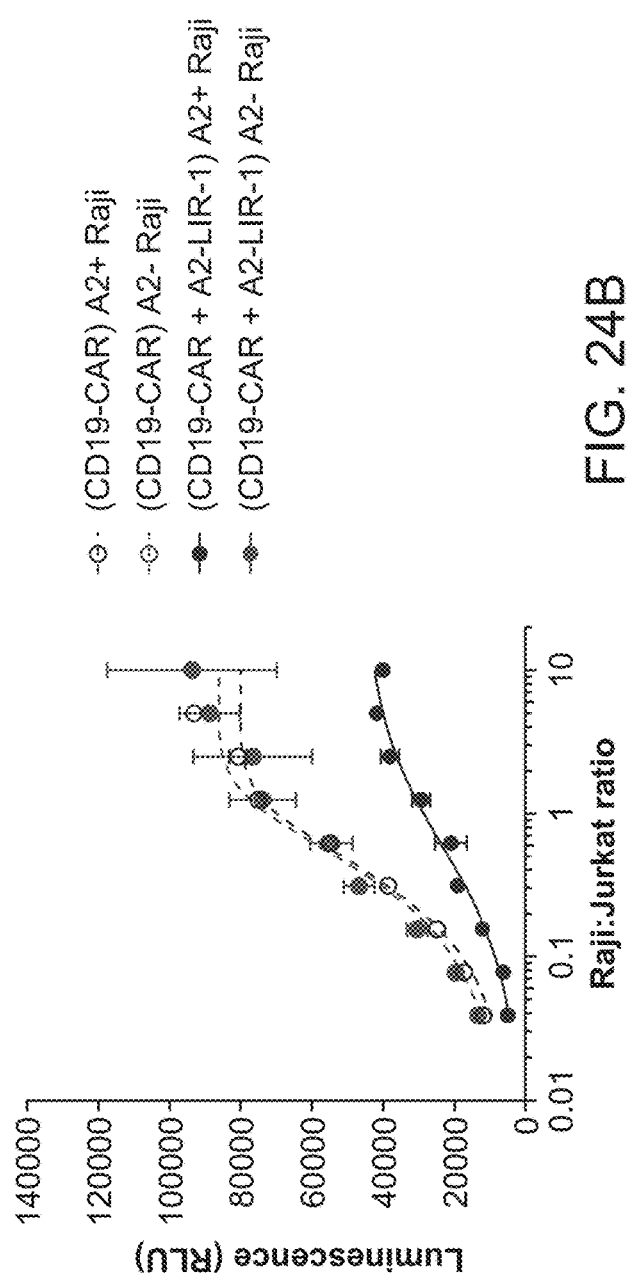
FIG. 24A
FIG. 24B

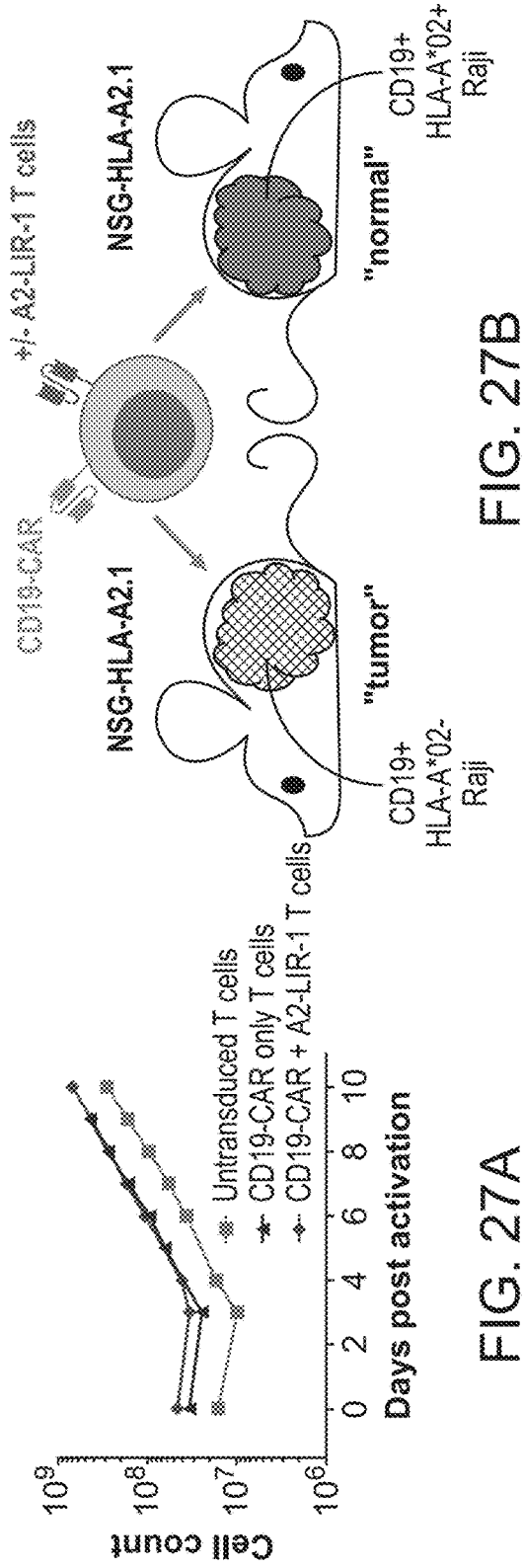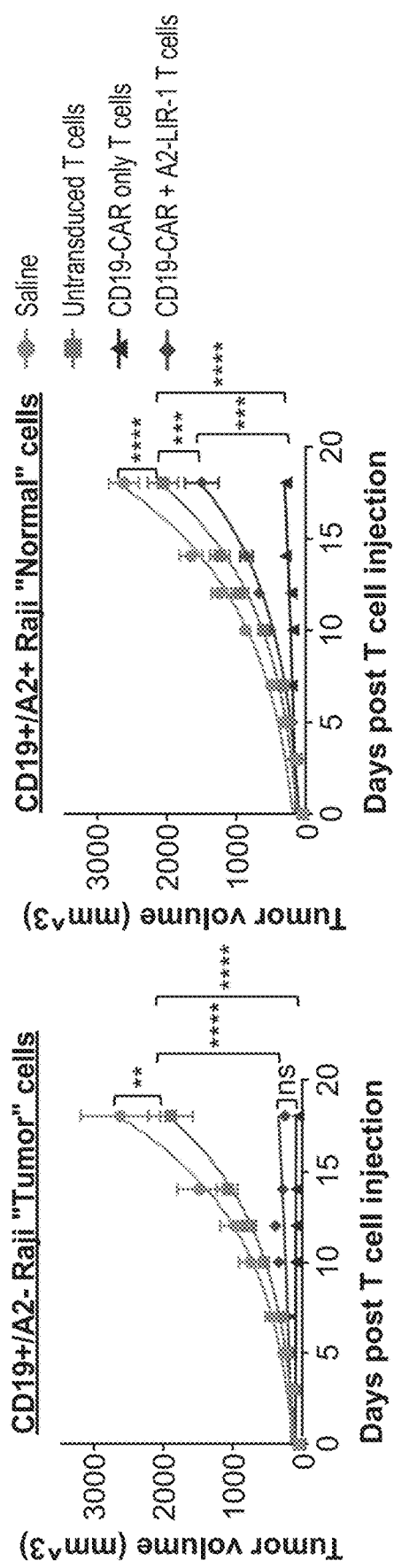
FIG. 27A
FIG. 27B
FIG. 27C

SEQUENCE LISTING

<160> NUMBER OF SEQ ID NOS: 129

<210> SEQ ID NO 1
<211> LENGTH: 670
<212> TYPE: PRT
<213> ORGANISM: Homo sapiens

<400> SEQUENCE: 1

Met Thr Pro Ile Leu Thr Val Leu Ile Cys Leu Gly Leu Ser Leu Gly

-continued

```
1               5                   10                  15
Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
            35                  40                  45

Cys Gln Gly Gly Gln Glu Thr Gln Glu Tyr Arg Leu Tyr Arg Glu Lys
50                          55                  60

Lys Thr Ala Leu Trp Ile Thr Arg Ile Pro Gln Glu Leu Val Lys Lys
65                      70                  75                  80

Gly Gln Phe Pro Ile Pro Ser Ile Thr Trp Glu His Ala Gly Arg Tyr
                    85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
            115                 120                 125

Ala Gln Pro Ser Pro Val Val Asn Ser Gly Gly Asn Val Ile Leu Gln
130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
                195                 200                 205

Ser Leu Pro Ser Asp Leu Leu Glu Leu Leu Val Leu Gly Val Ser Lys
            210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
                260                 265                 270

Pro Gln Ala Gly Leu Ser Gln Ala Asn Phe Thr Leu Gly Pro Val Ser
            275                 280                 285

Arg Ser Tyr Gly Gly Gln Tyr Arg Cys Tyr Gly Ala His Asn Leu Ser
            290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
            355                 360                 365

Leu Arg Ser Thr Tyr Gln Ser Gln Lys Tyr Gln Ala Glu Phe Pro Met
            370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
            405                 410                 415

Leu Val Val Ser Gly Pro Ser Gly Gly Pro Ser Ser Pro Thr Thr Gly
            420                 425                 430
```

```
Pro Thr Ser Thr Ser Gly Pro Glu Asp Gln Pro Leu Thr Pro Thr Gly
            435                 440                 445

Ser Asp Pro Gln Ser Gly Leu Gly Arg His Leu Gly Val Val Ile Gly
        450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                    500                 505                 510

Thr Asp Arg Gly Leu Gln Trp Arg Ser Ser Pro Ala Ala Asp Ala Gln
            515                 520                 525

Glu Glu Asn Leu Tyr Ala Ala Val Lys His Thr Gln Pro Glu Asp Gly
        530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
                    580                 585                 590

Ala Glu Glu Asp Arg Gln Met Asp Thr Glu Ala Ala Ala Ser Glu Ala
            595                 600                 605

Pro Gln Asp Val Thr Tyr Ala Gln Leu His Ser Leu Thr Leu Arg Arg
        610                 615                 620

Glu Ala Thr Glu Pro Pro Pro Ser Gln Glu Gly Pro Ser Pro Ala Val
625                 630                 635                 640

Pro Ser Ile Tyr Ala Thr Leu Ala Ile His Pro Ser Gln Glu Gly Pro
                645                 650                 655

Ser Pro Ala Val Pro Ser Ile Tyr Ala Thr Leu Ala Ile His
                    660                 665                 670

<210> SEQ ID NO 2
<211> LENGTH: 253
<212> TYPE: PRT
<213> ORGANISM: Homo sapiens

<400> SEQUENCE: 2

Tyr Gly Ser Gln Ser Ser Lys Pro Tyr Leu Thr His Pro Ser Asp
1               5                   10                  15

Pro Leu Glu Leu Val Val Ser Gly Pro Ser Gly Gly Pro Ser Ser Pro
                20                  25                  30

Thr Thr Gly Pro Thr Ser Thr Ser Gly Pro Glu Asp Gln Pro Leu Thr
            35                  40                  45

Pro Thr Gly Ser Asp Pro Gln Ser Gly Leu Gly Arg His Leu Gly Val
        50                  55                  60

Val Ile Gly Ile Leu Val Ala Val Ile Leu Leu Leu Leu Leu Leu Leu
65                  70                  75                  80

Leu Leu Phe Leu Ile Leu Arg His Arg Arg Gln Gly Lys His Trp Thr
                85                  90                  95

Ser Thr Gln Arg Lys Ala Asp Phe Gln His Pro Ala Gly Ala Val Gly
                    100                 105                 110

Pro Glu Pro Thr Asp Arg Gly Leu Gln Trp Arg Ser Ser Pro Ala Ala
            115                 120                 125

Asp Ala Gln Glu Glu Asn Leu Tyr Ala Ala Val Lys His Thr Gln Pro
```

```
                130                 135                 140
Glu Asp Gly Val Glu Met Asp Thr Arg Ser Pro His Asp Glu Asp Pro
145                 150                 155                 160

Gln Ala Val Thr Tyr Ala Glu Val Lys His Ser Arg Pro Arg Arg Glu
                165                 170                 175

Met Ala Ser Pro Pro Ser Pro Leu Ser Gly Glu Phe Leu Asp Thr Lys
                180                 185                 190

Asp Arg Gln Ala Glu Glu Asp Arg Gln Met Asp Thr Glu Ala Ala Ala
                195                 200                 205

Ser Glu Ala Pro Gln Asp Val Thr Tyr Ala Gln Leu His Ser Leu Thr
                210                 215                 220

Leu Arg Arg Glu Ala Thr Glu Pro Pro Pro Ser Gln Glu Gly Pro Ser
225                 230                 235                 240

Pro Ala Val Pro Ser Ile Tyr Ala Thr Leu Ala Ile His
                245                 250
```

```
<210> SEQ ID NO 3
<211> LENGTH: 233
<212> TYPE: PRT
<213> ORGANISM: Homo sapiens

<400> SEQUENCE: 3

Val Val Ser Gly Pro Ser Gly Gly Pro Ser Ser Pro Thr Thr Gly Pro
1               5                   10                  15

Thr Ser Thr Ser Gly Pro Glu Asp Gln Pro Leu Thr Pro Thr Gly Ser
                20                  25                  30

Asp Pro Gln Ser Gly Leu Gly Arg His Leu Gly Val Val Ile Gly Ile
                35                  40                  45

Leu Val Ala Val Ile Leu Leu Leu Leu Leu Leu Leu Leu Leu Phe Leu
                50                  55                  60

Ile Leu Arg His Arg Arg Gln Gly Lys His Trp Thr Ser Thr Gln Arg
65                  70                  75                  80

Lys Ala Asp Phe Gln His Pro Ala Gly Ala Val Gly Pro Glu Pro Thr
                85                  90                  95

Asp Arg Gly Leu Gln Trp Arg Ser Ser Pro Ala Ala Asp Ala Gln Glu
                100                 105                 110

Glu Asn Leu Tyr Ala Ala Val Lys His Thr Gln Pro Glu Asp Gly Val
                115                 120                 125

Glu Met Asp Thr Arg Ser Pro His Asp Glu Asp Pro Gln Ala Val Thr
130                 135                 140

Tyr Ala Glu Val Lys His Ser Arg Pro Arg Arg Glu Met Ala Ser Pro
145                 150                 155                 160

Pro Ser Pro Leu Ser Gly Glu Phe Leu Asp Thr Lys Asp Arg Gln Ala
                165                 170                 175

Glu Glu Asp Arg Gln Met Asp Thr Glu Ala Ala Ala Ser Glu Ala Pro
                180                 185                 190

Gln Asp Val Thr Tyr Ala Gln Leu His Ser Leu Thr Leu Arg Arg Glu
                195                 200                 205

Ala Thr Glu Pro Pro Pro Ser Gln Glu Gly Pro Ser Pro Ala Val Pro
                210                 215                 220

Ser Ile Tyr Ala Thr Leu Ala Ile His
225                 230
```

```
<210> SEQ ID NO 4
<211> LENGTH: 63
```

```
<212> TYPE: PRT
<213> ORGANISM: Homo sapiens

<400> SEQUENCE: 4

Tyr Gly Ser Gln Ser Ser Lys Pro Tyr Leu Thr His Pro Ser Asp
 1               5                  10                  15

Pro Leu Glu Leu Val Val Ser Gly Ser Gly Pro Ser Ser Pro
             20                  25                  30

Thr Thr Gly Pro Thr Ser Thr Ser Gly Pro Glu Asp Gln Pro Leu Thr
             35                  40                  45

Pro Thr Gly Ser Asp Pro Gln Ser Gly Leu Gly Arg His Leu Gly
         50                  55                  60

<210> SEQ ID NO 5
<211> LENGTH: 23
<212> TYPE: PRT
<213> ORGANISM: Homo sapiens

<400> SEQUENCE: 5

Val Val Ile Gly Ile Leu Val Ala Val Ile Leu Leu Leu Leu Leu
 1               5                  10                  15

Leu Leu Leu Phe Leu Ile Leu
             20

<210> SEQ ID NO 6

<400> SEQUENCE: 6

000

<210> SEQ ID NO 7
<211> LENGTH: 167
<212> TYPE: PRT
<213> ORGANISM: Homo sapiens

<400> SEQUENCE: 7

Arg His Arg Arg Gln Gly Lys His Trp Thr Ser Thr Gln Arg Lys Ala
 1               5                  10                  15

Asp Phe Gln His Pro Ala Gly Ala Val Gly Pro Glu Pro Thr Asp Arg
             20                  25                  30

Gly Leu Gln Trp Arg Ser Ser Pro Ala Ala Asp Ala Gln Glu Glu Asn
             35                  40                  45

Leu Tyr Ala Ala Val Lys His Thr Gln Pro Glu Asp Gly Val Glu Met
         50                  55                  60

Asp Thr Arg Ser Pro His Asp Glu Asp Pro Gln Ala Val Thr Tyr Ala
 65                  70                  75                  80

Glu Val Lys His Ser Arg Pro Arg Arg Glu Met Ala Ser Pro Pro Ser
                 85                  90                  95

Pro Leu Ser Gly Glu Phe Leu Asp Thr Lys Asp Arg Gln Ala Glu Glu
                100                 105                 110

Asp Arg Gln Met Asp Thr Glu Ala Ala Ala Ser Glu Ala Pro Gln Asp
            115                 120                 125

Val Thr Tyr Ala Gln Leu His Ser Leu Thr Leu Arg Arg Glu Ala Thr
        130                 135                 140

Glu Pro Pro Pro Ser Gln Glu Gly Pro Ser Pro Ala Val Pro Ser Ile
145                 150                 155                 160

Tyr Ala Thr Leu Ala Ile His
                165
```

-continued

```
<210> SEQ ID NO 8
<211> LENGTH: 6
<212> TYPE: PRT
<213> ORGANISM: Homo sapiens

<400> SEQUENCE: 8

Asn Leu Tyr Ala Ala Val
1               5

<210> SEQ ID NO 9
<211> LENGTH: 6
<212> TYPE: PRT
<213> ORGANISM: Homo sapiens

<400> SEQUENCE: 9

Val Thr Tyr Ala Glu Val
1               5

<210> SEQ ID NO 10
<211> LENGTH: 6
<212> TYPE: PRT
<213> ORGANISM: Homo sapiens

<400> SEQUENCE: 10

Val Thr Tyr Ala Gln Leu
1               5

<210> SEQ ID NO 11
<211> LENGTH: 6
<212> TYPE: PRT
<213> ORGANISM: Homo sapiens

<400> SEQUENCE: 11

Ser Ile Tyr Ala Thr Leu
1               5

<210> SEQ ID NO 12
<211> LENGTH: 35
<212> TYPE: PRT
<213> ORGANISM: Homo sapiens

<400> SEQUENCE: 12

Asn Leu Tyr Ala Ala Val Lys His Thr Gln Pro Glu Asp Gly Val Glu
1               5                   10                  15

Met Asp Thr Arg Ser Pro His Asp Glu Asp Pro Gln Ala Val Thr Tyr
            20                  25                  30

Ala Glu Val
        35

<210> SEQ ID NO 13
<211> LENGTH: 58
<212> TYPE: PRT
<213> ORGANISM: Homo sapiens

<400> SEQUENCE: 13

Val Thr Tyr Ala Glu Val Lys His Ser Arg Pro Arg Arg Glu Met Ala
1               5                   10                  15

Ser Pro Pro Ser Pro Leu Ser Gly Glu Phe Leu Asp Thr Lys Asp Arg
            20                  25                  30

Gln Ala Glu Glu Asp Arg Gln Met Asp Thr Glu Ala Ala Ala Ser Glu
        35                  40                  45

Ala Pro Gln Asp Val Thr Tyr Ala Gln Leu
```

```
                50                  55

<210> SEQ ID NO 14
<211> LENGTH: 36
<212> TYPE: PRT
<213> ORGANISM: Homo sapiens

<400> SEQUENCE: 14

Val Thr Tyr Ala Gln Leu His Ser Leu Thr Leu Arg Arg Glu Ala Thr
1               5                   10                  15

Glu Pro Pro Pro Ser Gln Glu Gly Pro Ser Pro Ala Val Pro Ser Ile
            20                  25                  30

Tyr Ala Thr Leu
        35

<210> SEQ ID NO 15
<211> LENGTH: 87
<212> TYPE: PRT
<213> ORGANISM: Homo sapiens

<400> SEQUENCE: 15

Asn Leu Tyr Ala Ala Val Lys His Thr Gln Pro Glu Asp Gly Val Glu
1               5                   10                  15

Met Asp Thr Arg Ser Pro His Asp Glu Asp Pro Gln Ala Val Thr Tyr
            20                  25                  30

Ala Glu Val Lys His Ser Arg Pro Arg Arg Glu Met Ala Ser Pro Pro
        35                  40                  45

Ser Pro Leu Ser Gly Glu Phe Leu Asp Thr Lys Asp Arg Gln Ala Glu
    50                  55                  60

Glu Asp Arg Gln Met Asp Thr Glu Ala Ala Ala Ser Glu Ala Pro Gln
65                  70                  75                  80

Asp Val Thr Tyr Ala Gln Leu
                85

<210> SEQ ID NO 16
<211> LENGTH: 88
<212> TYPE: PRT
<213> ORGANISM: Homo sapiens

<400> SEQUENCE: 16

Val Thr Tyr Ala Glu Val Lys His Ser Arg Pro Arg Arg Glu Met Ala
1               5                   10                  15

Ser Pro Pro Ser Pro Leu Ser Gly Glu Phe Leu Asp Thr Lys Asp Arg
            20                  25                  30

Gln Ala Glu Glu Asp Arg Gln Met Asp Thr Glu Ala Ala Ala Ser Glu
        35                  40                  45

Ala Pro Gln Asp Val Thr Tyr Ala Gln Leu His Ser Leu Thr Leu Arg
    50                  55                  60

Arg Glu Ala Thr Glu Pro Pro Pro Ser Gln Glu Gly Pro Ser Pro Ala
65                  70                  75                  80

Val Pro Ser Ile Tyr Ala Thr Leu
                85

<210> SEQ ID NO 17
<211> LENGTH: 117
<212> TYPE: PRT
<213> ORGANISM: Homo sapiens

<400> SEQUENCE: 17
```

```
Asn Leu Tyr Ala Ala Val Lys His Thr Gln Pro Glu Asp Gly Val Glu
1               5                   10                  15

Met Asp Thr Arg Ser Pro His Asp Glu Asp Pro Gln Ala Val Thr Tyr
            20                  25                  30

Ala Glu Val Lys His Ser Arg Pro Arg Arg Glu Met Ala Ser Pro Pro
                35                  40                  45

Ser Pro Leu Ser Gly Glu Phe Leu Asp Thr Lys Asp Arg Gln Ala Glu
        50                  55                  60

Glu Asp Arg Gln Met Asp Thr Glu Ala Ala Ser Glu Ala Pro Gln
65                  70                  75                  80

Asp Val Thr Tyr Ala Gln Leu His Ser Leu Thr Leu Arg Arg Glu Ala
                85                  90                  95

Thr Glu Pro Pro Pro Ser Gln Glu Gly Pro Ser Pro Ala Val Pro Ser
            100                 105                 110

Ile Tyr Ala Thr Leu
            115
```

```
<210> SEQ ID NO 18
<211> LENGTH: 20
<212> TYPE: PRT
<213> ORGANISM: Homo sapiens

<400> SEQUENCE: 18

Tyr Gly Ser Gln Ser Ser Lys Pro Tyr Leu Leu Thr His Pro Ser Asp
1               5                   10                  15

Pro Leu Glu Leu
            20
```

```
<210> SEQ ID NO 19
<211> LENGTH: 43
<212> TYPE: PRT
<213> ORGANISM: Homo sapiens

<400> SEQUENCE: 19

Val Val Ser Gly Pro Ser Gly Pro Ser Ser Pro Thr Thr Gly Pro
1               5                   10                  15

Thr Ser Thr Ser Gly Pro Glu Asp Gln Pro Leu Thr Pro Thr Gly Ser
            20                  25                  30

Asp Pro Gln Ser Gly Leu Gly Arg His Leu Gly
            35                  40
```

```
<210> SEQ ID NO 20
<211> LENGTH: 86
<212> TYPE: PRT
<213> ORGANISM: Homo sapiens

<400> SEQUENCE: 20

Tyr Gly Ser Gln Ser Ser Lys Pro Tyr Leu Leu Thr His Pro Ser Asp
1               5                   10                  15

Pro Leu Glu Leu Val Val Ser Gly Pro Ser Gly Pro Ser Ser Pro
            20                  25                  30

Thr Thr Gly Pro Thr Ser Thr Ser Gly Pro Glu Asp Gln Pro Leu Thr
            35                  40                  45

Pro Thr Gly Ser Asp Pro Gln Ser Gly Leu Gly Arg His Leu Gly Val
            50                  55                  60

Val Ile Gly Ile Leu Val Ala Val Ile Leu Leu Leu Leu Leu Leu
65                  70                  75                  80

Leu Leu Phe Leu Ile Leu
```

<210> SEQ ID NO 21
<211> LENGTH: 190
<212> TYPE: PRT
<213> ORGANISM: Homo sapiens

<400> SEQUENCE: 21

Val Val Ile Gly Ile Leu Val Ala Val Ile Leu Leu Leu Leu Leu
1               5                   10                  15

Leu Leu Leu Phe Leu Ile Leu Arg His Arg Arg Gln Gly Lys His Trp
            20                  25                  30

Thr Ser Thr Gln Arg Lys Ala Asp Phe Gln His Pro Ala Gly Ala Val
        35                  40                  45

Gly Pro Glu Pro Thr Asp Arg Gly Leu Gln Trp Arg Ser Ser Pro Ala
    50                  55                  60

Ala Asp Ala Gln Glu Glu Asn Leu Tyr Ala Ala Val Lys His Thr Gln
65                  70                  75                  80

Pro Glu Asp Gly Val Glu Met Asp Thr Arg Ser Pro His Asp Glu Asp
                85                  90                  95

Pro Gln Ala Val Thr Tyr Ala Glu Val Lys His Ser Arg Pro Arg Arg
            100                 105                 110

Glu Met Ala Ser Pro Pro Ser Pro Leu Ser Gly Glu Phe Leu Asp Thr
        115                 120                 125

Lys Asp Arg Gln Ala Glu Glu Asp Arg Gln Met Asp Thr Glu Ala Ala
130                 135                 140

Ala Ser Glu Ala Pro Gln Asp Val Thr Tyr Ala Gln Leu His Ser Leu
145                 150                 155                 160

Thr Leu Arg Arg Glu Ala Thr Glu Pro Pro Pro Ser Gln Glu Gly Pro
                165                 170                 175

Ser Pro Ala Val Pro Ser Ile Tyr Ala Thr Leu Ala Ile His
            180                 185                 190

<210> SEQ ID NO 22
<211> LENGTH: 16
<212> TYPE: PRT
<213> ORGANISM: Artificial Sequence
<220> FEATURE:
<223> OTHER INFORMATION: light chain CDR

<400> SEQUENCE: 22

Arg Ser Ser Gln Ser Ile Val His Ser Asn Gly Asn Thr Tyr Leu Glu
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: light chain CDR

<400> SEQUENCE: 23

Lys Val Ser Asn Arg Phe Ser Gly Val Pro Asp Arg
1               5                   10

<210> SEQ ID NO 24
<211> LENGTH: 9
<212> TYPE: PRT
<213> ORGANISM: Artificial Sequence
<220> FEATURE:
<223> OTHER INFORMATION: light chain CDR

```
<400> SEQUENCE: 24

Phe Gln Gly Ser His Val Pro Arg Thr
1               5

<210> SEQ ID NO 25
<211> LENGTH: 12
<212> TYPE: PRT
<213> ORGANISM: Artificial Sequence
<220> FEATURE:
<223> OTHER INFORMATION: heavy chain CDR

<400> SEQUENCE: 25

Ala Ser Gly Tyr Thr Phe Thr Ser Tyr His Ile His
1               5                   10

<210> SEQ ID NO 26
<211> LENGTH: 18
<212> TYPE: PRT
<213> ORGANISM: Artificial Sequence
<220> FEATURE:
<223> OTHER INFORMATION: heavy chain CDR

<400> SEQUENCE: 26

Trp Ile Tyr Pro Gly Asn Val Asn Thr Glu Tyr Asn Glu Lys Phe Lys
1               5                   10                  15

Gly Lys

<210> SEQ ID NO 27
<211> LENGTH: 9
<212> TYPE: PRT
<213> ORGANISM: Artificial Sequence
<220> FEATURE:
<223> OTHER INFORMATION: heavy chain CDR

<400> SEQUENCE: 27

Glu Glu Ile Thr Tyr Ala Met Asp Tyr
1               5

<210> SEQ ID NO 28
<211> LENGTH: 16
<212> TYPE: PRT
<213> ORGANISM: Artificial Sequence
<220> FEATURE:
<223> OTHER INFORMATION: light chain CDR

<400> SEQUENCE: 28

Arg Ser Ser Gln Ser Ile Val His Ser Asn Gly Asn Thr Tyr Leu Asp
1               5                   10                  15

<210> SEQ ID NO 29
<211> LENGTH: 12
<212> TYPE: PRT
<213> ORGANISM: Artificial Sequence
<220> FEATURE:
<223> OTHER INFORMATION: light chain CDR

<400> SEQUENCE: 29

Lys Val Ser Asn Arg Phe Ser Gly Val Pro Asp Arg
1               5                   10

<210> SEQ ID NO 30
<211> LENGTH: 9
<212> TYPE: PRT
<213> ORGANISM: Artificial Sequence
<220> FEATURE:
```

<223> OTHER INFORMATION: light chain CDR

<400> SEQUENCE: 30

Met Gln Gly Ser His Val Pro Arg Thr
1               5

<210> SEQ ID NO 31
<211> LENGTH: 11
<212> TYPE: PRT
<213> ORGANISM: Artificial Sequence
<220> FEATURE:
<223> OTHER INFORMATION: heavy chain CDR

<400> SEQUENCE: 31

Ser Gly Tyr Thr Phe Thr Ser Tyr His Met His
1               5                   10

<210> SEQ ID NO 32
<211> LENGTH: 17
<212> TYPE: PRT
<213> ORGANISM: Artificial Sequence
<220> FEATURE:
<223> OTHER INFORMATION: heavy chain CDR

<400> SEQUENCE: 32

Trp Ile Tyr Pro Gly Asp Gly Ser Thr Gln Tyr Asn Glu Lys Phe Lys
1               5                   10                  15

Gly

<210> SEQ ID NO 33
<211> LENGTH: 9
<212> TYPE: PRT
<213> ORGANISM: Artificial Sequence
<220> FEATURE:
<223> OTHER INFORMATION: heavy chain CDR

<400> SEQUENCE: 33

Glu Gly Thr Tyr Tyr Ala Met Asp Tyr
1               5

<210> SEQ ID NO 34
<211> LENGTH: 3229
<212> TYPE: DNA
<213> ORGANISM: Homo sapiens

<400> SEQUENCE: 34

```
aaatgagttt taaaaaggct tgtccaggaa gcacatatgg gagctggtca ctctgcattt      60
tgggccctcc tggaggtgtt tagaccttcc gagagagaaa ctgagacaca tgagagggaa     120
gaaatgactc agtggtgaga ccctgtggag tcccacccac aaccagcaca ctgtgaccca     180
ctgcacaaac ctctagccca cagctcactt cctcctttaa gaagagaaga gaaagagga     240 gaggagagga ggaacagaaa agaaaagaaa agaaaaagtg ggaaacaaat aatctaagaa     300
tgaggagaaa gcaagaagag tgacccccct gtgggcactc cattggtttt atggcgcctc     360
tactttctgg agtttgtgta aaacaaaaat attatggtct ttgtgcacat ttacatcaag     420
ctcagcctgg gcggcacagc cagatgcgag atgcgtctct gctgatctga gtctgcctgc     480
agcatggacc tgggtcttcc ctgaagcatc tccagggctg agggacgac tgccatgcac     540 cgagggctca tccatccaca gagcagggca gtgggaggag acgccatgac ccccatcctc     600
acggtcctga tctgtctcgg gctgagtctg ggccccgga cccacgtgca ggcagggcac     660
ctccccaagc ccaccctctg ggctgaacca ggctctgtga tcacccaggg gagtcctgtg     720
```

```
accctcaggt gtcagggggg ccaggagacc caggagtacc gtctatatag agaaaagaaa      780
acagcaccct ggattacacg gatcccacag gagcttgtga agaagggcca gttccccatc      840
ccatccatca cctgggaaca cacagggcgg tatcgctgtt actatggtag cgacactgca      900
ggccgctcag agagcagtga cccccctggag ctggtggtga caggagccta catcaaaccc     960
accctctcag cccagcccag ccccgtggtg aactcaggag ggaatgtaac cctccagtgt     1020
gactcacagg tggcatttga tggcttcatt ctgtgtaagg aaggagaaga tgaacaccca     1080
caatgcctga actcccagcc ccatgcccgt gggtcgtccc gcgccatctt ctccgtgggc     1140
cccgtgagcc cgagtcgcag gtggtggtac aggtgctatg cttatgactc gaactctccc     1200
tatgagtggt ctctacccag tgatctcctg gagctcctgg tcctaggtgt ttctaagaag     1260
ccatcactct cagtgcagcc aggtcctatc gtggcccctg aggagaccct gactctgcag     1320
tgtggctctg atgctggcta acagagattt gttctgtata aggacgggga acgtgacttc     1380
cttcagctcg ctggcgcaca gccccaggct gggctctccc aggccaactt caccctgggc     1440
cctgtgagcc gctcctacgg gggccagtac agatgctacg gtgcacacaa cctctcctcc     1500
gagtggtcgg cccccagcga ccccctggac atcctgatcg caggacagtt ctatgacaga     1560
gtctccctct cggtgcagcc gggccccacg gtggcctcag gagagaacgt gaccctgctg     1620
tgtcagtcac agggatggat gcaaactttc cttctgacca aggagggggc agctgatgac     1680
ccatggcgtc taagatcaac gtaccaatct caaaaatacc aggctgaatt ccccatgggt     1740
cctgtgacct cagcccatgc ggggacctac aggtgctacg gctcacagag ctccaaaccc     1800
tacctgctga ctcaccccag tgacccctg gagctcgtgg tctcaggacc gtctggggc      1860 cccagctccc cgacaacagg ccccacctcc acatctggcc ctgaggacca gcccctcacc     1920
cccaccgggt cggatcccca gagtggtctg ggaaggcacc tgggggttgt gatcggcatc     1980 ttggtgccg tcatcctact gctcctcctc ctcctcctcc tcttcctcat cctccgacat     2040
cgacgtcagg gcaaacactg gacatcgacc cagagaaagg ctgatttcca acatcctgca     2100
ggggctgtgg ggccagagcc cacagacaga ggcctgcagt ggaggtccag cccagctgcc     2160
gatgcccagg aagaaaacct ctatgctgcc gtgaagcaca cacagcctga ggatggggtg     2220
gagatggaca ctcggagccc acacgatgaa gaccccaggg cagtgacgta tgccgaggtg     2280
aaacactcca gacctaggag agaaatggcc tctcctcctt ccccactgtc tggggaattc     2340
ctggacacaa aggacagaca ggcggaagag gacaggcaga tggacactga ggctgctgca     2400
tctgaagccc cccaggatgt gacctacgcc cagctgcaca gcttgaccct cagacgggag     2460
gcaactgagc ctcctccatc ccaggaaggg ccctctccag ctgtgcccag catctacgcc     2520
actctggcca tccactagcc caggggggga cgcagacccc acactccatg gagtctggaa     2580
tgcatgggag ctgccccccc agtggacacc attggacccc acccagcctg gatctacccc     2640
aggagactct gggaactttt aggggtcact caattctgca gtataaataa ctaatgtctc     2700
tacaattttg aaataaagca acagacttct caataatcaa tgaagtagct gagaaaacta     2760
agtcagaaag tgcattaaac tgaatcacaa tgtaaatatt acacatcaag cgatgaaact     2820
ggaaaactac aagccacgaa tgaatgaatt aggaaagaaa aaagtagga aatgaatgat       2880 cttggctttc ctataagaaa tttagggcag ggcacggtgg ctcacgcctg taattccagc     2940
actttgggag gccgaggcgg gcagatcacg agttcaggag atcgagacca tcttggccaa     3000
catggtgaaa ccctgtctct cctaaaaata caaaaattag ctggatgtgg tggcagtgcc     3060
```

```
tgtaatccca gctatttggg aggctgaggc aggagaatcg cttgaaccag ggagtcagag    3120
gtttcagtga gccaagatcg caccactgct ctccagcctg gcgacagagg gagactccat    3180
ctcaaattaa aaaaaaaaaa aaaaagaaa gaaaaaaaaa aaaaaaaa                  3229
```

<210> SEQ ID NO 35
<211> LENGTH: 247
<212> TYPE: PRT
<213> ORGANISM: Artificial Sequence
<220> FEATURE:
<223> OTHER INFORMATION: C-001765 scFv antibody construct

<400> SEQUENCE: 35

```
Met Met Thr Gln Thr Pro Leu Ser Leu Pro Val Ser Leu Gly Asp Gln
1               5                   10                  15

Ala Ser Ile Ser Cys Arg Ser Ser Gln Ser Ile Val His Ser Asn Gly
            20                  25                  30

Asn Thr Tyr Leu Glu Trp Tyr Leu Gln Lys Pro Gly Gln Ser Pro Lys
        35                  40                  45

Leu Leu Ile Tyr Lys Val Ser Asn Arg Phe Ser Gly Val Pro Asp Arg
    50                  55                  60

Phe Ser Gly Ser Gly Ser Gly Thr Asp Phe Thr Leu Lys Ile Ser Arg
65                  70                  75                  80

Val Glu Ala Glu Asp Leu Gly Val Tyr Tyr Cys Phe Gln Gly Ser His
                85                  90                  95

Val Pro Arg Thr Ser Gly Gly Gly Thr Lys Leu Glu Ile Lys Gly Gly
            100                 105                 110

Gly Gly Ser Gly Gly Gly Gly Ser Gly Gly Gly Gly Ser Gly Gly Gln
        115                 120                 125

Val Gln Leu Gln Gln Ser Gly Pro Glu Leu Val Lys Pro Gly Ala Ser
    130                 135                 140

Val Arg Ile Ser Cys Lys Ala Ser Gly Tyr Thr Phe Thr Ser Tyr His
145                 150                 155                 160

Ile His Trp Val Lys Gln Arg Pro Gly Gln Gly Leu Glu Trp Ile Gly
                165                 170                 175

Trp Ile Tyr Pro Gly Asn Val Asn Thr Glu Tyr Asn Glu Lys Phe Lys
            180                 185                 190

Gly Lys Ala Thr Leu Thr Ala Asp Lys Ser Ser Ser Thr Ala Tyr Met
        195                 200                 205

His Leu Ser Ser Leu Thr Ser Glu Asp Ser Ala Val Tyr Phe Cys Ala
    210                 215                 220

Arg Glu Glu Ile Thr Tyr Ala Met Asp Tyr Trp Gly Gln Gly Thr Ser
225                 230                 235                 240

Val Thr Val Ser Ser Tyr Gly
                245
```

<210> SEQ ID NO 36
<211> LENGTH: 245
<212> TYPE: PRT
<213> ORGANISM: Artificial Sequence
<220> FEATURE:
<223> OTHER INFORMATION: C-002159 scFv antibody construct

<400> SEQUENCE: 36

```
Gln Leu Val Gln Ser Gly Ala Glu Val Lys Lys Pro Gly Ser Ser Val
1               5                   10                  15

Lys Val Ser Cys Lys Ala Ser Gly Tyr Thr Phe Thr Ser Tyr His Ile
            20                  25                  30
```

His Trp Val Arg Gln Ala Pro Gly Gln Gly Leu Glu Trp Met Gly Trp
                35                  40                  45

Ile Tyr Pro Gly Asn Val Asn Thr Glu Tyr Asn Glu Lys Phe Lys Gly
 50                  55                  60

Lys Ala Thr Ile Thr Ala Asp Lys Ser Thr Ser Thr Ala Tyr Met Glu
 65                  70                  75                  80

Leu Ser Ser Leu Arg Ser Glu Asp Thr Ala Val Tyr Tyr Cys Ala Arg
                85                  90                  95

Glu Glu Ile Thr Tyr Ala Met Asp Tyr Trp Gly Gln Gly Thr Thr Val
                100                 105                 110

Thr Val Ser Ser Gly Gly Gly Gly Ser Gly Gly Gly Gly Ser Gly Gly
                115                 120                 125

Gly Gly Ser Gly Gly Glu Ile Val Leu Thr Gln Ser Pro Gly Thr Leu
 130                 135                 140

Ser Leu Ser Pro Gly Glu Arg Ala Thr Leu Ser Cys Arg Ser Ser Gln
145                 150                 155                 160

Ser Ile Val His Ser Asn Gly Asn Thr Tyr Leu Glu Trp Tyr Gln Gln
                165                 170                 175

Lys Pro Gly Gln Ala Pro Arg Leu Leu Ile Tyr Lys Val Ser Asn Arg
                180                 185                 190

Phe Ser Gly Ile Pro Asp Arg Phe Ser Gly Ser Gly Ser Gly Thr Asp
                195                 200                 205

Phe Thr Leu Thr Ile Ser Arg Leu Glu Pro Glu Asp Phe Ala Val Tyr
 210                 215                 220

Tyr Cys Phe Gln Gly Ser His Val Pro Arg Thr Phe Gly Gly Gly Thr
225                 230                 235                 240

Lys Val Glu Ile Lys
                245

<210> SEQ ID NO 37
<211> LENGTH: 245
<212> TYPE: PRT
<213> ORGANISM: Artificial Sequence
<220> FEATURE:
<223> OTHER INFORMATION: C-002160 scFv antibody construct

<400> SEQUENCE: 37

Gln Leu Val Gln Ser Gly Ala Glu Val Lys Lys Pro Gly Ser Ser Val
 1               5                  10                  15

Lys Val Ser Cys Lys Ala Ser Gly Tyr Thr Phe Thr Ser Tyr His Ile
                20                  25                  30

His Trp Val Arg Gln Ala Pro Gly Gln Gly Leu Glu Trp Met Gly Trp
                35                  40                  45

Ile Tyr Pro Gly Asn Val Asn Thr Glu Tyr Asn Glu Lys Phe Lys Gly
 50                  55                  60

Lys Ala Thr Ile Thr Ala Asp Lys Ser Thr Ser Thr Ala Tyr Met Glu
 65                  70                  75                  80

Leu Ser Ser Leu Arg Ser Glu Asp Thr Ala Val Tyr Tyr Cys Ala Arg
                85                  90                  95

Glu Glu Ile Thr Tyr Ala Met Asp Tyr Trp Gly Gln Gly Thr Thr Val
                100                 105                 110

Thr Val Ser Ser Gly Gly Gly Gly Ser Gly Gly Gly Gly Ser Gly Gly
                115                 120                 125

Gly Gly Ser Gly Gly Asp Ile Val Met Thr Gln Thr Pro Leu Ser Leu
 130                 135                 140

Pro Val Thr Pro Gly Glu Pro Ala Ser Ile Ser Cys Arg Ser Ser Gln
145                 150                 155                 160

Ser Ile Val His Ser Asn Gly Asn Thr Tyr Leu Glu Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Phe Gln Gly Ser His Val Pro Arg Thr Phe Gly Gly Gly Thr
225                 230                 235                 240

Lys Val Glu Ile Lys
            245

<210> SEQ ID NO 38
<211> LENGTH: 245
<212> TYPE: PRT
<213> ORGANISM: Artificial Sequence
<220> FEATURE:
<223> OTHER INFORMATION: C-002161 scFv antibody construct

<400> SEQUENCE: 38

Gln Leu Val Glu Ser Gly Gly Gly Leu Val Lys Pro Gly Gly Ser Leu
1               5                   10                  15

Arg Leu Ser Cys Ala Ala Ser Gly Tyr Thr Phe Thr Ser Tyr His Ile
            20                  25                  30

His Trp Val Arg Gln Ala Pro Gly Lys Gly Leu Glu Trp Val Gly Trp
        35                  40                  45

Ile Tyr Pro Gly Asn Val Asn Thr Glu Tyr Asn Glu Lys Phe Lys Gly
    50                  55                  60

Arg Phe Thr Ile Ser Arg Asp Asp Ser Lys Asn Thr Leu Tyr Leu Gln
65                  70                  75                  80

Met Asn Ser Leu Lys Thr Glu Asp Thr Ala Val Tyr Tyr Cys Ala Arg
                85                  90                  95

Glu Glu Ile Thr Tyr Ala Met Asp Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Gly Gly Asp Ile Gln Met Thr Gln Ser Pro Ser Ser Leu
    130                 135                 140

Ser Ala Ser Val Gly Asp Arg Val Thr Ile Thr Cys Arg Ser Ser Gln
145                 150                 155                 160

Ser Ile Val His Ser Asn Gly Asn Thr Tyr Leu Glu Trp Tyr Gln Gln
                165                 170                 175

Lys Pro Gly Lys Ala Pro Lys Leu Leu Ile Tyr Lys Val Ser Asn Arg
            180                 185                 190

Phe Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Phe Gln Gly Ser His Val Pro Arg Thr Phe Gly Gly Gly Thr
225                 230                 235                 240

Lys Val Glu Ile Lys
            245

<210> SEQ ID NO 39
<211> LENGTH: 245
<212> TYPE: PRT
<213> ORGANISM: Artificial Sequence
<220> FEATURE:
<223> OTHER INFORMATION: C-002162 scFv antibody construct

<400> SEQUENCE: 39

Gln Leu Val Gln Ser Gly Ala Glu Val Lys Lys Pro Gly Ser Ser Val
1               5                   10                  15

Lys Val Ser Cys Lys Ala Ser Gly Tyr Thr Phe Thr Ser Tyr His Ile
            20                  25                  30

His Trp Val Arg Gln Ala Pro Gly Gln Gly Leu Glu Trp Ile Gly Trp
        35                  40                  45

Ile Tyr Pro Gly Asn Val Asn Thr Glu Tyr Asn Glu Lys Phe Lys Gly
    50                  55                  60

Lys Ala Thr Ile Thr Ala Asp Glu Ser Thr Asn Thr Ala Tyr Met Glu
65                  70                  75                  80

Leu Ser Ser Leu Arg Ser Glu Asp Thr Ala Val Tyr Tyr Cys Ala Arg
                85                  90                  95

Glu Glu Ile Thr Tyr Ala Met Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gly Gly Asp Ile Gln Met Thr Gln Ser Pro Ser Thr Leu
    130                 135                 140

Ser Ala Ser Val Gly Asp Arg Val Thr Ile Thr Cys Arg Ser Ser Gln
145                 150                 155                 160

Ser Ile Val His Ser Asn Gly Asn Thr Tyr Leu Glu Trp Tyr Gln Gln
                165                 170                 175

Lys Pro Gly Lys Ala Pro Lys Leu Leu Ile Tyr Lys Val Ser Asn Arg
            180                 185                 190

Phe Ser Gly Val Pro Ala Arg Phe Ser Gly Ser Gly Ser Gly Thr Glu
        195                 200                 205

Phe Thr Leu Thr Ile Ser Ser Leu Gln Pro Asp Asp Phe Ala Thr Tyr
    210                 215                 220

Tyr Cys Phe Gln Gly Ser His Val Pro Arg Thr Phe Gly Gln Gly Thr
225                 230                 235                 240

Lys Val Glu Val Lys
                245

<210> SEQ ID NO 40
<211> LENGTH: 245
<212> TYPE: PRT
<213> ORGANISM: Artificial Sequence
<220> FEATURE:
<223> OTHER INFORMATION: C-002163 scFv antibody construct

<400> SEQUENCE: 40

Gln Leu Val Gln Ser Gly Ala Glu Val Lys Lys Pro Gly Ser Ser Val
1               5                   10                  15

Lys Val Ser Cys Lys Ala Ser Gly Tyr Thr Phe Thr Ser Tyr His Met
            20                  25                  30

His Trp Val Arg Gln Ala Pro Gly Gln Gly Leu Glu Trp Ile Gly Tyr
        35                  40                  45

Ile Tyr Pro Gly Asn Val Asn Thr Glu Tyr Asn Glu Lys Phe Lys Gly

```
                  50                  55                  60

Lys Ala Thr Leu Thr Ala Asp Lys Ser Thr Asn Thr Ala Tyr Met Glu
 65                  70                  75                  80

Leu Ser Ser Leu Arg Ser Glu Asp Thr Ala Val Tyr Phe Cys Ala Arg
                     85                  90                  95

Glu Glu Ile Thr Tyr Ala Met Asp Tyr Trp Gly Gln Gly Thr Leu Val
                100                 105                 110

Thr Val Ser Ser Gly Gly Gly Gly Ser Gly Gly Gly Gly Ser Gly Gly
            115                 120                 125

Gly Gly Ser Gly Gly Asp Val Gln Met Thr Gln Ser Pro Ser Thr Leu
        130                 135                 140

Ser Ala Ser Val Gly Asp Arg Val Thr Ile Thr Cys Ser Ser Ser Gln
145                 150                 155                 160

Ser Ile Val His Ser Asn Gly Asn Thr Tyr Met Glu Trp Tyr Gln Gln
                165                 170                 175

Lys Pro Gly Lys Ala Pro Lys Leu Leu Ile Tyr Lys Val Ser Asn Arg
            180                 185                 190

Phe Ser Gly Val Pro Asp Arg Phe Ser Gly Ser Gly Ser Gly Thr Glu
        195                 200                 205

Phe Thr Leu Thr Ile Ser Ser Leu Gln Pro Asp Asp Phe Ala Thr Tyr
    210                 215                 220

Tyr Cys His Gln Gly Ser His Val Pro Arg Thr Phe Gly Gln Gly Thr
225                 230                 235                 240

Lys Val Glu Val Lys
            245

<210> SEQ ID NO 41
<211> LENGTH: 247
<212> TYPE: PRT
<213> ORGANISM: Artificial Sequence
<220> FEATURE:
<223> OTHER INFORMATION: C-002164 scFv antibody construct

<400> SEQUENCE: 41

Gln Val Gln Leu Gln Gln Ser Gly Pro Glu Leu Val Lys Pro Gly Ala
  1               5                  10                  15

Ser Val Lys Met Ser Cys Lys Ala Ser Gly Tyr Thr Phe Thr Ser Tyr
                 20                  25                  30

His Ile Gln Trp Val Lys Gln Arg Pro Gly Gln Gly Leu Glu Trp Ile
             35                  40                  45

Gly Trp Ile Tyr Pro Gly Asp Gly Ser Thr Gln Tyr Asn Glu Lys Phe
         50                  55                  60

Lys Gly Lys Thr Thr Leu Thr Ala Asp Lys Ser Ser Ser Thr Ala Tyr
 65                  70                  75                  80

Met Leu Leu Ser Ser Leu Thr Ser Glu Asp Ser Ala Ile Tyr Phe Cys
                 85                  90                  95

Ala Arg Glu Gly Thr Tyr Tyr Ala Met Asp Tyr Trp Gly Gln Gly Thr
                100                 105                 110

Ser Val Thr Val Ser Ser Gly Gly Gly Gly Ser Gly Gly Gly Gly Ser
            115                 120                 125

Gly Gly Gly Gly Ser Gly Gly Asp Val Leu Met Thr Gln Thr Pro Leu
        130                 135                 140

Ser Leu Pro Val Ser Leu Gly Asp Gln Val Ser Ile Ser Cys Arg Ser
145                 150                 155                 160

Ser Gln Ser Ile Val His Ser Asn Gly Asn Thr Tyr Leu Glu Trp Tyr
```

```
                    165                 170                 175
Leu Gln Lys Pro Gly Gln Ser Pro Lys Leu Leu Ile Tyr Lys Val Ser
                180                 185                 190

Asn Arg Phe Ser Gly Val Pro Asp Arg Phe Ser Gly Ser Gly Ser Gly
                195                 200                 205

Thr Asp Phe Thr Leu Lys Ile Ser Arg Val Glu Ala Glu Asp Leu Gly
            210                 215                 220

Val Tyr Tyr Cys Phe Gln Gly Ser His Val Pro Arg Thr Phe Gly Gly
225                 230                 235                 240

Gly Thr Lys Leu Glu Ile Lys
                245

<210> SEQ ID NO 42
<211> LENGTH: 247
<212> TYPE: PRT
<213> ORGANISM: Artificial Sequence
<220> FEATURE:
<223> OTHER INFORMATION: C-002165 scFv antibody construct

<400> SEQUENCE: 42

Gln Leu Gln Leu Gln Glu Ser Gly Pro Gly Leu Val Lys Pro Ser Glu
1               5                   10                  15

Thr Leu Ser Leu Thr Cys Thr Val Ser Gly Tyr Thr Phe Thr Ser Tyr
                20                  25                  30

His Ile Gln Trp Ile Arg Gln Pro Pro Gly Lys Gly Leu Glu Trp Ile
            35                  40                  45

Gly Trp Ile Tyr Pro Gly Asp Gly Ser Thr Gln Tyr Asn Glu Lys Phe
        50                  55                  60

Lys Gly Arg Ala Thr Ile Ser Val Asp Thr Ser Lys Asn Gln Phe Ser
65                  70                  75                  80

Leu Asn Leu Asp Ser Val Ser Ala Ala Asp Thr Ala Ile Tyr Tyr Cys
                85                  90                  95

Ala Arg Glu Gly Thr Tyr Tyr Ala Met Asp Tyr Trp Gly Lys Gly Ser
            100                 105                 110

Thr Val Thr Val Ser Ser Gly Gly Gly Gly Ser Gly Gly Gly Gly Ser
        115                 120                 125

Gly Gly Gly Gly Ser Gly Gly Asp Ile Gln Met Thr Gln Ser Pro Ser
    130                 135                 140

Ser Leu Ser Ala Ser Val Gly Asp Arg Val Thr Ile Thr Cys Arg Ser
145                 150                 155                 160

Ser Gln Ser Ile Val His Ser Asn Gly Asn Thr Tyr Leu Glu Trp Tyr
                165                 170                 175

Gln Gln Lys Pro Gly Lys Ala Pro Lys Leu Leu Ile Tyr Lys Val Ser
                180                 185                 190

Asn Arg Phe Ser Gly Val Pro Ser Arg Phe Ser Gly Ser Gly Ser Gly
                195                 200                 205

Thr Asp Phe Thr Phe Thr Ile Ser Ser Leu Gln Pro Glu Asp Ile Ala
            210                 215                 220

Thr Tyr Tyr Cys Phe Gln Gly Ser His Val Pro Arg Thr Phe Gly Pro
225                 230                 235                 240

Gly Thr Lys Val Asp Ile Lys
                245

<210> SEQ ID NO 43
<211> LENGTH: 247
<212> TYPE: PRT
```

<213> ORGANISM: Artificial Sequence
<220> FEATURE:
<223> OTHER INFORMATION: C-002166 scFv antibody construct

<400> SEQUENCE: 43

Glu Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Ser Tyr
                20                  25                  30

His Ile Gln Trp Val Lys Gln Ala Pro Gly Gln Gly Leu Glu Trp Ile
            35                  40                  45

Gly Trp Ile Tyr Pro Gly Asp Gly Ser Thr Gln Tyr Asn Glu Lys Phe
    50                  55                  60

Lys Gly Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Asp Ile Gln Met Thr Gln Ser Pro Ser
    130                 135                 140

Thr Leu Ser Ala Ser Val Gly Asp Arg Val Thr Ile Thr Cys Arg Ser
145                 150                 155                 160

Ser Gln Ser Ile Val His Ser Asn Gly Asn Thr Tyr Leu Glu Trp Tyr
                165                 170                 175

Gln Gln Lys Pro Gly Lys Ala Pro Lys Leu Leu Ile Tyr Lys Val Ser
            180                 185                 190

Asn Arg Phe Ser Gly Val Pro Ser Arg Phe Ser Gly Ser Gly Ser Gly
        195                 200                 205

Thr Asp Phe Thr Leu Thr Ile Ser Ser Leu Gln Pro Asp Asp Phe Ala
    210                 215                 220

Thr Tyr Tyr Cys Phe Gln Gly Ser His Val Pro Arg Thr Phe Gly Gln
225                 230                 235                 240

Gly Thr Lys Val Glu Val Lys
                245

<210> SEQ ID NO 44
<211> LENGTH: 247
<212> TYPE: PRT
<213> ORGANISM: Artificial Sequence
<220> FEATURE:
<223> OTHER INFORMATION: C-002167 scFv antibody construct

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Met
            35                  40                  45

Gly Trp Ile Tyr Pro Gly Asp Gly Ser Thr Gln Tyr Asn Glu Lys Phe
    50                  55                  60

Lys Gly Arg Val Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
             85                  90                  95

Ala Arg Glu Gly Thr Tyr Tyr Ala Met Asp Tyr Trp Gly Gln Gly Thr
            100                 105                 110

Thr Val Thr Val Ser Ser Gly Gly Gly Gly Ser Gly Gly Gly Gly Ser
            115                 120                 125

Gly Gly Gly Gly Ser Gly Glu Ile Val Leu Thr Gln Ser Pro Gly
            130                 135                 140

Thr Leu Ser Leu Ser Pro Gly Glu Arg Ala Thr Leu Ser Cys Arg Ser
145                 150                 155                 160

Ser Gln Ser Ile Val His Ser Asn Gly Asn Thr Tyr Leu Glu Trp Tyr
                165                 170                 175

Gln Gln Lys Pro Gly Gln Ala Pro Arg Leu Leu Ile Tyr Lys Val Ser
            180                 185                 190

Asn Arg Phe Ser Gly Ile Pro Asp Arg Phe Ser Gly Ser Gly Ser Gly
            195                 200                 205

Thr Asp Phe Thr Leu Thr Ile Ser Arg Leu Glu Pro Glu Asp Phe Ala
            210                 215                 220

Val Tyr Tyr Cys Phe Gln Gly Ser His Val Pro Arg Thr Phe Gly Gly
225                 230                 235                 240

Gly Thr Lys Val Glu Ile Lys
                245

<210> SEQ ID NO 45
<211> LENGTH: 247
<212> TYPE: PRT
<213> ORGANISM: Artificial Sequence
<220> FEATURE:
<223> OTHER INFORMATION: C-002168 scFv antibody construct

<400> SEQUENCE: 45

Gln Val Thr Leu Lys Gln Ser Gly Ala Glu Val Lys Lys Pro Gly Ser
1               5                   10                  15

Ser Val Lys Val Ser Cys Thr Ala Ser Gly Tyr Thr Phe Thr Ser Tyr
            20                  25                  30

His Val Ser Trp Val Arg Gln Ala Pro Gly Gln Gly Leu Glu Trp Leu
            35                  40                  45

Gly Arg Ile Tyr Pro Gly Asp Gly Ser Thr Gln Tyr Asn Glu Lys Phe
        50                  55                  60

Lys Gly Lys Val Thr Ile Thr Ala Asp Lys Ser Met Asp Thr Ser Phe
65                  70                  75                  80

Met Glu Leu Thr Ser Leu Thr Ser Glu Asp Thr Ala Val Tyr Tyr Cys
            85                  90                  95

Ala Arg Glu Gly Thr Tyr Tyr Ala Met Asp Leu Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Gly Glu Ile Val Leu Thr Gln Ser Pro Gly
            130                 135                 140

Thr Leu Ser Leu Ser Pro Gly Glu Arg Ala Thr Leu Ser Cys Arg Ser
145                 150                 155                 160

Ser Gln Ser Ile Val His Ser Asn Gly Asn Thr Tyr Leu Ala Trp Tyr
                165                 170                 175

Gln Gln Lys Pro Gly Gln Ala Pro Arg Leu Leu Ile Ser Lys Val Ser
            180                 185                 190
```

```
Asn Arg Phe Ser Gly Val Pro Asp Arg Phe Ser Gly Ser Gly
            195                 200                 205

Thr Asp Phe Thr Leu Thr Ile Ser Arg Leu Glu Pro Glu Asp Phe Ala
    210                 215                 220

Val Tyr Tyr Cys Gln Gln Gly Ser His Val Pro Arg Thr Phe Gly Gly
225             230                 235                 240

Gly Thr Lys Val Glu Ile Lys
                245
```

<210> SEQ ID NO 46
<211> LENGTH: 247
<212> TYPE: PRT
<213> ORGANISM: Artificial Sequence
<220> FEATURE:
<223> OTHER INFORMATION: C-002169 scFv antibody construct

<400> SEQUENCE: 46

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Met His Trp Val Arg Gln Ala Pro Gly Gln Arg Leu Glu Trp Met
            35                  40                  45

Gly Trp Ile Tyr Pro Gly Asp Gly Ser Thr Gln Tyr Asn Glu Lys Phe
        50                  55                  60

Lys Gly Lys Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Asp Ile Val Met Thr Gln Thr Pro Leu
    130                 135                 140

Ser Leu Pro Val Thr Pro Gly Glu Pro Ala Ser Ile Ser Cys Arg Ser
145                 150                 155                 160

Ser Gln Ser Ile Val His Ser Asn Gly Asn Thr Tyr Leu Asp Trp Tyr
                165                 170                 175

Leu Gln Lys Pro Gly Gln Ser Pro Gln Leu Leu Ile Tyr Lys Val Ser
            180                 185                 190

Asn Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Gly Ser His Val Pro Arg Thr Phe Gly Gly
225             230                 235                 240

Gly Thr Lys Val Glu Ile Lys
                245
```

<210> SEQ ID NO 47
<211> LENGTH: 511
<212> TYPE: PRT
<213> ORGANISM: Artificial Sequence
<220> FEATURE:
<223> OTHER INFORMATION: C563 chimeric antigen recetor consruct

<400> SEQUENCE: 47

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
            85                  90                  95

Ala Arg Ile Pro Phe Gly Asp Trp Trp Tyr Phe Asp Leu Trp Gly Arg
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Asp Ile Gln Met Thr Gln Ser
        130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
        210                 215                 220

Cys Gln Gln Ser Tyr Ser Phe Val Leu Thr Phe Gly Gly Gly Thr Lys
225                 230                 235                 240

Val Glu Ile Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
            275                 280                 285

Asp Phe Trp Val Leu Val Val Gly Gly Val Leu Ala Cys Tyr Ser
        290                 295                 300

Leu Leu Val Thr Val Ala Phe Ile Ile Phe Trp Val Arg Ser Lys Arg
305                 310                 315                 320

Ser Arg Leu Leu His Ser Asp Tyr Met Asn Met Thr Pro Arg Arg Pro
                325                 330                 335

Gly Pro Thr Arg Lys His Tyr Gln Pro Tyr Ala Pro Pro Arg Asp Phe
            340                 345                 350

Ala Ala Tyr Arg Ser Lys Arg Gly Arg Lys Lys Leu Leu Tyr Ile Phe
            355                 360                 365

Lys Gln Pro Phe Met Arg Pro Val Gln Thr Thr Gln Glu Glu Asp Gly
    370                 375                 380

Cys Ser Cys Arg Phe Pro Glu Glu Glu Glu Gly Gly Cys Glu Leu Arg
385                 390                 395                 400

Val Lys Phe Ser Arg Ser Ala Asp Ala Pro Ala Tyr Lys Gln Gly Gln
                405                 410                 415
```

Asn Gln Leu Tyr Asn Glu Leu Asn Leu Gly Arg Arg Glu Tyr Asp
            420                 425                 430

Val Leu Asp Lys Arg Arg Gly Arg Asp Pro Glu Met Gly Gly Lys Pro
            435                 440                 445

Arg Arg Lys Asn Pro Gln Glu Gly Leu Tyr Asn Glu Leu Gln Lys Asp
450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
            485                 490                 495

Lys Asp Thr Tyr Asp Ala Leu His Met Gln Ala Leu Pro Pro Arg
            500                 505                 510

<210> SEQ ID NO 48
<211> LENGTH: 403
<212> TYPE: PRT
<213> ORGANISM: Artificial Sequence
<220> FEATURE:
<223> OTHER INFORMATION: C1759 chimeric antigen recetor constuct

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
225                 230                 235                 240

Ser Phe Gly Ser Phe Arg Ala Leu Pro Cys Val Trp Ser Asn Ser Ser
                245                 250                 255

Asp Pro Leu Leu Val Ser Val Thr Gly Asn Pro Ser Ser Trp Pro
            260                 265                 270

```
Ser Pro Thr Glu Pro Ser Ser Lys Ser Gly Ile Cys Arg His Leu His
            275                 280                 285

Val Leu Ile Gly Thr Ser Val Val Ile Phe Leu Phe Ile Leu Leu Leu
        290                 295                 300

Phe Phe Leu Leu Tyr Arg Trp Cys Ser Asn Lys Lys Asn Ala Ala Val
305                 310                 315                 320

Met Asp Gln Glu Pro Ala Gly Asp Arg Thr Val Asn Arg Gln Asp Ser
                325                 330                 335

Asp Glu Gln Asp Pro Gln Glu Val Thr Tyr Ala Gln Leu Asp His Cys
                340                 345                 350

Val Phe Ile Gln Arg Lys Ile Ser Arg Pro Ser Gln Arg Pro Lys Thr
                355                 360                 365

Pro Leu Thr Asp Thr Ser Val Tyr Thr Glu Leu Pro Asn Ala Glu Pro
            370                 375                 380

Arg Ser Lys Val Val Ser Cys Pro Arg Ala Pro Gln Ser Gly Leu Glu
385                 390                 395                 400

Gly Val Phe

<210> SEQ ID NO 49
<211> LENGTH: 358
<212> TYPE: PRT
<213> ORGANISM: Artificial Sequence
<220> FEATURE:
<223> OTHER INFORMATION: C1760 chimeric antigen recetor constuct

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
```

```
            225                 230                 235                 240

Ser Phe Gly Ser Phe Arg Ala Leu Pro His Ala Trp Ser Asp Pro Ser
                245                 250                 255

Asp Pro Leu Pro Val Ser Val Thr Gly Asn Ser Arg Asn Leu His Val
                260                 265                 270

Leu Ile Gly Thr Ser Val Val Ile Ile Pro Phe Ala Ile Leu Leu Phe
                275                 280                 285

Phe Leu Leu His Arg Trp Cys Ala Asn Lys Lys Asn Ala Val Val Met
            290                 295                 300

Asp Gln Glu Pro Ala Gly Asn Arg Thr Val Asn Arg Glu Asp Ser Asp
305                 310                 315                 320

Glu Gln Asp Pro Gln Glu Val Thr Tyr Ala Gln Leu Asn His Cys Val
                325                 330                 335

Phe Thr Gln Arg Lys Ile Thr Arg Pro Ser Gln Arg Pro Lys Thr Pro
                340                 345                 350

Pro Thr Asp Thr Ser Val
            355

<210> SEQ ID NO 50
<211> LENGTH: 494
<212> TYPE: PRT
<213> ORGANISM: Artificial Sequence
<220> FEATURE:
<223> OTHER INFORMATION: C1761 chimeric antigen recetor constuct

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
                100                 105                 110

Gly Gly Gly Gly Ser Gly Gly Gly Ser Gly Gly Glu Val Gln Leu
            115                 120                 125

Val Glu Ser Gly Gly Gly Leu Val Gln Pro Gly Gly Ser Leu Arg Leu
130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
                180                 185                 190

Ser Arg Asp Asn Ser Lys Asn Thr Leu Tyr Leu Gln Met Asn Ser Leu
            195                 200                 205

Arg Ala Glu Asp Thr Ala Val Tyr Tyr Cys Ala Arg Tyr Ser Tyr Tyr
        210                 215                 220

Tyr Tyr Tyr Met Asp Val Trp Gly Lys Gly Thr Thr Val Thr Val Ser
```

```
                225                 230                 235                 240
Ser Tyr Gly Ser Gln Ser Ser Lys Pro Tyr Leu Leu Thr His Pro Ser
                245                 250                 255

Asp Pro Leu Glu Leu Val Val Ser Gly Pro Ser Gly Gly Pro Ser Ser
                260                 265                 270

Pro Thr Thr Gly Pro Thr Ser Thr Ser Gly Pro Glu Asp Gln Pro Leu
                275                 280                 285

Thr Pro Thr Gly Ser Asp Pro Gln Ser Gly Leu Gly Arg His Leu Gly
                290                 295                 300

Val Val Ile Gly Ile Leu Val Ala Val Ile Leu Leu Leu Leu Leu Leu
305                 310                 315                 320

Leu Leu Leu Phe Leu Ile Leu Arg His Arg Arg Gln Gly Lys His Trp
                325                 330                 335

Thr Ser Thr Gln Arg Lys Ala Asp Phe Gln His Pro Ala Gly Ala Val
                340                 345                 350

Gly Pro Glu Pro Thr Asp Arg Gly Leu Gln Trp Arg Ser Ser Pro Ala
                355                 360                 365

Ala Asp Ala Gln Glu Glu Asn Leu Tyr Ala Ala Val Lys His Thr Gln
                370                 375                 380

Pro Glu Asp Gly Val Glu Met Asp Thr Arg Ser Pro His Asp Glu Asp
385                 390                 395                 400

Pro Gln Ala Val Thr Tyr Ala Glu Val Lys His Ser Arg Pro Arg Arg
                405                 410                 415

Glu Met Ala Ser Pro Pro Ser Pro Leu Ser Gly Glu Phe Leu Asp Thr
                420                 425                 430

Lys Asp Arg Gln Ala Glu Glu Asp Arg Gln Met Asp Thr Glu Ala Ala
                435                 440                 445

Ala Ser Glu Ala Pro Gln Asp Val Thr Tyr Ala Gln Leu His Ser Leu
                450                 455                 460

Thr Leu Arg Arg Glu Ala Thr Glu Pro Pro Pro Ser Gln Glu Gly Pro
465                 470                 475                 480

Ser Pro Ala Val Pro Ser Ile Tyr Ala Thr Leu Ala Ile His
                485                 490

<210> SEQ ID NO 51
<211> LENGTH: 385
<212> TYPE: PRT
<213> ORGANISM: Artificial Sequence
<220> FEATURE:
<223> OTHER INFORMATION: C1762 chimeric antigen recetor constuct

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
```

```
              100                 105                 110
Gly Gly Gly Gly Ser Gly Gly Gly Ser Gly Gly Glu Val Gln Leu
            115                 120                 125

Val Glu Ser Gly Gly Gly Leu Val Gln Pro Gly Gly Ser Leu Arg Leu
        130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
225                 230                 235                 240

Ser Thr Glu Arg Arg Ala Glu Val Pro Thr Ala His Pro Ser Pro Ser
                245                 250                 255

Pro Arg Pro Ala Gly Gln Phe Gln Thr Leu Val Val Gly Val Val Gly
            260                 265                 270

Gly Leu Leu Gly Ser Leu Val Leu Leu Val Trp Val Leu Ala Val Ile
        275                 280                 285

Cys Ser Arg Ala Ala Arg Gly Thr Ile Gly Ala Arg Arg Thr Gly Gln
    290                 295                 300

Pro Leu Lys Glu Asp Pro Ser Ala Val Pro Val Phe Ser Val Asp Tyr
305                 310                 315                 320

Gly Glu Leu Asp Phe Gln Trp Arg Glu Lys Thr Pro Glu Pro Pro Val
                325                 330                 335

Pro Cys Val Pro Glu Gln Thr Glu Tyr Ala Thr Ile Val Phe Pro Ser
            340                 345                 350

Gly Met Gly Thr Ser Ser Pro Ala Arg Arg Gly Ser Ala Asp Gly Pro
        355                 360                 365

Arg Ser Ala Gln Pro Leu Arg Pro Glu Asp Gly His Cys Ser Trp Pro
    370                 375                 380

Leu
385

<210> SEQ ID NO 52
<211> LENGTH: 439
<212> TYPE: PRT
<213> ORGANISM: Artificial Sequence
<220> FEATURE:
<223> OTHER INFORMATION: C2057 chimeric antigen recetor constuct

<400> SEQUENCE: 52

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
```

```
            65                  70                  75                  80
Leu Asn Ala Ser Leu Asp Lys Ser Ser Gly Arg Ser Thr Leu Tyr Ile
                    85                  90                  95

Ala Ala Ser Gln Pro Gly Asp Ser Ala Thr Tyr Leu Cys Ala Val Arg
                100                 105                 110

Pro Leu Tyr Gly Gly Ser Tyr Ile Pro Thr Phe Gly Arg Gly Thr Ser
                115                 120                 125

Leu Ile Val His Pro Tyr Ile Gln Asn Pro Asp Pro Ala Val Tyr Gln
            130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                    165                 170                 175

Ile Thr Asp Lys Cys Val Leu Asp Met Arg Ser Met Asp Phe Lys Ser
                180                 185                 190

Asn Ser Ala Val Ala Trp Ser Asn Lys Ser Asp Phe Ala Cys Ala Asn
                195                 200                 205

Ala Phe Asn Asn Ser Ile Ile Pro Glu Asp Thr Phe Phe Pro Ser Pro
            210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Val Ile Gly Ile Leu Val
                    245                 250                 255

Ala Val Ile Leu Leu Leu Leu Leu Leu Leu Phe Leu Ile Leu
                260                 265                 270

Arg His Arg Arg Gln Gly Lys His Trp Thr Ser Thr Gln Arg Lys Ala
            275                 280                 285

Asp Phe Gln His Pro Ala Gly Ala Val Gly Pro Glu Pro Thr Asp Arg
290                 295                 300

Gly Leu Gln Trp Arg Ser Ser Pro Ala Ala Asp Ala Gln Glu Glu Asn
305                 310                 315                 320

Leu Tyr Ala Ala Val Lys His Thr Gln Pro Glu Asp Gly Val Glu Met
                    325                 330                 335

Asp Thr Arg Ser Pro His Asp Glu Asp Pro Gln Ala Val Thr Tyr Ala
                340                 345                 350

Glu Val Lys His Ser Arg Pro Arg Arg Glu Met Ala Ser Pro Pro Ser
                355                 360                 365

Pro Leu Ser Gly Glu Phe Leu Asp Thr Lys Asp Arg Gln Ala Glu Glu
            370                 375                 380

Asp Arg Gln Met Asp Thr Glu Ala Ala Ser Glu Ala Pro Gln Asp
385                 390                 395                 400

Val Thr Tyr Ala Gln Leu His Ser Leu Thr Leu Arg Arg Glu Ala Thr
                    405                 410                 415

Glu Pro Pro Pro Ser Gln Glu Gly Pro Ser Pro Ala Val Pro Ser Ile
                420                 425                 430

Tyr Ala Thr Leu Ala Ile His
            435

<210> SEQ ID NO 53
<211> LENGTH: 466
<212> TYPE: PRT
<213> ORGANISM: Artificial Sequence
<220> FEATURE:
<223> OTHER INFORMATION: C2058 chimeric antigen recetor constuct
```

```
<400> SEQUENCE: 53

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Val Val Gly Ile Leu Val Ala Val Ile Leu Leu
        275                 280                 285

Leu Leu Leu Leu Leu Leu Leu Phe Leu Ile Leu Arg His Arg Arg Gln
290                 295                 300

Gly Lys His Trp Thr Ser Thr Gln Arg Lys Ala Asp Phe Gln His Pro
305                 310                 315                 320

Ala Gly Ala Val Gly Pro Glu Pro Thr Asp Arg Gly Leu Gln Trp Arg
                325                 330                 335

Ser Ser Pro Ala Ala Asp Ala Gln Glu Glu Asn Leu Tyr Ala Ala Val
            340                 345                 350

Lys His Thr Gln Pro Glu Asp Gly Val Glu Met Asp Thr Arg Ser Pro
        355                 360                 365

His Asp Glu Asp Pro Gln Ala Val Thr Tyr Ala Glu Val Lys His Ser
370                 375                 380

Arg Pro Arg Arg Glu Met Ala Ser Pro Pro Ser Pro Leu Ser Gly Glu
385                 390                 395                 400

Phe Leu Asp Thr Lys Asp Arg Gln Ala Glu Glu Asp Arg Gln Met Asp
                405                 410                 415
```

```
Thr Glu Ala Ala Ala Ser Glu Ala Pro Gln Asp Val Thr Tyr Ala Gln
            420                 425                 430

Leu His Ser Leu Thr Leu Arg Arg Glu Ala Thr Glu Pro Pro Ser
        435                 440                 445

Gln Glu Gly Pro Ser Pro Ala Val Pro Ser Ile Tyr Ala Thr Leu Ala
    450                 455                 460

Ile His
465

<210> SEQ ID NO 54
<211> LENGTH: 421
<212> TYPE: PRT
<213> ORGANISM: Artificial Sequence
<220> FEATURE:
<223> OTHER INFORMATION: C2070 chimeric antigen recetor construct

<400> SEQUENCE: 54

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300
```

Lys Arg Lys Asp Ser Arg Gly Gly Gly Ser Gly Gly Gly
305             310             315             320

Ser Gly Gly Gly Ser Arg Ala Ala Arg Gly Thr Ile Gly Ala Arg
            325             330             335

Arg Thr Gly Gln Pro Leu Lys Glu Asp Pro Ser Ala Val Pro Val Phe
        340             345             350

Ser Val Asp Tyr Gly Glu Leu Asp Phe Gln Trp Arg Glu Lys Thr Pro
        355             360             365

Glu Pro Pro Val Pro Cys Val Pro Glu Gln Thr Glu Tyr Ala Thr Ile
        370             375             380

Val Phe Pro Ser Gly Met Gly Thr Ser Ser Pro Ala Arg Arg Gly Ser
385             390             395             400

Ala Asp Gly Pro Arg Ser Ala Gln Pro Leu Arg Pro Glu Asp Gly His
            405             410             415

Cys Ser Trp Pro Leu
            420

<210> SEQ ID NO 55
<211> LENGTH: 416
<212> TYPE: PRT
<213> ORGANISM: Artificial Sequence
<220> FEATURE:
<223> OTHER INFORMATION: C2071 chimeric antigen recetor constuct

<400> SEQUENCE: 55

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

```
Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Gly Gly Ser Gly Gly Gly Gly Gly
305                 310                 315                 320

Ser Gly Gly Gly Gly Ser Asn Lys Lys Asn Ala Ala Val Met Asp Gln
                325                 330                 335

Glu Pro Ala Gly Asp Arg Thr Val Asn Arg Gln Asp Ser Asp Glu Gln
            340                 345                 350

Asp Pro Gln Glu Val Thr Tyr Ala Gln Leu Asp His Cys Val Phe Ile
        355                 360                 365

Gln Arg Lys Ile Ser Arg Pro Ser Gln Arg Pro Lys Thr Pro Leu Thr
    370                 375                 380

Asp Thr Ser Val Tyr Thr Glu Leu Pro Asn Ala Glu Pro Arg Ser Lys
385                 390                 395                 400

Val Val Ser Cys Pro Arg Ala Pro Gln Ser Gly Leu Glu Gly Val Phe
                405                 410                 415

<210> SEQ ID NO 56
<211> LENGTH: 493
<212> TYPE: PRT
<213> ORGANISM: Artificial Sequence
<220> FEATURE:
<223> OTHER INFORMATION: C2072 chimeric antigen recetor constuct

<400> SEQUENCE: 56

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190
```

```
Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Ser Arg Gly Gly Gly Gly Ser Gly Gly Gly Gly
305                 310                 315                 320

Ser Gly Gly Gly Gly Ser Arg His Arg Gln Gly Lys His Trp Thr
                325                 330                 335

Ser Thr Gln Arg Lys Ala Asp Phe Gln His Pro Ala Gly Ala Val Gly
            340                 345                 350

Pro Glu Pro Thr Asp Arg Gly Leu Gln Trp Arg Ser Pro Ala Ala
            355                 360                 365

Asp Ala Gln Glu Glu Asn Leu Tyr Ala Ala Val Lys His Thr Gln Pro
370                 375                 380

Glu Asp Gly Val Glu Met Asp Thr Arg Ser Pro His Asp Glu Asp Pro
385                 390                 395                 400

Gln Ala Val Thr Tyr Ala Glu Val Lys His Ser Arg Pro Arg Arg Glu
                405                 410                 415

Met Ala Ser Pro Pro Ser Pro Leu Ser Gly Glu Phe Leu Asp Thr Lys
                420                 425                 430

Asp Arg Gln Ala Glu Glu Asp Arg Gln Met Asp Thr Glu Ala Ala Ala
            435                 440                 445

Ser Glu Ala Pro Gln Asp Val Thr Tyr Ala Gln Leu His Ser Leu Thr
    450                 455                 460

Leu Arg Arg Glu Ala Thr Glu Pro Pro Pro Ser Gln Glu Gly Pro Ser
465                 470                 475                 480

Pro Ala Val Pro Ser Ile Tyr Ala Thr Leu Ala Ile His
                485                 490

<210> SEQ ID NO 57
<211> LENGTH: 704
<212> TYPE: PRT
<213> ORGANISM: Artificial Sequence
<220> FEATURE:
<223> OTHER INFORMATION: C2106 chimeric antigen recetor constuct

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Glu Val Gln Leu
            115                 120                 125

Val Glu Ser Gly Gly Gly Leu Val Gln Pro Gly Gly Ser Leu Arg Leu
            130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
            195                 200                 205

Arg Ala Glu Asp Thr Ala Val Tyr Tyr Cys Ala Arg Tyr Ser Tyr Tyr
210                 215                 220

Tyr Tyr Tyr Met Asp Val Trp Gly Lys Gly Thr Thr Val Thr Val Ser
225                 230                 235                 240

Ser Thr Thr Thr Pro Ala Pro Arg Pro Pro Thr Pro Ala Pro Thr Ile
            245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Ile Tyr
            275                 280                 285

Ile Trp Ala Pro Leu Ala Gly Thr Cys Gly Val Leu Leu Leu Ser Leu
290                 295                 300

Val Ile Thr Leu Tyr Cys Asn His Asp Arg Glu Lys Lys Pro Arg Gln
305                 310                 315                 320

His Ser Gly Asp His Glu Asn Leu Met Asn Val Pro Ser Asp Lys Glu
            325                 330                 335

Met Phe Ser Arg Ser Val Thr Ser Leu Ala Thr Asp Ala Pro Ala Ser
            340                 345                 350

Ser Glu Gln Asn Gly Ala Leu Thr Asn Gly Asp Ile Leu Ser Glu Asp
            355                 360                 365

Ser Thr Leu Thr Cys Met Gln His Tyr Glu Glu Val Gln Thr Ser Ala
370                 375                 380

Ser Asp Leu Leu Asp Ser Gln Asp Ser Thr Gly Lys Pro Lys Cys His
385                 390                 395                 400

Gln Ser Arg Glu Leu Pro Arg Ile Pro Pro Glu Ser Ala Val Asp Thr
            405                 410                 415

Met Leu Thr Ala Arg Ser Val Asp Gly Asp Gln Gly Leu Gly Met Glu
            420                 425                 430

Gly Pro Tyr Glu Val Leu Lys Asp Ser Ser Ser Gln Glu Asn Met Val
            435                 440                 445

Glu Asp Cys Leu Tyr Glu Thr Val Lys Glu Ile Lys Glu Val Ala Ala
            450                 455                 460

Ala Ala His Leu Glu Lys Gly His Ser Gly Lys Ala Lys Ser Thr Ser
465                 470                 475                 480
```

```
Ala Ser Lys Glu Leu Pro Gly Pro Gln Thr Glu Gly Lys Ala Glu Phe
            485                 490                 495
Ala Glu Tyr Ala Ser Val Asp Arg Asn Lys Lys Cys Arg Gln Ser Val
        500                 505                 510
Asn Val Glu Ser Ile Leu Gly Asn Ser Cys Asp Pro Glu Glu Glu Ala
        515                 520                 525
Pro Pro Pro Val Pro Val Lys Leu Leu Asp Glu Asn Glu Asn Leu Gln
    530                 535                 540
Glu Lys Glu Gly Gly Glu Ala Glu Glu Ser Ala Thr Asp Thr Thr Ser
545                 550                 555                 560
Glu Thr Asn Lys Arg Phe Ser Ser Leu Ser Tyr Lys Ser Arg Glu Glu
                565                 570                 575
Asp Pro Thr Leu Thr Glu Glu Glu Ile Ser Ala Met Tyr Ser Ser Val
            580                 585                 590
Asn Lys Pro Gly Gln Leu Val Asn Lys Ser Gly Gln Ser Leu Thr Val
        595                 600                 605
Pro Glu Ser Thr Tyr Thr Ser Ile Gln Gly Asp Pro Gln Arg Ser Pro
    610                 615                 620
Ser Ser Cys Asn Asp Leu Tyr Ala Thr Val Lys Asp Phe Glu Lys Thr
625                 630                 635                 640
Pro Asn Ser Thr Leu Pro Pro Ala Gly Arg Pro Ser Glu Glu Pro Glu
                645                 650                 655
Pro Asp Tyr Glu Ala Ile Gln Thr Leu Asn Arg Glu Glu Glu Lys Ala
            660                 665                 670
Thr Leu Gly Thr Asn Gly His His Gly Leu Val Pro Lys Glu Asn Asp
        675                 680                 685
Tyr Glu Ser Ile Ser Asp Leu Gln Gln Gly Arg Asp Ile Thr Arg Leu
    690                 695                 700

<210> SEQ ID NO 58
<211> LENGTH: 702
<212> TYPE: PRT
<213> ORGANISM: Artificial Sequence
<220> FEATURE:
<223> OTHER INFORMATION: C2107 chimeric antigen recetor construct

<400> SEQUENCE: 58

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Leu
                85                  90                  95
Thr Phe Gly Gly Gly Thr Lys Val Glu Ile Lys Gly Gly Gly Gly Ser
            100                 105                 110
Gly Gly Gly Gly Ser Gly Gly Gly Ser Gly Glu Val Gln Leu
        115                 120                 125
Val Glu Ser Gly Gly Gly Leu Val Gln Pro Gly Gly Ser Leu Arg Leu
    130                 135                 140
```

```
Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
            165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
            195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
225                 230                 235                 240

Ser Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Leu Trp
            275                 280                 285

Gly Ser Leu Ala Ala Val Ala Ile Phe Phe Val Ile Thr Phe Leu Ile
    290                 295                 300

Phe Leu Cys Ser Ser Cys Asp Arg Glu Lys Lys Pro Arg Gln His Ser
305                 310                 315                 320

Gly Asp His Glu Asn Leu Met Asn Val Pro Ser Asp Lys Glu Met Phe
                325                 330                 335

Ser Arg Ser Val Thr Ser Leu Ala Thr Asp Ala Pro Ala Ser Ser Glu
            340                 345                 350

Gln Asn Gly Ala Leu Thr Asn Gly Asp Ile Leu Ser Glu Asp Ser Thr
            355                 360                 365

Leu Thr Cys Met Gln His Tyr Glu Glu Val Gln Thr Ser Ala Ser Asp
    370                 375                 380

Leu Leu Asp Ser Gln Asp Ser Thr Gly Lys Pro Lys Cys His Gln Ser
385                 390                 395                 400

Arg Glu Leu Pro Arg Ile Pro Pro Glu Ser Ala Val Asp Thr Met Leu
                405                 410                 415

Thr Ala Arg Ser Val Asp Gly Asp Gln Gly Leu Gly Met Glu Gly Pro
            420                 425                 430

Tyr Glu Val Leu Lys Asp Ser Ser Gln Glu Asn Met Val Glu Asp
            435                 440                 445

Cys Leu Tyr Glu Thr Val Lys Glu Ile Lys Glu Val Ala Ala Ala Ala
    450                 455                 460

His Leu Glu Lys Gly His Ser Gly Lys Ala Lys Ser Thr Ser Ala Ser
465                 470                 475                 480

Lys Glu Leu Pro Gly Pro Gln Thr Glu Gly Lys Ala Glu Phe Ala Glu
                485                 490                 495

Tyr Ala Ser Val Asp Arg Asn Lys Lys Cys Arg Gln Ser Val Asn Val
            500                 505                 510

Glu Ser Ile Leu Gly Asn Ser Cys Asp Pro Glu Glu Glu Ala Pro Pro
    515                 520                 525

Pro Val Pro Val Lys Leu Leu Asp Glu Asn Glu Leu Gln Glu Lys
            530                 535                 540

Glu Gly Gly Glu Ala Glu Ser Ala Thr Asp Thr Thr Ser Glu Thr
545                 550                 555                 560

Asn Lys Arg Phe Ser Ser Leu Ser Tyr Lys Ser Arg Glu Glu Asp Pro
```

-continued

```
                565                 570                 575

Thr Leu Thr Glu Glu Ile Ser Ala Met Tyr Ser Ser Val Asn Lys
            580                 585                 590

Pro Gly Gln Leu Val Asn Lys Ser Gly Gln Ser Leu Thr Val Pro Glu
        595                 600                 605

Ser Thr Tyr Thr Ser Ile Gln Gly Asp Pro Gln Arg Ser Pro Ser Ser
    610                 615                 620

Cys Asn Asp Leu Tyr Ala Thr Val Lys Asp Phe Glu Lys Thr Pro Asn
625                 630                 635                 640

Ser Thr Leu Pro Pro Ala Gly Arg Pro Ser Glu Glu Pro Glu Pro Asp
                645                 650                 655

Tyr Glu Ala Ile Gln Thr Leu Asn Arg Glu Glu Lys Ala Thr Leu
            660                 665                 670

Gly Thr Asn Gly His His Gly Leu Val Pro Lys Glu Asn Asp Tyr Glu
                675                 680                 685

Ser Ile Ser Asp Leu Gln Gln Gly Arg Asp Ile Thr Arg Leu
        690                 695                 700

<210> SEQ ID NO 59
<211> LENGTH: 481
<212> TYPE: PRT
<213> ORGANISM: Artificial Sequence
<220> FEATURE:
<223> OTHER INFORMATION: C2153 chimeric antigen recetor constuct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
```

```
                225                 230                 235                 240
Ser Thr Thr Thr Pro Ala Pro Arg Pro Pro Thr Pro Ala Pro Thr Ile
                245                 250                 255

Ala Ser Gln Pro Leu Ser Leu Arg Pro Glu Ala Cys Arg Pro Ala Ala
            260                 265                 270

Gly Gly Ala Val His Thr Arg Gly Leu Asp Phe Ala Cys Asp Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Leu Arg His Arg Arg Gln Gly
305                 310                 315                 320

Lys His Trp Thr Ser Thr Gln Arg Lys Ala Asp Phe Gln His Pro Ala
                325                 330                 335

Gly Ala Val Gly Pro Glu Pro Thr Asp Arg Gly Leu Gln Trp Arg Ser
            340                 345                 350

Ser Pro Ala Ala Asp Ala Gln Glu Glu Asn Leu Tyr Ala Ala Val Lys
        355                 360                 365

His Thr Gln Pro Glu Asp Gly Val Glu Met Asp Thr Arg Ser Pro His
    370                 375                 380

Asp Glu Asp Pro Gln Ala Val Thr Tyr Ala Glu Val Lys His Ser Arg
385                 390                 395                 400

Pro Arg Arg Glu Met Ala Ser Pro Pro Ser Pro Leu Ser Gly Glu Phe
                405                 410                 415

Leu Asp Thr Lys Asp Arg Gln Ala Glu Glu Asp Arg Gln Met Asp Thr
            420                 425                 430

Glu Ala Ala Ala Ser Glu Ala Pro Gln Asp Val Thr Tyr Ala Gln Leu
        435                 440                 445

His Ser Leu Thr Leu Arg Arg Glu Ala Thr Glu Pro Pro Pro Ser Gln
    450                 455                 460

Glu Gly Pro Ser Pro Ala Val Pro Ser Ile Tyr Ala Thr Leu Ala Ile
465                 470                 475                 480

His

<210> SEQ ID NO 60
<211> LENGTH: 444
<212> TYPE: PRT
<213> ORGANISM: Artificial Sequence
<220> FEATURE:
<223> OTHER INFORMATION: C2156 chimeric antigen recetor constuct

<400> SEQUENCE: 60

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
            85                  90                  95

Ala Ala Ser Gln Pro Gly Asp Ser Ala Thr Tyr Leu Cys Ala Val Arg
        100                 105                 110
```

Pro Leu Tyr Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Cys Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Leu Ile Leu
                245                 250                 255

Leu Leu Leu Val Ala Gly Phe Asn Leu Leu Met Thr Leu Leu Leu Trp
            260                 265                 270

Ser Ser Leu Ile Leu Arg His Arg Arg Gln Gly Lys His Trp Thr Ser
        275                 280                 285

Thr Gln Arg Lys Ala Asp Phe Gln His Pro Ala Gly Ala Val Gly Pro
    290                 295                 300

Glu Pro Thr Asp Arg Gly Leu Gln Trp Arg Ser Ser Pro Ala Ala Asp
305                 310                 315                 320

Ala Gln Glu Glu Asn Leu Tyr Ala Ala Val Lys His Thr Gln Pro Glu
                325                 330                 335

Asp Gly Val Glu Met Asp Thr Arg Ser Pro His Asp Glu Asp Pro Gln
            340                 345                 350

Ala Val Thr Tyr Ala Glu Val Lys His Ser Arg Pro Arg Arg Glu Met
        355                 360                 365

Ala Ser Pro Pro Ser Pro Leu Ser Gly Glu Phe Leu Asp Thr Lys Asp
    370                 375                 380

Arg Gln Ala Glu Glu Asp Arg Gln Met Asp Thr Glu Ala Ala Ala Ser
385                 390                 395                 400

Glu Ala Pro Gln Asp Val Thr Tyr Ala Gln Leu His Ser Leu Thr Leu
                405                 410                 415

Arg Arg Glu Ala Thr Glu Pro Pro Pro Ser Gln Glu Gly Pro Ser Pro
            420                 425                 430

Ala Val Pro Ser Ile Tyr Ala Thr Leu Ala Ile His
        435                 440

<210> SEQ ID NO 61
<211> LENGTH: 471
<212> TYPE: PRT
<213> ORGANISM: Artificial Sequence
<220> FEATURE:
<223> OTHER INFORMATION: C2157 chimeric antigen recetor constuct

<400> SEQUENCE: 61

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
    35                  40                  45

Glu Tyr Met Ser Trp Tyr Arg Gln Asp Pro Gly Met Gly Leu Arg Leu
 50                  55                  60

Ile His Tyr Ser Val Gly Ala Gly Ile Thr Asp Gln Gly Glu Val Pro
 65                  70                  75                  80

Asn Gly Tyr Asn Val Ser Arg Ser Thr Thr Glu Asp Phe Pro Leu Arg
                 85                  90                  95

Leu Leu Ser Ala Ala Pro Ser Gln Thr Ser Val Tyr Phe Cys Ala Ser
                100                 105                 110

Ser Tyr Val Gly Asn Thr Gly Glu Leu Phe Phe Gly Glu Gly Ser Arg
            115                 120                 125

Leu Thr Val Leu Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Leu Ile Leu Leu Gly Leu Ala
        275                 280                 285

Thr Leu Tyr Ala Val Leu Val Ser Ala Leu Val Leu Met Leu Ile Leu
    290                 295                 300

Arg His Arg Arg Gln Gly Lys His Trp Thr Ser Thr Gln Arg Lys Ala
305                 310                 315                 320

Asp Phe Gln His Pro Ala Gly Ala Val Gly Pro Glu Pro Thr Asp Arg
                325                 330                 335

Gly Leu Gln Trp Arg Ser Ser Pro Ala Ala Asp Ala Gln Glu Glu Asn
            340                 345                 350

Leu Tyr Ala Ala Val Lys His Thr Gln Pro Glu Asp Gly Val Glu Met
        355                 360                 365

Asp Thr Arg Ser Pro His Asp Glu Asp Pro Gln Ala Val Thr Tyr Ala
    370                 375                 380

Glu Val Lys His Ser Arg Pro Arg Arg Glu Met Ala Ser Pro Pro Ser
385                 390                 395                 400

Pro Leu Ser Gly Glu Phe Leu Asp Thr Lys Asp Arg Gln Ala Glu Glu
                405                 410                 415

Asp Arg Gln Met Asp Thr Glu Ala Ala Ala Ser Glu Ala Pro Gln Asp
            420                 425                 430

Val Thr Tyr Ala Gln Leu His Ser Leu Thr Leu Arg Arg Glu Ala Thr
        435                 440                 445

-continued

Glu Pro Pro Ser Gln Glu Gly Pro Ser Pro Ala Val Pro Ser Ile
    450                 455                 460

Tyr Ala Thr Leu Ala Ile His
465                 470

<210> SEQ ID NO 62
<211> LENGTH: 484
<212> TYPE: PRT
<213> ORGANISM: Artificial Sequence
<220> FEATURE:
<223> OTHER INFORMATION: C2158 chimeric antigen recetor constuct

<400> SEQUENCE: 62

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Ile Pro Phe Gly Asp Trp Trp Tyr Phe Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Phe Val Leu Thr Phe Gly Gly Gly Thr Lys
225                 230                 235                 240

Val Glu Ile Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Phe Trp Val Leu Val Val Val Gly Gly Val Leu Ala Cys Tyr Ser
    290                 295                 300

Leu Leu Val Thr Val Ala Phe Ile Ile Phe Trp Val Leu Arg His Arg
305                 310                 315                 320

Arg Gln Gly Lys His Trp Thr Ser Thr Gln Arg Lys Ala Asp Phe Gln
                325                 330                 335

-continued

```
His Pro Ala Gly Ala Val Gly Pro Glu Pro Thr Asp Arg Gly Leu Gln
                340                 345                 350

Trp Arg Ser Ser Pro Ala Ala Asp Ala Gln Glu Glu Asn Leu Tyr Ala
            355                 360                 365

Ala Val Lys His Thr Gln Pro Glu Asp Gly Val Glu Met Asp Thr Arg
        370                 375                 380

Ser Pro His Asp Glu Asp Pro Gln Ala Val Thr Tyr Ala Glu Val Lys
385                 390                 395                 400

His Ser Arg Pro Arg Arg Glu Met Ala Ser Pro Pro Ser Pro Leu Ser
                405                 410                 415

Gly Glu Phe Leu Asp Thr Lys Asp Arg Gln Ala Glu Glu Asp Arg Gln
            420                 425                 430

Met Asp Thr Glu Ala Ala Ala Ser Glu Ala Pro Gln Asp Val Thr Tyr
        435                 440                 445

Ala Gln Leu His Ser Leu Thr Leu Arg Arg Glu Ala Thr Glu Pro Pro
    450                 455                 460

Pro Ser Gln Glu Gly Pro Ser Pro Ala Val Pro Ser Ile Tyr Ala Thr
465                 470                 475                 480

Leu Ala Ile His

<210> SEQ ID NO 63
<211> LENGTH: 414
<212> TYPE: PRT
<213> ORGANISM: Artificial Sequence
<220> FEATURE:
<223> OTHER INFORMATION: C2179 chimeric antigen recetor constuct

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
```

```
               210                 215                 220
Tyr Tyr Tyr Met Asp Val Trp Gly Lys Gly Thr Thr Val Thr Val Ser
225                 230                 235                 240

Ser Tyr Gly Ser Gln Ser Ser Lys Pro Tyr Leu Leu Thr His Pro Ser
                245                 250                 255

Asp Pro Leu Glu Leu Val Val Ser Gly Pro Ser Gly Gly Pro Ser Ser
                260                 265                 270

Pro Thr Thr Gly Pro Thr Ser Thr Ser Gly Pro Glu Asp Gln Pro Leu
                275                 280                 285

Thr Pro Thr Gly Ser Asp Pro Gln Ser Gly Leu Gly Arg His Leu Gly
                290                 295                 300

Val Val Ile Gly Ile Leu Val Ala Val Ile Leu Leu Leu Leu Leu Leu
305                 310                 315                 320

Leu Leu Leu Phe Leu Ile Leu Arg His Arg Arg Gln Arg Pro Arg Arg
                325                 330                 335

Glu Met Ala Ser Pro Pro Ser Pro Leu Ser Gly Glu Phe Leu Asp Thr
                340                 345                 350

Lys Asp Arg Gln Ala Glu Glu Asp Arg Gln Met Asp Thr Glu Ala Ala
                355                 360                 365

Ala Ser Glu Ala Pro Gln Asp Val Thr Tyr Ala Gln Leu His Ser Leu
                370                 375                 380

Thr Leu Arg Arg Glu Ala Thr Glu Pro Pro Pro Ser Gln Glu Gly Pro
385                 390                 395                 400

Ser Pro Ala Val Pro Ser Ile Tyr Ala Thr Leu Ala Ile His
                405                 410

<210> SEQ ID NO 64
<211> LENGTH: 576
<212> TYPE: PRT
<213> ORGANISM: Artificial Sequence
<220> FEATURE:
<223> OTHER INFORMATION: C2180 chimeric antigen recetor construct

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
                100                 105                 110

Gly Gly Gly Gly Ser Gly Gly Gly Ser Gly Gly Glu Val Gln Leu
                115                 120                 125

Val Glu Ser Gly Gly Gly Leu Val Gln Pro Gly Gly Ser Leu Arg Leu
                130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
```

```
            165                 170                 175
Gly Gly Ser Thr Tyr Tyr Ala Asp Ser Val Lys Gly Arg Phe Thr Ile
        180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
        210                 215                 220

Tyr Tyr Tyr Met Asp Val Trp Gly Lys Gly Thr Thr Val Thr Val Ser
225                 230                 235                 240

Ser Tyr Gly Ser Gln Ser Ser Lys Pro Tyr Leu Leu Thr His Pro Ser
                245                 250                 255

Asp Pro Leu Glu Leu Val Val Ser Gly Pro Ser Gly Pro Ser Ser
                260                 265                 270

Pro Thr Thr Gly Pro Thr Ser Thr Ser Gly Pro Glu Asp Gln Pro Leu
                275                 280                 285

Thr Pro Thr Gly Ser Asp Pro Gln Ser Gly Leu Gly Arg His Leu Gly
                290                 295                 300

Val Val Ile Gly Ile Leu Val Ala Val Ile Leu Leu Leu Leu Leu Leu
305                 310                 315                 320

Leu Leu Leu Phe Leu Ile Leu Arg His Arg Arg Gln Gly Lys His Trp
                325                 330                 335

Thr Ser Thr Gln Arg Lys Ala Asp Phe Gln His Pro Ala Gly Ala Val
                340                 345                 350

Gly Pro Glu Pro Thr Asp Arg Gly Leu Gln Trp Arg Ser Ser Pro Ala
                355                 360                 365

Ala Asp Ala Gln Glu Glu Asn Leu Tyr Ala Ala Val Lys His Thr Gln
                370                 375                 380

Pro Glu Asp Gly Val Glu Met Asp Thr Arg Ser Pro His Asp Glu Asp
385                 390                 395                 400

Pro Gln Ala Val Thr Tyr Ala Glu Val Lys His Ser Arg Pro Arg Arg
                405                 410                 415

Glu Met Ala Ser Pro Pro Ser Pro Leu Ser Gly Glu Phe Leu Asp Thr
                420                 425                 430

Lys Asp Arg Gln Ala Glu Glu Asp Arg Gln Met Asp Thr Glu Ala Ala
                435                 440                 445

Ala Ser Glu Ala Pro Gln Asp Val Thr Tyr Ala Gln Leu His Ser Leu
                450                 455                 460

Thr Leu Arg Arg Glu Ala Thr Glu Pro Pro Pro Ser Gln Glu Gly Pro
465                 470                 475                 480

Ser Pro Ala Val Pro Ser Ile Tyr Ala Thr Leu Ala Ile His Arg Pro
                485                 490                 495

Arg Arg Glu Met Ala Ser Pro Pro Ser Pro Leu Ser Gly Glu Phe Leu
                500                 505                 510

Asp Thr Lys Asp Arg Gln Ala Glu Glu Asp Arg Gln Met Asp Thr Glu
                515                 520                 525

Ala Ala Ala Ser Glu Ala Pro Gln Asp Val Thr Tyr Ala Gln Leu His
                530                 535                 540

Ser Leu Thr Leu Arg Arg Glu Ala Thr Glu Pro Pro Pro Ser Gln Glu
545                 550                 555                 560

Gly Pro Ser Pro Ala Val Pro Ser Ile Tyr Ala Thr Leu Ala Ile His
                565                 570                 575
```

<210> SEQ ID NO 65

```
<211> LENGTH: 496
<212> TYPE: PRT
<213> ORGANISM: Artificial Sequence
<220> FEATURE:
<223> OTHER INFORMATION: C2181 chimeric antigen recetor constuct

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
225                 230                 235                 240

Ser Tyr Gly Ser Gln Ser Ser Lys Pro Tyr Leu Leu Thr His Pro Ser
                245                 250                 255

Asp Pro Leu Glu Leu Val Val Ser Gly Pro Ser Gly Gly Pro Ser Ser
            260                 265                 270

Pro Thr Thr Gly Pro Thr Ser Thr Ser Gly Pro Glu Asp Gln Pro Leu
        275                 280                 285

Thr Pro Thr Gly Ser Asp Pro Gln Ser Gly Leu Gly Arg His Leu Gly
    290                 295                 300

Val Val Ile Gly Ile Leu Val Ala Val Ile Leu Leu Leu Leu Leu Leu
305                 310                 315                 320

Leu Leu Leu Phe Leu Ile Leu Arg His Arg Gln Arg Pro Arg Arg
                325                 330                 335

Glu Met Ala Ser Pro Pro Ser Pro Leu Ser Gly Glu Phe Leu Asp Thr
            340                 345                 350

Lys Asp Arg Gln Ala Glu Glu Asp Arg Gln Met Asp Thr Glu Ala Ala
        355                 360                 365

Ala Ser Glu Ala Pro Gln Asp Val Thr Tyr Ala Gln Leu His Ser Leu
    370                 375                 380
```

Thr Leu Arg Arg Glu Ala Thr Glu Pro Pro Ser Gln Glu Gly Pro
385                 390                 395                 400

Ser Pro Ala Val Pro Ser Ile Tyr Ala Thr Leu Ala Ile His Arg Pro
            405                 410                 415

Arg Arg Glu Met Ala Ser Pro Pro Ser Pro Leu Ser Gly Glu Phe Leu
        420                 425                 430

Asp Thr Lys Asp Arg Gln Ala Glu Glu Asp Arg Gln Met Asp Thr Glu
        435                 440                 445

Ala Ala Ala Ser Glu Ala Pro Gln Asp Val Thr Tyr Ala Gln Leu His
        450                 455                 460

Ser Leu Thr Leu Arg Arg Glu Ala Thr Glu Pro Pro Ser Gln Glu
465                 470                 475                 480

Gly Pro Ser Pro Ala Val Pro Ser Ile Tyr Ala Thr Leu Ala Ile His
                485                 490                 495

<210> SEQ ID NO 66
<211> LENGTH: 494
<212> TYPE: PRT
<213> ORGANISM: Artificial Sequence
<220> FEATURE:
<223> OTHER INFORMATION: C2182 chimeric antigen recetor constuct

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
225                 230                 235                 240

Ser Tyr Gly Ser Gln Ser Ser Lys Pro Tyr Leu Leu Thr His Pro Ser
                245                 250                 255

```
Asp Pro Leu Glu Leu Val Val Ser Gly Pro Gly Gly Pro Ser Ser
                260                 265                 270

Pro Thr Thr Gly Pro Thr Ser Thr Ser Gly Pro Glu Asp Gln Pro Leu
            275                 280                 285

Thr Pro Thr Gly Ser Asp Pro Gln Ser Gly Leu Gly Arg His Leu Gly
290                 295                 300

Val Val Ile Gly Ile Leu Val Ala Val Ile Leu Leu Leu Leu Leu Leu
305                 310                 315                 320

Leu Leu Leu Phe Leu Ile Leu Arg His Arg Arg Gln Gly Lys His Trp
                325                 330                 335

Thr Ser Thr Gln Arg Lys Ala Asp Phe Gln His Pro Ala Gly Ala Val
            340                 345                 350

Gly Pro Glu Pro Thr Asp Arg Gly Leu Gln Trp Arg Ser Ser Pro Ala
            355                 360                 365

Ala Asp Ala Gln Glu Glu Asn Leu Phe Ala Ala Val Lys His Thr Gln
370                 375                 380

Pro Glu Asp Gly Val Glu Met Asp Thr Arg Ser Pro His Asp Glu Asp
385                 390                 395                 400

Pro Gln Ala Val Thr Phe Ala Glu Val Lys His Ser Arg Pro Arg Arg
                405                 410                 415

Glu Met Ala Ser Pro Pro Ser Pro Leu Ser Gly Glu Phe Leu Asp Thr
            420                 425                 430

Lys Asp Arg Gln Ala Glu Glu Asp Arg Gln Met Asp Thr Glu Ala Ala
            435                 440                 445

Ala Ser Glu Ala Pro Gln Asp Val Thr Phe Ala Gln Leu His Ser Leu
450                 455                 460

Thr Leu Arg Arg Glu Ala Thr Glu Pro Pro Pro Ser Gln Glu Gly Pro
465                 470                 475                 480

Ser Pro Ala Val Pro Ser Ile Phe Ala Thr Leu Ala Ile His
                485                 490

<210> SEQ ID NO 67
<211> LENGTH: 494
<212> TYPE: PRT
<213> ORGANISM: Artificial Sequence
<220> FEATURE:
<223> OTHER INFORMATION: C2183 chimeric antigen recetor construct

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Glu Val Gln Leu
        115                 120                 125
```

Val Glu Ser Gly Gly Gly Leu Val Gln Pro Gly Gly Ser Leu Arg Leu
130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
            165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
210                 215                 220

Tyr Tyr Tyr Met Asp Val Trp Gly Lys Gly Thr Thr Val Thr Val Ser
225                 230                 235                 240

Ser Tyr Gly Ser Gln Ser Ser Lys Pro Tyr Leu Leu Thr His Pro Ser
            245                 250                 255

Asp Pro Leu Glu Leu Val Val Ser Gly Pro Ser Gly Pro Ser Ser
            260                 265                 270

Pro Thr Thr Gly Pro Thr Ser Thr Ser Gly Pro Glu Asp Gln Pro Leu
            275                 280                 285

Thr Pro Thr Gly Ser Asp Pro Gln Ser Gly Leu Gly Arg His Leu Gly
        290                 295                 300

Val Val Ile Gly Ile Leu Val Ala Val Ile Leu Leu Leu Leu Leu
305                 310                 315                 320

Leu Leu Leu Phe Leu Ile Leu Arg His Arg Gln Gly Lys His Trp
            325                 330                 335

Thr Ser Thr Gln Arg Lys Ala Asp Phe Gln His Pro Ala Gly Ala Val
            340                 345                 350

Gly Pro Glu Pro Thr Asp Arg Gly Leu Gln Trp Arg Ser Ser Pro Ala
            355                 360                 365

Ala Asp Ala Gln Glu Glu Asn Leu Phe Ala Ala Val Lys His Thr Gln
370                 375                 380

Pro Glu Asp Gly Val Glu Met Asp Thr Arg Ser Pro His Asp Glu Asp
385                 390                 395                 400

Pro Gln Ala Val Thr Phe Ala Glu Val Lys His Ser Arg Pro Arg Arg
            405                 410                 415

Glu Met Ala Ser Pro Pro Ser Pro Leu Ser Gly Glu Phe Leu Asp Thr
            420                 425                 430

Lys Asp Arg Gln Ala Glu Glu Asp Arg Gln Met Asp Thr Glu Ala Ala
        435                 440                 445

Ala Ser Glu Ala Pro Gln Asp Val Thr Tyr Ala Gln Leu His Ser Leu
450                 455                 460

Thr Leu Arg Arg Glu Ala Thr Glu Pro Pro Pro Ser Gln Glu Gly Pro
465                 470                 475                 480

Ser Pro Ala Val Pro Ser Ile Tyr Ala Thr Leu Ala Ile His
            485                 490

<210> SEQ ID NO 68
<211> LENGTH: 494
<212> TYPE: PRT
<213> ORGANISM: Artificial Sequence
<220> FEATURE:
<223> OTHER INFORMATION: C2184 chimeric antigen recetor constuct

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
225                 230                 235                 240

Ser Tyr Gly Ser Gln Ser Ser Lys Pro Tyr Leu Leu Thr His Pro Ser
                245                 250                 255

Asp Pro Leu Glu Leu Val Val Ser Gly Pro Ser Gly Pro Ser Ser
            260                 265                 270

Pro Thr Thr Gly Pro Thr Ser Thr Ser Gly Pro Glu Asp Gln Pro Leu
        275                 280                 285

Thr Pro Thr Gly Ser Asp Pro Gln Ser Gly Leu Gly Arg His Leu Gly
    290                 295                 300

Val Val Ile Gly Ile Leu Val Ala Val Ile Leu Leu Leu Leu Leu Leu
305                 310                 315                 320

Leu Leu Leu Phe Leu Ile Leu Arg His Arg Arg Gln Gly Lys His Trp
                325                 330                 335

Thr Ser Thr Gln Arg Lys Ala Asp Phe Gln His Pro Ala Gly Ala Val
            340                 345                 350

Gly Pro Glu Pro Thr Asp Arg Gly Leu Gln Trp Arg Ser Ser Pro Ala
        355                 360                 365

Ala Asp Ala Gln Glu Glu Asn Leu Tyr Ala Ala Val Lys His Thr Gln
    370                 375                 380

Pro Glu Asp Gly Val Glu Met Asp Thr Arg Ser Pro His Asp Glu Asp
385                 390                 395                 400

Pro Gln Ala Val Thr Tyr Ala Glu Val Lys His Ser Arg Pro Arg Arg
                405                 410                 415
```

-continued

Glu Met Ala Ser Pro Pro Ser Pro Leu Ser Gly Glu Phe Leu Asp Thr
            420             425                 430

Lys Asp Arg Gln Ala Glu Glu Asp Arg Gln Met Asp Thr Glu Ala Ala
435             440                 445

Ala Ser Glu Ala Pro Gln Asp Val Thr Phe Ala Gln Leu His Ser Leu
    450             455                 460

Thr Leu Arg Arg Glu Ala Thr Glu Pro Pro Ser Gln Glu Gly Pro
465             470             475                 480

Ser Pro Ala Val Pro Ser Ile Phe Ala Thr Leu Ala Ile His
                485                 490

<210> SEQ ID NO 69
<211> LENGTH: 438
<212> TYPE: PRT
<213> ORGANISM: Artificial Sequence
<220> FEATURE:
<223> OTHER INFORMATION: C2218 chimeric antigen recetor constuct

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
225                 230                 235                 240

Ser Tyr Gly Ser Gln Ser Ser Lys Pro Tyr Leu Leu Thr His Pro Ser
                245                 250                 255

Asp Pro Leu Glu Leu Val Val Ser Gly Pro Ser Gly Gly Pro Ser Ser
            260                 265                 270

Pro Thr Thr Gly Pro Thr Ser Thr Ser Gly Pro Glu Asp Gln Pro Leu
        275                 280                 285

```
Thr Pro Thr Gly Ser Asp Pro Gln Ser Gly Leu Gly Arg His Leu Gly
    290                 295                 300

Val Val Ile Gly Ile Leu Val Ala Val Ile Leu Leu Leu Leu Leu Leu
305                 310                 315                 320

Leu Leu Leu Phe Leu Ile Leu Arg Arg His Gln Gly Lys Gln Asn Glu
            325                 330                 335

Leu Ser Asp Thr Ala Gly Arg Glu Ile Asn Leu Val Asp Ala His Leu
        340                 345                 350

Lys Ser Glu Gln Thr Glu Ala Ser Thr Arg Gln Asn Ser Gln Val Leu
    355                 360                 365

Leu Ser Glu Thr Gly Ile Tyr Asp Asn Asp Pro Asp Leu Cys Phe Arg
    370                 375                 380

Met Gln Glu Gly Ser Glu Val Tyr Ser Asn Pro Cys Leu Glu Glu Asn
385                 390                 395                 400

Lys Pro Gly Ile Val Tyr Ala Ser Leu Asn His Ser Val Ile Gly Pro
                405                 410                 415

Asn Ser Arg Leu Ala Arg Asn Val Lys Glu Ala Pro Thr Glu Tyr Ala
            420                 425                 430

Ser Ile Cys Val Arg Ser
            435

<210> SEQ ID NO 70
<211> LENGTH: 437
<212> TYPE: PRT
<213> ORGANISM: Artificial Sequence
<220> FEATURE:
<223> OTHER INFORMATION: C2219 chimeric antigen recetor constuct

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205
```

Arg Ala Glu Asp Thr Ala Val Tyr Tyr Cys Ala Arg Tyr Ser Tyr Tyr
210                 215                 220

Tyr Tyr Tyr Met Asp Val Trp Gly Lys Gly Thr Thr Val Thr Val Ser
225                 230                 235                 240

Ser Tyr Gly Ser Gln Ser Ser Lys Pro Tyr Leu Leu Thr His Pro Ser
            245                 250                 255

Asp Pro Leu Glu Leu Val Val Ser Gly Pro Ser Gly Gly Pro Ser Ser
        260                 265                 270

Pro Thr Thr Gly Pro Thr Ser Thr Ser Gly Pro Glu Asp Gln Pro Leu
        275                 280                 285

Thr Pro Thr Gly Ser Asp Pro Gln Ser Gly Leu Gly Arg His Leu Gly
        290                 295                 300

Val Leu Leu Pro Leu Gly Gly Leu Pro Leu Leu Ile Thr Thr Cys Phe
305                 310                 315                 320

Cys Leu Phe Cys Cys Leu Arg Arg His Gln Gly Lys Gln Asn Glu Leu
                325                 330                 335

Ser Asp Thr Ala Gly Arg Glu Ile Asn Leu Val Asp Ala His Leu Lys
            340                 345                 350

Ser Glu Gln Thr Glu Ala Ser Thr Arg Gln Asn Ser Gln Val Leu Leu
        355                 360                 365

Ser Glu Thr Gly Ile Tyr Asp Asn Asp Pro Asp Leu Cys Phe Arg Met
        370                 375                 380

Gln Glu Gly Ser Glu Val Tyr Ser Asn Pro Cys Leu Glu Glu Asn Lys
385                 390                 395                 400

Pro Gly Ile Val Tyr Ala Ser Leu Asn His Ser Val Ile Gly Pro Asn
            405                 410                 415

Ser Arg Leu Ala Arg Asn Val Lys Glu Ala Pro Thr Glu Tyr Ala Ser
        420                 425                 430

Ile Cys Val Arg Ser
        435

<210> SEQ ID NO 71
<211> LENGTH: 397
<212> TYPE: PRT
<213> ORGANISM: Artificial Sequence
<220> FEATURE:
<223> OTHER INFORMATION: C2220 chimeric antigen recetor constuct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Glu Val Gln Leu
        115                 120                 125

```
Val Glu Ser Gly Gly Leu Val Gln Pro Gly Gly Ser Leu Arg Leu
130                 135                 140
Ser Cys Ala Ala Ser Gly Phe Thr Val Tyr Asp Tyr Met Ser Trp Val
145                 150                 155                 160
Arg Gln Ala Pro Gly Lys Gly Leu Glu Trp Val Ser Val Ile Tyr Ser
                165                 170                 175
Gly Gly Ser Thr Tyr Tyr Ala Asp Ser Val Lys Gly Arg Phe Thr Ile
            180                 185                 190
Ser Arg Asp Asn Ser Lys Asn Thr Leu Tyr Leu Gln Met Asn Ser Leu
        195                 200                 205
Arg Ala Glu Asp Thr Ala Val Tyr Tyr Cys Ala Arg Tyr Ser Tyr Tyr
210                 215                 220
Tyr Tyr Tyr Met Asp Val Trp Gly Lys Gly Thr Thr Val Thr Val Ser
225                 230                 235                 240
Ser Thr Asp Val Lys Ser Ala Ser Glu Arg Pro Ser Lys Asp Glu Met
                245                 250                 255
Ala Ser Arg Pro Trp Leu Leu Tyr Arg Leu Pro Leu Gly Gly Leu
            260                 265                 270
Pro Leu Leu Ile Thr Thr Cys Phe Cys Leu Phe Cys Cys Leu Arg Arg
        275                 280                 285
His Gln Gly Lys Gln Asn Glu Leu Ser Asp Thr Ala Gly Arg Glu Ile
    290                 295                 300
Asn Leu Val Asp Ala His Leu Lys Ser Glu Gln Thr Glu Ala Ser Thr
305                 310                 315                 320
Arg Gln Asn Ser Gln Val Leu Leu Ser Glu Thr Gly Ile Tyr Asp Asn
                325                 330                 335
Asp Pro Asp Leu Cys Phe Arg Met Gln Glu Gly Ser Glu Val Tyr Ser
            340                 345                 350
Asn Pro Cys Leu Glu Glu Asn Lys Pro Gly Ile Val Tyr Ala Ser Leu
        355                 360                 365
Asn His Ser Val Ile Gly Pro Asn Ser Arg Leu Ala Arg Asn Val Lys
    370                 375                 380
Glu Ala Pro Thr Glu Tyr Ala Ser Ile Cys Val Arg Ser
385                 390                 395

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000
```

<210> SEQ ID NO 76

<400> SEQUENCE: 76

000

<210> SEQ ID NO 77
<211> LENGTH: 578
<212> TYPE: PRT
<213> ORGANISM: Artificial Sequence
<220> FEATURE:
<223> OTHER INFORMATION: C2302 chimeric antigen recetor constuct

<400> SEQUENCE: 77

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
225                 230                 235                 240

Ser Tyr Gly Ser Gln Ser Ser Lys Pro Tyr Leu Leu Thr His Pro Ser
                245                 250                 255

Asp Pro Leu Glu Leu Val Val Ser Gly Pro Ser Gly Pro Ser Ser
            260                 265                 270

Pro Thr Thr Gly Pro Thr Ser Thr Ser Gly Pro Glu Asp Gln Pro Leu
        275                 280                 285

Thr Pro Thr Gly Ser Asp Pro Gln Ser Gly Leu Gly Arg His Leu Gly
    290                 295                 300

Val Val Ile Gly Ile Leu Val Ala Val Ile Leu Leu Leu Leu Leu Leu
305                 310                 315                 320

Leu Leu Leu Phe Leu Ile Leu Arg His Arg Arg Gln Arg Pro Arg Arg
                325                 330                 335
```

```
Glu Met Ala Ser Pro Ser Pro Leu Ser Gly Glu Phe Leu Asp Thr
            340                 345                 350

Lys Asp Arg Gln Ala Glu Glu Asp Arg Gln Met Asp Thr Glu Ala Ala
        355                 360                 365

Ala Ser Glu Ala Pro Gln Asp Val Thr Tyr Ala Gln Leu His Ser Leu
    370                 375                 380

Thr Leu Arg Arg Glu Ala Thr Glu Pro Pro Ser Gln Glu Gly Pro
385                 390                 395                 400

Ser Pro Ala Val Pro Ser Ile Tyr Ala Thr Leu Ala Ile His Arg Pro
                405                 410                 415

Arg Arg Glu Met Ala Ser Pro Ser Pro Leu Ser Gly Glu Phe Leu
            420                 425                 430

Asp Thr Lys Asp Arg Gln Ala Glu Glu Asp Arg Gln Met Asp Thr Glu
        435                 440                 445

Ala Ala Ala Ser Glu Ala Pro Gln Asp Val Thr Tyr Ala Gln Leu His
    450                 455                 460

Ser Leu Thr Leu Arg Arg Glu Ala Thr Glu Pro Pro Ser Gln Glu
465                 470                 475                 480

Gly Pro Ser Pro Ala Val Pro Ser Ile Tyr Ala Thr Leu Ala Ile His
                485                 490                 495

Arg Pro Arg Arg Glu Met Ala Ser Pro Ser Pro Leu Ser Gly Glu
            500                 505                 510

Phe Leu Asp Thr Lys Asp Arg Gln Ala Glu Glu Asp Arg Gln Met Asp
        515                 520                 525

Thr Glu Ala Ala Ala Ser Glu Ala Pro Gln Asp Val Thr Tyr Ala Gln
    530                 535                 540

Leu His Ser Leu Thr Leu Arg Arg Glu Ala Thr Glu Pro Pro Ser
545                 550                 555                 560

Gln Glu Gly Pro Ser Pro Ala Val Pro Ser Ile Tyr Ala Thr Leu Ala
                565                 570                 575

Ile His

<210> SEQ ID NO 78
<211> LENGTH: 600
<212> TYPE: PRT
<213> ORGANISM: Artificial Sequence
<220> FEATURE:
<223> OTHER INFORMATION: CT138 chimeric antigen recetor constuct

<400> SEQUENCE: 78

Met Gly Pro Val Thr Cys Ser Val Leu Val Leu Leu Met Leu Arg
1               5                   10                  15

Arg Ser Asn Gly Asp Gly Asp Ser Val Thr Gln Thr Glu Gly Leu Val
            20                  25                  30

Thr Leu Thr Glu Gly Leu Pro Val Met Leu Asn Cys Thr Tyr Gln Thr
        35                  40                  45

Ile Tyr Ser Asn Pro Phe Leu Phe Trp Tyr Val Gln His Leu Asn Glu
    50                  55                  60

Ser Pro Arg Leu Leu Leu Lys Ser Phe Thr Asp Asn Lys Arg Thr Glu
65                  70                  75                  80

His Gln Gly Phe His Ala Thr Leu His Lys Ser Ser Ser Phe His
            85                  90                  95

Leu Gln Lys Ser Ser Ala Gln Leu Ser Asp Ser Ala Leu Tyr Tyr Cys
            100                 105                 110
```

```
Ala Phe Asp Thr Asn Thr Tyr Lys Val Ile Phe Gly Lys Gly Thr His
            115                 120                 125
Leu His Val Leu Pro Asn Ile Gln Asn Pro Glu Pro Ala Val Tyr Gln
        130                 135                 140
Leu Lys Asp Pro Arg Ser Gln Asp Ser Thr Leu Cys Leu Phe Thr Asp
145                 150                 155                 160
Phe Asp Ser Gln Ile Asn Val Pro Lys Thr Met Glu Ser Gly Thr Phe
                165                 170                 175
Ile Thr Asp Lys Thr Val Leu Asp Met Lys Ala Met Asp Ser Lys Ser
            180                 185                 190
Asn Gly Ala Ile Ala Trp Ser Asn Gln Thr Ser Phe Thr Cys Gln Asp
        195                 200                 205
Ile Phe Lys Glu Thr Asn Thr Thr Tyr Pro Ser Ser Asp Val Pro Cys
    210                 215                 220
Asp Ala Thr Leu Thr Glu Lys Ser Phe Glu Thr Asp Met Asn Leu Asn
225                 230                 235                 240
Phe Gln Asn Leu Ser Val Met Gly Leu Arg Ile Leu Leu Leu Lys Val
                245                 250                 255
Ala Gly Phe Asn Leu Leu Met Thr Leu Arg Leu Trp Ser Ser Arg Ala
            260                 265                 270
Lys Arg Ser Gly Ser Gly Ala Thr Asn Phe Ser Leu Leu Lys Gln Ala
        275                 280                 285
Gly Asp Val Glu Glu Asn Pro Gly Pro Met Arg Val Arg Leu Ile Ser
    290                 295                 300
Ala Val Val Leu Cys Ser Leu Gly Thr Gly Leu Val Asp Met Lys Val
305                 310                 315                 320
Thr Gln Met Pro Arg Tyr Leu Ile Lys Arg Met Gly Glu Asn Val Leu
                325                 330                 335
Leu Glu Cys Gly Gln Asp Met Ser His Glu Thr Met Tyr Trp Tyr Arg
            340                 345                 350
Gln Asp Pro Gly Leu Gly Leu Gln Leu Ile Tyr Ile Ser Tyr Asp Val
        355                 360                 365
Asp Ser Asn Ser Glu Gly Asp Ile Pro Lys Gly Tyr Arg Val Ser Arg
    370                 375                 380
Lys Lys Arg Glu His Phe Ser Leu Ile Leu Asp Ser Ala Lys Thr Asn
385                 390                 395                 400
Gln Thr Ser Val Tyr Phe Cys Ala Ser Ser Ser Thr Asn Thr Glu Val
                405                 410                 415
Phe Phe Gly Lys Gly Thr Arg Leu Thr Val Val Glu Asp Leu Arg Asn
            420                 425                 430
Val Thr Pro Pro Lys Val Ser Leu Phe Glu Pro Ser Lys Ala Glu Ile
        435                 440                 445
Ala Asn Lys Gln Lys Ala Thr Leu Val Cys Leu Ala Arg Gly Phe Phe
    450                 455                 460
Pro Asp His Val Glu Leu Ser Trp Trp Val Asn Gly Lys Glu Val His
465                 470                 475                 480
Ser Gly Val Ser Thr Asp Pro Gln Ala Tyr Lys Glu Ser Asn Tyr Ser
                485                 490                 495
Tyr Cys Leu Ser Ser Arg Leu Arg Val Ser Ala Thr Phe Trp His Asn
            500                 505                 510
Pro Arg Asn His Phe Arg Cys Gln Val Gln Phe His Gly Leu Ser Glu
        515                 520                 525
Glu Asp Lys Trp Pro Glu Gly Ser Pro Lys Pro Val Thr Gln Asn Ile
```

```
                530             535             540
Ser Ala Glu Ala Trp Gly Arg Ala Asp Cys Gly Ile Thr Ser Ala Ser
545                 550                 555                 560

Tyr Gln Gln Gly Val Leu Ser Ala Thr Ile Leu Tyr Glu Ile Leu Leu
                565                 570                 575

Gly Lys Ala Thr Leu Tyr Ala Val Leu Val Ser Thr Leu Val Val Met
                580                 585                 590

Ala Met Val Lys Arg Lys Asn Ser
                595                 600

<210> SEQ ID NO 79
<211> LENGTH: 605
<212> TYPE: PRT
<213> ORGANISM: Artificial Sequence
<220> FEATURE:
<223> OTHER INFORMATION: CT139 chimeric antigen recetor constuct

<400> SEQUENCE: 79

Met Val Leu Val Thr Ile Leu Leu Leu Ser Ala Phe Phe Ser Leu Arg
1               5                   10                  15

Gly Asn Ser Ala Gln Ser Val Asp Gln Pro Asp Ala His Val Thr Leu
                20                  25                  30

Ser Glu Gly Ala Ser Leu Glu Leu Arg Cys Ser Tyr Ser Tyr Ser Ala
                35                  40                  45

Ala Pro Tyr Leu Phe Trp Tyr Val Gln Tyr Pro Gly Gln Ser Leu Gln
        50                  55                  60

Phe Leu Leu Lys Tyr Ile Thr Gly Asp Thr Val Val Lys Gly Thr Lys
65                  70                  75                  80

Gly Phe Glu Ala Glu Phe Arg Lys Ser Asn Ser Ser Phe Asn Leu Lys
                85                  90                  95

Lys Ser Pro Ala His Trp Ser Asp Ser Ala Lys Tyr Phe Cys Ala Leu
                100                 105                 110

Glu Gly Pro Asp Thr Gly Asn Tyr Lys Tyr Val Phe Gly Ala Gly Thr
                115                 120                 125

Arg Leu Lys Val Ile Ala His Ile Gln Asn Pro Glu Pro Ala Val Tyr
        130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
                180                 185                 190

Ser Asn Gly Ala Ile Ala Trp Ser Asn Gln Thr Ser Phe Thr Cys Gln
                195                 200                 205

Asp Ile Phe Lys Glu Thr Asn Ala Thr Tyr Pro Ser Ser Asp Val Pro
        210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser Arg
                260                 265                 270

Ala Lys Arg Ser Gly Ser Gly Ala Thr Asn Phe Ser Leu Leu Lys Gln
                275                 280                 285

Ala Gly Asp Val Glu Glu Asn Pro Gly Pro Met Gly Ile Gln Thr Leu
```

```
                290                 295                 300
Cys Cys Val Ile Phe Tyr Val Leu Ile Ala Asn His Thr Asp Ala Gly
305                 310                 315                 320

Val Thr Gln Thr Pro Arg His Glu Val Ala Glu Lys Gly Gln Thr Ile
                325                 330                 335

Ile Leu Lys Cys Glu Pro Val Ser Gly His Asn Asp Leu Phe Trp Tyr
            340                 345                 350

Arg Gln Thr Lys Ile Gln Gly Leu Glu Leu Leu Ser Tyr Phe Arg Ser
        355                 360                 365

Lys Ser Leu Met Glu Asp Gly Ala Phe Lys Asp Arg Phe Lys Ala
    370                 375                 380

Glu Met Leu Asn Ser Ser Phe Ser Thr Leu Lys Ile Gln Pro Thr Glu
385                 390                 395                 400

Pro Arg Asp Ser Ala Val Tyr Leu Cys Ala Ser Ser Phe Gly Thr Ala
                405                 410                 415

Ser Ala Glu Thr Leu Tyr Phe Gly Ser Gly Thr Arg Leu Thr Val Leu
            420                 425                 430

Glu Asp Leu Arg Asn Val Thr Pro Pro Lys Val Ser Leu Phe Glu Pro
        435                 440                 445

Ser Lys Ala Glu Ile Ala Asn Lys Gln Lys Ala Thr Leu Val Cys Leu
    450                 455                 460

Ala Arg Gly Phe Phe Pro Asp His Val Glu Leu Ser Trp Trp Val Asn
465                 470                 475                 480

Gly Lys Glu Val His Ser Gly Val Ser Thr Asp Pro Gln Ala Tyr Lys
                485                 490                 495

Glu Ser Asn Tyr Ser Tyr Cys Leu Ser Ser Arg Leu Arg Val Ser Ala
            500                 505                 510

Thr Phe Trp His Asn Pro Arg Asn His Phe Arg Cys Gln Val Gln Phe
        515                 520                 525

His Gly Leu Ser Glu Glu Asp Lys Trp Pro Glu Gly Ser Pro Lys Pro
    530                 535                 540

Val Thr Gln Asn Ile Ser Ala Glu Ala Trp Gly Arg Ala Asp Cys Gly
545                 550                 555                 560

Ile Thr Ser Ala Ser Tyr His Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Gly Leu Val Leu Met Ala Met Val Lys Lys Lys Asn Ser
        595                 600                 605

<210> SEQ ID NO 80
<211> LENGTH: 64
<212> TYPE: PRT
<213> ORGANISM: Homo sapiens

<400> SEQUENCE: 80

Tyr Gly Ser Gln Ser Ser Lys Pro Tyr Leu Leu Thr His Pro Ser Asp
1               5                   10                  15

Pro Leu Glu Leu Val Val Ser Gly Pro Ser Gly Gly Pro Ser Ser Pro
            20                  25                  30

Thr Thr Gly Pro Thr Ser Thr Ser Gly Pro Glu Asp Gln Pro Leu Thr
        35                  40                  45

Pro Thr Gly Ser Asp Pro Gln Ser Gly Leu Gly Arg His Leu Gly Val
    50                  55                  60
```

```
<210> SEQ ID NO 81
<211> LENGTH: 44
<212> TYPE: PRT
<213> ORGANISM: Homo sapiens

<400> SEQUENCE: 81

Val Val Ser Gly Pro Ser Gly Gly Pro Ser Ser Pro Thr Thr Gly Pro
1               5                   10                  15

Thr Ser Thr Ser Gly Pro Glu Asp Gln Pro Leu Thr Thr Gly Ser
            20                  25                  30

Asp Pro Gln Ser Gly Leu Gly Arg His Leu Gly Val
        35                  40

<210> SEQ ID NO 82
<211> LENGTH: 67
<212> TYPE: PRT
<213> ORGANISM: Artificial Sequence
<220> FEATURE:
<223> OTHER INFORMATION: Made in Lab - long hinge 1 sequence

<400> SEQUENCE: 82

Ala Gly Ser Gly Gly Ser Gly Gly Ser Gly Gly Ser Pro Val Pro Ser
1               5                   10                  15

Thr Pro Pro Thr Pro Ser Pro Ser Thr Pro Pro Thr Pro Ser Pro Ser
            20                  25                  30

Gly Gly Ser Gly Asn Ser Ser Gly Ser Gly Gly Ser Pro Val Pro Ser
        35                  40                  45

Thr Pro Pro Thr Pro Ser Pro Ser Thr Pro Pro Thr Pro Ser Pro Ser
    50                  55                  60

Ala Ser Val
65

<210> SEQ ID NO 83
<211> LENGTH: 75
<212> TYPE: PRT
<213> ORGANISM: Artificial Sequence
<220> FEATURE:
<223> OTHER INFORMATION: Made in Lab - long hinge 2 sequence

<400> SEQUENCE: 83

Ala Gly Ser Gly Gly Ser Gly Gly Ser Gly Gly Ser Pro Val Pro Ser
1               5                   10                  15

Thr Pro Pro Thr Asn Ser Ser Ser Thr Pro Pro Thr Pro Ser Pro Ser
            20                  25                  30

Pro Val Pro Ser Thr Pro Pro Thr Asn Ser Ser Thr Pro Pro Thr
        35                  40                  45

Pro Ser Pro Ser Pro Val Pro Ser Thr Pro Pro Thr Asn Ser Ser Ser
    50                  55                  60

Thr Pro Pro Thr Pro Ser Pro Ser Ala Ser Val
65                  70                  75

<210> SEQ ID NO 84
<211> LENGTH: 85
<212> TYPE: PRT
<213> ORGANISM: Artificial Sequence
<220> FEATURE:
<223> OTHER INFORMATION: Made in Lab - 2x short hinge sequence

<400> SEQUENCE: 84

Val Val Ser Gly Pro Ser Gly Gly Pro Ser Ser Pro Thr Thr Gly Pro
1               5                   10                  15
```

```
Thr Ser Thr Ser Gly Pro Glu Asp Gln Pro Leu Thr Pro Thr Gly Ser
            20                  25                  30

Asp Pro Gln Ser Gly Leu Gly Arg His Val Val Ser Gly Pro Ser Gly
            35                  40                  45

Gly Pro Ser Ser Pro Thr Thr Gly Pro Thr Ser Thr Ser Gly Pro Glu
50                      55                  60

Asp Gln Pro Leu Thr Pro Thr Gly Ser Asp Pro Gln Ser Gly Leu Gly
65                  70                  75                  80

Arg His Leu Gly Val
                85

<210> SEQ ID NO 85

<400> SEQUENCE: 85

000

<210> SEQ ID NO 86

<400> SEQUENCE: 86

000

<210> SEQ ID NO 87
<211> LENGTH: 111
<212> TYPE: PRT
<213> ORGANISM: Homo sapiens

<400> SEQUENCE: 87

Arg Arg His Gln Gly Lys Gln Asn Glu Leu Ser Asp Thr Ala Gly Arg
1               5                   10                  15

Glu Ile Asn Leu Val Asp Ala His Leu Lys Ser Glu Gln Thr Glu Ala
            20                  25                  30

Ser Thr Arg Gln Asn Ser Gln Val Leu Leu Ser Glu Thr Gly Ile Tyr
        35                  40                  45

Asp Asn Asp Pro Asp Leu Cys Phe Arg Met Gln Glu Gly Ser Glu Val
50                  55                  60

Tyr Ser Asn Pro Cys Leu Glu Glu Asn Lys Pro Gly Ile Val Tyr Ala
65                  70                  75                  80

Ser Leu Asn His Ser Val Ile Gly Pro Asn Ser Arg Leu Ala Arg Asn
                85                  90                  95

Val Lys Glu Ala Pro Thr Glu Tyr Ala Ser Ile Cys Val Arg Ser
            100                 105                 110

<210> SEQ ID NO 88
<211> LENGTH: 132
<212> TYPE: PRT
<213> ORGANISM: Homo sapiens

<400> SEQUENCE: 88

Leu Leu Pro Leu Gly Gly Leu Pro Leu Ile Thr Thr Cys Phe Cys
1               5                   10                  15

Leu Phe Cys Cys Leu Arg Arg His Gln Gly Lys Gln Asn Glu Leu Ser
            20                  25                  30

Asp Thr Ala Gly Arg Glu Ile Asn Leu Val Asp Ala His Leu Lys Ser
            35                  40                  45

Glu Gln Thr Glu Ala Ser Thr Arg Gln Asn Ser Gln Val Leu Leu Ser
50                  55                  60
```

Glu Thr Gly Ile Tyr Asp Asn Asp Pro Asp Leu Cys Phe Arg Met Gln
65                  70                  75                  80

Glu Gly Ser Glu Val Tyr Ser Asn Pro Cys Leu Glu Glu Asn Lys Pro
            85                  90                  95

Gly Ile Val Tyr Ala Ser Leu Asn His Ser Val Ile Gly Pro Asn Ser
            100                 105                 110

Arg Leu Ala Arg Asn Val Lys Glu Ala Pro Thr Glu Tyr Ala Ser Ile
            115                 120                 125

Cys Val Arg Ser
       130

<210> SEQ ID NO 89
<211> LENGTH: 500
<212> TYPE: PRT
<213> ORGANISM: Artificial Sequence
<220> FEATURE:
<223> OTHER INFORMATION: PA2.1.14 scFv LIR1 HTICD construct

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Gly Leu Glu Trp Ile
        35                  40                  45

Gly Trp Ile Tyr Pro Gly Asn Val Asn Thr Glu Tyr Asn Glu Lys Phe
    50                  55                  60

Lys Gly Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Glu Ile Thr Tyr Ala Met Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Gly Gly Asp Ile Gln Met Thr Gln Ser Pro Ser
        130                 135                 140

Thr Leu Ser Ala Ser Val Gly Asp Arg Val Thr Ile Thr Cys Arg Ser
145                 150                 155                 160

Ser Gln Ser Ile Val His Ser Asn Gly Asn Thr Tyr Leu Glu Trp Tyr
            165                 170                 175

Gln Gln Lys Pro Gly Lys Ala Pro Lys Leu Leu Ile Tyr Lys Val Ser
            180                 185                 190

Asn Arg Phe Ser Gly Val Pro Ala Arg Phe Ser Gly Ser Gly Ser Gly
            195                 200                 205

Thr Glu Phe Thr Leu Thr Ile Ser Ser Leu Gln Pro Asp Asp Phe Ala
        210                 215                 220

Thr Tyr Tyr Cys Phe Gln Gly Ser His Val Pro Arg Thr Phe Gly Gln
225                 230                 235                 240

Gly Thr Lys Val Glu Val Lys Tyr Gly Ser Gln Ser Ser Lys Pro Tyr
            245                 250                 255

Leu Leu Thr His Pro Ser Asp Pro Leu Glu Leu Val Val Ser Gly Pro
            260                 265                 270

Ser Gly Gly Pro Ser Ser Pro Thr Thr Gly Pro Thr Ser Thr Ser Gly
        275                 280                 285

```
Pro Glu Asp Gln Pro Leu Thr Pro Thr Gly Ser Asp Pro Gln Ser Gly
    290                 295                 300
Leu Gly Arg His Leu Gly Val Ile Gly Ile Leu Val Ala Val Ile
305                 310                 315                 320
Leu Leu Leu Leu Leu Leu Leu Leu Phe Leu Ile Leu Arg His Arg
                325                 330                 335
Arg Gln Gly Lys His Trp Thr Ser Thr Gln Arg Lys Ala Asp Phe Gln
                340                 345                 350
His Pro Ala Gly Ala Val Gly Pro Glu Pro Thr Asp Arg Gly Leu Gln
            355                 360                 365
Trp Arg Ser Ser Pro Ala Ala Asp Ala Gln Glu Glu Asn Leu Tyr Ala
370                 375                 380
Ala Val Lys His Thr Gln Pro Glu Asp Gly Val Glu Met Asp Thr Arg
385                 390                 395                 400
Ser Pro His Asp Glu Asp Pro Gln Ala Val Thr Tyr Ala Glu Val Lys
                405                 410                 415
His Ser Arg Pro Arg Arg Glu Met Ala Ser Pro Pro Ser Pro Leu Ser
                420                 425                 430
Gly Glu Phe Leu Asp Thr Lys Asp Arg Gln Ala Glu Glu Asp Arg Gln
            435                 440                 445
Met Asp Thr Glu Ala Ala Ala Ser Glu Ala Pro Gln Asp Val Thr Tyr
450                 455                 460
Ala Gln Leu His Ser Leu Thr Leu Arg Arg Glu Ala Thr Glu Pro Pro
465                 470                 475                 480
Pro Ser Gln Glu Gly Pro Ser Pro Ala Val Pro Ser Ile Tyr Ala Thr
                485                 490                 495
Leu Ala Ile His
            500

<210> SEQ ID NO 90
<211> LENGTH: 480
<212> TYPE: PRT
<213> ORGANISM: Artificial Sequence
<220> FEATURE:
<223> OTHER INFORMATION: PA2.1.14 scFv LIR1 sHTICD construct

<400> SEQUENCE: 90

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Ser Tyr
            20                  25                  30
His Ile His Trp Val Arg Gln Ala Pro Gly Gln Gly Leu Glu Trp Ile
        35                  40                  45
Gly Trp Ile Tyr Pro Gly Asn Val Asn Thr Glu Tyr Asn Glu Lys Phe
    50                  55                  60
Lys Gly Lys Ala Thr Ile Thr Ala Asp Glu Ser Thr Asn Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Glu Ile Thr Tyr Ala Met Asp Tyr Trp Gly Gln Gly Thr
            100                 105                 110
Leu Val Thr Val Ser Ser Gly Gly Gly Gly Ser Gly Gly Gly Gly Ser
        115                 120                 125
Gly Gly Gly Gly Ser Gly Gly Asp Ile Gln Met Thr Gln Ser Pro Ser
    130                 135                 140
```

```
Thr Leu Ser Ala Ser Val Gly Asp Arg Val Thr Ile Thr Cys Arg Ser
145                 150                 155                 160

Ser Gln Ser Ile Val His Ser Asn Gly Asn Thr Tyr Leu Glu Trp Tyr
            165                 170                 175

Gln Gln Lys Pro Gly Lys Ala Pro Lys Leu Leu Ile Tyr Lys Val Ser
        180                 185                 190

Asn Arg Phe Ser Gly Val Pro Ala Arg Phe Ser Gly Ser Gly Ser Gly
    195                 200                 205

Thr Glu Phe Thr Leu Thr Ile Ser Ser Leu Gln Pro Asp Asp Phe Ala
210                 215                 220

Thr Tyr Tyr Cys Phe Gln Gly Ser His Val Pro Arg Thr Phe Gly Gln
225                 230                 235                 240

Gly Thr Lys Val Glu Val Lys Val Val Ser Gly Pro Ser Gly Gly Pro
            245                 250                 255

Ser Ser Pro Thr Thr Gly Pro Thr Ser Thr Ser Gly Pro Glu Asp Gln
        260                 265                 270

Pro Leu Thr Pro Thr Gly Ser Asp Pro Gln Ser Gly Leu Gly Arg His
    275                 280                 285

Leu Gly Val Val Ile Gly Ile Leu Val Ala Val Ile Leu Leu Leu Leu
290                 295                 300

Leu Leu Leu Leu Leu Phe Leu Ile Leu Arg His Arg Arg Gln Gly Lys
305                 310                 315                 320

His Trp Thr Ser Thr Gln Arg Lys Ala Asp Phe Gln His Pro Ala Gly
            325                 330                 335

Ala Val Gly Pro Glu Pro Thr Asp Arg Gly Leu Gln Trp Arg Ser Ser
        340                 345                 350

Pro Ala Ala Asp Ala Gln Glu Glu Asn Leu Tyr Ala Ala Val Lys His
    355                 360                 365

Thr Gln Pro Glu Asp Gly Val Glu Met Asp Thr Arg Ser Pro His Asp
370                 375                 380

Glu Asp Pro Gln Ala Val Thr Tyr Ala Glu Val Lys His Ser Arg Pro
385                 390                 395                 400

Arg Arg Glu Met Ala Ser Pro Pro Ser Pro Leu Ser Gly Glu Phe Leu
            405                 410                 415

Asp Thr Lys Asp Arg Gln Ala Glu Glu Asp Arg Gln Met Asp Thr Glu
        420                 425                 430

Ala Ala Ala Ser Glu Ala Pro Gln Asp Val Thr Tyr Ala Gln Leu His
    435                 440                 445

Ser Leu Thr Leu Arg Arg Glu Ala Thr Glu Pro Pro Pro Ser Gln Glu
450                 455                 460

Gly Pro Ser Pro Ala Val Pro Ser Ile Tyr Ala Thr Leu Ala Ile His
465                 470                 475                 480

<210> SEQ ID NO 91
<211> LENGTH: 500
<212> TYPE: PRT
<213> ORGANISM: Artificial Sequence
<220> FEATURE:
<223> OTHER INFORMATION: PA2.1.14 (VL:VH) scFv LIR1 HTICD construct

<400> SEQUENCE: 91

Asp Ile Gln Met Thr Gln Ser Pro Ser Thr Leu Ser Ala Ser Val Gly
1               5                   10                  15

Asp Arg Val Thr Ile Thr Cys Arg Ser Ser Gln Ser Ile Val His Ser
            20                  25                  30
```

```
Asn Gly Asn Thr Tyr Leu Glu Trp Tyr Gln Gln Lys Pro Gly Lys Ala
            35                  40                  45

Pro Lys Leu Leu Ile Tyr Lys Val Ser Asn Arg Phe Ser Gly Val Pro
 50                  55                  60

Ala Arg Phe Ser Gly Ser Gly Ser Gly Thr Glu Phe Thr Leu Thr Ile
 65                  70                  75                  80

Ser Ser Leu Gln Pro Asp Asp Phe Ala Thr Tyr Tyr Cys Phe Gln Gly
                 85                  90                  95

Ser His Val Pro Arg Thr Phe Gly Gln Gly Thr Lys Val Glu Val Lys
                100                 105                 110

Gly Gly Gly Gly Ser Gly Gly Gly Ser Gly Gly Gly Gly Ser Gly
                115                 120                 125

Gly Gln Val Gln Leu Val Gln Ser Gly Ala Glu Val Lys Lys Pro Gly
130                 135                 140

Ser Ser Val Lys Val Ser Cys Lys Ala Ser Gly Tyr Thr Phe Thr Ser
145                 150                 155                 160

Tyr His Ile His Trp Val Arg Gln Ala Pro Gly Gln Gly Leu Glu Trp
                165                 170                 175

Ile Gly Trp Ile Tyr Pro Gly Asn Val Asn Thr Glu Tyr Asn Glu Lys
                180                 185                 190

Phe Lys Gly Lys Ala Thr Ile Thr Ala Asp Glu Ser Thr Asn Thr Ala
            195                 200                 205

Tyr Met Glu Leu Ser Ser Leu Arg Ser Glu Asp Thr Ala Val Tyr Tyr
            210                 215                 220

Cys Ala Arg Glu Glu Ile Thr Tyr Ala Met Asp Tyr Trp Gly Gln Gly
225                 230                 235                 240

Thr Leu Val Thr Val Ser Ser Tyr Gly Ser Gln Ser Ser Lys Pro Tyr
                245                 250                 255

Leu Leu Thr His Pro Ser Asp Pro Leu Glu Leu Val Val Ser Gly Pro
                260                 265                 270

Ser Gly Gly Pro Ser Ser Pro Thr Thr Gly Pro Thr Ser Thr Ser Gly
            275                 280                 285

Pro Glu Asp Gln Pro Leu Thr Pro Thr Gly Ser Asp Pro Gln Ser Gly
290                 295                 300

Leu Gly Arg His Leu Gly Val Val Ile Gly Ile Leu Val Ala Val Ile
305                 310                 315                 320

Leu Leu Leu Leu Leu Leu Leu Leu Phe Leu Ile Leu Arg His Arg
                325                 330                 335

Arg Gln Gly Lys His Trp Thr Ser Thr Gln Arg Lys Ala Asp Phe Gln
            340                 345                 350

His Pro Ala Gly Ala Val Gly Pro Glu Pro Thr Asp Arg Gly Leu Gln
            355                 360                 365

Trp Arg Ser Ser Pro Ala Ala Asp Ala Gln Glu Glu Asn Leu Tyr Ala
370                 375                 380

Ala Val Lys His Thr Gln Pro Glu Asp Gly Val Glu Met Asp Thr Arg
385                 390                 395                 400

Ser Pro His Asp Glu Asp Pro Gln Ala Val Thr Tyr Ala Glu Val Lys
                405                 410                 415

His Ser Arg Pro Arg Arg Glu Met Ala Ser Pro Pro Ser Pro Leu Ser
            420                 425                 430

Gly Glu Phe Leu Asp Thr Lys Asp Arg Gln Ala Glu Glu Asp Arg Gln
            435                 440                 445

Met Asp Thr Glu Ala Ala Ala Ser Glu Ala Pro Gln Asp Val Thr Tyr
```

Ala Gln Leu His Ser Leu Thr Leu Arg Arg Glu Ala Thr Glu Pro Pro
465                 470                 475                 480

Pro Ser Gln Glu Gly Pro Ser Pro Ala Val Pro Ser Ile Tyr Ala Thr
            485                 490                 495

Leu Ala Ile His
            500

<210> SEQ ID NO 92
<211> LENGTH: 407
<212> TYPE: PRT
<213> ORGANISM: Artificial Sequence
<220> FEATURE:
<223> OTHER INFORMATION: PA2.1.14 (VL:VH) scFv LIR1 sHTICD construct

<400> SEQUENCE: 92

Thr Glu Phe Thr Leu Thr Ile Ser Ser Leu Gln Pro Asp Asp Phe Ala
1               5                   10                  15

Thr Tyr Tyr Cys Phe Gln Gly Ser His Val Pro Arg Thr Phe Gly Gln
            20                  25                  30

Gly Thr Lys Val Glu Val Lys Gly Gly Gly Gly Ser Gly Gly Gly Gly
        35                  40                  45

Ser Gly Gly Gly Gly Ser Gly Gly Gln Val Gln Leu Val Gln Ser Gly
    50                  55                  60

Ala Glu Val Lys Lys Pro Gly Ser Ser Val Lys Val Ser Cys Lys Ala
65                  70                  75                  80

Ser Gly Tyr Thr Phe Thr Ser Tyr His Ile His Trp Val Arg Gln Ala
                85                  90                  95

Pro Gly Gln Gly Leu Glu Trp Ile Gly Trp Ile Tyr Pro Gly Asn Val
            100                 105                 110

Asn Thr Glu Tyr Asn Glu Lys Phe Lys Gly Lys Ala Thr Ile Thr Ala
        115                 120                 125

Asp Glu Ser Thr Asn Thr Ala Tyr Met Glu Leu Ser Ser Leu Arg Ser
    130                 135                 140

Glu Asp Thr Ala Val Tyr Tyr Cys Ala Arg Glu Glu Ile Thr Tyr Ala
145                 150                 155                 160

Met Asp Tyr Trp Gly Gln Gly Thr Leu Val Thr Val Ser Ser Val Val
                165                 170                 175

Ser Gly Pro Ser Gly Gly Pro Ser Ser Pro Thr Thr Gly Pro Thr Ser
            180                 185                 190

Thr Ser Gly Pro Glu Asp Gln Pro Leu Thr Pro Thr Gly Ser Asp Pro
        195                 200                 205

Gln Ser Gly Leu Gly Arg His Leu Gly Val Val Ile Gly Ile Leu Val
    210                 215                 220

Ala Val Ile Leu Leu Leu Leu Leu Leu Leu Leu Phe Leu Ile Leu
225                 230                 235                 240

Arg His Arg Arg Gln Gly Lys His Trp Thr Ser Thr Gln Arg Lys Ala
                245                 250                 255

Asp Phe Gln His Pro Ala Gly Ala Val Gly Pro Glu Pro Thr Asp Arg
            260                 265                 270

Gly Leu Gln Trp Arg Ser Ser Pro Ala Ala Asp Ala Gln Glu Glu Asn
        275                 280                 285

Leu Tyr Ala Ala Val Lys His Thr Gln Pro Glu Asp Gly Val Glu Met
    290                 295                 300

Asp Thr Arg Ser Pro His Asp Glu Asp Pro Gln Ala Val Thr Tyr Ala

```
                    305                 310                 315                 320
Glu Val Lys His Ser Arg Pro Arg Arg Glu Met Ala Ser Pro Pro Ser
                325                 330                 335

Pro Leu Ser Gly Glu Phe Leu Asp Thr Lys Asp Arg Gln Ala Glu Glu
            340                 345                 350

Asp Arg Gln Met Asp Thr Glu Ala Ala Ala Ser Glu Ala Pro Gln Asp
        355                 360                 365

Val Thr Tyr Ala Gln Leu His Ser Leu Thr Leu Arg Arg Glu Ala Thr
    370                 375                 380

Glu Pro Pro Pro Ser Gln Glu Gly Pro Ser Pro Ala Val Pro Ser Ile
385                 390                 395                 400

Tyr Ala Thr Leu Ala Ile His
                405

<210> SEQ ID NO 93
<211> LENGTH: 32
<212> TYPE: PRT
<213> ORGANISM: Homo sapiens

<400> SEQUENCE: 93

Thr Thr Gly Pro Thr Ser Thr Ser Gly Pro Glu Asp Gln Pro Leu Thr
1               5                   10                  15

Pro Thr Gly Ser Asp Pro Gln Ser Gly Leu Gly Arg His Leu Gly Val
            20                  25                  30

<210> SEQ ID NO 94
<211> LENGTH: 10
<212> TYPE: PRT
<213> ORGANISM: Homo sapiens

<400> SEQUENCE: 94

Met Ala Met Val Lys Arg Lys Asp Ser Arg
1               5                   10

<210> SEQ ID NO 95
<211> LENGTH: 30
<212> TYPE: DNA
<213> ORGANISM: Homo sapiens

<400> SEQUENCE: 95
atggccatgg tcaagagaaa ggattccaga                                          30

<210> SEQ ID NO 96
<211> LENGTH: 23
<212> TYPE: PRT
<213> ORGANISM: Homo sapiens

<400> SEQUENCE: 96

Val Ile Gly Phe Arg Ile Leu Leu Leu Lys Val Ala Gly Phe Asn Leu
1               5                   10                  15

Leu Met Thr Leu Arg Leu Trp
            20

<210> SEQ ID NO 97
<211> LENGTH: 69
<212> TYPE: DNA
<213> ORGANISM: Homo sapiens

<400> SEQUENCE: 97
gtgattgggt tccgaatcct cctcctgaaa gtggccgggt taatctgct catgacgctg        60
```

-continued cggctgtgg                                                              69

<210> SEQ ID NO 98
<211> LENGTH: 23
<212> TYPE: PRT
<213> ORGANISM: Homo sapiens

<400> SEQUENCE: 98

Thr Ile Leu Tyr Glu Ile Leu Leu Gly Lys Ala Thr Leu Tyr Ala Val
1               5                   10                  15

Leu Val Ser Ala Leu Val Leu
            20

<210> SEQ ID NO 99
<211> LENGTH: 69
<212> TYPE: DNA
<213> ORGANISM: Homo sapiens

<400> SEQUENCE: 99
accatcctct atgagatctt gctagggaag gccaccttgt atgccgtgct ggtcagtgcc    60
ctcgtgctg                                                              69

<210> SEQ ID NO 100
<211> LENGTH: 27
<212> TYPE: PRT
<213> ORGANISM: Homo sapiens

<400> SEQUENCE: 100

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 101
<211> LENGTH: 81
<212> TYPE: DNA
<213> ORGANISM: Homo sapiens

<400> SEQUENCE: 101
ttctgggtgc tggtcgttgt gggcggcgtg ctggcctgct acagcctgct ggtgacagtg    60
gccttcatca tcttttgggt g                                                81

<210> SEQ ID NO 102
<211> LENGTH: 45
<212> TYPE: PRT
<213> ORGANISM: Homo sapiens

<400> SEQUENCE: 102

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 103
<211> LENGTH: 135
<212> TYPE: DNA
<213> ORGANISM: Homo sapiens

<400> SEQUENCE: 103

```
accacgacgc cagcgccgcg accaccaaca ccggcgccca ccatcgcgtc gcagcccctg    60
tccctgcgcc cagaggcgtg ccggccagcg gcgggggggcg cagtgcacac gagggggctg   120
gacttcgcct gtgat                                                    135
```

<210> SEQ ID NO 104
<211> LENGTH: 41
<212> TYPE: PRT
<213> ORGANISM: Homo sapiens

<400> SEQUENCE: 104

```
Cys Thr Ile Glu Val Met Tyr Pro Pro Tyr Leu Asp Asn Glu Lys
1               5                   10                  15

Ser Asn Gly Thr Ile Ile His Val Lys Gly Lys His Leu Cys Pro Ser
            20                  25                  30

Pro Leu Phe Pro Gly Pro Ser Lys Pro
        35                  40
```

<210> SEQ ID NO 105
<211> LENGTH: 123
<212> TYPE: DNA
<213> ORGANISM: Homo sapiens

<400> SEQUENCE: 105

```
tgtaccattg aagttatgta tcctcctcct tacctagaca atgagaagag caatggaacc    60
attatccatg tgaagggaa acacctttgt ccaagtcccc tatttcccgg accttctaag   120
ccc                                                                 123
```

<210> SEQ ID NO 106
<211> LENGTH: 9
<212> TYPE: PRT
<213> ORGANISM: Homo sapiens

<400> SEQUENCE: 106

```
Phe Leu Trp Gly Pro Arg Ala Leu Val
1               5
```

<210> SEQ ID NO 107
<211> LENGTH: 9
<212> TYPE: PRT
<213> ORGANISM: Homo sapiens

<400> SEQUENCE: 107

```
Ser Leu Leu Met Trp Ile Thr Gln Val
1               5
```

<210> SEQ ID NO 108
<211> LENGTH: 11
<212> TYPE: PRT
<213> ORGANISM: Homo sapiens

<400> SEQUENCE: 108

```
Met Pro Lys Val Ala Glu Leu Val His Phe Leu
1               5                   10
```

<210> SEQ ID NO 109
<211> LENGTH: 10
<212> TYPE: PRT
<213> ORGANISM: Human papillomavirus

<400> SEQUENCE: 109

```
Thr Ile His Asp Ile Ile Leu Glu Cys Val
```

<210> SEQ ID NO 110
<211> LENGTH: 9
<212> TYPE: PRT
<213> ORGANISM: Human papillomavirus

<400> SEQUENCE: 110

Tyr Met Leu Asp Leu Gln Pro Glu Thr
1               5

<210> SEQ ID NO 111
<211> LENGTH: 1503
<212> TYPE: DNA
<213> ORGANISM: Artificial Sequence
<220> FEATURE:
<223> OTHER INFORMATION: Polynucleotide encoding PA2.1.14 scFv LIR1
      HTICD construct

<400> SEQUENCE: 111

```
caggtgcagc tggtgcagtc tggggctgag gtgaagaagc ctgggtcctc agtgaaggtt      60
tcctgcaagg cttctggata caccttcact agctatcata cacttgggt gcgccaggcc     120
cccggacaag ggcttgagtg gatcggatgg atctaccctg caatgttaa cacagaatat     180
aatgagaagt tcaagggcaa agccaccatt accgcggacg aatccacgaa cacagcctac     240
atggagctga gcagcctgag atctgaagac acggctgtgt attactgtgc gagggaggaa     300
attacctacg ctatggacta ctggggccag ggaaccctgg tcaccgtgtc ctcaggcgga     360
ggtgaagcg aggggggagg atctggcggc ggaggaagcg aggcgacat tcaaatgacc      420
cagagcccat ccaccctgag cgcatctgta ggtgaccggg tcaccatcac ttgtagatcc     480
agtcagagta ttgtacacag taatgggaac acctatttgg aatggtatca gcagaaacca     540
ggtaaagccc caaaattgct catctacaaa gtctctaaca gatttagtgg tgtaccagcc     600
aggttcagcg gttccggaag tggtactgaa ttcaccctca cgatctcctc tctccagcca     660
gatgatttcg ccacttatta ctgttttcaa ggttcacatg tgccgcgcac attcggtcag     720
ggtactaaag tagaagtcaa atacggctca cagagctcca aaccctacct gctgactcac     780
cccagtgacc ccctggagct cgtggtctca ggaccgtctg ggggcccccag ctccccgaca     840
acaggcccca cctccacatc tggccctgag accagccccc tcaccccac cgggtcggat     900
ccccagagtg gtctgggaag gcacctgggg gttgtgatcg gcatcttggt ggccgtcatc     960
ctactgctcc tcctcctcct cctcctcttc ctcatcctcc gacatcgacg tcagggcaaa    1020
cactggacat cgacccagag aaaggctgat ttccaacatc ctgcaggggc tgtggggcca    1080
gagcccacag acagaggcct gcagtggagg tccagcccag ctgccgatgc caggaagaa    1140
aacctctatg ctgccgtgaa gcacacacag cctgaggatg gggtggagat ggacactcgg    1200
agcccacacg atgaagaccc ccaggcagtg acgtatgccg aggtgaaaca ctccagacct    1260
aggagagaaa tggcctctcc tccttcccca ctgtctgggg aattcctgga cacaaaggac    1320
agacaggcgg aagaggacag gcagatggac actgaggctg ctgcatctga gccccccag    1380
gatgtgacct acgccagct gcacagcttg accctcagac gggaggcaac tgagcctcct    1440
ccatcccagg aagggccctc tccagctgtg cccagcatct acgccactct ggccatccac    1500
tag                                                                    1503
```

<210> SEQ ID NO 112
<211> LENGTH: 1443

```
<212> TYPE: DNA
<213> ORGANISM: Artificial Sequence
<220> FEATURE:
<223> OTHER INFORMATION: Polynucleotide encoding PA2.1.14 scFv LIR1
      sHTICD construct

<400> SEQUENCE: 112
caggtgcagc tggtgcagtc tggggctgag gtgaagaagc ctgggtcctc agtgaaggtt      60
tcctgcaagg cttctggata caccttcact agctatcata tacattgggt gcgccaggcc    120
cccggacaag ggcttgagtg gatcggatgg atctaccctg caatgttaa cacagaatat     180
aatgagaagt tcaagggcaa agccaccatt accgcggacg aatccacgaa cacagcctac    240
atggagctga gcagcctgag atctgaagac acggctgtgt attactgtgc gagggaggaa    300
attacctacg ctatggacta ctggggccag ggaaccctgg tcaccgtgtc ctcaggcgga    360
ggtggaagcg agggggagg atctggcggc ggaggaagcg aggcgacat tcaaatgacc      420
cagagcccat ccaccctgag cgcatctgta ggtgaccggg tcaccatcac ttgtagatcc    480
agtcagagta ttgtacacag taatgggaac acctatttgg aatggtatca gcagaaacca    540
ggtaaagccc caaaattgct catctacaaa gtctctaaca gatttagtgg tgtaccagcc    600
aggttcagcg gttccggaag tggtactgaa ttcaccctca cgatctcctc tctccagcca    660
gatgatttcg ccacttatta ctgttttcaa ggttcacatg tgccgcgcac attcggtcag    720
ggtactaaag tagaagtcaa agtggtctca ggaccgtctg ggggcccag ctccccgaca     780
acaggcccca cctccacatc tggccctgag accagccccc tcaccccac cgggtcggat     840
ccccagagtg tctgggaag caccctgggg gttgtgatcg catcttggt ggccgtcatc      900
ctactgctcc tcctcctcct cctcctcttc ctcatcctcc gacatcgacg tcagggcaaa    960
cactggacat cgacccagag aaaggctgat ttcaacatc tgcagggc tgtgggggca      1020
gagcccacag acagaggcct gcagtggagg tccagcccag ctgccgatgc caggaagaa    1080
aacctctatg ctgccgtgaa gcacacacag cctgaggatg gggtggagat ggacactcgg    1140
agcccacacg atgaagaccc ccaggcagtg acgtatgccg aggtgaaaca ctccagacct    1200
aggagagaaa tggcctctcc tccttcccca ctgtctgggg aattcctgga cacaaaggac    1260
agacaggcgg aagaggacag gcagatggac actgaggctg ctgcatctga agccccccag    1320
gatgtgaccct acgccagct gcacagcttg accctcagac gggaggcaac tgagcctcct    1380
ccatcccagg aagggccctc tccagctgtg cccagcatct acgccactct ggccatccac    1440
tag                                                                 1443

<210> SEQ ID NO 113
<211> LENGTH: 1503
<212> TYPE: DNA
<213> ORGANISM: Artificial Sequence
<220> FEATURE:
<223> OTHER INFORMATION: Polynucleotide PA2.1.14 (VL:VH) scFv LIR1 HTICD
      construct

<400> SEQUENCE: 113
gacattcaaa tgacccagag cccatccacc ctgagcgcat ctgtaggtga ccgggtcacc      60
atcacttgta gatccagtca gagtattgta cacagtaatg ggaacaccta tttggaatgg    120
tatcagcaga aaccaggtaa agccccaaaa ttgctcatct acaaagtctc taacagattt    180
agtggtgtac cagccaggtt cagcggttcc ggaagtggta ctgaattcac cctcacgatc    240
tcctctctcc agccagatga tttcgccact tattactgtt ttcaaggttc acatgtgccg    300
```

| | |
|---|---|
| cgcacattcg gtcagggtac taaagtagaa gtcaaaggcg gaggtggaag cggaggggga | 360 |
| ggatctggcg gcggaggaag cggaggccag gtgcagctgg tgcagtctgg ggctgaggtg | 420 |
| aagaagcctg gtcctcagt gaaggtttcc tgcaaggctt ctggatacac cttcactagc | 480 |
| tatcatatac attgggtgcg ccaggccccc ggacaagggc ttgagtggat cggatggatc | 540 |
| taccctggca atgttaacac agaatataat gagaagttca agggcaaagc caccattacc | 600 |
| gcggacgaat ccacgaacac agcctacatg agctgagca gcctgagatc tgaagacacg | 660 |
| gctgtgtatt actgtgcgag ggaggaaatt acctacgcta tggactactg gggccaggga | 720 |
| accctggtca ccgtgtcctc atacggctca cagagctcca acccctacct gctgactcac | 780 |
| cccagtgacc ccctggagct cgtggtctca ggaccgtctg ggggccccag ctccccgaca | 840 |
| acaggcccca cctccacatc tggccctgag accagcccc tcaccccac cgggtcggat | 900 |
| ccccagagtg gtctgggaag gcacctgggg gttgtgatcg gcatcttggt ggccgtcatc | 960 |
| ctactgctcc tcctcctcct cctcctcttc ctcatcctcc gacatcgacg tcagggcaaa | 1020 |
| cactggacat cgacccagag aaaggctgat ttccaacatc ctgcagggc tgtggggcca | 1080 |
| gagcccacag acagaggcct gcagtggagg tccagcccag ctgccgatgc caggaagaa | 1140 |
| aacctctatg ctgccgtgaa gcacacacag cctgaggatg ggtggagat ggacactcgg | 1200 |
| agcccacacg atgaagaccc ccaggcagtg acgtatgccg aggtgaaaca ctccagacct | 1260 |
| aggagagaaa tggcctctcc tccttcccca ctgtctgggg aattcctgga cacaaaggac | 1320 |
| agacaggcgg aagaggacag gcagatggac actgaggctg ctgcatctga agcccccccag | 1380 |
| gatgtgacct acgccagct gcacagcttg accctcagac gggaggcaac tgagcctcct | 1440 |
| ccatcccagg aagggccctc tccagctgtg cccagcatct acgccactct ggccatccac | 1500 |
| tag | 1503 |

<210> SEQ ID NO 114
<211> LENGTH: 1443
<212> TYPE: DNA
<213> ORGANISM: Artificial Sequence
<220> FEATURE:
<223> OTHER INFORMATION: Polynucleotide encoding PA2.1.14 (VL:VH) scFv
    LIR1 sHTICD construct

<400> SEQUENCE: 114

| | |
|---|---|
| gacattcaaa tgacccagag cccatccacc ctgagcgcat ctgtaggtga ccgggtcacc | 60 |
| atcacttgta gatccagtca gagtattgta cacagtaatg gaacaccta tttggaatgg | 120 |
| tatcagcaga aaccaggtaa agcccccaaa ttgctcatct acaaagtctc taacagattt | 180 |
| agtggtgtac cagccaggtt cagcggttcc ggaagtggta ctgaattcac cctcacgatc | 240 |
| tcctctctcc agccagatga tttcgccact tattactgtt tcaaggttc acatgtgccg | 300 |
| cgcacattcg gtcagggtac taaagtagaa gtcaaaggcg gaggtggaag cggaggggga | 360 |
| ggatctggcg gcggaggaag cggaggccag gtgcagctgg tgcagtctgg ggctgaggtg | 420 |
| aagaagcctg gtcctcagt gaaggtttcc tgcaaggctt ctggatacac cttcactagc | 480 |
| tatcatatac attgggtgcg ccaggccccc ggacaagggc ttgagtggat cggatggatc | 540 |
| taccctggca atgttaacac agaatataat gagaagttca agggcaaagc caccattacc | 600 |
| gcggacgaat ccacgaacac agcctacatg agctgagca gcctgagatc tgaagacacg | 660 |
| gctgtgtatt actgtgcgag ggaggaaatt acctacgcta tggactactg gggccaggga | 720 |
| accctggtca ccgtgtcctc agtggtctca ggaccgtctg ggggccccag ctccccgaca | 780 |

```
acaggcccca cctccacatc tggccctgag gaccagcccc tcaccccccac cgggtcggat    840 ccccagagtg gtctgggaag gcacctgggg gttgtgatcg gcatcttggt ggccgtcatc    900
ctactgctcc tcctcctcct cctcctcttc ctcatcctcc gacatcgacg tcagggcaaa    960
cactggacat cgaccagag aaaggctgat ttccaacatc ctgcagggc tgtggggcca    1020 gagcccacag acagaggcct gcagtggagg tccagcccag ctgccgatgc ccaggaagaa   1080
aacctctatg ctgccgtgaa gcacacacag cctgaggatg gggtggagat ggacactcgg    1140
agcccacacg atgaagaccc ccaggcagtg acgtatgccg aggtgaaaca ctccagacct    1200
aggagagaaa tggcctctcc tccttcccca ctgtctgggg aattcctgga cacaaaggac    1260
agacaggcgg aagaggacag gcagatggac actgaggctg ctgcatctga agccccccag    1320
gatgtgacct acgcccagct gcacagcttg accctcagac gggaggcaac tgagcctcct    1380
ccatcccagg aagggccctc tccagctgtg cccagcatct acgccactct ggccatccac    1440
tag                                                                 1443
```

<210> SEQ ID NO 115
<211> LENGTH: 71
<212> TYPE: PRT
<213> ORGANISM: Homo sapiens

<400> SEQUENCE: 115

Ser Ser Tyr Gly Ser Gln Ser Ser Lys Pro Tyr Leu Leu Thr His Pro
1               5                   10                  15

Ser Asp Pro Leu Glu Leu Val Val Ser Gly Pro Ser Gly Gly Pro Ser
            20                  25                  30

Ser Pro Thr Thr Gly Pro Thr Ser Thr Ser Gly Pro Glu Asp Gln Pro
        35                  40                  45

Leu Thr Pro Thr Gly Ser Asp Pro Gln Ser Gly Leu Gly Arg His Leu
    50                  55                  60

Gly Val Val Ile Gly Ile Leu
65                  70

<210> SEQ ID NO 116
<211> LENGTH: 39
<212> TYPE: PRT
<213> ORGANISM: Homo sapiens

<400> SEQUENCE: 116

Ser Ser Thr Thr Gly Pro Thr Ser Thr Ser Gly Pro Glu Asp Gln Pro
1               5                   10                  15

Leu Thr Pro Thr Gly Ser Asp Pro Gln Ser Gly Leu Gly Arg His Leu
            20                  25                  30

Gly Val Val Ile Gly Ile Leu
        35

<210> SEQ ID NO 117
<211> LENGTH: 74
<212> TYPE: PRT
<213> ORGANISM: Artificial Sequence
<220> FEATURE:
<223> OTHER INFORMATION: Made in Lab - hinge sequence

<400> SEQUENCE: 117

Ser Ser Ala Gly Ser Gly Gly Ser Gly Gly Ser Gly Gly Ser Pro Val
1               5                   10                  15

Pro Ser Thr Pro Pro Thr Pro Ser Pro Ser Thr Pro Pro Thr Pro Ser
            20                  25                  30

```
Pro Ser Gly Gly Ser Gly Asn Ser Gly Ser Gly Gly Ser Pro Val
        35                  40                  45

Pro Ser Thr Pro Pro Thr Pro Ser Pro Ser Thr Pro Pro Thr Pro Ser
50                  55                  60

Pro Ser Ala Ser Val Val Ile Gly Ile Leu
65                  70
```

<210> SEQ ID NO 118
<211> LENGTH: 82
<212> TYPE: PRT
<213> ORGANISM: Artificial Sequence
<220> FEATURE:
<223> OTHER INFORMATION: Made in Lab - hinge sequence

<400> SEQUENCE: 118

```
Ser Ser Ala Gly Ser Gly Gly Ser Gly Gly Ser Gly Gly Ser Pro Val
1               5                   10                  15

Pro Ser Thr Pro Pro Thr Asn Ser Ser Ser Thr Pro Pro Thr Pro Ser
                20                  25                  30

Pro Ser Pro Val Pro Ser Thr Pro Pro Thr Asn Ser Ser Ser Thr Pro
            35                  40                  45

Pro Thr Pro Ser Pro Ser Pro Val Pro Ser Thr Pro Pro Thr Asn Ser
        50                  55                  60

Ser Ser Thr Pro Pro Thr Pro Ser Pro Ser Ala Ser Val Val Ile Gly
65                  70                  75                  80

Ile Leu
```

<210> SEQ ID NO 119
<211> LENGTH: 92
<212> TYPE: PRT
<213> ORGANISM: Artificial Sequence
<220> FEATURE:
<223> OTHER INFORMATION: Made in Lab - hinge sequence

<400> SEQUENCE: 119

```
Ser Ser Val Val Ser Gly Pro Ser Gly Gly Pro Ser Ser Pro Thr Thr
1               5                   10                  15

Gly Pro Thr Ser Thr Ser Gly Pro Glu Asp Gln Pro Leu Thr Pro Thr
                20                  25                  30

Gly Ser Asp Pro Gln Ser Gly Leu Gly Arg His Val Val Ser Gly Pro
            35                  40                  45

Ser Gly Gly Pro Ser Ser Pro Thr Thr Gly Pro Thr Ser Thr Ser Gly
        50                  55                  60

Pro Glu Asp Gln Pro Leu Thr Pro Thr Gly Ser Asp Pro Gln Ser Gly
65                  70                  75                  80

Leu Gly Arg His Leu Gly Val Val Ile Gly Ile Leu
                85                  90
```

<210> SEQ ID NO 120
<211> LENGTH: 522
<212> TYPE: PRT
<213> ORGANISM: Artificial Sequence
<220> FEATURE:
<223> OTHER INFORMATION: C1765 chimeric antigen recetor constuct with
      signal peptide

<400> SEQUENCE: 120

```
Met Asp Met Arg Val Pro Ala Gln Leu Leu Gly Leu Leu Leu Leu Trp
1               5                   10                  15
```

-continued

```
Leu Arg Gly Ala Arg Cys Asp Val Leu Met Thr Gln Thr Pro Leu Ser
             20                  25                  30
Leu Pro Val Ser Leu Gly Asp Gln Ala Ser Ile Ser Cys Arg Ser Ser
         35                  40                  45
Gln Ser Ile Val His Ser Asn Gly Asn Thr Tyr Leu Glu Trp Tyr Leu
 50                  55                  60
Gln Lys Pro Gly Gln Ser Pro Lys Leu Leu Ile Tyr Lys Val Ser Asn
65                  70                  75                  80
Arg Phe Ser Gly Val Pro Asp Arg Phe Ser Gly Ser Gly Ser Gly Thr
                 85                  90                  95
Asp Phe Thr Leu Lys Ile Ser Arg Val Glu Ala Glu Asp Leu Gly Val
            100                 105                 110
Tyr Tyr Cys Phe Gln Gly Ser His Val Pro Arg Thr Ser Gly Gly Gly
        115                 120                 125
Thr Lys Leu Glu Ile Lys Gly Gly Gly Ser Gly Gly Gly Gly Ser
    130                 135                 140
Gly Gly Gly Gly Ser Gly Gly Gln Val Gln Leu Gln Gln Ser Gly Pro
145                 150                 155                 160
Glu Leu Val Lys Pro Gly Ala Ser Val Arg Ile Ser Cys Lys Ala Ser
                165                 170                 175
Gly Tyr Thr Phe Thr Ser Tyr His Ile His Trp Val Lys Gln Arg Pro
            180                 185                 190
Gly Gln Gly Leu Glu Trp Ile Gly Trp Ile Tyr Pro Gly Asn Val Asn
        195                 200                 205
Thr Glu Tyr Asn Glu Lys Phe Lys Gly Lys Ala Thr Leu Thr Ala Asp
    210                 215                 220
Lys Ser Ser Ser Thr Ala Tyr Met His Leu Ser Ser Leu Thr Ser Glu
225                 230                 235                 240
Asp Ser Ala Val Tyr Phe Cys Ala Arg Glu Glu Ile Thr Tyr Ala Met
                245                 250                 255
Asp Tyr Trp Gly Gln Gly Thr Ser Val Thr Val Ser Ser Tyr Gly Ser
            260                 265                 270
Gln Ser Ser Lys Pro Tyr Leu Leu Thr His Pro Ser Asp Pro Leu Glu
        275                 280                 285
Leu Val Val Ser Gly Pro Ser Gly Pro Ser Ser Pro Thr Thr Gly
    290                 295                 300
Pro Thr Ser Thr Ser Gly Pro Glu Asp Gln Pro Leu Thr Pro Thr Gly
305                 310                 315                 320
Ser Asp Pro Gln Ser Gly Leu Gly Arg His Leu Gly Val Val Ile Gly
                325                 330                 335
Ile Leu Val Ala Val Ile Leu Leu Leu Leu Leu Leu Leu Leu Leu Phe
            340                 345                 350
Leu Ile Leu Arg His Arg Arg Gln Gly Lys His Trp Thr Ser Thr Gln
        355                 360                 365
Arg Lys Ala Asp Phe Gln His Pro Ala Gly Ala Val Gly Pro Glu Pro
    370                 375                 380
Thr Asp Arg Gly Leu Gln Trp Arg Ser Ser Pro Ala Ala Asp Ala Gln
385                 390                 395                 400
Glu Glu Asn Leu Tyr Ala Ala Val Lys His Thr Gln Pro Glu Asp Gly
                405                 410                 415
Val Glu Met Asp Thr Arg Ser Pro His Asp Glu Asp Pro Gln Ala Val
            420                 425                 430
Thr Tyr Ala Glu Val Lys His Ser Arg Pro Arg Arg Glu Met Ala Ser
```

|         | 435             | 440             | 445             |
|---------|-----------------|-----------------|-----------------|

Pro Pro Ser Pro Leu Ser Gly Glu Phe Leu Asp Thr Lys Asp Arg Gln
        450                 455                 460

Ala Glu Glu Asp Arg Gln Met Asp Thr Glu Ala Ala Ser Glu Ala
465             470              475                 480

Pro Gln Asp Val Thr Tyr Ala Gln Leu His Ser Leu Thr Leu Arg Arg
                485                 490                 495

Glu Ala Thr Glu Pro Pro Pro Ser Gln Glu Gly Pro Ser Pro Ala Val
            500                 505                 510

Pro Ser Ile Tyr Ala Thr Leu Ala Ile His
        515                 520

<210> SEQ ID NO 121
<211> LENGTH: 1569
<212> TYPE: DNA
<213> ORGANISM: Artificial Sequence
<220> FEATURE:
<223> OTHER INFORMATION: Polynucleotide encoding C1765 chimeric antigen
      recetor constuct with signal peptide

<400> SEQUENCE: 121

| atggacatga | gggtccccgc | tcagctcctg | gggctcctgc | tactctggct | ccgaggtgcc | 60 |
|---|---|---|---|---|---|---|
| agatgtgatg | ttttgatgac | ccaaactcca | ctctccctgc | ctgtcagtct | tggagatcaa | 120 |
| gcctccatct | cttgcagatc | tagtcagagc | attgtacata | gtaatggaaa | cacctattta | 180 |
| gaatggtacc | tgcagaaacc | aggccagtct | ccaaagctcc | tgatctacaa | agtttccaac | 240 |
| cgattttctg | ggtccccaga | caggttcagt | ggcagtggat | cagggacaga | tttcacactc | 300 |
| aagatcagta | gagtggaggc | tgaggatctg | ggagtttatt | actgctttca | aggttcacat | 360 |
| gttcctcgga | cgtccggtgg | aggcaccaag | ctggaaatca | aaggcggagg | tggaagcgga | 420 |
| gggggaggat | ctggcggcgg | aggaagcgga | ggccaggtcc | agctgcagca | gtctggacct | 480 |
| gagctggtga | agcctgggc | ttcagtgagg | atatcctgca | aggcttctgg | ctacaccttc | 540 |
| acaagttacc | atatacattg | ggtgaagcag | aggcctggac | agggacttga | gtggattgga | 600 |
| tggatttatc | ctggaaatgt | taatactgag | tacaatgaga | agttcaaggg | caaggccaca | 660 |
| ctgactgcag | acaaatcgtc | cagcacagcc | tacatgcacc | tcagcagcct | gacctctgag | 720 |
| gactctgcgg | tctatttctg | tgccagagag | gagattacct | atgctatgga | ctactggggt | 780 |
| caaggaacct | cagtcaccgt | gtcctcatac | ggctcacaga | gctccaaacc | ctacctgctg | 840 |
| actcacccca | gtgaccccct | ggagctcgtg | gtctcaggac | cgtctggggg | ccccagctcc | 900 |
| ccgacaacag | gccccacctc | cacatctggc | cctgaggacc | agccctcac | ccccaccggg | 960 |
| tcggatcccc | agagtggtct | gggaaggcac | ctggggttg | tgatcggcat | cttggtggcc | 1020 |
| gtcatcctac | tgctcctcct | cctcctcctc | ctcttcctca | tcctccgaca | tcgacgtcag | 1080 |
| ggcaaacact | ggacatcgac | ccagagaaag | gctgatttcc | aacatcctgc | aggggctgtg | 1140 |
| gggccagagc | ccacagacag | aggcctgcag | tggaggtcca | gccagctgc | cgatgcccag | 1200 |
| gaagaaaacc | tctatgctgc | cgtgaagcac | acacagcctg | aggatggggt | ggagatggac | 1260 |
| actcggagcc | cacacgatga | agaccccag | gcagtgacgt | atgccgaggt | gaaacactcc | 1320 |
| agacctagga | gagaaatggc | ctctcctcct | tccccactgt | ctggggaatt | cctggacaca | 1380 |
| aaggacagac | aggcggaaga | ggacaggcag | atggacactg | aggctgctgc | atctgaagcc | 1440 |
| ccccaggatg | tgacctacgc | ccagctgcac | agcttgaccc | tcagacggga | ggcaactgag | 1500 |
| cctcctccat | cccaggaagg | gccctctcca | gctgtgccca | gcatctacgc | cactctggcc | 1560 | atccactag                                                          1569

<210> SEQ ID NO 122
<211> LENGTH: 500
<212> TYPE: PRT
<213> ORGANISM: Artificial Sequence
<220> FEATURE:
<223> OTHER INFORMATION: C1765 chimeric antigen recetor constuct without
      signal peptide

<400> SEQUENCE: 122

```
Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Arg Thr Ser Gly Gly Gly Thr Lys Leu Glu Ile Lys
            100                 105                 110

Gly Gly Gly Gly Ser Gly Gly Gly Ser Gly Gly Gly Gly Ser Gly
        115                 120                 125

Gly Gln Val Gln Leu Gln Gln Ser Gly Pro Glu Leu Val Lys Pro Gly
    130                 135                 140

Ala Ser Val Arg Ile Ser Cys Lys Ala Ser Gly Tyr Thr Phe Thr Ser
145                 150                 155                 160

Tyr His Ile His Trp Val Lys Gln Arg Pro Gly Gln Gly Leu Glu Trp
                165                 170                 175

Ile Gly Trp Ile Tyr Pro Gly Asn Val Asn Thr Glu Tyr Asn Glu Lys
            180                 185                 190

Phe Lys Gly Lys Ala Thr Leu Thr Ala Asp Lys Ser Ser Ser Thr Ala
        195                 200                 205

Tyr Met His Leu Ser Ser Leu Thr Ser Glu Asp Ser Ala Val Tyr Phe
    210                 215                 220

Cys Ala Arg Glu Glu Ile Thr Tyr Ala Met Asp Tyr Trp Gly Gln Gly
225                 230                 235                 240

Thr Ser Val Thr Val Ser Ser Tyr Gly Ser Gln Ser Ser Lys Pro Tyr
                245                 250                 255

Leu Leu Thr His Pro Ser Asp Pro Leu Glu Leu Val Val Ser Gly Pro
            260                 265                 270

Ser Gly Gly Pro Ser Ser Pro Thr Thr Gly Pro Thr Ser Thr Ser Gly
        275                 280                 285

Pro Glu Asp Gln Pro Leu Thr Pro Thr Gly Ser Asp Pro Gln Ser Gly
    290                 295                 300

Leu Gly Arg His Leu Gly Val Val Ile Gly Ile Leu Val Ala Val Ile
305                 310                 315                 320

Leu Leu Leu Leu Leu Leu Leu Leu Phe Leu Ile Leu Arg His Arg
                325                 330                 335

Arg Gln Gly Lys His Trp Thr Ser Thr Gln Arg Lys Ala Asp Phe Gln
            340                 345                 350
```

His Pro Ala Gly Ala Val Gly Pro Glu Pro Thr Asp Arg Gly Leu Gln
        355                 360                 365

Trp Arg Ser Ser Pro Ala Ala Asp Ala Gln Glu Glu Asn Leu Tyr Ala
    370                 375                 380

Ala Val Lys His Thr Gln Pro Glu Asp Gly Val Glu Met Asp Thr Arg
385                 390                 395                 400

Ser Pro His Asp Glu Asp Pro Gln Ala Val Thr Tyr Ala Glu Val Lys
            405                 410                 415

His Ser Arg Pro Arg Arg Glu Met Ala Ser Pro Ser Pro Leu Ser
        420                 425                 430

Gly Glu Phe Leu Asp Thr Lys Asp Arg Gln Ala Glu Asp Arg Gln
    435                 440                 445

Met Asp Thr Glu Ala Ala Ala Ser Glu Ala Pro Gln Asp Val Thr Tyr
450                 455                 460

Ala Gln Leu His Ser Leu Thr Leu Arg Arg Glu Ala Thr Glu Pro Pro
465                 470                 475                 480

Pro Ser Gln Glu Gly Pro Ser Pro Ala Val Pro Ser Ile Tyr Ala Thr
            485                 490                 495

Leu Ala Ile His
        500

<210> SEQ ID NO 123
<211> LENGTH: 1503
<212> TYPE: DNA
<213> ORGANISM: Artificial Sequence
<220> FEATURE:
<223> OTHER INFORMATION: Polynucleotide encoding C1765 chimeric antigen
      recetor construct without signal peptide

<400> SEQUENCE: 123
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga accaggcca gtctccaaag ctcctgatct acaaagtttc caaccgattt      180
tctggggtcc cagacaggtt cagtggcagt ggatcaggga cagatttcac actcaagatc     240
agtagagtgg aggctgagga tctgggagtt tattactgct ttcaaggttc acatgttcct     300
cggacgtccg gtgaggcac aagctgaa atcaaaggcg aggtggaag cggagggga      360 ggatctggcg gcggaggaag cggaggccag gtccagctgc agcagtctgg acctgagctg     420
gtgaagcctg ggcttcagt gaggatatcc tgcaaggctt ctggctacac cttcacaagt     480
taccatatac attgggtgaa gcagaggcct ggacaggac ttgagtggat tggatggatt      540
tatcctggaa atgttaatac tgagtacaat gagaagttca aggcaaggc cacactgact      600 gcagacaaat cgtccagcac agcctacatg cacctcagca gcctgacctc tgaggactct     660
gcggtctatt tctgtgccag agaggagatt acctatgcta ggactactg ggtcaagga      720 acctcagtca ccgtgtcctc atacggctca cagagctcca aaccctacct gctgactcac     780
cccagtgacc cctggagct cgtggtctca ggaccgtctg ggggcccag ctccccgaca      840 acaggcccca cctccacatc tggccctgag accagcccc tcaccccac cgggtcggat      900 ccccagagtg gtctgggaag caacctgggg gttgtgatcg catcttggt ggccgtcatc     960 ctactgctcc tcctcctcct cctcctcttc ctcatcctcc acatcgacg tcagggcaaa    1020 cactggacat cgacccagag aaaggctgat ttccaacatc ctgcaggggc tgtgggca     1080 gagcccacag acagaggcct gcagtggagg tccagcccag ctgccgatgc caggaagaa    1140

```
aacctctatg ctgccgtgaa gcacacacag cctgaggatg gggtggagat ggacactcgg    1200
agcccacacg atgaagaccc ccaggcagtg acgtatgccg aggtgaaaca ctccagacct    1260
aggagagaaa tggcctctcc tccttcccca ctgtctgggg aattcctgga cacaaaggac    1320
agacaggcgg aagaggacag gcagatggac actgaggctg ctgcatctga agcccccag     1380 gatgtgacct acgcccagct gcacagcttg accctcagac gggaggcaac tgagcctcct    1440
ccatcccagg aagggccctc tccagctgtg cccagcatct acgccactct ggccatccac    1500
tag                                                                   1503

<210> SEQ ID NO 124
<211> LENGTH: 6
<212> TYPE: PRT
<213> ORGANISM: Artificial Sequence
<220> FEATURE:
<223> OTHER INFORMATION: immunoreceptor tyrosine-based inhibitory motif
<220> FEATURE:
<221> NAME/KEY: MISC_FEATURE
<222> LOCATION: (1)..(1)
<223> OTHER INFORMATION: Xaa = Ser, Ile, Val or Leu
<220> FEATURE:
<221> NAME/KEY: MISC_FEATURE
<222> LOCATION: (2)..(2)
<223> OTHER INFORMATION: Xaa = Any amino acid
<220> FEATURE:
<221> NAME/KEY: MISC_FEATURE
<222> LOCATION: (4)..(5)
<223> OTHER INFORMATION: Xaa = Any amino acid
<220> FEATURE:
<221> NAME/KEY: MISC_FEATURE
<222> LOCATION: (6)..(6)
<223> OTHER INFORMATION: Xaa = Ile, Val or Leu

<400> SEQUENCE: 124

Xaa Xaa Tyr Xaa Xaa Xaa
1               5

<210> SEQ ID NO 125
<211> LENGTH: 247
<212> TYPE: PRT
<213> ORGANISM: Artificial Sequence
<220> FEATURE:
<223> OTHER INFORMATION: C-001765 scFv antibody construct

<400> SEQUENCE: 125

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Arg Thr Ser Gly Gly Gly Thr Lys Leu Glu Ile Lys
            100                 105                 110

Gly Gly Gly Gly Ser Gly Gly Gly Ser Gly Gly Gly Gly Ser
        115                 120                 125

Gly Gln Val Gln Leu Gln Gln Ser Gly Pro Glu Leu Val Lys Pro Gly
```

```
                130             135                140
Ala Ser Val Arg Ile Ser Cys Lys Ala Ser Gly Tyr Thr Phe Thr Ser
145                 150                 155                 160

Tyr His Ile His Trp Val Lys Gln Arg Pro Gly Gln Gly Leu Glu Trp
                165                 170                 175

Ile Gly Trp Ile Tyr Pro Gly Asn Val Asn Thr Glu Tyr Asn Glu Lys
                180                 185                 190

Phe Lys Gly Lys Ala Thr Leu Thr Ala Asp Lys Ser Ser Ser Thr Ala
                195                 200                 205

Tyr Met His Leu Ser Ser Leu Thr Ser Glu Asp Ser Ala Val Tyr Phe
    210                 215                 220

Cys Ala Arg Glu Glu Ile Thr Tyr Ala Met Asp Tyr Trp Gly Gln Gly
225                 230                 235                 240

Thr Ser Val Thr Val Ser Ser
                245

<210> SEQ ID NO 126
<211> LENGTH: 759
<212> TYPE: DNA
<213> ORGANISM: Homo sapiens

<400> SEQUENCE: 126
tacggctcac agagctccaa accctacctg ctgactcacc ccagtgaccc cctggagctc      60
gtggtctcag gaccgtctgg gggccccagc tccccgacaa caggccccac ctccacatct     120
ggccctgagg accagcccct caccccccac gggtcggatc cccagagtgg tctgggaagg     180
cacctggggg ttgtgatcgg catcttggtg gccgtcatcc tactgctcct cctcctcctc     240
ctcctcttcc tcatcctccg acatcgacgt cagggcaaac actggacatc gacccagaga     300
aaggctgatt ccaacatcc tgcaggggct gtggggccag agcccacaga cagaggcctg      360
cagtggaggt ccagcccagc tgccgatgcc aggaagaaa acctctatgc tgccgtgaag      420
cacacacagc ctgaggatgg ggtggagatg gacactcgga gcccacacga tgaagacccc     480
caggcagtga cgtatgccga ggtgaaacac tccagaccta ggagagaaat ggcctctcct     540
ccttccccac tgtctgggga attcctggac acaaaggaca gacaggcgga agaggacagg     600
cagatggaca ctgaggctgc tgcatctgaa gcccccagg atgtgaccta cgcccagctg      660
cacagcttga ccctcagacg ggaggcaact gagcctcctc catcccagga agggccctct     720
ccagctgtgc ccagcatcta cgccactctg gccatccac                            759

<210> SEQ ID NO 127
<211> LENGTH: 741
<212> TYPE: DNA
<213> ORGANISM: Artificial Sequence
<220> FEATURE:
<223> OTHER INFORMATION: C-001765 scFv antibody construct polynucleotide

<400> SEQUENCE: 127
gatgttttga tgacccaaac tccactctcc ctgcctgtca gtcttggaga tcaagcctcc      60
atctcttgca gatctagtca gagcattgta catagtaatg aaacaccta tttagaatgg     120 tacctgcaga aaccaggcca gtctccaaag ctcctgatct acaaagtttc caaccgattt     180
```

```
tctggggtcc cagacaggtt cagtggcagt ggatcaggga cagatttcac actcaagatc      240
agtagagtgg aggctgagga tctgggagtt tattactgct ttcaaggttc acatgttcct      300
cggacgtccg gtggaggcac caagctggaa atcaaaggcg gaggtggaag cggaggggga      360
ggatctggcg gcggaggaag cggaggccag gtccagctgc agcagtctgg acctgagctg      420
gtgaagcctg gggcttcagt gaggatatcc tgcaaggctt ctggctacac cttcacaagt      480
taccatatac attgggtgaa gcagaggcct ggacagggac ttgagtggat tggatggatt      540
tatcctggaa atgttaatac tgagtacaat gagaagttca agggcaaggc cacactgact      600
gcagacaaat cgtccagcac agcctacatg cacctcagca gcctgacctc tgaggactct      660
gcggtctatt tctgtgccag agaggagatt acctatgcta tggactactg gggtcaagga      720
acctcagtca ccgtgtcctc a                                                741

<210> SEQ ID NO 128
<211> LENGTH: 22
<212> TYPE: PRT
<213> ORGANISM: Homo sapiens

<400> SEQUENCE: 128

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 129
<211> LENGTH: 66
<212> TYPE: DNA
<213> ORGANISM: Homo sapiens

<400> SEQUENCE: 129
atggacatga gggtccccgc tcagctcctg gggctcctgc tactctggct ccgaggtgcc      60
agatgt                                                                 66
```

US 12,195,513 B2

LILRB1-BASED CHIMERIC ANTIGEN RECEPTOR

CROSS REFERENCE TO RELATED APPLICATIONS

This application is a divisional of U.S. application Ser. No. 17/230,637, filed Apr. 14, 2021, which is a continuation of International Application No. PCT/US2020/064607, filed on Dec. 11, 2020, which claims priority to and benefit of U.S. Provisional Patent Application Nos. 63/085,969 filed on Sep. 30, 2020, and 62/946,888, filed on Dec. 11, 2019, the contents of each of which are incorporated herein by reference in their entireties.

INCORPORATION BY REFERENCE OF SEQUENCE LISTING

This application contains a Sequence Listing which has been submitted in ASCII format via EFS-WEB and is hereby incorporated by reference in its entirety. Said ASCII copy, created on Jan. 31, 2022 is named A2BI_015_06US_SeqList_ST25.txt and is 228 KB in size.

BACKGROUND

Chimeric antigen receptor (CAR) T cell therapy, and T Cell Receptor (TCR) therapy, is proving to be an effective therapeutic approach to various diseases, particularly hematological malignancies but also other cancers. CAR NK cells may also have clinical applications. Conventional CARs provide a stimulatory signal to the engineered immune cell (e.g. a T cell or an NK cell). In CAR-T cells, this results in killing activity towards the target cell identified by the antigen-binding domain of the CAR. Inhibitory CARs (iCARs) have been developed as a means to control cell activity or restrict the activity of an activator CAR to specific cell types. Fedorov et al. *Sci. Transl. Med.* 5(215):215ra172 (2013). The inhibitory CAR generally has the intracellular domain of an inhibitory signaling molecule (such as PD-1 or CTLA-4) fused to an antigen-binding domain (e.g., a single-chain variable fragment, scFv) through a transmembrane region and optionally a hinge region.

Numerous alternative iCAR architectures have been described in the art. However, there remains an unmet need for novel alternative inhibitory receptors and identification of particular inhibitory receptor architectures having superior performance, along with associated compositions and methods of use thereof.

SUMMARY

In one aspect, the disclosure provides chimeric antigen receptors having the hinge, transmembrane region, and/or intracellular domain of LILRB1, or functional fragments or variants thereof. The chimeric antigen receptor may include single polypeptide, or more than one polypeptide. The receptors may include one or more, or all of the following: (a) an LILRB1 hinge domain or functional fragment or variant thereof; (b) an LILRB1 transmembrane domain or a functional variant thereof; and (c) an LILRB1 intracellular domain or a functional variant thereof, such as an LILRB1 intracellular domain and/or an intracellular domain comprising at least one immunoreceptor tyrosine-based inhibitory motif (ITIM) found in the polypeptide sequence of LILRB1. In some embodiments, the receptor comprises at least two ITIMS found in the polypeptide sequence of LILRB1. The ITIMs of LILRB1 are NLYAAV (SEQ ID NO: 8), VTYAEV (SEQ ID NO: 9), VTYAQL (SEQ ID NO: 10), and SIYATL (SEQ ID NO: 11). The receptor may include one, two, three, four, five, six, or more of these ITIMs, in any combination including multiple copies of the same ITIM.

In some embodiments of the receptors of the disclosure, the intracellular domain comprises both ITIMs NLYAAV (SEQ ID NO: 8) and VTYAEV (SEQ ID NO: 9). In some embodiments, the intracellular domain comprises a sequence at least 95% identical to SEQ ID NO: 12. In some embodiments, the intracellular domain comprises both ITIMs VTYAEV (SEQ ID NO: 9) and VTYAQL (SEQ ID NO: 10). In some embodiments, the intracellular domain comprises a sequence at least 95% identical to SEQ ID NO: 13. In some embodiments, the intracellular domain comprises both ITIMs VTYAQL (SEQ ID NO: 10) and SIYATL (SEQ ID NO: 11). In some embodiments, the intracellular domain comprises a sequence at least 95% identical to SEQ ID NO: 14. In some embodiments, the polypeptide comprises an intracellular domain comprising at least three immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11). In some embodiments, the intracellular domain comprises the ITIMs NLYAAV (SEQ ID NO: 8), VTYAEV (SEQ ID NO: 9), and VTYAQL (SEQ ID NO: 10). In some embodiments, the intracellular domain comprises a sequence at least 95% identical to SEQ ID NO: 15. In some embodiments, the intracellular domain comprises the ITIMs VTYAEV (SEQ ID NO: 9), VTYAQL (SEQ ID NO: 10), and SIYATL (SEQ ID NO: 11). In some embodiments, the intracellular domain comprises a sequence at least 95% identical to SEQ ID NO: 16. In some embodiments, the intracellular domain comprises the ITIMs NLYAAV (SEQ ID NO: 8), VTYAEV (SEQ ID NO: 9), VTYAQL (SEQ ID NO: 10), and SIYATL (SEQ ID NO: 11). In some embodiments, the intracellular domain comprises a sequence at least 95% identical to SEQ ID NO: 17. In some embodiments, the intracellular domain comprises a sequence at least 95% identical to the LILRB1 intracellular domain (SEQ ID NO: 7). In some embodiments, the intracellular domain comprises a sequence of SEQ ID NOS: 12-17.

In some embodiments of the receptors of the disclosure, the polypeptide comprises the LILRB1 transmembrane domain or a functional variant thereof. In some embodiments, the LILRB1 transmembrane domain or a functional variant thereof comprises a sequence at least 95% identical to SEQ ID NO: 5. In some embodiments, the LILRB1 transmembrane domain comprises SEQ ID NO: 5.

In some embodiments of the receptors of the disclosure, the polypeptide comprises the LILRB1 hinge domain or functional fragment or variant thereof. In some embodiments, the LILRB1 hinge domain or functional fragment or variant thereof comprises a sequence at least 95% identical to SEQ ID NO: 4, SEQ ID NO: 18, SEQ ID NO: 19, SEQ ID NO: 80, SEQ ID NO: 81, SEQ ID NO: 82, SEQ ID NO: 83, SEQ ID NO: 84 or SEQ ID NO: 93. In some embodiments, the LILRB1 hinge domain comprises a sequence identical to SEQ ID NO: 4, SEQ ID NO: 18, SEQ ID NO: 19, SEQ ID NO: 80, SEQ ID NO: 81, SEQ ID NO: 82, SEQ ID NO: 83, SEQ ID NO: 84 or SEQ ID NO: 93. In some embodiments, the LILRB1 hinge domain or functional fragment or variant thereof comprises a sequence at least 95% identical to SEQ ID NO: 4, SEQ ID NO: 18, SEQ ID NO: 19, SEQ ID NO: 80, SEQ ID NO:81, SEQ ID NO: 82, SEQ ID NO: 83 or SEQ ID NO: 84. In some embodiments, the LILRB1 hinge domain comprises a sequence identical to SEQ ID NO: 4, SEQ ID NO: 18, SEQ ID NO: 19, SEQ ID NO: 80, SEQ ID NO: 81, SEQ ID NO: 82, SEQ ID NO: 83 or SEQ ID NO: 84.

In some embodiments of the receptors of the disclosure, the polypeptide comprises: (a) an LILRB1 hinge domain or functional fragment or variant thereof, and (b) the LILRB1 transmembrane domain or a functional variant thereof. In some embodiments, the polypeptide comprises a sequence at least 95% identical to SEQ ID NO: 20.

In some embodiments of the receptors of the disclosure, the polypeptide comprises: (a) the LILRB1 transmembrane domain or a functional variant thereof, and (b) an LILRB1 intracellular domain and/or an intracellular domain comprising at least two immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11). In some embodiments, the polypeptide comprises a sequence at least 95% identical to SEQ ID NO: 21. In some embodiments, the polypeptide comprises a sequence of SEQ ID NO. 21.

In some embodiments of the receptors of the disclosure, the polypeptide comprises: (a) an LILRB1 hinge domain or functional fragment or variant thereof, (b) an LILRB1 transmembrane domain or a functional variant thereof; and (c) an LILRB1 intracellular domain and/or an intracellular domain comprising at least two immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In some embodiments of the receptors of the disclosure, the polypeptide comprises a sequence at least 95% identical to SEQ ID NO: 2 or SEQ ID NO: 3. In some embodiments, the polypeptide comprises a sequence at least 99% identical to SEQ ID NO: 20. In some embodiments, the polypeptide comprises a sequence at least 99% identical to SEQ ID NO: 21. In some embodiments, the polypeptide comprises a sequence at least 99% identical to SEQ ID NO: 2 or SEQ ID NO: 3. In some embodiments, the polypeptide comprises a sequence identical to SEQ ID NO: 20. In some embodiments, the polypeptide comprises a sequence identical to SEQ ID NO: 21. In some embodiments, the polypeptide comprises a sequence identical to SEQ ID NO: 2 or SEQ ID NO: 3.

In some embodiments of the receptors of the disclosure, the polypeptide comprises antigen-binding domain. In some embodiments, the antigen-binding domain is an antigen-binding domain other than the LILRB1 extracellular ligand binding protein. In some embodiments, the polypeptide comprises two or more antigen-binding domains. In some embodiments, the antigen-binding domain comprises a single chain variable fragment (scFv). In some embodiments, the receptor comprises a second polypeptide. In some embodiments, the first polypeptide comprises a first chain of an antibody and the second polypeptide comprise a second chain of said antibody. In some embodiments, the receptor comprises a Fab fragment of an antibody. In some embodiments, (a) the first polypeptide comprises an antigen-binding fragment of the heavy chain of the antibody, and (b) the second polypeptide comprises an antigen-binding fragment of the light chain of the antibody. In some embodiments, (a) the first polypeptide comprises an antigen-binding fragment of the light chain of the antibody, and (b) the second polypeptide comprises an antigen-binding fragment of the heavy chain of the antibody. In some embodiments, the first polypeptide comprises a first chain of a T-cell receptor (TCR) and the second polypeptide comprises a second chain of said TCR. In some embodiments, in the receptor comprises an extracellular fragment of a T cell receptor (TCR). In some embodiments, (a) the first polypeptide comprises an antigen-binding fragment of an alpha chain of the TCR, and (b) the second polypeptide comprises an antigen-binding fragment of the beta chain of the TCR. In some embodiments, (a) the first polypeptide comprises an antigen-binding fragment of the beta chain of the TCR, and (b) the second polypeptide comprises an antigen-binding fragment of the alpha chain of the TCR. In some embodiments, the receptor comprises a single-chain TCR. In some embodiments, the scFv comprises the complementarity determined regions (CDRs) of any one of SEQ ID NOS: 22-33. In some embodiments, the scFv comprises a sequence at least 95% identical to any one of SEQ ID NOS: 35-46 or 125. In some embodiments, the scFv comprises a sequence at least 95% identical to any one of SEQ ID NOS: 35, 39, 46 or 125. In some embodiments, the scFv comprises a sequence identical to any one of SEQ ID NOS: 35-46 or 125. In some embodiments, the scFv comprises a sequence identical to any one of SEQ ID NOS: 35, 39, 46 or 125. In some embodiments, the heavy chain of the antibody comprises the heavy chain CDRs of any one of SEQ ID NOS: 25-27 or 31-33, and wherein the light chain of the antibody comprises the light chain CDRs of any one of SEQ ID NOS: 22-24 or 28-30. In some embodiments, the heavy chain of the antibody comprises a sequence at least 95% identical to the heavy chain portion of any one of SEQ ID NOS: 35-46 or 125, and wherein the light chain of the antibody comprises a sequence at least 95% identical to the light chain portion of any one of SEQ ID NOS: 35-46 or 125. In some embodiments, the heavy chain of the antibody comprises a sequence identical to the heavy chain portion of any one of SEQ ID NOS: 35-46 or 125, and wherein the light chain of the antibody comprises a sequence identical to the light chain portion of any one of SEQ ID NOS: 35-46 or 125. In some embodiments, the heavy chain of the antibody comprises a sequence identical to the heavy chain portion of any one of SEQ ID NOS: 35, 39, 46 or 125, and wherein the light chain of the antibody comprises a sequence identical to the light chain portion of any one of SEQ ID NOS: 35, 39, 46 or 125.

In some embodiments of the receptors of the disclosure, the receptor comprises an amino acid sequence at least 95% identical to any one of SEQ ID NOS: 47-71, 77-79, 89-92, 120 or 122. In some embodiments, the receptor comprises an amino acid sequence of SEQ ID NOS: 47-71, 77-79, 89-92, 120 or 122.

In some embodiments of the receptors of the disclosure, the receptor is an inhibitory receptor.

The disclosure provides a polynucleotide comprising a nucleic acid sequence encoding the receptor or polypeptide of the disclosure.

The disclosure provides a vector comprising the polynucleotide of the disclosure. In some embodiments, the vector further comprises a sequence encoding a promoter operably linked to the polynucleotide.

The disclosure provides an immune cell comprising the receptor, polynucleotide, polypeptide or receptor of the disclosure. In some embodiments, the immune cell activation is reduced when the cell is contacted with the antigen or a cell expressing the antigen on its surface. In some embodiments, immune cell activation comprises expression of a gene operatively linked to an NFAT promoter. In some embodiments, the immune cell is a T cell. In some embodiments, further comprises an activator receptor. In some embodiments, the activator receptor is a chimeric antigen receptor or a T cell receptor.

The disclosure provides methods making an immune cell, comprising introducing the polynucleotide or vector of the disclosure into the immune cell. In some embodiments, the immune cell expresses the receptor. In some embodiments, the cell is an immune cell. In some embodiments, the immune cell is a T cell. In some embodiments, immune cell activation is reduced when the cell is contacted with an antigen specific to the chimeric antigen receptor, or a cell expressing the antigen on its surface. In some embodiments, immune cell activation comprises expression of a gene operatively linked to an NFAT promoter.

The disclosure provides methods of treating a subject with a disease or a disorder, comprising administering to the subject a plurality of the immune cells of the disclosure. In some embodiments, the disease or disorder is cancer.

The disclosure provides a kit, comprising the receptor, polypeptide, polynucleotide, vector or immune cell of the disclosure.

The disclosure provides an immune cell comprising a chimeric antigen receptor comprising a polypeptide, wherein the polypeptide sequence shares at least 95% identity or at least 100% identity to SEQ ID NO: 21.

In some embodiments of the immune cells of the disclosure, the polypeptide sequence shares at least 95% identity or at least 100% identity to SEQ ID NO: 3. In some embodiments, the polypeptide sequence shares at least 95% identity or at least 100% identity to SEQ ID NO: 2. In some embodiments, the chimeric antigen receptor comprises an antigen-binding domain comprising CDR-L1, CDR-L2, CDR-L3, CDR-H1, CDR-H2, CDR-H3 sequences according to SEQ ID NO: 22-27, respectively. In some embodiments, the chimeric antigen receptor comprises an antigen-binding domain comprising CDR-L1, CDR-L2, CDR-L3, CDR-H1, CDR-H2, CDR-H3 sequences according to SEQ ID NO: 28-33, respectively. In some embodiments, the polypeptide sequence shares at least 95% identity or at least 100% identity to SEQ ID NO: 122. In some embodiments, the polypeptide sequence shares at least 95% identity or at least 100/6 identity with any one of SEQ ID NOS: 35, 39, 46 or 125 in combination with SEQ ID NO: 2.

In some embodiments, the immune cell is a T cell. In some embodiments, the T cell comprises a chimeric antigen receptor or T cell receptor that specifically binds to a target expressed on tumor cells. In some embodiments, the T cell comprises a chimeric antigen receptor or T cell receptor that specifically binds to a target selected from etiolate receptor, αvββ integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, EGFR family including ErbB2 (HER2), EGFRvIII, EPCAM, EphA2, EpCAM, FAP, FBP, fetal acetylcholine receptor, Fzd7, GD2, GD3, Glypican-3 (GPC3), h5T4, IL-11R, IL13R-a2, KDR, κ light chain, λ light chain, LeY, LI CAM, MAGE-A1, mesothelin, MHC presented peptides, MUC1, MUC16, NCAM, NKG2D ligands, Notch1, Notch2/3, NY-ESO-1, PRAME, PSCA, PSMA, Survivin, TAG-72, TEMs, TERT, VEGFR2, and ROR1.

The disclosure provide methods of treating and/or preventing cancer in a subject in need thereof, comprising administering to the subject the immune cells of the disclosure. In some embodiments, the method comprises treating and/or preventing cancer in a subject in need thereof, comprising administering to the subject the immune cells of the disclosure.

Illustrative CARs provided herein include, without limitation, antibody-based CARs such as single-chain variable fragment (scFv) CARs, Fab CARs, or others; and T cell receptor (TCR)-based CARs.

In other aspects, the disclosure provides polynucleotides encoding such receptors; vectors for delivery of such polynucleotides; and immune cells with such polynucleotide and receptors.

In further aspects, the disclosure provides methods of introducing polynucleotide or vectors encoding such receptors into a cell. Advantageously, immune cell activation is reduced when the cell is contacted with the antigen or a cell expressing the antigen on its surface.

Yet further aspects and embodiments of the invention are provided in the detailed description that follows.

BRIEF DESCRIPTION OF DRAWINGS

FIGS. 2A-2B show illustrative diagrams of domain arrangements in embodiments having a ligand binding domain (LBD), hinge, transmembrane (TM), and intracellular signaling domain (ICD). When the ligand binding domain comprises two peptides, for example a heterodimeric LDB from a T Cell Receptor, each peptide may be fused with a hinge, TM and intracellular domain (FIG. 2A). Alternatively, only one peptide of the ligand binding domain may be fused to the hinge, TM and intracellular domain (FIG. 2B).

FIG. 22A is a pair of plots showing that Jurkat cells transfected with MSLN LBD1-CAR or MSLN LBD1-CAR & A2-LIR-1 co-cultured with K562 cells expressing either MSLN or MSLN & HLA-A*02 shows blocking of activation by a high-density antigen with A2-LIR-1 blocker only in the presence of HLA-A*02.

FIG. 22B is a pair of plots showing that killing of endogenous MSLN+ HeLa cells by MLSN LBD1-CAR T cells is blocked in the presence of HLA-A*02 with the A2-LIR-1 blocker.

FIG. 24A is a pair of plots showing that A2-LIR-1 blocks Jurkat activation in A2+ Raji cells but not WT Raji cells. Histograms show Raji WT "tumor" cells and Raji A2+"normal" cells have identical CD19 surface expression while HLA-A*02 is expressed only in Raji A2 "normal" cells.

FIG. 24B is a plot showing that A2-LIR-1 blocks Jurkat activation in A2+ Raji cells but not WT Raji cells. Jurkat cells transfected with either CD19 or CD19+A2-LIR-1 were co-cultured with either WT (A2-) Raji cells or A2+ Raji cells at various cell ratios. RLU=relative light units, error bars indicate f SD (n=2).

FIG. 27A is a plot showing primary T cells transduced with CD19 CAR activator and HLA-A*02 blocker demonstrates ~20-fold expansion with CD3/28 stimulation over 10 days.

FIG. 27B is a diagram showing an experiment to show that CAR-T cells expressing a LIR-1 blocker receptor selectively kill tumors in a xenograft model. HLA-A*02 NSG mice were administered either "tumor cells" (A2-negative Raji cells) or "normal cells" (A2-positive Raji cells) subcutaneously and primary T cells (human, HLA-A*02-negative donor 4) were injected into the tail vein when Raji xenografts averaged ~70 mm³.

FIGS. 27C-27E are each a pair of plots that show readouts by caliper measurement (FIG. 27C), human T cell counts in peripheral blood by flow cytometry (FIG. 27D), and survival (FIG. 27E). Error bars in C-D indicate f SEM (n=7). $*p<0.05$, $p<0.01$, $*p<0.001$, $****p<0.0001$, determined using a two-way ANOVA followed by Tukey's multiple-comparisons test.

DETAILED DESCRIPTION

Figure 1:
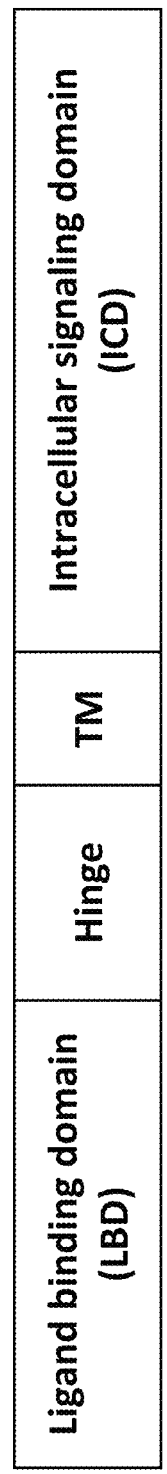
FIG. 1 shows an illustrative diagram of domain arrangement in an embodiment having a ligand binding domain (LBD), hinge, transmembrane (TM), and intracellular signaling domain (ICD).
Figure 3:
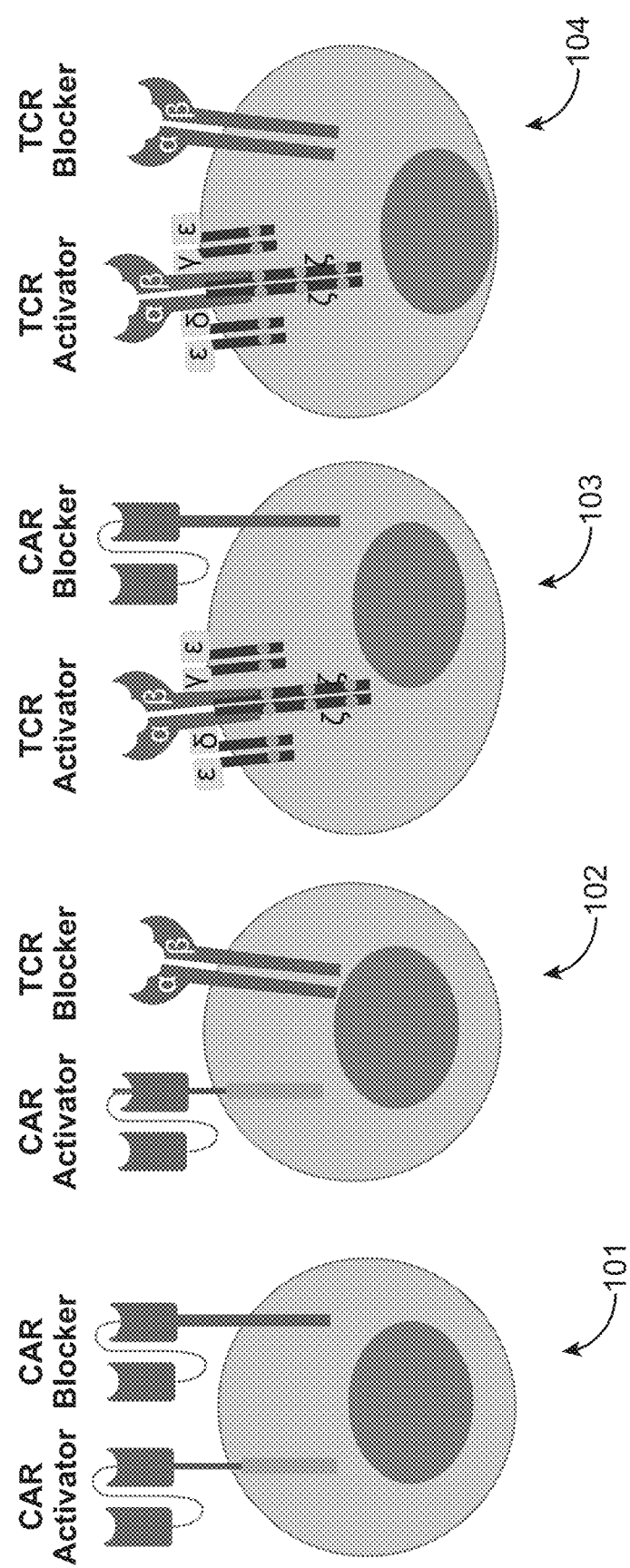
FIG. 3 shows four illustrative embodiments of immune cells having an activator scFv-based chimeric antigen receptor (CAR) [101 and 102] or activator T cell receptor [103 and 104] and an inhibitory scFv based CAR [101 and 103] or inhibitory TCR-based CAR [102 and 104].

The present disclosure describes receptors having one or more domains from Leukocyte immunoglobulin-like receptor subfamily B member 1 (LILRB1, sometimes referred to as LIR1 or LIR-1). Numerous receptors, engineered cells, and uses thereof are contemplated herein. The inventors have found that chimeric receptors comprising an antigen-binding domain and one or more LILRB1 domains, including the LILRB1 intracellular domain, can inhibit immune cell signaling even in the presence of activatory chimeric antigen receptors (CARs) or T cell receptors (TCRs).

The term "chimeric antigen receptors" or "CARs" as used herein, may refer to artificial T-cell receptors, chimeric T-cell receptors, or chimeric immunoreceptors, for example, and encompass engineered receptors that graft an artificial specificity onto a particular immune effector cell, such as a helper T cell (CD4+), cytotoxic T cell (CD8+) or NK cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen. In some embodiments, CARs comprise an intracellular signaling domain, a transmembrane domain, and an extracellular domain comprising an antigen-binding region. In some embodiments, CARs comprise fusions of single-chain variable fragments (scFvs) or scFabs derived from monoclonal antibodies, fused to a transmembrane domain and intracellular signaling domain(s). The fusion may also comprise a hinge. Either heavy-light (H-L) and light-heavy (L-H) scFvs may be used. The specificity of CAR designs may be derived from ligands of receptors (e.g., peptides). Depending on the type of intracellular domain, a CAR can be an activatory receptor or an inhibitory receptor. In some embodiments, for example when the CAR is an activatory receptor, the CAR comprises domains for additional co-stimulatory signaling, such as CD3, FcR, CD27, CD28, CD137, DAP10, and/or OX40. In some embodiments, molecules can be co-expressed with the CAR, including co-stimulatory molecules, reporter genes for imaging (e.g., for positron emission tomography), gene products that conditionally ablate the T cells upon addition of a prodrug, homing receptors, cytokines, and cytokine receptors. As used herein, characteristics attributed to a chimeric antigen receptor may be understood to refer to the receptor itself or to a host cell comprising the receptor.

As used herein, a "TCR", sometimes also called a "TCR complex" or "TCR/CD3 complex" refers to a protein complex comprising a TCR alpha chain, a TCR beta chain, and one or more of the invariant CD3 chains (zeta, gamma, delta and epsilon), sometimes referred to as subunits. The TCR alpha and beta chains can be disulfide-linked to function as a heterodimer to bind to peptide-MHC complexes. Once the TCR alpha/beta heterodimer engages peptide-MHC, conformational changes in the TCR complex in the associated invariant CD3 subunits are induced, which leads to their phosphorylation and association with downstream proteins, thereby transducing a primary stimulatory signal. In an exemplary TCR complex, the TCR alpha and TCR beta polypeptides form a heterodimer, CD3 epsilon and CD3 delta form a heterodimer, CD3 epsilon and CD3 gamma for a heterodimer, and two CD3 zeta form a homodimer.

The term "stimulation" refers to a primary response induced by binding of a stimulatory domain or stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, and/or reorganization of cytoskeletal structures, and the like.

The term "stimulatory molecule" or "stimulatory domain" refers to a molecule or portion thereof that, when natively expressed by a T-cell, provides the primary cytoplasmic signaling sequence(s) that regulate activation of the TCR complex in a stimulatory way for at least some aspect of the T-cell signaling pathway. TCR alpha and/or TCR beta chains of wild type TCR complexes do not contain stimulatory domains and require association with CD3 subunits such as CD3 zeta to initiate signaling. In one aspect, the primary stimulatory signal is initiated by, for instance, binding of a TCR/CD3 complex with an a major histocompatibility complex (MHC) bound to peptide, and which leads to mediation of a T-cell response, including, but not limited to, proliferation, activation, differentiation, and the like. One or more stimulatory domains, as described herein, can be fused to the intracellular portion of any one or more subunits of the TCR complex, including TCR alpha, TCR beta, CD3 delta, CD3 gamma and CD3 epsilon.

As used herein, a "domain capable of providing a stimulatory signal" refers to any domain that, either directly or indirectly, can provide a stimulatory signal that enhances or increases the effectiveness of signaling mediated by the TCR complex to enhance at least some aspect of T-cell signaling. The domain capable of providing a stimulatory signal can provide this signal directly, for example with the domain capable of providing the stimulatory signal is a primary stimulatory domain or co-stimulatory domain. Alternatively, or in addition, the domain capable of providing the stimulatory signal can act indirectly. For example, the domain can be a scaffold that recruits stimulatory proteins to the TCR, or provide an enzymatic activity, such as kinase activity, that acts through downstream targets to provide a stimulatory signal.

As used herein, a "domain capable of providing an inhibitory signal" refers to any domain that, either directly or indirectly, can provide an inhibitory signal that inhibits or decreases the effectiveness signaling mediated by the TCR complex. The domain capable of providing an inhibitory signal can reduce, or block, totally or partially, at least some aspect of T-cell signaling or function. The domain capable of providing an inhibitory signal can provide this signal directly, for example with the domain capable of providing the inhibitory signal provides a primary inhibitory signal. Alternatively, or in addition, the domain capable of providing the stimulatory signal can act indirectly. For example, the domain can recruit additional inhibitory proteins to the TCR, or can provide an enzymatic activity that acts through downstream targets to provide an inhibitory signal.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

In general, "sequence identity" or "sequence homology" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%.

As used herein, a "subsequence" refers to a length of contiguous amino acids or nucleotides that form a part of a sequence described herein. A subsequence may be identical to a part of a full length sequence when aligned to the full length sequence, or less than 100% identical to the part of the full length sequence to which it aligns (e.g., 90% identical to 50% of the full sequence, or the like).

The term "exogenous" is used herein to refer to any molecule, including nucleic acids, protein or peptides, small molecular compounds, and the like that originate from outside the organism. In contrast, the term "endogenous" refers to any molecule that originates from inside the organism (i.e., naturally produced by the organism).

A polynucleotide is "operably linked" to another polynucleotide when it is placed into a functional relationship with the other polynucleotide. For example, a promoter or enhancer is operably linked to a coding sequence if it affects the transcription of the sequence. A peptide is "operably linked" to another peptide when the polynucleotides encoding them are operably linked, preferably they are in the same open reading frame.

A "promoter" is a sequence of DNA needed to turn a gene on or off. Promoters are located immediately upstream and/or overlapping the transcription start site, and are usually between about one hundred to several hundred base pairs in length.

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%.

All publications, patents, and patent applications mentioned in this specification are herein incorporated by reference to the same extent as if each individual publication, patent, or patent application was specifically and individually indicated to be incorporated by reference.

Leukocyte Immunoglobulin-Like Receptor Subfamily B Member 1 (LILRB1)

The present disclosure describes receptors having one or more domains from Leukocyte immunoglobulin-like receptor subfamily B member 1 (LILRB1, or LIR1). Numerous receptors, engineered cells, and uses thereof are contemplated herein.

Leukocyte immunoglobulin-like receptor subfamily B member 1 (LILRB1), also known as Leukocyte immunoglobulin-like receptor B1, as well as ILT2, LIR1, MIR7, PIRB, CD85J, ILT-2 LIR-1, MIR-7 and PIR-B, is a member of the leukocyte immunoglobulin-like receptor (LIR) family. The LILRB1 protein belongs to the subfamily B class of LIR receptors. These receptors contain two to four extracellular immunoglobulin domains, a transmembrane domain, and two to four cytoplasmic immunoreceptor tyrosine-based inhibitory motifs (ITIMs). The LILRB1 receptor is expressed on immune cells, where it binds to MHC class I molecules on antigen-presenting cells and transduces a negative signal that inhibits stimulation of an immune response. LILRB1 is thought to regulate inflammatory responses, as well as cytotoxicity, and to play a role in limiting auto-reactivity. Multiple transcript variants encoding different isoforms of LILRB1 exist, all of which are contemplated as within the scope of the instant disclosure.

In some embodiments of the receptors having one or domains of LILRB1, the one or more domains of LILRB1 comprise an amino acid sequence that is at least 80%/o, at least 90%, at least 95%, at least 96%, at least 97%, at least 98%, at least 99% or is identical to a sequence or subsequence of SEQ ID NO: 1. In some embodiments, the one or more domains of LILRB1 comprise an amino acid sequence that is identical to a sequence or subsequence of SEQ ID NO: 1. In some embodiments, the one or more domains of LILRB1 consist of an amino acid sequence that is at least 80%, at least 90%, at least 95%, at least 96%, at least 97%, at least 98%, at least 99% or is identical to a sequence or subsequence of SEQ ID NO: 1. In some embodiments, the one or more domains of LILRB1 consist of an amino acid sequence that is identical to a sequence or subsequence of SEQ ID NO: 1.

In some embodiments of the receptors having one or domains of LILRB1, the one or more domains of LILRB1 are encoded by a polynucleotide sequence that is at least 80%, at least 90%, at least 95%, at least 96%, at least 97%, at least 98%, at least 99% or is identical to a sequence or subsequence of SEQ ID NO: 34.

In some embodiments of the receptors having one or domains of LILRB1, the one or more domains of LILRB1 are encoded by a polynucleotide sequence that is identical to a sequence or subsequence of SEQ ID NO: 34.

Receptors

In various embodiments, a chimeric antigen receptor is provided, comprising a polypeptide, wherein the polypeptide comprises one or more of: an LILRB1 hinge domain or functional fragment or variant thereof; an LILRB1 transmembrane domain or a functional variant thereof; and an LILRB1 intracellular domain or an intracellular domain comprising at least one, or at least two immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

Intracellular Domain

The disclosure provides chimeric antigen receptors, the chimeric antigen receptors comprising a polypeptide. In some embodiments, the polypeptide comprises an intracellular domain. In some embodiments, the intracellular domain is an LILRB1 intracellular domain or a functional variant thereof.

As used herein, "intracellular domain" refers to the cytoplasmic or intracellular domain of a protein, such as a receptor, that interacts with the interior of the cell, and carries out a cytosolic function. As used herein, "cytosolic function" refers to a function of a protein or protein complex that is carried out in the cytosol of a cell. For example, intracellular signal transduction cascades are cytosolic functions.

As used herein an "immunoreceptor tyrosine-based inhibitory motif" or "ITIM" refers to a conserved sequence of amino acids with a consensus sequence of S/I/V/LxYxxI/V/L (SEQ ID NO. 124), or the like, that is found in the cytoplasmic tails of many inhibitory receptors of the immune system. After ITIM-possessing inhibitory receptors interact with their ligand, the ITIM motif is phosphorylated, allowing the inhibitory receptor to recruit other enzymes, such as the phosphotyrosine phosphatases SHP-1 and SHP-2, or the inositol-phosphatase called SHIP.

In some embodiments, the polypeptide comprises an intracellular domain comprising at least one immunoreceptor tyrosine-based inhibitory motif (ITIM), at least two ITIMs, at least 3 ITIMs, at least 4 ITIMs, at least 5 ITIMs or at least 6 ITIMs. In some embodiments, the intracellular domain has 1, 2, 3, 4, 5, or 6 ITIMs.

In some embodiments, the polypeptide comprises an intracellular domain comprising at least one ITIM selected from the group of ITIMs consisting of NLYAAV (SEQ ID NO: 8), VTYAEV (SEQ ID NO: 9), VTYAQL (SEQ ID NO: 10), and SIYATL (SEQ ID NO: 11).

In further particular embodiments, the polypeptide comprises an intracellular domain comprising at least two immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In some embodiments, the intracellular domain comprises both ITIMs NLYAAV (SEQ ID NO: 8) and VTYAEV (SEQ ID NO: 9). In some embodiments, the intracellular domain comprises a sequence at least 95% identical to SEQ ID NO: 12. In some embodiments, the intracellular domain comprises or consists essentially of a sequence identical to SEQ ID NO: 12.

In some embodiments, the intracellular domain comprises both ITIMs VTYAEV (SEQ ID NO: 9) and VTYAQL (SEQ ID NO: 10). In some embodiments, the intracellular domain comprises a sequence at least 95% identical to SEQ ID NO: 13. In some embodiments, the intracellular domain comprises or consists essentially of a sequence identical to SEQ ID NO: 13.

In some embodiments, the intracellular domain comprises both ITIMs VTYAQL (SEQ ID NO: 10) and SIYATL (SEQ ID NO: 11). In some embodiments, the intracellular domain comprises a sequence at least 95% identical to SEQ ID NO: 14. In some embodiments, the intracellular domain comprises or consists essentially of a sequence identical to SEQ ID NO: 14.

In some embodiments, the intracellular domain comprises the ITIMs NLYAAV (SEQ ID NO: 8), VTYAEV (SEQ ID NO: 9), and VTYAQL (SEQ ID NO: 10). In some embodiments, the intracellular domain comprises a sequence at least 95% identical to SEQ ID NO: 15. In some embodiments, the intracellular domain comprises or consists essentially of a sequence identical to SEQ ID NO: 15.

In some embodiments, the intracellular domain comprises the ITIMs VTYAEV (SEQ ID NO: 9), VTYAQL (SEQ ID NO: 10), and SIYATL (SEQ ID NO: 11). In some embodiments, the intracellular domain comprises a sequence at least 95% identical to SEQ ID NO: 16. In some embodiments, the intracellular domain comprises or consists essentially of a sequence identical to SEQ ID NO: 16.

In some embodiments, the intracellular domain comprises the ITIMs NLYAAV (SEQ ID NO: 8), VTYAEV (SEQ ID NO: 9), VTYAQL (SEQ ID NO: 10), and SIYATL (SEQ ID NO: 11). In embodiments, the intracellular domain comprises a sequence at least 95% identical to SEQ ID NO: 17. In some embodiments, the intracellular domain comprises or consists essentially of a sequence identical to SEQ ID NO: 17.

In some embodiments, the intracellular domain comprises a sequence at least 95% identical to the LILRB1 intracellular domain (SEQ ID NO: 7). In some embodiments, the intracellular domain comprises or consists essentially of a sequence identical to the LILRB1 intracellular domain (SEQ ID NO: 7).

LILRB1 intracellular domains or functional variants thereof of the disclosure can have at least 1, at least 2, at least 4, at least 4, at least 5, at least 6, at least 7, or at least 8 ITIMs. In some embodiments, the LILRB1 intracellular domain or functional variant thereof has 2, 3, 4, 5, or 6 ITIMs.

In particular embodiments, the polypeptide comprises an intracellular domain comprising two, three, four, five, or six immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In particular embodiments, the polypeptide comprises an intracellular domain comprising at least three immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In particular embodiments, the polypeptide comprises an intracellular domain comprising three immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In particular embodiments, the polypeptide comprises an intracellular domain comprising four immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In particular embodiments, the polypeptide comprises an intracellular domain comprising five immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In particular embodiments, the polypeptide comprises an intracellular domain comprising six immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In particular embodiments, the polypeptide comprises an intracellular domain comprising at least seven immunoreceptor tyrosine-based inhibitory motifs (ITIMs), wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In some embodiments, the intracellular domain comprises a TCR alpha intracellular domain. In some embodiments, the intracellular domain comprises a TCR alpha intracellular domain and an LILRB1 intracellular domain, as described herein. In some embodiments, a TCR alpha intracellular domain comprises Ser-Ser. In some embodiments, a TCR alpha intracellular domain is encoded by a sequence of TCCAGC.

In some embodiments, the intracellular domain comprises a TCR beta intracellular domain. In some embodiments, the intracellular domain comprises a TCR beta intracellular domain and an LILRB1 intracellular domain, as described herein. In some embodiments, the TCR beta intracellular domain comprises an amino acid sequence having at least 80% identity, at least 90% identity, or is identical to a sequence of: MAMVKRKDSR (SEQ ID NO: 94). In some embodiments, the TCR beta intracellular domain comprises, or consists essentially of MAMVKRKDSR (SEQ ID NO: 94). In some embodiments, the TCR beta intracellular domain is encoded by a sequence of ATGGCCATGGT-CAAGAGAAAGGATTCCAGA (SEQ ID NO: 95).

Transmembrane Domain

The disclosure provides chimeric antigen receptors the receptors comprising a polypeptide. In some embodiments, the polypeptide comprises a transmembrane domain. In some embodiments, the transmembrane domain is a LILRB1 transmembrane domain or a functional variant thereof.

A "transmembrane domain", as used herein, refers to a domain of a protein that spans membrane of the cell. Transmembrane domains typically consist predominantly of non-polar amino acids, and may traverse the lipid bilayer once or several times. Transmembrane domains usually comprise alpha helices, a configuration which maximizes internal hydrogen bonding.

Transmembrane domains isolated or derived from any source are envisaged as within the scope of the fusion proteins of the disclosure.

In particular embodiments, the polypeptide comprises an LILRB1 transmembrane domain or a functional variant thereof.

In some embodiments, the LILRB1 transmembrane domain or a functional variant thereof comprises a sequence at least 95% identical, at least 96% identical, at least 97% identical, at least 98% identical or at least 99% to SEQ ID NO: 5. In some embodiments, the LILRB1 transmembrane domain or a functional variant thereof comprises a sequence at least 95% identical to SEQ ID NO: 5. In some embodiments, the LILRB1 transmembrane domain comprises a sequence identical to SEQ ID NO: 5. In embodiments, the LILRB1 transmembrane domain consists essentially of a sequence identical to SEQ ID NO: 5.

In some embodiments of the chimeric antigen receptors of the disclosure, the transmembrane domain is not a LILRB1 transmembrane domain. In some embodiments, the transmembrane domain is one that is associated with one of the other domains of the fusion protein, or isolated or derived from the same protein as one of the other domains of the fusion protein.

The transmembrane domain may be derived either from a natural or from a recombinant source. Where the source is natural, the domain may be derived from any membrane-bound or transmembrane protein. Exemplary transmembrane domains may include at least the transmembrane region(s) of e.g., the alpha, beta or zeta chain of the TCR, CD3 delta, CD3 epsilon or CD3 gamma, CD28, CD3 epsilon, CD45, CD4, CD5, CD8, CD9, CD16, CD22, CD33, CD37, CD64, CD80, CD86, CD134, CD137, CD154.

In some embodiments, the transmembrane comprises a TCR alpha transmembrane domain. In some embodiments, the TCR alpha transmembrane domain comprises an amino acid sequence having at least 85% identity, at least 90% identity, at least 95% identity, at least 96% identity, at least 97% identity, at least 98% identity, at least 99% identity or is identical to a sequence of: VIGFRILLLKVAGFNLL-MTLRLW (SEQ ID NO: 96). In some embodiments, the TCR alpha transmembrane domain comprises, or consists essentially of, VIGFRILLLKVAGFNLLMTLRLW (SEQ ID NO: 96). In some embodiments, the TCR alpha transmembrane domain is encoded by a sequence of:

```
                              (SEQ ID NO: 97)
GTGATTGGGTTCCGAATCCTCCTCCTGAAAGTGGCCGGGT

TTAATCTGCTCATGACGCTGCGGCTGTGG.
```

In some embodiments, the transmembrane comprises a TCR beta transmembrane domain. In some embodiments, the TCR beta transmembrane domain comprises an amino acid sequence having at least 85% identity, at least 90% identity, at least 95% identity, at least 96% identity, at least 97% identity, at least 98% identity, at least 99% identity or is identical to a sequence of: TILYEILLGKAT-LYAVLVSALVL (SEQ ID NO: 98). In some embodiments, the TCR beta transmembrane domain comprises, or consists essentially of TILYEILLGKATLYAVLVSALVL (SEQ ID NO: 98). In some embodiments, the TCR beta transmembrane domain is encoded by a sequence of

```
                              (SEQ ID NO: 99)
ACCATCCTCTATGAGATCTTGCTAGGGAAGGCCACCTTG

TATGCCGTGCTGGTCAGTGCCCTCGTGCTG.
```

In some embodiments, the TCR alpha and/or TCR beta transmembrane domain comprises one or more mutations that attenuate or abolish interaction of the TCR with the TCR CD3 subunit. In some embodiments, the TCR alpha transmembrane domain comprises a R253L mutation. In some embodiments, the TCR beta transmembrane domain comprises a K288L mutation.

In some embodiments the transmembrane domain comprise a CD28 transmembrane domain. In some embodiments, the CD28 transmembrane domain comprises an amino acid sequence having at least 80% identity, at least 90% identity, at least 95% identity, at least 99% identity or is identical to a sequence of FWVLVVVGGVLACYSLL-VTVAFIIFWV (SEQ ID NO: 100). In some embodiments, the CD28 transmembrane domain comprises or consists essentially of FWVLVVVGGVLACYSLLVTVAFIIFWV (SEQ ID NO: 100). In some embodiments, the CD28 transmembrane domain is encoded by a nucleotide sequence having at least 80% identity, at least 90% identity, at least 95% identity, at least 99% identity or is identical to a sequence of

```
                              (SEQ ID NO: 101)
TTCTGGGTGCTGGTCGTTGTGGGCGGCGTGCTGGCCTG

CTACAGCCTGCTGGTCACAGTGGCCTTCATCATCTTTT

GGGTG.
```

In some embodiments, the transmembrane domain can be attached to the extracellular region chimeric antigen receptor, e.g., the antigen-binding domain or ligand binding domain, via a hinge, e.g., a hinge from a human protein. For example, in some embodiments, the hinge can be a human immunoglobulin (Ig) hinge, e.g., an IgG4 hinge, a CD8a hinge or an LILRB1 hinge.

Hinge Domain

The disclosure provides chimeric antigen receptors, the receptors comprising a polypeptide. In some embodiments, the polypeptide comprises a hinge domain. In some embodiments, the hinge domain is a LILRB1 hinge domain or a functional variant thereof.

The LILRB1 protein has four immunoglobulin (Ig) like domains termed D1, D2, D3 and D4. In some embodiments, the LILRB1 hinge domain comprises an LILRB1 D3D4 domain or a functional variant thereof. In some embodiments, the LILRB1 D3D4 domain comprises a sequence at least 95%, at least 96%, at least 97%, at least 98%, at least 99% or identical to SEQ ID NO: 18. In some embodiments, the LILRB1 D3D4 domain comprises or consists essentially of SEQ ID NO: 18.

In some embodiments, the polypeptide comprises the LILRB1 hinge domain or functional fragment or variant thereof. In embodiments, the LILRB1 hinge domain or functional fragment or variant thereof comprises a sequence at least 95%, at least 96%, at least 97%, at least 98%, at least 99% identical or identical to SEQ ID NO: 4, SEQ ID NO: 18, or SEQ ID NO: 19. In embodiments, the LILRB1 hinge domain or functional fragment or variant thereof comprises a sequence at least 95% identical to SEQ ID NO: 4, SEQ ID NO: 18, or SEQ ID NO: 19.

In some embodiments, the LILRB1 hinge domain comprises a sequence identical to SEQ ID NO: 4, SEQ ID NO: 18, or SEQ ID NO: 19.

In some embodiments, the LILRB1 hinge domain consists essentially of a sequence identical to SEQ ID NO: 4, SEQ ID NO: 18, or SEQ ID NO: 19.

In some embodiments the chimeric antigen receptors of the disclosure, the polypeptide comprises a hinge that is not isolated or derived from LILRB1.

In some embodiments, the hinge is isolated or derived from CD8a or CD28. In some embodiments, the CD8a hinge comprises an amino acid sequence having at least 80% identity, at least 90% identity, at least 95% identity, at least 99% identity or is identical to a sequence of TTTPAPRPPT-PAPTIASQPLSLRPEACRPAAGGAVHTRGLDFACD (SEQ ID NO: 102). In some embodiments, the CD8a hinge comprises TTTPAPRPPTPAPTIASQPLSLRPEACR-PAAGGAVHTRGLDFACD (SEQ ID NO: 102). In some embodiments, the CD8a hinge consists essentially of TTT-PAPRPPTPAPTIASQPLSLRPEACRPAAGGAVHTR-GLDFACD (SEQ ID NO: 102). In some embodiments, the CD8a hinge is encoded by a nucleotide sequence having at least 80% identity, at least 90% identity, at least 95% identity, at least 99% identity or is identical to a sequence

```
                                      (SEQ ID NO: 103)
accacgacgccagcgccgcgaccaccaacaccggcgcccac catcgcgtcgcagcccctgtccctgcgcccagaggcgtgcc ggccagcggcgggggcgcagtgcacacgagggggctggac ttcgcctgtgat.
```

In some embodiments, the CD28 hinge comprises an amino acid sequence having at least 80% identity, at least 90% identity, at least 95% identity, at least 99% identity or is identical to a sequence of CTIEVMYPPPYLD-NEKSNGTIIHVKGKHLCPSPLFPGPSKP (SEQ ID NO: 104). In some embodiments, the CD28 hinge comprises or consists essentially of CTIEVMYPPPYLD-NEKSNGTIIHVKGKHLCPSPLFPGPSKP (SEQ ID NO: 104). In some embodiments, the CD28 hinge is encoded by a nucleotide sequence having at least 80% identity, at least 90% identity, at least 95% identity, at least 99% identity or is identical to a sequence of

```
                                      (SEQ ID NO: 105)
tgtaccattgaagttatgtatcctcctccttacctagacaa tgagaagagcaatggaaccattatccatgtgaaagggaaac acctttgtccaagtcccctatttccggaccttctaagccc.
```

Combinations of LILRB1 Domains

In some embodiments, the chimeric antigen receptors of the disclosure comprise a polypeptide comprising more than one LILRB1 domain or functional equivalent thereof. For example, in some embodiments, the polypeptide comprises an LILRB1 transmembrane domain and intracellular domain, or an LILRB1 hinge domain, transmembrane domain and intracellular domain.

In particular embodiments, the polypeptide comprises an LILRB1 hinge domain or functional fragment or variant thereof, and the LILRB1 transmembrane domain or a functional variant thereof. In some embodiments, the polypeptide comprises a sequence at least 95% identical, at least 96% identical, at least 97% identical, at least 98% identical, at least 99% identical or identical to SEQ ID NO: 20. In some embodiments, the polypeptide comprises a sequence at least 95% identical to SEQ ID NO: 20. In some embodiments, the polypeptide comprises a sequence identical to SEQ ID NO: 20.

In further embodiments, the polypeptide comprises: the LILRB1 transmembrane domain or a functional variant thereof, and an LILRB1 intracellular domain and/or an intracellular domain comprising at least one immunoreceptor tyrosine-based inhibitory motif (ITIM), wherein the ITIM is selected from NLYAAV (SEQ ID NO: 8), VTYAEV (SEQ ID NO: 9), VTYAQL (SEQ ID NO: 10), and SIYATL (SEQ ID NO: 11). In some embodiments, the polypeptide comprises the LILRB1 transmembrane domain or a functional variant thereof, and an LILRB1 intracellular domain and/or an intracellular domain comprising at least two ITIM, wherein each ITIM is independently selected from NLYAAV (SEQ ID NO: 8), VTYAEV (SEQ ID NO: 9), VTYAQL (SEQ ID NO: 10), and SIYATL (SEQ ID NO: 11).

In some embodiments, the polypeptide comprises a LILRB1 transmembrane domain and intracellular domain. In some embodiments, the polypeptide comprises a sequence at least 95% identical, at least 96% identical, at least 97% identical, at least 98% identical, at least 99% identical or identical to SEQ ID NO: 21. In some embodiments, the polypeptide comprises a sequence at least 95% identical to SEQ ID NO: 21. In some embodiments, the polypeptide comprises a sequence identical to SEQ ID NO: 21.

In preferred embodiments, the polypeptide comprises: an LILRB1 hinge domain or functional fragment or variant thereof; an LILRB1 transmembrane domain or a functional variant thereof; and an LILRB1 intracellular domain and/or an intracellular domain comprising at least two immunoreceptor tyrosine-based inhibitory motifs (ITIMs), wherein each ITIM is independently selected from LYAAV (SEQ ID NO: 8), VTYAE (SEQ ID NO:9), VTYAQL (SEQ ID NO: 10), and SIYATL (SEQ ID NO: 11).

In some embodiments, the polypeptide comprises a sequence at least 95% identical to SEQ ID NO: 2 or SEQ ID NO: 3, or at least 99% identical to SEQ ID NO: 2 or SEQ ID NO: 3, or identical to SEQ ID NO: 2 or SEQ ID NO: 3.

In some embodiments, the polypeptide comprises a sequence at least 99% identical to SEQ ID NO. 20, or at least 99% identical to SEQ ID NO: 20, or identical to SEQ ID NO: 20.

In some embodiments, the polypeptide comprises a sequence at least 99% identical to SEQ ID NO: 21, or at least 99% identical to SEQ ID NO: 21, or identical to SEQ ID NO: 21.

Extracellular Domains

The disclosure provides chimeric antigen receptors comprising a polypeptide. In some embodiments, the polypeptide comprises a ligand binding domain, such as an antigen-binding domain. Suitable antigen-binding domains include, but are not limited to antigen-binding domains from antibodies, antibody fragments, scFv, antigen-binding domains derived from T cell receptors, and the like. All forms of antigen-binding domains known in the art are envisaged as within the scope of the disclosure.

An "extracellular domain", as used herein, refers to the extracellular portion of a protein. For example, the TCR alpha and beta chains each comprise an extracellular domain, which comprise a constant and a variable region involved in peptide-MHC recognition. The "extracellular domain" can also comprise a fusion domain, for example of fusions between additional domains capable of binding to and targeting a specific antigen and the endogenous extracellular domain of the TCR subunit.

The term "antibody," as used herein, refers to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources.

The terms "antibody fragment" or "antibody binding domain" refer to at least one portion of an antibody, or recombinant variants thereof, that contains the antigen-binding domain, i.e., an antigenic determining variable region of an intact antibody, that is sufficient to confer recognition and specific binding of the antibody fragment to a target, such as an antigen and its defined epitope. Examples of antibody fragments include, but are not limited to, Fab, Fab', F(ab')2, and Fv fragments, single-chain (sc)Fv ("scFv") antibody fragments, linear antibodies, single domain antibodies (abbreviated "sdAb") (either VL or VH), camelid VHH domains, and multi-specific antibodies formed from antibody fragments.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived.

"Heavy chain variable region" or "VH" (or, in the case of single domain antibodies, e.g., nanobodies, "VHH") with regard to an antibody refers to the fragment of the heavy chain that contains three CDRs interposed between flanking stretches known as framework regions, these framework regions are generally more highly conserved than the CDRs and form a scaffold to support the CDRs.

Unless specified, as used herein a scFv may have the VL and VH variable regions in either order, e.g., with respect to the N-terminal and C-terminal ends of the polypeptide, the scFv may comprise VL-linker-VH or may comprise VH-linker-VL.

The term "antibody light chain," refers to the smaller of the two types of polypeptide chains present in antibody molecules in their naturally occurring conformations. Kappa ("κ") and lambda ("λ") light chains refer to the two major antibody light chain isotypes.

The term "recombinant antibody" refers to an antibody that is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

In some embodiments, for example those embodiments wherein the receptor comprises a first and a second polypeptide, the antigen-binding domain is isolated or derived from a T cell receptor (TCR) extracellular domain or an antibody.

In preferred embodiments, the polypeptide comprises antigen-binding domain, e.g., an antigen-binding domain other than the LILRB1 antigen-binding protein. An illustrative embodiments of receptor having a single antigen-binding domain is depicted in FIG. 1. The disclosure contemplated chimeric antigen receptors have two, three, four or more antigen-binding domains. The antigen-binding domains may be provided on the same or a different chain of the chimeric antigen receptor. In embodiments, the chimeric antigen receptor is a DARIC as described, for example in Leung et al. *JCI Insight.* 2019 Jun. 6; 4(11):e124430, WO2015017214A1; and WO2017156484A1.

In some embodiments, the receptor is an inhibitory chimeric antigen receptor (iCAR). Various methods and composition suitable for use with the embodiments disclosure herein include those provided in US2018/0044399A1; WO2018148454A1; and WO2017087723A1, each of which is incorporated herein for all purposes.

In some embodiments, the antigen-binding domain comprises a single chain variable fragment (scFv).

In some embodiments, the receptor comprises a second polypeptide. The disclosure provides receptors having two polypeptides each having a part of a ligand-binding domain (e.g. cognates of a heterodimeric LDB, such as a TCRα/β- or Fab-based LBD) and each having an intracellular domain, as depicted in FIG. 2A. The disclosure further provides receptors having two polypeptides, each having a part of a ligand-binding domain (e.g. cognates of a heterodimeric LDB, such as a TCRα/β- or Fab-based LBD) and one part of the ligand binding domain is fused to a hinge or transmembrane domain, while the other part of the ligand binding domain has no intracellular domain, as depicted in FIG. 2B. Further variations include receptors where each polypeptide has a hinge domain, and where each polypeptide has a hinge and transmembrane domain. In some embodiments, the hinge domain is absent. In other embodiments, the hinge domain is a membrane proximal extracellular region (MPER), such as the LILRB1 D3D4 domain. In any of the embodiments disclosed herein, the domains may be fused adjacent to one another with linkers between them.

In some embodiments, the first polypeptide comprises a first chain of an antibody and the second polypeptide comprise a second chain of said antibody.

In some embodiments, the receptor comprises a Fab fragment of an antibody. In embodiments, an antigen-binding fragment of the heavy chain of the antibody, and the second polypeptide comprises an antigen-binding fragment of the light chain of the antibody. In embodiments, the first polypeptide comprises an antigen-binding fragment of the light chain of the antibody, and the second polypeptide comprises an antigen-binding fragment of the heavy chain of the antibody.

In some embodiments, the first polypeptide comprises a first chain of a T-cell receptor (TCR) and the second polypeptide comprises a second chain of said TCR. In embodiments, the receptor comprises an extracellular fragment of a T cell receptor (TCR). In embodiments, the first polypeptide comprises an antigen-binding fragment of the alpha chain of the TCR, and the second polypeptide comprises an antigen-binding fragment of the beta chain of the TCR. In some embodiments, the first polypeptide comprises an antigen-binding fragment of the beta chain of the TCR, and the second polypeptide comprises an antigen-binding fragment of the alpha chain of the TCR.

In some embodiments, the receptor comprises a single-chain TCR, such as, without limitation, those disclosed in WO2017091905A1.

Illustrative Antigen-Binding Domains

Various single variable domains known in the art or disclosed herein are suitable for use in embodiments. Such scFv's include, for example and without limitation the following mouse and humanized scFv antibodies that bind HLA-A*02 in a peptide-independent way (complementarity determining regions underlined):

```
C-001765
MMTQTPLSLPVSLGDQASISCRSSQSIVHSNGNTY
LEWYLQKPGQSPKLLIYKVSNRFSGVPDRFSGSGS
GTDPTLKISRVEAEPLGVYYCFQGSHVPRTSGGGT
KLEIKGGGGSGGGGSGGGGSGGQVQLQQSGPELVK
PGASVRISCKASGYTFTSYHIHWVKQRPGQGLEWI
GWIYPGNVNTEYNEKFKGKATLTAPKSSSTAYMHL
SSLTSEPSAVYFCAREEITYAMDYWGQGTSVTVSS
YG;
(SEQ ID NO: 35) or

PVLMTQTPLSLPVSLGDQASISCRSSQSIVHSNGN
TYLEWYLQKPGQSPKLLIYKVSNRFSGVPDRFSGS
GSGTDFTLKISRVEAEDLGVYYCFQGSHVPRTSGG
GTKLEIKGGGGSGGGGSGGGGSGGQVQLQQSGPEL
VKPGASVRISCKASGYTFTSYHIHWVKQRPGQGLE
WIGWIYPGNVNTEYNEKFKGKATLTADKSSSTAYM
HLSSLTSEDSAVYFCAREEITYAMDYWGQGTSVTV
SS
(SEQ ID NO. 125, the corresponding
Polynucleotide sequence is provided
as SEQ ID NO: 127)

C-002159
QLVQSGAEVKKPGSSVKVSCKASGYTFTSYHIHWV
RQAPGQGLEWMGWIYPGNVNTEYNEKFKGKATITA
DKSTSTAYMELSSLRSEDTAVYYCAREEITYAMDY
WGQGTTVTVSSGGGGSGGGGSGGGGSGGEIVLTQS
PGTLSLSPGERATLSCRSSQSIVHSNGNTYLEWYQ
QKPGQAPRLLIYKVSNRFSGIPDRFSGSGSGTPFT
LTISRLEPEPFAVYYCFQGSHVPRTFGGGTKVEIK
(SEQ ID NO: 36)

C-002160
QLVQSGAEVKKPGSSVKVSCKASGYTFTSYHIHWV
RQAPGQGLEWMGWIYPGNVNTEYNEKFKGKATITA
DKSTSTAYMELSSLRSEDTAVYYCAREEITYAMDY
WGQGTTVTVSSGGGGSGGGGSGGGGSGGDIVMTQT
PLSLPVTPGEPASISCRSSQSIVHSNGNTYLEWYL
QKPGQSPQLLIYKVSNRFSGVPDRFSGSGSGTDFT
LKISRVEAEDVGVYYCFQGSHVPRTFGGGTKVEIK
(SEQ ID NO: 37)

C-002161
QLVESGGGLVKPGGSLRLSCAASGYTFTSYHIHWV
RQAPGKGLEWVGWIYPGNVNTEYNEKFKGRFTISR
DDSKNTLYLQMNSLKTEDTAWYCAREEITYAMDYW
GQGTTVTVSSGGGGSGGGGSGGGGSGGDIQMTQSP
SSLSASVGDRVTITCRSSQSIVHSNGNTYLEWYQQ
KPGKAPKLLIYKVSNRFSGVPSRFSGSGSGTDFTL
TISSLQPEDFATYYCFQGSHVPRTFGGGTKVEIK
(SEQ ID NO: 38)

C-002162
QLVQSGAEVKKPGSSVKVSCKASGYTFTSYHIHWV
RQAPGQGLEWIGWIYPGNVNTEYNEKFKGKATITA
DESTNTAYMELSSLRSEDTAVYYCAREEITYAMDY
WGQGTLVTVSSGGGGSGGGGSGGGGSGGDIQMTQS
PSTLSASVGDRVTITCRSSQSIVIISNGNTYLEWY
QQKPGKAPKLLIYKVSNRFSGVPARFSGSGSGTEF
TLTISSLQPDDFATYYCFQGSHVPRTFGQGTKVEV
K
(SEQ ID NO: 39)

C-002163
QLVQSGAEVKKPGSSVKVSCKASGYTFTSYHMHWV
RQAPGQGLEWIGYIYPGNVNTEYNEKFKGKATLTA
DKSTNTAYMELSSLRSEDTAVYFCAREEFITAMDY
WGQGTLVTVSSGGGGSGGGGSGGGGSGGDVQMTQS
PSTLSASVGPRVTITCSSSQSIVHSNGNTYMEWYQ
QKPGKAPKLLIYKVSNRFSGVPDRFSGSGSGTEFT
LTISSLQPDDFATYYCHQGSHVTRTFGQGTKVEVK
(SEQ ID NO: 40)

C-002164
QVQLQQSGPELVKPGASVKMSCKASGYTFTSYHIQ
WVKQRPGQGLEWIGWIYPGPGSTQYNEKFKGKTTL
TADKSSSTAYMLLSSLTSEDSAIYFCAREGTYYAM
DYWGQGTSVTVSSGGGGSGGGGSGGGGSGGDVLMT
QTPLSLPVSLGDQVSISCRSSQSIVHSNGNTYLEW
YLQKPGQSPKLLIYKVSNRFSGVPDRFSGSGSGTD
FTLKISRVEAEDLGVYYCFQGSHVPRTFGGGTKLE
TK(SEQ ID NO: 41)

C-002165
QLQLQESGPGLVKPSETLSLTCTVSGYTFTSYHIQ
WIRQPPGKGLEWIGWIYPGDGSTQYNEKFKGRATI
SVDTSKNQFSLNLDSVSAADTAIYYCAREGTYYAM
DYWGKGSTVTVSSGGGGSGGGGSGGGGSGGDIQMT
QSPSSLSASVGDRVTITCRSSQSIVHSNGNTYLEW
YQQKPGKAPKLLIYKVSNRFSGVPSRFSGSGSGTD
FTFTISSLQPEDIATYYCFQGSHVPRTFGPGTKVD
DC(SEQ ID NO: 42)

C-002166
EVQLVQSGAELKKPGSSVKVSCKASGYTFTSYHIQ
WVKQAPGQGLEWIGWIYPGPGSTQYNEKFKGKATL
TVDKSTNTAYMELSSLRSEDTAVYYCAREGTYYAM
DYWGQGTLVTVSSGGGGSGGGGSGGGGSGGDIQMT
QSPSTLSASVGDRVTITCRSSQSIVHSNGNTYLEW
YQQKPGKAPKLLIYKVSNRFSGVPSRFSGSGSGTD
FTLTISSLQPDDFATYYCFQGSHVPRTFGQGTKVE
(SEQ ID NO: 43)

WC-002167
QVQLVQSGAEVKKPGSSVKVSCKASGYTFTSYHIQ
WVRQAPGQGLEWMGWIYPGDGSTQYNEKFKGRVTI
TADKSTSTAYMELSSLRSEDTAVYYCAREGTYYAM
DYWGQGTTVTVSSGGGGSGGGGSGGGGSGGEIVLT
QSPGTLSLSPGERATLSCRSSQSIVHSNGNTYLEW
YQQKPGQAPRLLIYKVSNRFSGIPDRFSGSGSGTD
FTLTISRLEPFDFAVYYCFQGSHVPRTFGGGTKVE
IK
(SEQ ID NO: 44)
```

-continued

```
C-002168
QVTLKQSGAEVKKPGSSVKVSCTASGYTFTSYHVS
WVRQAPGQGLEWLGRIYPGDGSTQYNEKFKGKVTI
TADKSMPTSFMELTSLTSEPTAVYYCAREGTYYAM
DLWGQGTLVTVSSGGGGSGGGGSGGGGSGGEIVLT
QSPGTLSLSPGERATLSCRSSQSIVHSNGNTYLAW
YQQKPGQAPRLLISKVSNRFSGVPDRFSGSGSGTD
FTLTISRLEPEDFAVYYCQQGSHVPRTFGGGTKVE
IK
(SEQ ID NO: 45)

C-002169
QVQLVQSGAEVKKPGASVKVSCKASGYTFTSYHMH
WVRQAPGQRLEWMGWIYPGDGSTQYNEKFKGKVTI
TRDTSASTAYMELSSLRSEDTAVYYCAREGTYYAM
DYWGQGTLVTVSSGGGGSGGGGSGGGGSGGDIVMT
QTPLSLPVTPGEPASISCRSSQSIVHSNGNTYLDW
YLQKPGQSPQLLIYKVSNRFSGVPDRFSGSGSGTP
FTLKISRVEAEDVGVYYCMQGSHVPRTFGGGTKVE
IK
(SEQ ID NO: 46)
```

| CDR-L1 | CDR-L2 | CDR-L3 | CDR-H1 | CDR-H2 | CDR-H3 |
|---|---|---|---|---|---|
| RSSQ SIVH SNGN TYLE (SEQ ID NO: 22) | KVSN RFSG VPDR (SEQ ID NO: 23) | FQGS HVPR T (SEQ ID NO: 24) | ASGY TFTS YHIH EKFK GK (SEQ ID NO: 25) | WIYP GNVN TEYN (SEQ ID NO: 26) | EEIT YAMD Y (SEQ ID NO: 27) |
| RSSQ SIVH SNGN TYLD (SEQ ID NO: 28) | KVSN RFSG VPDR (SEQ ID NO: 29) | MQGS HVPR T (SEQ ID NO: 30) | SGYT FTSY HMH EKFK G (SEQ ID NO: 31) | WIYP GDGS TQYN (SEQ ID NO: 32) | EGTY YAMD Y (SEQ ID NO: 33) |

In some embodiments, the scFv comprises the complementarity determined regions (CDRs) of any one of SEQ ID NOS: 22-33. In some embodiments, the scFv comprises a sequence at least 95% identical to any one of SEQ ID NOS: 22-33. In some embodiments, the scFv comprises a sequence identical to any one of SEQ ID NOS: 22-33. In some embodiments, the heavy chain of the antibody comprises the heavy chain CDRs of any one of SEQ ID NOS: 25-27 or 31-33, and the light chain of the antibody comprises the light chain CDRs of any one of SEQ ID NOS: 22-24 or 28-30. In some embodiments, the heavy chain of the antibody comprises a sequence at least 95% identical to the heavy chain portion of any one of SEQ ID NOS: 35-46 or 125, and wherein the light chain of the antibody comprises a sequence at least 95% identical to the light chain portion of any one of SEQ ID NOS: 35-46 or 125. In some embodiments, the heavy chain comprises all of SEQ ID NOS: 25-27, and the light chain comprises all of SEQ ID NOS: 22-24. In some embodiments, the heavy chain comprises all of SEQ ID NOS: 31-33, and the light chain comprises all of SEQ ID NOS: 28-30.

In some embodiments, the heavy chain of the antibody comprises a sequence identical to the heavy chain portion of any one of SEQ ID NOS: 35-46 or 125, and wherein the light chain of the antibody comprises a sequence identical to the light chain portion of any one of SEQ ID NOS: 35-46 or 125.

In some embodiments, the ScFv comprises a sequence at least 95% identical, at least 96% identical, at least 97% identical, at least 98% identical, at least 99% identical or identical to any one of SEQ ID NOS: 35-46 or 125.

B- and T-Lymphocyte Attenuator (BTLA) Domains

In some embodiments, the polypeptide comprises a B- and T-lymphocyte attenuator (BTLA) hinge domain, transmembrane domain, intracellular domain or a functional variant, derivative or combination thereof.

In some embodiments, the polypeptide comprises a BTLA intracellular domain. In some embodiments, the BTLA intracellular domain comprises a sequence of RRHQGKQNELSDTAGREINLVDAHLKSEQTEASTRQNSQVLLSETGIYDNDPDLCFRMQ EGSEVYSNPCLEENKPGIVYASLNHSVIGPNSRLARNVKEAPTEYASICVRS (SEQ ID NO: 87). In some embodiments, the BTLA intracellular domain comprises SEQ ID NO: 87, or a sequence with at least 95% identity thereto. In some embodiments, the BTLA intracellular domain consists essentially SEQ ID NO: 87.

In some embodiments, the BTLA transmembrane domain and intracellular domain comprises a sequence at least 95% identical to a sequence of LLPLGGLPLLITTCFCLFCCLRRHQGKQNELSDTAGREINLVDAHLKSEQTEASTRQNSQ VLLSETGIYDNDPDLCFRMQEGSEVYSNPCLEENKPGIVYASLNHSVIGPNSRLARNVKE APTEYASICVRS (SEQ ID NO: 88). In some embodiments, the BTLA transmembrane domain and intracellular domain comprises or consists essentially of a sequence of SEQ ID NO: 88.

Signal Peptides

In some embodiments, the polypeptide comprises a signal peptide. For example, the polypeptide comprises a VK1 signal peptide. In some embodiments, the signal peptide is an N-terminal signal peptide. In some embodiments, the signal peptide comprises a sequence at least 95% identical to a sequence of MDMRVPAQLLGLLLLWLRGARC (SEQ ID NO: 128). In some embodiments, the signal peptide comprises a sequence of MDMRVPAQLLGLLLLWLRGARC (SEQ ID NO: 128). In some embodiments, the signal peptide is encoded by a sequence at least 95% identical to a sequence of ATGGACATGAGGGTCCCCGCTCAGCTCCTGGGGCTCCTGCTACTCTGGCTCCGAGGTGCCAGATGT (SEQ ID NO: 129), or a sequence identical thereto.

Antigens

The skilled artisan will understand that any macromolecule, including virtually all proteins or peptides, can serve as an antigen for the LILRB1-based receptors described herein. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

In some embodiments, the antigen-binding domain specifically binds to a target selected from etiolate receptor, αvββ integrin, TNF receptor superfamily member 17 (BCMA), CD276 molecule (B7-H3), natural killer cell cytotoxicity receptor 3 ligand 1 (B7-H6), carbonic anhydrase 9

(CAIX), CD19 molecule (CD19), membrane spanning 4-domains A1 (CD20), CD22 molecule (CD22), TNF receptor superfamily member 8 (CD30), CD33 molecule (CD33), CD37 molecule (CD37), CD44 molecule (CD44), CD44v6, CD44v7/8, CD70 molecule (CD70), interleukin 3 receptor subunit alpha (CD123), syndecan 1 (CD138), L1 cell adhesion molecule (CD171), CEA cell adhesion molecule (CEA), delta like canonical Notch ligand 4 (DLL4), epithelial cell adhesion molecule (EGP-2), epithelial cell adhesion molecule (EGP-40), chondroitin sulfate proteoglycan 4 (CSPG4), epidermal growth factor receptor (EGFR), EGFR family including ErbB2 (HER2), EGFRvIII, epithelial cell adhesion molecule (EPCAM), EPH receptor A2 (EphA2), EpCAM, fibroblast activation protein alpha (FAP), folate receptor alpha (FBP), fetal acetylcholine receptor, frizzled class receptor 7 (Fzd7), diganglioside GD2 (GD2), ganglioside GD3 (GD3), Glypican-3 (GPC3), trophoblast glycoprotein (h5T4), interleukin 11 receptor subunit alpha (IL-1 1R), interleukin 13 receptor subunit alpha 2 (IL13R-a2), kinase insert domain receptor (KDR), κ light chain, λ light chain, LeY, L1 cell adhesion molecule (L1 CAM), MAGE-A1, mesothelin, MHC presented peptides, mucin 1, cell surface associated (MUC1), mucin 16, cell surface associated (MUC16), neural cell adhesion molecule 1 (NCAM), killer cell lectin like receptor K1 (NKG2D) ligands, Notch1, Notch2/3, NY-ESO-1, PRAME nuclear receptor transcriptional regulator (PRAME), prostate stem cell antigen (PSCA), folate hydrolase 1 (PSMA), Survivin, TAG-72, TEMs, telomerase reverse transcriptase (TERT), kinase insert domain receptor (VEGFR2), and receptor tyrosine kinase like orphan receptor 1 (ROR1).

In some embodiments, the antigen-binding domain specifically binds to a target selected from CD33, CD38, a human leukocyte antigen (HLA), an organ specific antigen, a blood-brain barrier specific antigen, an Epithelial-mesenchymal transition (EMT) antigen, E-cadherin, cytokeratin, Opioid-binding protein/cell adhesion molecule (OPCML), HYLA2, Deleted in Colorectal Carcinoma (DCC), Scaffold/Matrix attachment region-binding protein 1 (SMAR1), cell surface carbohydrate and mucin type 0-glycan.

In some embodiments, the extracellular domain of the LILRB1-based receptors described herein comprises an antigen-binding domain specific to an antigen that is lost through loss of heterozygosity in cells of a subject.

As used herein, "loss of heterozygosity (LOH)" refers to a genetic change that occurs at high frequency in cancers, whereby one of the two alleles is deleted, leaving a single mono-allelic (hemizygous) locus.

In some embodiments, the LILRB1-based receptor comprises an antigen-binding domain specific to a minor histocompatibility antigen (MiHA). MiHAs are peptides derived from proteins that contain nonsynonymous differences between alleles and are displayed by common HLA alleles. The non-synonymous differences can arise from SNPs, deletions, frameshift mutations or insertions in the coding sequence of the gene encoding the MiHA. Exemplary MiHAs can be about 9-12 amino acids in length and can bind to MHC class I and MHC class II proteins. Binding of the TCR to the MHC complex displaying the MiHA can activate T cells. The genetic and immunological properties of MiHAs will be known to the person of ordinary skill in the art, and specific MiHas described in PCT/US2020/045228, the contents of which are incorporated by reference.

In some embodiments, the LILRB1-based receptor comprises an antigen-binding domain specific to an antigen that is lost in cancer cells of a subject through loss of Y chromosome.

In some embodiments, the LILRB1-based receptor comprises an antigen-binding domain specific to an HLA class I allele. The major histocompatibility complex (MHC) class I is a protein complex that displays antigens to cells of the immune system, triggering immune response. The Human Leukocyte Antigens (HLAs) corresponding to MHC class I are HLA-A, HLA-B and HLA-C. HLA-E is known in the art as a non-classical MHC class I molecule. In some embodiments, the antigen for the LILR1-based receptor comprises an HLA class I allele. In some embodiments, allele of HLA class I is lost in a target cell, such as a cancer cell, through loss of heterozygosity (LOH).

HLA-A is a group of human leukocyte antigens (HLA) of the major histocompatibility complex (MHC) that are encoded by the HLA-A locus. HLA-A is one of three major types of human MHC class I cell surface receptors. The receptor is a heterodimer comprising a heavy α chain and smaller β chain. The α chain is encoded by a variant of HLA-A, while the β chain (β2-microglobulin) is invariant. There are several thousand HLA-A variants, all of which fall within the scope of the instant disclosure.

In some embodiments, the LILRB1-based receptor comprises an antigen-binding domain specific to an HLA-B allele. The HLA-B gene has many possible variations (alleles). Hundreds of versions (alleles) of the HLA-B gene are known, each of which is given a particular number (such as HLA-B27).

In some embodiments, the LILRB1-based receptor comprises an antigen-binding domain specific to an HLA-C allele. HLA-C belongs to the HLA class I heavy chain paralogues. This class I molecule is a heterodimer consisting of a heavy chain and a light chain (beta-2 microglobulin).

In some embodiments, the HLA class I allele has broad or ubiquitous RNA expression.

In some embodiments, the HLA class I allele has a known, or generally high minor allele frequency.

In some embodiments, the HLA class I allele does not require a peptide-MHC antigen, for example when the HLA class I allele is recognized by a pan-HLA ligand binding domain.

In some embodiments, the LILRB1-based receptor comprises an antigen-binding domain specific to an HLA-A allele. In some embodiments the HLA-A allele comprises HLA-A*02. Various single variable domains known in the art or disclosed herein that bind to and recognize HLA-A*02 are suitable for use in embodiments, and are described herein.

In some embodiments, the antigen-binding domain specifically binds to an HLA-A*02 antigen. In some embodiments, the antigen-binding domain specifically binds to an HLA-A*02 antigen in a peptide-independent manner.

Polynucleotides and Vectors

In other aspects, the disclosure provides polynucleotides comprising a nucleic acid sequence encoding receptors of the disclosure. In some embodiments, the polynucleotides encode one or more of an LILRB1 hinge domain, an LILRB1 transmembrane domain and an LILRB1 intracellular domain or a functional derivative or fragment thereof.

In some embodiments, the polynucleotide comprises a nucleic acid sequence that encodes a polypeptide that is at least 95% identical to any one of SEQ ID NOS: 1-7 or 12-21. In some embodiments, the polynucleotide comprises a nucleic acid sequence that encodes a polypeptide that is at least 95% identical to any one of SEQ ID NOS: 47-71, 77-79, 89-92, 120 or 122. In some embodiments, the polynucleotide comprises a nucleic acid sequence that encodes a polypeptide that is at least 95% identical to the heavy chain portion or the light chain portion of any one of SEQ ID NOS: 35-46 or 125. In some embodiments, the polynucleotide comprises a nucleic acid sequence that encodes a polypeptide that is at least 95% identical to the heavy chain portion or the light chain portion of any one of SEQ ID NOS. 35, 39, 46 or 125. In some embodiments, the polynucleotide comprises a nucleic acid sequence that encodes a polypeptide that is identical to the heavy chain portion or the light chain portion of any one of SEQ ID NOS: 35, 39, 46 or 125. In another aspect, the disclosure provides vectors comprising the polynucleotides encoding receptors of the disclosure.

In some embodiments, the polynucleotide comprises a sequence at least 95% identical to SEQ ID NO: 121 or 123. In some embodiments, the polynucleotide comprises SEQ ID NO: 121 or 123.

In some embodiments, the polynucleotide comprises a sequence of a LILRB1 hinge, transmembrane and intracellular domain. In some embodiments, the polynucleotide comprises a sequence at least 95% identical to SEQ ID NO: 126. In some embodiments, the polynucleotide comprises a sequence of SEQ ID NO: 126.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression of natural or synthetic nucleic acids encoding receptors is typically achieved by operably linking a nucleic acid encoding receptor or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The polynucleotides encoding the receptors can be cloned into a number of types of vectors. For example, the polynucleotides can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to cells, such as immune cells, in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

In some embodiments, the vector comprises a promoter. Vectors can also include additional regulatory elements. Additional regulatory elements, e.g., enhancers, regulate the frequency of transcriptional initiation. Typically, these are located in the region 30-110 basepairs (bp) upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of receptor the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). One method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Engineered Cells

In another aspect, the disclosure provides immune cells comprising a nucleic acid sequence or vector encoding receptors of the disclosure and/or expressing receptors of the disclosure.

In embodiments, immune cell activation is reduced when the cell is contacted with the antigen of the LILRB1 based receptors of the disclosure, or a cell expressing the antigen on its surface. In embodiments, immune cell activation comprises expression of a gene operatively linked to an NFAT promoter. Immune cell activation and/or inhibition of activation can be measured by various other methods known in the art. In some embodiments, the immune cell comprises an additional exogenous receptor, for example an activator receptor such as a chimeric antigen receptor (CAR) or TCR.

In embodiments, the immune cell is a T cell.

As used herein, the term "immune cell" refers to a cell involved in the innate or adaptive (acquired) immune systems. Exemplary innate immune cells include phagocytic cells such as neutrophils, monocytes and macrophages, Natural Killer (NK) cells, polymophonuclear leukocytes such as neutrophils eosinophils and basophils and mononuclear cells such as monocytes, macrophages and mast cells. Immune cells with roles in acquired immunity include lymphocytes such as T-cells and B-cells.

As used herein, a "T-cell" refers to a type of lymphocyte that originates from a bone marrow precursor that develops in the thymus gland. There are several distinct types of T-cells which develop upon migration to the thymus, which include, helper CD4+ T-cells, cytotoxic CD8+ T cells, memory T cells, regulatory CD4+ T-cells and stem memory T-cells. Different types of T-cells can be distinguished by the ordinarily skilled artisan based on their expression of markers. Methods of distinguishing between T-cell types will be readily apparent to the ordinarily skilled artisan.

Method of Making Engineered Cells

In another aspect, the disclosure provides methods comprising introducing a polynucleotide of the disclosure into cells, optionally using vectors of the disclosure. In embodiments, the resulting cell expresses LILRB1 based receptor encoded by the polynucleotide. In embodiments, the cell is an immune cell. In embodiments, the immune cell is a T cell.

Methods of transforming populations of immune cells, such as T cells, with the vectors of the instant disclosure will be readily apparent to the person of ordinary skill in the art. For example, CD3+ T cells can be isolated from PBMCs using a CD3+ T cell negative isolation kit (Miltenyi), according to manufacturer's instructions. T cells can be cultured at a density of $1\times10^{\wedge}6$ cells/mL in X-Vivo 15 media supplemented with 5% human A/B serum and 1% Pen/strep in the presence of CD3/28 Dynabeads (1:1 cell to bead ratio) and 300 Units/mL of IL-2 (Miltenyi). After 2 days, T cells can be transduced with viral vectors, such as lentiviral vectors using methods known in the art. In some embodiments, the viral vector is transduced at a multiplicity of infection (MOI) of 5. Cells can then be cultured in IL-2 or other cytokines such as combinations of IL-7/15/21 for an additional 5 days prior to enrichment. Methods of isolating and culturing other populations of immune cells, such as B cells, or other populations of T cells, will be readily apparent to the person of ordinary skill in the art. Although this method outlines a potential approach it should be noted that these methodologies are rapidly evolving. For example excellent viral transduction of peripheral blood mononuclear cells can be achieved after 5 days of growth to generate a >99% CD3+ highly transduced cell population.

Methods of activating and culturing populations of T cells comprising the receptors, polynucleotides or vectors of the disclosure will be readily apparent to the person of ordinary skill in the art.

Whether prior to or after genetic modification, T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041, 10,040,846; and U.S. Pat. Appl. Pub. No. 2006/0121005.

In some embodiments, T cells of the instant disclosure are expanded and activated in vitro. Generally, the T cells of the instant disclosure are expanded in vitro by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In some embodiments, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. In some embodiments, a ratio of 1:1 cells to beads is used. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached to contact the T cells. In one embodiment the cells (for example, CD4+ T cells) and beads (for example, DYNABEADS CD3/CD28 T paramagnetic beads at a ratio of 1:1) are combined in a buffer. Again, those of ordinary skill in the art can readily appreciate any cell concentration may be used. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. In some embodiments, cells that are cultured at a density of $1 \times 10^6$ cells/mL are used.

In some embodiments, the mixture may be cultured for several hours (about 3 hours) to about 14 days or any hourly integer value in between. In another embodiment, the beads and T cells are cultured together for 2-3 days. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$, IL-4, IL-7, GM-CSF, IL-10, IL-12, IL-15, TGF$\beta$, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. In some embodiments, the media comprises X-VIVO-15 media supplemented with 5% human A/B serum, 1% penicillin/streptomycin (pen/strep) and 300 Units/ml of IL-2 (Miltenyi).

The T cells are maintained under conditions necessary to support growth, for example, an appropriate temperature (e.g., 37° C.) and atmosphere (e.g., air plus 5% CO2).

In some embodiments, the T cells comprising receptors of the disclosure are autologous. Prior to expansion and genetic modification, a source of T cells is obtained from a subject. Immune cells such as T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation.

In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In alternative embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In some embodiments, immune cells such as T cells are isolated from peripheral blood lymphocytes by lysing the red blood cells and depleting the monocytes, for example, by centrifugation through a PERCOLL™ gradient or by counterflow centrifugal elutriation. Specific subpopulations of immune cells, such as T cells, B cells, or CD4+ T cells can be further isolated by positive or negative selection techniques. For example, in one embodiment, T cells are isolated by incubation with anti-CD4-conjugated beads, for a time period sufficient for positive selection of the desired T cells.

Enrichment of an immune cell population, such as a T cell population, by negative selection can be accomplished with a combination of antibodies directed to surface markers unique to the negatively selected cells. One method is cell sorting and/or selection via negative magnetic immuneadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD 14, CD20, CD 11b, CD 16, HLA-DR, and CD8.

For isolation of a desired population of immune cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads.

In some embodiments, the cells may be incubated on a rotator for varying lengths of time at varying speeds at either 2-10° C. or at room temperature.

T cells for stimulation, or PBMCs from which immune cells such as T cells are isolated, can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Assaying Signaling

In some embodiments, immune cell activation is reduced when the cell is contacted with the antigen corresponding to the LILRB1 based receptor of the disclosure, or a cell expressing the antigen on its surface. In some embodiments, immune cell activation comprises expression of a gene operatively linked to an NFAT promoter. Nuclear factor of activated T-cells (NFAT) is a family of transcription factors shown to be important in immune response. The NFAT transcription factor family consists of five members NFATc1, NFATc2, NFATc3, NFATc4, and NFAT5. NFAT plays a role in regulating inflammation.

As used herein, an NFAT promoter is a promoter that is regulated (i.e., activated or repressed) when NFAT is expressed in a cell. NFAT target promoters are described in Badran, B. M. et al. (2002) J. Biological Chemistry Vol. 277: 47136-47148, and contain NFAT consensus sequences such as GGAAA.

Methods of assessing the effects of receptor activation on gene expression are known in the art, and include the use of reporter genes, whose expression can be quantified. Reporter genes are used for identifying potentially transfected or transduced cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoterdriven transcription. In exemplary embodiments, an NFAT promoter operably linked to a reporter gene is used to evaluate the expression of the receptors of the disclosure on NFAT signaling.

Pharmaceutical Compositions

The disclosure provides pharmaceutical compositions comprising immune cells comprising the LILRB1-based receptors of the disclosure a pharmaceutically acceptable diluent, carrier or excipient.

Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; and preservatives.

Methods of Treating Disease

Provided herein are methods of treating a subject in need thereof, comprising administering to the subject a therapeutically effective amount of a composition comprising a plurality of immune cells comprising the LILRB1-based receptors described herein. In some embodiments, the immune cells further comprise an activator receptor, such as an activator CAR or TCR.

Additional methods of treating subjects, and activator receptors combination combined with inhibitory receptors, are described in PCT/US2020/045228, the contents of which are incorporated by reference herein in their entirety.

In some embodiments, the subject in need thereof has cancer. In some embodiments, the methods of treating the subject comprise administering to the subject a plurality of immune cells comprising the LILRB1-receptors of the disclosure. In some embodiments, the plurality of immune cells further comprises an activator receptor, such as a CAR or a TCR. In some embodiments, the CAR or TCR comprises an antigen-binding domain specific to a cancer antigen. Activator receptors specific for cancer antigens can comprise antigen-binding domains isolated or derived from any antibody or antigen-binding domain known in the art, including, but not limited to, urelumab, utomilumab, oleclumab, naptumomab, ascrinvacumab, tacatuzumab, nesvacumab, vanucizumab, belimumab, tabalumab, tibulizumab, belantamab, igovomab, oregovomab, sofituzumab, mogamulizumab, talacotuzumab, tavolimab, vonlerolizumab, ipilimumab, duvortuxizumab, blinatumomab, coltuximab, denintuzumab, inebilizumab, loncastuximab, taplitumomab, ibritumomab, obinutuzumab, ocaratuzumab, ocrelizumab, ofatumumab, rituximab, tositumomab, veltuzumab, samalizumab, bectumomab, epratuzumab, inotuzumab, moxetumomab, pinatuzumab, gomiliximab, lumiliximab, camidanlumab, basiliximab, inolimomab, daclizumab, varlilumab, enoblituzumab, omburtamab, brentuximab, iratumumab, gemtuzumab, lintuzumab, vadastuximab, lilotomab, otlertuzumab, tetulomab, daratumumab, isatuximab, bivatuzumab, abituzumab, intetumumab, lorvotuzumab, itolizumab, cusatuzumab, vorsetuzumab, milatuzumab, polatuzumab, iladatuzumab, galiximab, altumomab, arcitumomab, labetuzumab, cibisatamab, zolbetuximab, lacnotuzumab, cabiralizumab, emactuzumab, gimsilumab, lenzilumab, otilimab, mavrilimumab, tremelimumab, ulocuplumab, tepoditamab, rovalpituzumab, demcizumab, drozitumab, parsatuzumab, cetuximab, depatuxizumab, futuximab, imgatuzumab, laprituximab, matuzumab, necitumumab, nimotuzumab, panitumumab, zalutumumab, modotuximab, amivantamab, tomuzotuximab, losatuxizumab, adecatumumab, citatuzumab, edrecolomab, oportuzumab, solitomab, tucotuzumab, catumaxomab, ifabotuzumab, duligotuzumab, elgemtumab, lumretuzumab, patritumab, seribantumab, zenocutuzumab, aprutumab, bemarituzumab, vantictumab, dinutuximab, ecromeximab, mitumomab, codrituzumab, glembatumumab, zatuximab, ertumaxomab, margetuximab, timiguтuzumab, gancotamab, pertuzumab, trastuzumab, ficlatuzumab, rilotumumab, telisotuzumab, emibetuzumab, cixutumumab, dalotuzumab, figitumumab, ganitumab, robatumumab, teprotumumab, flotetuzumab, bermekimab, cergutuzumab, volociximab, etaracizumab, relatlimab, carluzumab, amatuximab, clivatuzumab, gatipotuzumab, pemtumomab, cantuzumab, pankomab, racotumomab, brontictuzumab, tarextumabm vesencumab, camrelizumab, cetrelimab, nivolumab, pembrolizumab, pidilizumab, cemiplimab, spartalizumab, atezolizumab, avelumab, durvalumab, cirmtuzumab, tenatumomab, fresolimumab, brolucizumab, bevacizumab, ranibizumab, varisacumab, faricimab, icrucumab, alacizumab, and ramucirumab.

In some embodiments, the LILRB1-based receptor of the disclosure comprises an antigen-binding domain specific to an antigen that is lost in the cancer cells through loss of heterozygosity. In some embodiments, the antigen is a minor histocompatibility antigen (MiHA). In some embodiments, the antigen is an HLA class I allele. In some embodiments, the HLA class I allele comprises HLA-A, HLA-B or HLA-C. In some embodiments, the HLA class I allele comprises HLA-E. In some embodiments, the HLA class I allele is an HLA-A*02 allele. In some embodiments, the antigen is not expressed in the target cell due to loss of Y chromosome. In some embodiments, the antigen specific to the LILRB1-based receptor is an HLA-A*02 antigen.

In some embodiments, the subject in need thereof has cancer. Cancer is a disease in which abnormal cells divide without control and spread to nearby tissue. In some embodiments, the cancer comprises a liquid tumor or a solid tumor. Exemplary liquid tumors include leukemias and lymphomas. Further cancers that are liquid tumors can be those that occur, for example, in blood, bone marrow, and lymph nodes, and can include, for example, leukemia, myeloid leukemia, lymphocytic leukemia, lymphoma, Hodgkin's lymphoma, melanoma, and multiple myeloma. Leukemias include, for example, acute lymphoblastic leukemia (ALL), acute myeloid leukemia (AML), chronic lymphocytic leukemia (CLL), chronic myelogenous leukemia (CML), and hairy cell leukemia. Exemplary solid tumors include sarcomas and carcinomas. Cancers can arise in virtually an organ in the body, including blood, bone marrow, lung, breast, colon, bone, central nervous system, pancreas, prostate and ovary. Further cancers that are solid tumors include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer, squamous cell skin cancer, renal cancer, head and neck cancers, throat cancer, squamous carcinomas that form on the moist mucosal linings of the nose, mouth, throat, bladder cancer, osteosarcoma, cervical cancer, endometrial cancer, esophageal cancer, liver cancer, and kidney cancer. In some embodiments, the condition treated by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

Any cancer wherein a plurality of the cancer cells express the first, activator ligand and do not express the second, inhibitor ligand is envisaged as within the scope of the instant disclosure. For example, CEA positive cancers that can be treated using the methods described herein include colorectal cancer, pancreatic cancer, esophageal cancer, gastric cancer, lung adenocarcinoma, head and neck cancer, diffuse large B cell cancer or acute myeloid leukemia cancer.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or 1a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%, more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Kits and Articles of Manufacture

The disclosure provides kits and articles of manufacture comprising the polynucleotides and vectors encoding the receptors described herein. In some embodiments, the kit comprises articles such as vials, syringes and instructions for use.

In some embodiments, the kit comprises a polynucleotide or vector comprising a sequence encoding one or more chimeric antigen receptors of the disclosure. For example, the polynucleotide or vector comprises a sequence one or more LILRB1 domains as described herein.

In some embodiments, the kit comprises a plurality of immune cells comprising a chimeric antigen receptor as described herein. In some embodiments, the plurality of immune cells comprises a plurality of T cells.

| Polypeptide Sequences for Elements of Illustrative Chimeric Antigen Receptors | |
|---|---|
| Name | Sequence |
| LILRB1 | MTPILTVLICLGLSL GPRTHVQAGHLPKPT LWAEPGSVITQGSPV TLRCQGGQETQEYRL YREKKTALWITRIPQ ELVKKGQFPIPSITW EHAGRYRCYYGSDTA GRSESSDPLELVVTG AYIKPTLSAQPSPVV NSGGNVILQCDSQVA FDGFSLCKEGEDEHP QCLNSQPHARGSSRA IFSVGPVSPSRRWWY RCYAYDSNSPYEWSL PSDLLELLVLGVSKK PSLSVQPGPIVAPEE TLT LQCGSDAGYNRFVLY KDGERDFLQLAGAQP QAGLSQANFTLGPVS RSYGGQYRCYGAHNL SSEWSAPSDPLDILI AGQFYDRVSLSVQPG PTVASGENVTLLCQS QGWMQTFLLTKEGAA DDPWRLRSTYQSQKY QAEFPMGPVTSAHAG TYRCYGSQSSKPYLL THPSDPLELVVSGPS GGPSSPTTGPTSTSG PEDQPLTPTGSDPQS GLGRHLGVVIGILVA VILLLLLLLLLFLIL RHRRQGKHWTSTQRK ADFQHPAGAVGPEPT DRGLQWRSSPAADAQ EENLYAAVKHTQPED GVEMDTRSPHDEDPQ AVTYAEVKHSRPRRE MASPPSPLSGEFLDT KDRQAEEDRQMDTEA AASEAPQDVTYAQLH SLTLRREATEPPPSQ EGPSPAVPSIYATLA IHPSQEGPSPAVPSI YATLAIH SEQ ID NO: 1 |
| LILRB1 hinge-transmembrane-intracelluiar domain (SEQ ID NO: 126 is the polynucleotide sequence) | YGSQSSKPYLLTHPS DPLELVVSGPSGGPS SPITGPTSTSGPEDQ PLTPTGSDPQSGLGR HLGVVIGILVAVILL LLLLLLLFLILRHRR QGKHWTSTQRKADFQ HPAGAVGPEPTDRGL QWRSSPAADAQEENL YAAVKHTQPEDGVEM DTRSPHDEDPQAVTY AEVKHSRPRREMASP PSPLSGEFLDTKDRQ AEEDRQMDTEAAASE APQDVTYAQLHSLTL RREATEPPPSQEGPS PAVPSIYATLAIH SEQ ID NO: 2 |
| LILRB1 hinge-transmembrane-intraceilular domain (w/o YGSQSSKPYLLTHPSD PLEL, SEQ ID NO: 18) | VVSGPSGGPSSPTTG PTSTSGPEDQPLTPT GSDPQSGLGRHLGVV IGILVAVILLLLLLL LLFLILRHRRQGKHW TSTQRKADFQHPAGA VGPEPTDRGLQWRSS PAADAQEENLYAAVK HTQPEDGVEMDTRSP |

| | |
|---|---|
| | HDEDPQAVTYAEVKH SRPRREMASPPSPLS GEFLDTKDRQAEEDR QMDTEAAASEAPQDV TYAQLHSLTLRREAT EPPPSQEGPSPAVPS IYATLAIH SEQ ID NO: 3 |
| LILRB1 hinge domain | YGSQSSKPYLLTHPS DPLELVVSGPSGGPS SPTTGPTSTSGPEDQP LTPTGSDPQSQLGRHL G SEQ ID NO: 4 |
| LILRB1 transmembrane domain | VVIGILVAVILLLLL LLLLFLIL SEQ ID NO: 5 |
| LILRB1 intracellular domain | RHRRQGKHWTSTQRK ADFQHPAGAVGPEPT DRGLQWRSSPAADAQ EENLYAAV KHTQPEDGVEMDTRS PHDEDPQAVTYAEVK HSRPRREMASPPSPL SGEFLDTKDRQAEED RQMDTEAAASEAPQD VTYAQLHSLTLRREA TEPPPSQEGPSPAVP SIYATLAIH SEQ ID NO: 7 |
| ITIM1 | NLYAAV SEQ ID NO. 8 |
| ITIM2 | VTYAEV SEQ ID NO: 9 |
| ITIM3 | VTYAQL SEQ ID NO: 10 |
| ITLM4 | SIYATL SEQ ID NO: 11 |
| ITIM 1-2 | NLYAAVKHTQPEDGV EMDTRSPHDEDPQAV TYAEV SEQ ID NO: 12 |
| ITIM2-3 | VTYAEVKHSRPRREM ASPPSPLSGEFLDTK DRQAEEDRQMDTEAA ASEAPQDVTYAQL SEQ ID NO: 13 |
| ITIM3-4 | VTYAQLHSLTLRREA TEPPPSQEGPSPAVP SIYATL SEQ ID NO: 14 |
| ITIM1-3 | NLYAAVKHTQPEDGV EMDTRSPHDEDPQAV TYAEVKHSRPRREMA SPPSPLSGEFLDTKD RQAEEDRQMDTEAAA SEAPQDVTYAQL SEQ ID NO: 15 |
| ITIM2-4 | VTYAEVKHSRPRREM ASPPSPLSGEFLDTK DRQAEEDRQMDTEAA ASEAPQDVTYAQLHS LTLRREATEPPPSQE GPSPAVPSIYATL SEQ ID NO: 16 |
| ITIM1-4 | NLYAAVKHTQPEDGV EMDTRSPHDEDPQAV TYAEVKHSRPRREMA SPPSPLSGEFLDTKD RQAEEDRQMDTEAAA SEA PQDVTYAQLHSLTLR REATEPPPSQEGPSP AVPSIYATL SEQ ID NO: 17 |
| D3D4 domain | YGSQSSKPYLLTHPS DPLEL SEQ ID NO: 18 |
| Short hinge | VVSGPSGGPSSPTTG PTSTSGPEDQPLTPT GSDPQSGLGRH LG SEQ ID NO: 19 |
| Hinge (iTIM hinge) | YGSQSSKPYLLTHPS DPLELVVSGPSGGPS SPTTGPTSTSGP EDQPLTPTGSDPQSG LGRHLGV (SEQ ID NO: 80) |
| Short hinge 2 | VVSGPSGGPSSPTTG PTSTSGPBDQPLTPT GSDPQSGLGRH LGV (SEQ ID NO: 81) |
| Long hinge 1 | AGSGGSGGSGGSPVP STPPTPSPSTPPTPS PSGGSGNSSGSG GSPVPSTPPTPSPST PPTPSPSASV (SEQ ID NO: 82) |
| Long hinge 2 | AGSGGSGGSGGSPVP STPPTNSSSTPPTPS PSPVPSTPPTNSS STPPTPSPSVPSTP PTNSSSTPPTPSPSA SV (SEQ ID NO: 83) |
| 2X short hinge | WSGPSGGPSSPTTGP TSTSGPEDQPLTPTG SDPQSGLGRH VVSGPSGGPSSPTTG PTSTSGPEDQPLTPT GSDPQSGLGRHLGV (SEQ ID NO: 84) |
| Hinge (truncated) | TTGPTSTSGPEDQPL TPTGSDPQSGLGRHL GV (SEQ ID NO: 93) |
| Hinge-transmembrane | YGSQSSKPYLLTHPS DPLEL VVSGPSGGPS SPTTGPTSTSGPEDQ PLTPTGSDPQSGLGR HLGVVIGILVAVILL LLLLLLLFLIL SEQ ID NO: 20 |
| Transmembrane-intracellular domain | VVIGILVAVILLLLL LLLLFLILRHRRQGK HWTSTQRKADFQHPA GAVGPEPTDRGLQWR SSPAADAQEENLYAAV KHTQPEDGVEMDTRS PHDEDPQAVTYAEVK HSRPRREMASPPSPL SGEFLDTKDRQAEED RQMDTEAAASEAPQD |

| Polypeptide Sequences for Illustrative Chimeric Antigen Receptors | |
|---|---|
| Name | Sequence |
| | VTYAQLHSLTLRREA |
| | TEPPPSQEGPSPAVP |
| | SIYATLAIH |
| | SEQ ID NO: 21 |
| C563 (SEQ ID NO: 47) | QVQLQESGPGLVKPS |
| | DTLSLTCAVSGYSIS |
| | SSNWWGWIRQPPGKG |
| | LEWIGYIYYSGSTYY |
| | NPSLKSRVTMSVDTS |
| | KNQFSLKLSSVTAVD |
| | TAVYYCARIPFGDWW |
| | YFDLWGRGTLVTVSS |
| | GGGGSGGGGSGGGGS |
| | GGDIQMTQSPSSLSA |
| | SVGDRVTITCRASQS |
| | ISSYLNWYQQKPGKA |
| | PKLLIYAASSLQSGV |
| | PSRFSGSGSGTDFTL |
| | TISSLQPEDFATYYC |
| | QQSYSFVLTFGGGTK |
| | VEIKTTTPAPRPPIP |
| | APTIASQPLSLRPEA |
| | CRPAAGGAVHTRGLD |
| | FACDFWVLVVVGGVL |
| | ACYSLLVTVAFIIFW |
| | VRSKRSRLLHSDYMN |
| | MTPRRPGPTRKHYQP |
| | YAPPRDFAAYRSKRG |
| | RKKLLYIFKQPFMRP |
| | VQTTQEEDGCSCRFP |
| | EEEEGGCELRVKFSR |
| | SADAPAYKQGQNQLY |
| | NELNLGRREEYDVLD |
| | KRRGRDPEMGGKPRR |
| | KNPQEGLYNELQKDK |
| | MAEAYSEIGMKGER |
| | RRGKGHDGL |
| | YQGLSTATKDTYDAL |
| | FIMQALPPR |
| C1759 (SEQ ID NO: 48) | DIQMTQSPSSLSASV |
| | GDRVTITCRASQSIS |
| | SYLNWYQQKPGKAPK |
| | LLIYAASSLQSGVPS |
| | RFSGSGSGTDFTLTI |
| | SSLQPEDFATYYCQQ |
| | SYSTPLTFGGGTKVE |
| | IKGGGGSGGGGSGGG |
| | GSGGEVQLVESGGGL |
| | VQPGGSLRLSCAASG |
| | FTVYDYMSWVRQAPG |
| | KGLEWVSIYSGGST |
| | YYADSVKGRFTISRD |
| | NSKNTLYLQMNSLRA |
| | EDTAVYYCARYSYYY |
| | YYMDVWGKGTTVTVS |
| | SFGSFRALPCWSNSS |
| | DPLLVSVTGNPSSSW |
| | PSPTEPSSKSGICRH |
| | LHVLIGTSVVIF |
| | LFILLLFFLLYRWCS |
| | NKKNAAVMDQEPAGD |
| | RTVNRQDSDEQDPQE |
| | VTYAQLDFICVFIQR |
| | KISRPSQRPKTPLTD |
| | TSVYTELPNAEPRSK |
| | WSCPRAPQSGLEGVF |
| C1760 (SEQ ID NO: 49) | DIQMTQSPSSLSASV |
| | GDRVTITCRASQSIS |
| | SYLNWYQQKPGKAPK |
| | UJYAASSLQSGVPSR |
| | FSGSGSGTDFTLTIS |
| | SLQPEDFATYYCQQS |
| | YSTPLTFGGGTKVEI |
| | KGGGGSGGGGSGGGG |
| | SGGEVQLVESGGGLV |
| | QPGGSLRLSCAASGF |
| | TVYDYMSWVRQAPGK |
| | GLEWVSIYSGGSTY |
| | YADSVKGRFTISRDN |
| | SKNTLYLQMNSLRAE |
| | DTAVYYCARYSYYTY |
| | YMDVWGKGTTVTVSS |
| | FGSFRALPHAWSDPS |
| | DPLPVSVTGNSRNLH |
| | VLIGTSVVIIPPAI |
| | LLFFLLHRWCA |
| | NKKNAVVMDQEPAGN |
| | RTVNREDSDEQDPQE |
| | VTYAQLNHCVFTQRK |
| | ITRPSQRPKTPPTDT |
| | SV |
| C1761 (SEQ ID NO: 50) | DIQMTQSPSSLSASV |
| | GDRVTITCRASQSIS |
| | SYLNWYQQKPGKAPK |
| | LLIYAASSLQSGVPS |
| | RFSGSGSGTDFTLTI |
| | SSLQPEDF |
| | ATYYCQQSYSTPLTF |
| | GGGTKVEIKGGGGSG |
| | GGGSGGGGSGGEVQL |
| | VESGGGLVQPGGSLR |
| | LSCAASGFTVYDYMS |
| | WVRQAPGKGLEWVSV |
| | IYSGGSTYYADSVKG |
| | RFTISRDNSKNTLYL |
| | QMNSLRAEDTAVYYC |
| | ARYSYYYYMDVWGK |
| | GTTVTVSSYGSQSSK |
| | PYLLTHPSDPIFIVV |
| | SGPSGGPSSPTTGPT |
| | STSGPEDQPLTPTGS |
| | DPQSGLGRHLGVVIG |
| | ILVAVILLLLLLLL |
| | FLILRHRRQGKHWTS |
| | TQRKADFQHPAGAVG |
| | PEPTDRGLQWRSSPA |
| | ADAQEENLYAAVKHT |
| | QPEDGVEMDTRSPHD |
| | EDPQAVTYAEVKHSR |
| | PRREMASPPSPLSGE |
| | FLDTKDRQAEEDRQM |
| | DTEAAASEAPQDVTY |
| | AQLHSLTLRREATEP |
| | PPSQEGPSPAVPSIY |
| | ATLAIIT |
| C1762 (SEQ ID NO: 51) | DIQMTQSPSSLSASV |
| | GDRVTITCRASQSIS |
| | SYENWYQQKPGKAPK |
| | LLIYAASSLQSGVPS |
| | RFSGSGSGTDFTLTI |
| | SSLQPEDFATYYCQQ |
| | SYSTPLTFGGGTKVE |
| | IKGGGGSGGGGSGGG |
| | GSGGEVQLVESGGGL |
| | VQPGGSERSCAASG |
| | FTVYDYMSWVRQAPG |
| | KGLEWVSIYSGGST |
| | YYADSVKGRFTISRD |
| | NSKNTLYLQMNSLRA |
| | EDTAVYYCARYSYYY |
| | YYMDVWGKGTTVTVS |
| | STERRAEVPTAHPSP |
| | SPRPAGQFQTLWGWG |
| | GLLGSLVLLVWVLAV |
| | ICSRAARGTIGARRT |
| | GQPLKEDPSAVPVFS |
| | VDYGELDFQWREKTP |
| | EPPVPCVPEQTEYAT |

| | |
|---|---|
| | IVFPSGMGTSSPARR<br>GSADGPRSAQPLRPE<br>DGHCSWPL |
| C2057 (SEQ ID NO: 52) | METLLGELILWLQLQ<br>WVSSKQEVTQIPAAL<br>SVPEGENLVLNCSFT<br>DSAIYNLQWFRQDPG<br>KGLTSLLLIQSSQRE<br>QTSGRLNASLDKSSG<br>RSTLYIAASQPGDSA<br>TYLCAVRPLYGGSYI<br>PTFGRGTSLFVHPYI<br>QNPDDAVYQLRDSKS<br>SDKSVCLFTDFDSQT<br>NVSQSKDSDVYITDK<br>CVLDMRSMDFKSNSA<br>VAWSNKSDFACANAF<br>NNSIIPEDTFFPSPE<br>SSCDVKLVEKSFETD<br>TNLNFQNLSVVIGIL<br>VAVILLLLLLLLLFL<br>ILRHRRQGKFIWTST<br>QRKADFQHPAGAVGP<br>EPTDRGLQWRSSPAA<br>DAQEENLYAAVKIIT<br>QPEDGVEMDTRSPHD<br>EDPQAVTYAEVKHSR<br>PRREMASPPSPLSGE<br>FLDTKDRQAEEDRQM<br>DTEAAASEAPQDVTY<br>AQLHSLILRREATEP<br>PPSQEGPSPAVPSIY<br>ATLAIH |
| C2058 (SEQ ID NO: 53) | MSIGLLCCAALSLLW<br>AGPVNAGVTQTPKFQ<br>VLKTGQSMTLQCAQD<br>MNHEYMSWYRQDPGM<br>GLRLIHYSVGAGITD<br>QGEVPNGYNVSRSTT<br>EDFPLRLLSAAPSQT<br>SVYFCASSYVGNTGE<br>LFFGEGSRLTVLEDL<br>KNVFPPEVAVFEPSE<br>AEISHTQKATLVCLA<br>TGFYPDHVELSWWVT<br>JGKEVHSGVCTDPQP<br>LKEQPALNDSRYCLS<br>SRLRVSATFWQNPRN<br>HFRCQVQFYGLSEND<br>EWTQDRAKPVTQIVS<br>AEAWGRADCGFTSES<br>YQQGVLSVVIGILVA<br>VTLLLLLLLLLLFLIL<br>RHRRQGKHWTSTQRK<br>ADFQHPAGAVGPEPT<br>DRGLQWRSSPAADAQ<br>EENLYAAVKHTQPED<br>GVEMDTRSPHDEDPQ<br>AVTYAEVKHSRPRRE<br>MASPPSPLSGEFLDT<br>KDRQAEEDRQMDTEA<br>AASEAPQDVTYAQLH<br>SLTLRREATEPPPSQ<br>EGPSPAVPSIYATLA<br>IH |
| C2070 (SEQ ID NO: 54) | MSIGLLCCAALSLLW<br>AGPVNAGVTQTPKFQ<br>VLKTGQSMTLQCAQD<br>MNHEYMSWYRQDPGM<br>GLRLIHYSVGAGITD<br>QG<br>ATYYCQQSYSTPLTF<br>GGGTKVEIKGGGGSG<br>GGGSGGGGSGGEVQL<br>VESGGGLVQPGGSLR<br>LSCAASGFTVYDYMS |
| | YVVRQAPGKGLEWVS<br>VIYSGGSTYYADSVK<br>GRFTISRDNSKNTLY<br>LQMNSLRAEDTAVYY<br>CARYSYYYYMDVWG<br>KGTTVTVSSYGSQSS<br>KPYLLTHPSDPIFIW<br>SGPSGGPSSPTTGPT<br>STSGPEDQPLTPTGS<br>DPQSGLGRHLGVVIG<br>ILVAVILLLLLLLLL<br>FLILRHRRQGKHWTS<br>TQRKADFQHPAGAVG<br>PEPTDRGLQWRSSPA<br>ADAQEENLYAAVKIT<br>FQPEDGVEMDTRSPH<br>DEDPQAVTYAEVKHS<br>RPRREMASPPSPLSG<br>EFLDTKDRQAEEDRQ<br>MDTEAAASEAPQDVT<br>YAQLHSLTLRREATE<br>PPPSQEGPSPAVPSI<br>YATLAIIT |
| C1762 (SEQ ID NO: 51) | DIQMTQSPSSLSASV<br>GDRVTITCRASQSIS<br>SYLNWYQQKPGKAPK<br>LLIYAASSLQSGVPS<br>RFSGSGSGTDFTLTI<br>SSLQPEDFATYYCQQ<br>SYSTPLTFGGGTKVE<br>IKGGGGSGGGGSGGG<br>GSGGEVQLVESGGGL<br>VQPGGSLRESCAASG<br>FTVYDYMSWVRQAPG<br>KGLEWVSVIYSGGST<br>YYADSVKGRFTISRD<br>NSKNTLYLQMNSLRA<br>EDTAVYYCARYSYYY<br>YYMDVWGKGTTVTVS<br>STERRAEVPTAHPSP<br>SPRPAGQFQTLWGWG<br>GLLGSLVLLWVLAV<br>ICSRAARGTIGARRT<br>GQPLKEDPSAVPVFS<br>VDYGELDFQWREKTP<br>EPPVPCVPEQTEYAT<br>IVFPSGMTSSPARR<br>GSADGPRSAQPLRPE<br>DGHCSWPL |
| C2057 (SEQ ID NO 52) | METLLGLLILWLQLQ<br>WVSSKQEVTQIPAAL<br>SVPEGENLVLNCSFT<br>DSAIYNLQWFRQDPG<br>KGLTSLLLIQSSQRE<br>QTSGRLNASLDKSSG<br>RSTLYIAASQPGDSA<br>TYLCAVRPLYGGSYI<br>PTFGRGTSLFVHPYI<br>QNPDDAVYQLRDSKS<br>SDKSVCLFTDFDSQT<br>NVSQSKDSDVYITDK<br>CVLDMRSMDFKSNSA<br>VAWSNKSDFACANAF<br>NNSHPEDTFFPSPES<br>SCDVKLVEKSFETDT<br>NLNFQNLSVVIGILV<br>AVILLLLLLLLLFLI<br>LRHRRQGKFIWTSTQ<br>RKADFQHPAGAVGPE<br>PTDRGLQWRSSPAAD<br>AQEENLYAAVKIITQ<br>PEDGVEMDTRSPHDE<br>DPQAVTYAEVKHSRP<br>RREMASPPSPLSGEF |

| | |
|---|---|
| C2058 (SEQ ID NO: 53) | LDTKDRQAEEDRQMD
TEAAASEAPQDVTYA
QLHSLTLRREATEPP
PSQEGPSPAVPSIYA
TLAIH
MSIGLLCCAALSLLW
AGPVNAGVTQTPKFQ
VLKTGQSMTLQCAQD
MNHEYMSWYRQDPGM
GLRLIHYSVGAGITD
QGEVPNGYNVSRSTT
EDFPLRLLSAAPSQT
SVYFCASSYVGNTGE
LFFGEGSRLTVLEDL
KNVFPPEVAVFEPSE
AEISHTQKATLVCLA
TGFYTPHVELSWWVN
GKEVHSGVCTDPQPL
KEQPALNDSRYCLSS
RLRVSATFWQNPRNH
FRCQVQFYGLSENDE
WTQDRAKPVTQIVSA
EAWGRADCGFTSESY
QQGVLSVVIGILVAV
ILLLLLLLLLFLILR
HRRQGKHWTSTQRKA
DFQHPAGAVGPEPTD
RGLQWRSSPAADAQE
ENLYAAVKHTQPEDG
VEMDTRSPHDEDPQA
VTYAEVKHSRPRREM
ASPPSPLSGEFLDTK
DRQAEEDRQMDTEAA
ASEAPQDVTYAQLHS
LTLRREATEPPPSQE
GPSPAVPSIYATLAI
H |
| C2070 (SEQ ID NO: 54) | MSIGLLCCAALSLLW
AGPVNAGVTQTPKFQ
VLKTGQSMTLQCAQD
MNHEYMSWYRQDPGM
GLRLIHYSVGAGITD
QGEVPNGYNVSRSTT
EDFPLRLLSAAPSQT
SVYFCASSYVGNTGE
LFFGEGSRLTVLEDL
KNVFPPEVAVFEPSE
AEISHTQKATLVCLA
TGFYPDHVELSWWVN
GKEVHSGVCTDPQPL
KEQPALNDSRYCLSS
RLRVSATFWQNPRNH
FRCQVQFYGLSENDE
WTQDRAKPVTQIVSA
EAWGRADGGFTSESY
QQGVLSATILYEILL
GKATLYAVLVSALVL
MAMVKRKDSRGGGGG
SGGGGSGGGGSRAAR
GTIGARRTGQPLKED
PSAVPVFSVDYGELD
FQWREKTPEPPVPCV
PEQTEYATIVFPSGM
GTSSPARRGSADGPR
SAQPLRPEDGHCSWP
L |
| C2071 (SEQ ID NO: 55) | MSIGLLCCAALSLLW
AGPVNAGVTQTPKFQ
VLKTGQSMTLQCAQD
MNHEYMSWYRQDPGM
GLRLIHYSVGAGITD
QGIEVPNGYNVSRST
TEDFPLRLLSAAPSQ
TSVYFCASSYVGNTG
ELFFGEGSRLTVLED
LKNVFPPEVAVFEPS |

| | |
|---|---|
| | EAEISHTQKATLVCL
ATGFYPDHVELSWWV
NGKEVHSGVCTDPQP
LKEQPALNDSRYCLS
SRLRVSATFWQNPRN
HFRCQVQFYGLSEND
EWTQDRAKPVTQIVS
AEAWGRADCGFTSES
YQQGVLSATILYEIL
LGKATLYAVLVSALV
LMAMVKRKDSRGGGG
GSGGGGSGGGGSNKK
NAAVMDQEPAGDRTV
NRQDSDEQDPQEVTY
AQLDHCVFIQRKISR
PSQRPKTPLTDTSVY
TELPNAEPRSKVVSC
PRAPQSGLEGVF |
| C2072 (SEQ ID NO: 56) | MSIGLLCCAALSLLW
AGPVNAGVTQTPKFQ
VLKTGQSMTLQCAQD
MNHEYMSWYRQDPGM
GLRLIHYSVGAGITD
QGEVPNGYNVSRSTT
EDFPLRLLSAAPSQT
SVYFCASSYVGNTGE
LFFGEGSRLTVLEDL
KNVFPPEVAVFEPSE
AEISHTQKATLVCLA
TGFYPDHVELSWWVN
GKEVHSGVCTDPQPL
KEQPALNDSRYCLSS
RLRVSATFWQNPRNH
FRCQVQFYGLSENDE
WTQDRAKPVTQIVSA
EAWGRADCGFTSESY
QQGVLSATILYEILL
GKATLYAVLVSALVL
MAMVKRKDSRGGGGG
SGGGGSGGGGSRHRR
QGKHWTSTQRKADFQ
HPAGAVGPEPTDRGL
QWRSSPAADAQEENL
YAAVKHTQPEDGYEM
DTRSPHDEDPQAVTY
AEVKHSRPRREMASP
PSPLSGEFLDTKDRQ
AEEDRQMDTEAAASE
APQDVTYAQLHSLTL
RREATEPPPSQEGPS
PAVPSIYATLAIH |
| C2106 (SEQ ID NO: 57) | DIQMIQSPSSLSASV
GDRVIITCRASQSIS
SYLNWYQQKPGKAPK
LLIYAASSLQSGVPS
RFSGSGSGTDFTLTI
SSLQPEDFATYYCQQ
SYSTPLTFGGGTKVE
IKGGGGSGGGGSGGG
GSGGEVQLVESGGGL
VQPGGSLRLSCAASG
FTVYDYMSWVRQAPG
KGLEWVSVIYSGGST
YYADSVKGRFTISRD
NSKNTLYLQMNS
LRAEDTAVYYCARYS
YYYYYMDVWGKGTTV
TVSSTTTPAPRPPTP
APTIASQPLSLRPEA
CRPAAGGAVHTRGLD
FACDIYIYVAPLAGT
CGVLLLSLVITLYCN
HDREKKPRQHSGDHE
NEMNVPSDKEMFSRS
VTSLATDAPASSEQN
GALTNGDILSEDSTL
TCMQHYEEVQTSASD |

|  | |
|---|---|
|  | LLDSQDSTGKPKCFI<br>QSRELPRIPPESAVD<br>TMLTARSVDGDQGLG<br>MEGPYEVLKDSSQE<br>NMVEDCLYETVKEIK<br>EVAAAAHLEKGHSGK<br>AKSTSASKELPGPQT<br>EGKAEFAEYASVDRN<br>KKCRQSVNVESI<br>LGNSCDPEEEAPPPV<br>PVKLLDENENLQEKE<br>GGEAEESATDTTSE<br>TNKRFSSLSYKSR<br>EEDPTLTEEEISAMY<br>SSVNKPGQLVNKSGQ<br>SLTVPESTYTSIQGD<br>PQRSPSSCNDLYATV<br>KDFEKTPNSTLPPAG<br>RPSEEPEPDYEAIQT<br>LNREEEKATLGTNGH<br>HGLVPKENDYESISD<br>LQQGRDITRL |
| C2107 (SEQ ID NO: 58) | DIQMTQSPSSLSASV<br>GDRVTITCRASQSIS<br>SYLNWY<br>QQKPGKAPKLLIYAA<br>SSLQSGVPSRFSGSG<br>SGTDFTLTISSLQPE<br>DFATYYCQQSYSTPL<br>TFGGGTKVEIKGGGG<br>SGGGGSGGGGSGGEV<br>QLVESGGGLVQPGGS<br>LRLSCAASGFTVYDY<br>MSWVRQAPGKGLEWV<br>SVIYSGGSTYYADSV<br>KGRFTISRDNSKNTL<br>YLQMNSLRAEDTAVY<br>YCARYSYYYYMDVW<br>GKGTTVTVSSTTTPA<br>PRPPTPAPTIASQPL<br>SLRPEACRPAAGGAV<br>HTRGLDFACDLWGSL<br>AAVAIFFVITFLIPL<br>CSSCDREKKPRQHSG<br>DHENLMNVPSDKEMF<br>SRSVTSLATDAPASS<br>EQNGALTNGDILSED<br>STLTCMQHYEEVQTS<br>ASDLLDSQDSTGKPK<br>CHQSRELPRIPPESA<br>VDTMLTARSVDGDQG<br>LGMEGPYEVLKDSSS<br>QENMVEDCLYETVKE<br>IKEVAAAAHLEKGHS<br>GKAKSTSASKELPGP<br>QTEGKAEFAEYASVD<br>RNKKCRQSVNVESIL<br>GNSCDPEEEAPPPVP<br>VKLLDENENLQEKEG<br>GEAEESATDTTSETN<br>KRFSSLSYKSREEDP<br>TLTEEEISAMYSSVN<br>KPGQLVNKSGQSLTV<br>PESTYTSIQGDPQRS<br>PSSCNDLYATVKDFE<br>KTPNSTLPPAGRPSE<br>EPEPDYEAIQTLNRE<br>EEKATLGTNGHHGLV<br>PKENDYESISDLQQG<br>RDITRL |
| C2153 (SEQ ID NO: 59) | DIQMTQSPSSLSASV<br>GDRVTITCRASQSI<br>SSYLNWY<br>QQKPGKAPKLLIYAA<br>SSLQSGVPSRFSGSG<br>SGTDFTLTISSLQPE<br>DFATYYCQQSYSTPL<br>TFGGGTKVEIKGGGG<br>SGGGGSGGGGSGGEV<br>QLVESGGGLVQPGGS<br>LRLSCAASGFTVYDY<br>MSWVRQAPGKGLEWV<br>SVIYSGGSTYYADSV<br>KGRFTISRDNSKNTL<br>YLQMNSLRAEDTAVY<br>YCARYSYYYYMDVW<br>GKGTTVTVSSTTTPA<br>PRPPTPAPTIASQPL<br>SLRPEACRPAAGGAV<br>HTRGLDFACDFWVLW<br>VGGVLACYSLLVTVA<br>FIIFWVLRHRRQGKH<br>WTSTQRKADFQHPAG<br>AVGPEPTDRGLQWRS<br>SPAADAQEENLYAAV<br>KHTQPEDGVEMDTRS<br>PHDEDPQAVTYAEVK<br>HSRPRREMASPPSPL<br>SGEFLDTKDRQAEED<br>RQMDTEAAASEAPQD<br>VTYAQLHSLTLRREA<br>TEPPPSQEGPSPAVP<br>SIYATLAIH |
| C2156 (SEQ ID NO: 60) | METLLGLLILWLQLQ<br>WVSSKQEVTQIPAAL<br>SVPEGENLVLNCSFT<br>DSAIYNLQWFRQDPG<br>KGLTSLLLIQSSQRE<br>QTSGRLNASLDKSSG<br>RSTLYIAASQPGDSA<br>TYLCAVRPLYGGSYI<br>PTFGRGTSLIVHPYI<br>QNPDPAVYQLRDSKS<br>SDKSVCLFTDFDSQT<br>NVSQSKDSDVYITDK<br>CVLDMRSMDFKSNSA<br>VAWSNKSDFACANAF<br>NNSIIPEDTFFPSPE<br>SSCDVKLVEKSFETD<br>TNLNFQNLSVIGFLI<br>LLLLVAGFNLLMTLL<br>LWSSLILRHRRQGKH<br>WTSTQRKADFQHPAG<br>AVGPEPTDRGLQWRS<br>SPAADAQEENLYAAV<br>KHTQPEDGVEMDTRS<br>PHDEDPQAVTYAEVK<br>HS<br>RPRREMASPPSPLSG<br>EFLDTKDRQAEEDRQ<br>MDTEAAASEAPQDVT<br>YAQLHSLTLRREATE<br>PPPSQEGPSPAVPSI<br>YATLAIH |
| C2157 (SEQ ID NO: 61) | MSIGLLCCAALSLLW<br>AGPVNAGVTQTPKFQ<br>VLKTGQSMTLQCAQD<br>MNHEYMSWYRQDPGM<br>GLRLIHYSVGAGITD<br>QGEVPNGYNVSRSTT<br>EDFPLRLLSAAPSQT<br>SVYFCASSYVGNTGE<br>LFFGEGSRLTVLEDL<br>KNWPPEVAVFEPSEA<br>EISHTQKATLVCLAT<br>GFYPDIIVELSWWVN<br>GKEVHSGVCTDPQPL<br>KEQPALNDSRYCLSS<br>RLRVSATFWQNPRNH<br>FRCQVQFYGLSENDE<br>WTQDRAKPVTQIVSA<br>EAWGRADCGFTSESY<br>QQGVLSATILYLILL<br>GLATLYAVLVSALVL |

| | |
|---|---|
| | MLILRIIRRQGKHWT |
| | STQRKADFQHPAGAV |
| | GPEPTDRGLQWRSSP |
| | AADAQEENLYAAVKH |
| | TQPEDGVEMDTRSPH |
| | DEDPQAVTYAEVKHS |
| | RPRREMASPPSPLSG |
| | EFLDTKDRQAEEDRQ |
| | MDTEAAASEAPQDVT |
| | YAQLHSLTLRREATE |
| | PPPSQEGPSPAVPSI |
| | YATLAIH |
| C2158 (SEQ ID NO: 62) | QVQLQESGPGLVKPS |
| | DTLSLTCAVSGYSIS |
| | SSNWWGWIRQPPGKG |
| | LEWIGYIYYSGSTYY |
| | NPSLKSRVTMSVDTS |
| | KNQFSLKLSSVTAVD |
| | TAVYYCARIPFGDWW |
| | YFDLWGRGTLVTVSS |
| | GGGGSGGGGSGGGGS |
| | GGDIQMTQSPSSLSA |
| | SVGDRVTITCRASQS |
| | ISSYLNWYQQKPGKA |
| | PKLLIYAASSLQSGV |
| | PSRFSGSGSGTDFTL |
| | TISSLQPEDFATYYC |
| | QQSYSFVLTFGGGTK |
| | VEIKTTTPAPRPPTP |
| | APTIASQPLSLRPEA |
| | CRPAAGGAVHTRGLD |
| | FACDFWVLVVVGGVL |
| | ACYSLLVTVAFIIFV |
| | VVLRHRRQGKHWTST |
| | QRKADFQHPAGAVGP |
| | EPTDRGLQWRSSPAA |
| | DAQEENLYAAVKHTQ |
| | PEDGVEMDTRSPHDE |
| | DPQAVTYAEVKHSRP |
| | RREMASPPSPLSGEF |
| | LDTKDRQAEEDRQMD |
| | TEAAASEAPQDVTYA |
| | QLHSLTLRREATEPP |
| | PSQEGPSPAVPSIYA |
| | TLAIH |
| C2179 (SEQ ID NO: 63) | DIQMTQSPSSLSASV |
| | GDRVTITCRASQSIS |
| | SYLNWYQQKPGKAPK |
| | LLIYAASSLQSGVPS |
| | RFSGSGSGTDFTLTI |
| | SSLQPEDFATYYCQQ |
| | SYSTPLTFGGGTKVE |
| | IKGGGGSGGGGSGGG |
| | GSGGEVQLVESGGGL |
| | VQPGGSLRLSCAASG |
| | FTVYDYMSWVRQAPG |
| | KGLEWVSVIYSGGST |
| | YYADSVKGRFTISRD |
| | NSKNTLYLQMNSLRA |
| | EDTAVYYCARYSYYY |
| | YMDVWGKGTTVTVS |
| | SYGSQSSKPYLLTHP |
| | SDPLELVVSGPSGGP |
| | SSPTTGPTSTSGPED |
| | QPLTPTGSDPQSGLG |
| | RHLGVVIGILVAVIL |
| | LLLLLLLFLILRHR |
| | RQRPRREMASPPSPL |
| | SGEFLDTKDRQAEED |
| | RQMDTEAAASEAPQD |
| | VTYAQLHSLTLRREA |
| | TEPPPSQEGPSPAVP |
| | SIYATLAIH |
| C2180 (SEQ ID NO: 64) | DIQMTQSPSSLSASV |
| | GDRVTITCRASQSIS |
| | SYLNWYQQKPGKAPK |
| | LLIYAASSLQSGVPS |
| | RFSGSGSGTDFTLTI |
| | SSLQPEDFATYYCQQ |
| | SYSTPLTFGGGTKVE |
| | IKGGGGSGGGGSGGG |
| | GSGGEVQLVESGGGL |
| | VQPGGSLRLSCAASG |
| | FTVYDYMSWVRQAPG |
| | KGLEWVSVIYSGGST |
| | YYADSVKGRFTISRD |
| | NSKNTLYLQMNSLRA |
| | EDTAVYYCARYSYYY |
| | YMDVWGKGTTVTVS |
| | SYGSQSSKPYLLTHP |
| | SDPLELVVSGPSGGP |
| | SSPTTGPTSTSGPED |
| | QPLTPTGSDPQSGLG |
| | RHLGVVIGILVAVIL |
| | LLLLLL |
| | LFLILRHRRQGKHWT |
| | STQRKADFQHPAGAV |
| | GPEPTDRGLQWRSSP |
| | AADAQEENLYAAVKH |
| | TQPEDGVEMDTRSPH |
| | DEDPQAVTYAEVKFI |
| | SRPRREMASPPSPLS |
| | GEFLDTKDRQAEEDR |
| | QMDTEAAASEAPQDV |
| | TYAQLHSLTLRREAT |
| | EPPPSQEGPSPAVPS |
| | IYATLAIHRPRREMA |
| | SPPSPLSGEFLDTKD |
| | RQAEEDRQMDTEAAA |
| | SEAPQDVTYAQLHSL |
| | TLRREATEPPPSQEG |
| | PSPAVPSIYATLAIH |
| C2181 (SEQ ID NO: 65) | DIQMTQSPSSLSASV |
| | GDRVTITCRASQSIS |
| | SYLNWYQQKPGKAPK |
| | LLIYAASSLQSGVPS |
| | RFSGSGSGTDFTLTI |
| | SSLQPEDFATYYCQQ |
| | SYSTPLTFGGGTKVE |
| | IKGGGGSGGGGSGGG |
| | GSGGEVQLVESGGGL |
| | VQPGGSLRLSCAASG |
| | FTVYDYMSWVRQAPG |
| | KGLEWVSVIYSGGST |
| | YYADSVKGRITISRD |
| | NSKNTLYLQMNSLRA |
| | EDTAVYYCARYSYYY |
| | YMDVWGKGTTVTVS |
| | SYGSQSSKPYLLTHP |
| | SDPLELWSGPSGGPS |
| | SPTTGPTSTSGPEDQ |
| | PLTPTGSDPQSGLGR |
| | HLGVVIGILVAVILL |
| | LLLLLLLFLILRHRR |
| | QRPRREMASPPSPLS |
| | GEFLDTKDRQAEEDR |
| | QMDTEAAASEAPQDV |
| | TYAQLHSLTLRREAT |
| | EPPPSQEGPSPAVPS |
| | IYATLAIHRPRREMA |
| | SPPSPLSGEFLDTKD |
| | RQAEEDRQMDTEAAA |
| | SEAPQDVTYAQLHSL |
| | TLRREATEPPPSQEG |
| | PSPAVPSIYATLAIH |
| C2182 (SEQ ID NO: 66) | DIQMTQSPSSLSASV |
| | GDRVTITCRA |
| | SQSISSYLNWY |
| | QQKPGKAPKLLIYAA |
| | SSLQSGVPSRFSGSG |
| | SGTDFTLTISSLQPE |
| | DFATYYCQQSYSTPL |
| | TFGGGTKVEIKGGGG |

SGGGGSGGGGSGGEV
QLVESGGGLVQPGGS
LRLSCAASGFTVYDY
MSWVRQAPGKGLEWV
SVIYSGGSTYYADSV
KGRFTISRDNSKNTL
YLQMNSLRAEDTAVY
YCARYSYYYYMDVW
GKGTTVTVSSYGSQS
SKPYLLTHPSDPLEL
VVSGPSGGPSSPTTG
PTSTSGPEDQPLTPT
GSDPQSGLGRHLGVV
IGILVAVILLLLLLL
LLFLILRHRRQGKHW
TSTQRKADFQHPAGA
VGPEPTDRGLQWRSS
PAADAQEENLFAAVK
HTQPEDGVEMDTRSP
HDEDPQAVTFAEVKH
SRPRREMASPPSPLS
GEFLDTKDRQAEEDR
QMDIEAAASEAPQDV
TFAQLHSLTLRREAT
EPPPSQEGPSPAVPS
IFATLAIH

C2183 (SEQ ID NO. 67)
DIQMTQSPSSLSASV
GDRVTITCRASQSIS
SYLNWYQQKPGKAPK
LLIYAASSLQSGVPS
RFSGSGSGTDFTLTI
SSLQPEDFATYYCQQ
SYSTPLTFGGGTKVE
IKGGGGSGGGGSGGG
GSGGGEVQLVESGGGL
VQPGGSLRLSCAASG
FTVYDYMSWVRQAPG
KGLEWVSVIYSGGST
YYADSVKGRFTISRD
NSKNTLYLQMNSLRA
EDTAVYYCARYSYYY
YYMDVWGKGTTVTVS
SYGSQSSKPYLLTHP
SDPLELWSGPSGGPS
SPTTGPTSTGPEDQ
PLTPTGSDPQSGLGR
HLGVVIGILVAVILL
LLLLLLFLILRHRR
QGKHWTSTQRKADFQ
HPAGAVGPEPTDRGL
QWRSSPAADAQEENL
FAAVKHTQPEDGVEM
DTRSPHDEDPQAVTF
AEVKHSRPRREMASP
PSPLSGEFLDTKDRQ
AEEDRQMDTEAAASE
APQDVTYAQLHSLTL
RREATEPPPSQEGPS
PAVPSIYATLAIH

C2184 (SEQ ID NO: 68)
DIQMTQSPSSLSASV
GDRVTITCRASQSIS
SYLNWYQQKPGKAPK
LLIYAASSLQSGVPS
RFSGSGSGTDFTLTI
SSLQPEDFATYYCQQ
SYSTPLTFGGGTKVE
IKGGGGSGGGGSGGG
GSGGGEVQLVESGGGL
VQPGGSLRLSCAASG
FTVYDYMSWVRQAPG
KGLEWVSVIYSGGST
YYADSVKGRFTISRD
NSKNTLYLQMNSLRA
EDTAVYYCARYSYYY
YYMDVWGKGTTVTVS
SYGSQSSKPYLLTHP
SDPLELVVSGPSGGP
SSPTTGPTSTSGPED
QPLTPTGSDPQSGLG
RHLGVVIGILVAVIL
LLLLLLLFLILRHR
RQGKHWTSTQRKADF
QHPAGAVGPEPTDRG
LQWRSSPAADAQEEN
LYAAVKHTQPEDGVE
MDTRSPHDEDPQAVT
YAEVKFISRPRREMA
SPPSPLSGEFLDTKD
RQAEEDRQMDTEAAA
SEAPQDVTFAQLHSL
TLRREATEPPPSQEG
PSPAVPSIFATLAIH

C2218 (SEQ ID NO: 69)
DIQMTQSPSSLSASV
GDRVTITCRASQSIS
SYLNWYQQKPGKAPK
LLIYAASSLQSGVPS
RFSGSGSGTDFTLTI
SSLQPEDFATYYCQQ
SYSTPLTFGGGTKVE
IKGGGGSGGGGSGGG
GSGGGEVQLVESGGGL
VQPGGSLRLSCAASG
FTVYDYMSWVRQAPG
KGLEWVSVIYSGGS
TYYADSVKGRFTISR
DNSKNTLYLQMNSLR
AEDTAVYYCARYSYY
YYYMDVWGKGTTVTV
SSYGSQSSKPYLLTH
PSDPLELVVSGPSGG
PSSPTTGPTSTSGPE
DQPLTPTGSDPQSGL
GRHLGVVIGILVAVI
LLLLLLLLFLILRR
HQGKQNELSDTAGRE
INLVDAHLKSEQTEA
STRQNSQVLLSETGI
YDNDPDLCFRMQEGS
EVYSNPCLEENKPGI
VYASLNHSVIGPNSR
LARNYTCEAPTEYAS
ICVRS

C2219 (SEQ ID NO: 70)
DIQMTQSPSSLSASV
GDRVTITCRASQSIS
SYLNWYQQKPGKAPK
LLIYAASSLQSGVPS
RFSGSGSGTDFTLTI
SSLQPEDFATYYCQQ
SYSTPLTFGGGTKVE
IKGGGGSGGGGSGGG
GSGGGEVQLVESGGGL
VQPGGSLRLSCAASG
FTVYDYMSWVRQAPG
KGLEWVSVIYSGGST
YYADSVKGRFTISRD
NSKNTLYLQMNSLRA
EDTAVYYCARYSYYY
YYMDVWGKGTTVTVS
SYGSQSSKPYLLTHP
SDPLELVVSGPSGGP
SSPTTGPTSTSGPED
QPLTPTGSDPQSGLG
RHLGVLLPLGGLPLL
ITTCFCLFCCLRRHQ
GKQNELSDTAGREIN
LVDAHLKSEQTEAST
RQNSQVLLSETGIYD
NDPDLCFRMQEGSEV
YSNPCLEENKPGIVY
ASLNHSVIGPNSRLA
RNVKEAPTEYASICV
RS

| | |
|---|---|
| C2220 (SEQ ID NO: 71) | DIQMTQSPSSLSASV GDRVTITCRASQSIS SYLNWYQQKPGKAPK LLIYAASSLQSGVPS RFSGSGSGTDFTLTI SSLQPEDFATYYCQQ SYSTPLTFGGGTKVE IKGGGGSGGGGSGGG GSGGEVQLVESGGGL VQPGGSLRLSCAASG FTVYDYMSWVRQAPG KGLEWVSVIYSGGST YYADSVKGRFTISRD NSKNTLYLQMNSLRA EDTAVYYCARYSYYY YYMDVWGKGTTVTVS STDVKSASERPSKDE MASRPWLLYRLLPLG GLPLLITTCFCLFCC LRRHQGKQNELSDTA GREINLVDAHLKSEQ TEASTRQNSQVLLSE TGIYDNDPDLCFRMQ EGSEVYSNPCLEENK PGIVYASLNHSVIGP NSRLARNVKEAPTEY ASICVRS |
| C2302 (SEQ ID NO: 77) | DIQMTQSPSSLSASV GDRVTITCRASQSIS SYLNWYQQKPGKAPK LLIYAASSLQSGVPS RFSGSGSGTDFTLTI SSLQPEDFATYYCQQ SYSTPLTFGGGTKVE IKGGGGSGGGGSGGG GSGGEVQLVESGGGL VQPGGSLRLSCAASG FTVYDYMSWVRQAPG KGLEWVSVIYSGGST YYADSVKGRFTISRD NSKNTLYLQMNSLRA EDTAVYYCARYSYYY YYMDVWGKGTTVTVS SYGSQSSKPYLLTHP SDPLELVVSGPSGGP SSPTTGPTSTSGPED QPLTPTGSDPQSGLG RHLGVVIGILVAVIL LLLLLLLLFLILRHR RQRPRREMASPPSPL SGEFLDTKDRQAEED RQMDTEAAASEAPQD VTYAQLHSLTLRREA TEPPPSQEGPSPAVP SIYATLAIIIRPRRE MASPPSPLSGEFLDT KDRQAEEDRQMDTEA AASEAPQDVTYAQLH SLTLRREATEPPPSQ EGPSPAVPSIYAPLA OIRPRREMASPPSPL SGEFLDTKDRQAEED RQMDTEAAASEAPQD VTYAQLMSLTLRREA TEPPPSQEGPSPAVP SIYATLAIH |
| CT138 (SEQ ID NO: 78) | MGPVTCSVLVLLLML RRSNGDGDSVTQTEG LVTLTEGLPVMLNCT YQTIYSNPFLFWYVQ HLNESPRLLLKSFTD NKRTEHQGFHATLHK SSSSFHLQKSSAQLS DSALYYCAFDTNTYK VIFGKGTHLHVLPNI QNPEPAVYQLKDPRS QDSTLCLFTDFDSQI | NVPKTMESGTFITDK TVLDMKAMDSKSNGA IAWSNQTSFTCQDIF KETNTTYPSSDVPCD ATLTEKSFETDMNLN FQNLSVMGLRILLLK VAGFNLLMTLRLWSS RAKRSGSGATNFSLL KQAGDVEENPGPMRV RLISAVVLCSLGTGL VDMKVTQMPRYLIKR MGENYTLECGQDMSH ETMYWYRQDPGLGLQ LIYISYDVDSNSEGD IPKGYRVSRKKREHF SLILDSAKTNQTSVY FCASSSTNTEVFFGK GTRLTWEDLRNVTPP KVSLFEPSKAEIANK QKATLVCLARGFFPD HVELSWWVNGKEVHS GVSTDPQAYKESNYS YCLSSRLRVSATFWH NPRNHFRCQVQFHGL SEEDKWPEGSPKPVT QNISAEAWGRADCGI TSASYQQGVLSATIL YEILLGKATLYAVLV STLVVMAMVKRKNS |
| CT139 (SEQ ID NO: 79) | MVLVTILLLSAFFSL RGNSAQSVDQPDAFI VTLSEGASLELRCSY SYSAAPYLFVVYVQY PGQSLQFLLKYITGD TVVKGTKGFEAEFRK SNSSFNLKKSPAHWS DSAKYFCALEGPDTG NYKYVFGAGTRLKVI AHIQNPEPAVYQLKD PRSQDSTLCLFTDFD SQINWKTMESGTFIT DKTVLDMKAMDSKSN GAIAWSNQTSFTCQD IFKETNATYPSSDVP GDATLTEKSFETDMN LNFQNLSVMGLRILL LKVAGFNLLMTLRLW SSRAKRSGSGATNFS LLKQAGDVEENPGPM GIQTLCCVLFYVLIA NHTDAGVTQTPRHEV AEKGQTIILKCEPVS GHNDLFWYRQTKIQG LELLSYFRSKSLMED GGAFKDRFKAEMLNS SFSTLKIQPTEPRDS AVYLCASSFGTASAE TLYFGSGTRLTVLED LRNVTPPKVSLFEPS KAEIANKQKATLVCL ARGFFPDHVELSWWV NGKEVHSGVSTDPQA YKESNYSYCLSSRLR VSATFWHNPRNHFRC QVQFHGLSEEDKWPE GSPKPVTQNISAEAW GRADC GITSASYHQGVLSAT ILYEILLGKATLYAV LVSGLVLMAMVKKKN S |
| C1765 with signal peptide (SEQ ID NO: 120), LIR1 hinge, TM and ICD are | MDMRVPAQLLGLLLL WLRGARCDVLMTQTP LSLPVSLGDQASISC RSSQSIVHSNGNTYL EWYLQKPGQSPKLLI YKVSNRFSGVPDRFS |

-continued

| | |
|---|---|
| underlined Polynucleotide sequence - SEQ ID NO: 121 | GSGSGTDFTLKISRV EAEDLGVYYCFQGSH VPRTSGGGTKLEIKG GGGSGGGGSGGGGSG GQVQLQQSGPELVKP GASVRISCKASGYTF TSYHIHWVKQRPGQG LEWIGWIYPGNVNTE YNEKFKGKATLTADK SSSTAYMHLSSLTSE DSAVYFCAREEITYA MDYWGQGTSVTVSSY GSQSSKPYLLTHPSD PLELVVSGPSGGPSS PTTGPTSTSGPEDQP LTPTGSDPQSGLGRH LGVVIGILVAVILLL LLLLLLFLELRHRRQ GKHWTSTQRKADFQH PAGAVGPEPTDRGLQ WRSSPAADAQEENLY AAVKHTQPEDGVEMD TRSPHDEDPQAVTYA EVKHSRPRREMASPP SPLSGEFLDTKDRQA EEDRQMDTEAAASEA PQDVTYAQLHSLTLR REATEPPPSQEGPSP AVPSIYATLAIH |
| C1765 without signal peptide (SEQ ID NO: 122), LD11 hinge, TM and ICD are underlined Polynucleotide sequence - SEQ ID NO: 123 | DVLMTQTPLSLPVSL GDQASISCRSSQSIV HSNGNTYLEWYLQKP GQSPKLLIYKVSNRF SGWDRFSGSGSGTDF TLKISRVEAEDLGVY YCFQGSHVPRTSGGG TKLEIKGGGGSGGGG SGGGGSGGQVQLQQS GPELVKPGASVRISC KASGYTFTSYHIHWV KQRPGQGLEWIGWIY PGNVNTEYNEKFKGK ATLTADKSSSTAYMH LSSLTSEDSAVYFCA REEITYAMDYWGQGT SVTVSSYGSQSSKPY LLTHPSDPLELVVSG PSGGPSSPTTGPTST SGPEDQPLTPTGSDP QSGLGRHLGVVIGIL VAVILLLLLLLLLFL ILRHRRQGKHWTSTQ RKADFQHPAGAVGPE PTDRGLQWRSSPAAD AQEENLYAAVKHTQP EDGVEMDTRSPHDED PQAVTYAEVKHSRPR REMASPPSPLSGEFL DTKDRQAEEDRQMDT EAAASEAPQDVTYAQ LHSLTLRREATEPPP SQEGPSPAPSIYAIL AIH |

The present description sets forth numerous exemplary configurations, methods, parameters, and the like. It should be recognized, however, that such description is not intended as a limitation on the scope of the present disclosure, but is instead provided as a description of exemplary embodiments.

EXAMPLES

Example 1: LILRB1-Based Inhibitory scFv-CAR Compared to PD-1, EJR3DL2, EJR3DL3

The NY-ESO-1-responsive inhibitory construct was created by fusing the NY-ESO-1 ligand binding scFv domain (C-266) to domains of receptors including hinge, transmembrane region, and/or intracellular domain of Leukocyte immunoglobulin-like receptor subfamily B member 1, LILRB1 (LILRB1); Killer cell immunoglobulin-like receptor 3DL12, KIR3DL2; Killer cell immunoglobulin-like receptor 3DL3, KIR3DL3; and/or B- and T-lymphocyte attenuator, BTLA. Gene segments were combined using Golden Gate cloning and inserted downstream of an eF1α promoter contained in a lentiviral expression plasmid (pLenti1).

As reporter cells, Jurkat cells encoding an NFAT Luciferase reporter were maintained in RPMI media supplemented with 10% FBS, 1% Pen/Strep and 0.4 mg/mL G418/Geneticin. T2 cells (ATCC CLR-1992) were maintained in IMDM media+20% FBS and 1% Pen/Strep. For each construct to be evaluated, Jurkat cells were transfected via 100 μL format Neon electroporation system (Thermo Fisher) according to manufacturer's protocol using the following settings: 3 pulses, 1500V, 10 msec.

Co-transfection was performed with 3 μg of activating CAR construct (C-563) or TCR construct (CT-139) and 3 μg of either inactivating CAR construct or empty vector (pLenti0) per 1 million cells and recovered in RPMI media supplemented with 20% heat-inactivated FBS and 0.1% Pen/Strep.

Peptides, MAGE-A3 (FLWGPRALV) (SEQ ID NO: 106) and modified NY-ESO-1 (SLLMWITQV) (SEQ ID NO: 107), were synthesized by Genscript. Activating peptide, MAGE-A3, was serially diluted 5-fold starting at 50 μM. Inactivating peptide, NY-ESO-1, was diluted to 50 μM, 5 μM, 0.5 μM, or 0.05 uM and these constant amounts were added to the MAGE-A3 serial dilutions and subsequently loaded onto 10,000 T2 cells in 15 μL of RPMI supplemented with 1% BSA and 0.1% Pen/Strep and incubated in Corning® 384-well Low Flange White Flat Bottom Polystyrene TC-treated Microplates. The following day, 10,000 Jurkat cells were resuspended in 15 uL of RPMI supplemented with 10% heat-inactivated FBS and 0.1% Pen/Strep, added to the peptide-loaded T2 cells and co-cultured for 6 hours. ONE-Step Luciferase Assay System (BPS Bioscience) was used to evaluate Jurkat luminescence. Assays were performed in technical duplicates.

LILRB1 Compared to PD-1, KIR3DL2, KIR3DL3

Figure 4:
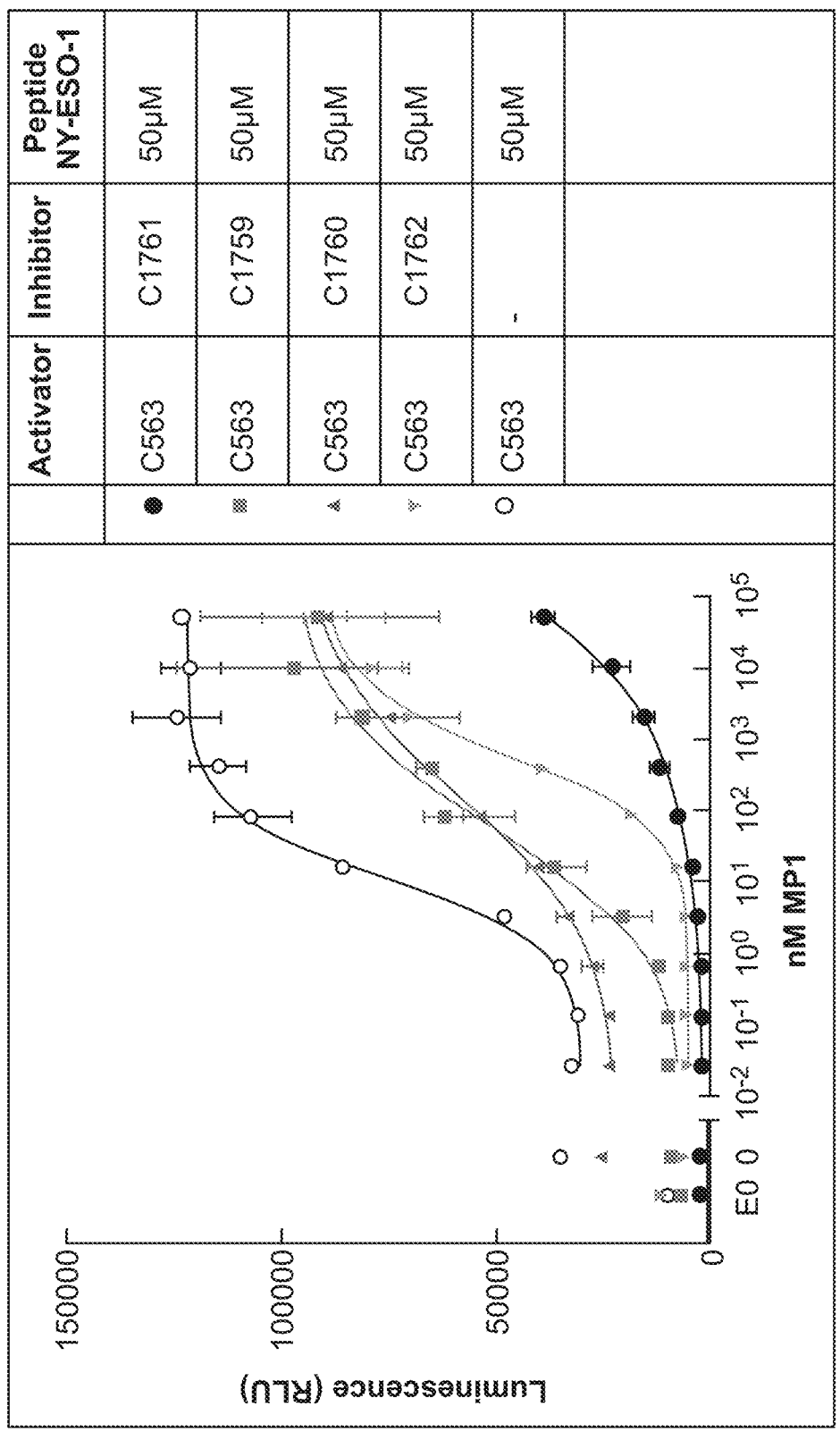
FIG. 4 shows a chart of luminescence in an NFAT-based reporter assay (relative luminescence units, RLU) at varying concentrations of MAGE-A3 activating peptide 1 (MP1, microliters, μM) for the indicated constructs in the presence of 50 μM NY-ESO-1 peptide.

FIG. 4 shows testing of the constructs provided in Table 1. The data show scFv-LILRB1 inhibits CAR activation in trans. Because the construct with an LILRB1 domain demonstrates inhibition of signaling at higher concentrations of MAGE-A3 activator peptide, the data demonstrate that a CAR with hinge, transmembrane domain, and intracellular domain from LILRB1 is superior to CARs generated with the same domains from PD-1, KIR3DL2, or KIR3DL3.

TABLE 1

|  | LBD | Hinge | TM | ICD |
|---|---|---|---|---|
| C563 | MAGE-A3 pep1 scFv | CD8[117-161] | CD28[135-161] | CD28[136-202] 41BB[197-238] CD3z[31-127] |
| C1761 | NY-ESO-1 scFv | LILRB1 | LILRB1 | LILRB1 |
| C1759 | NY-ESO-1 scFv | KIR3DL2 | KIR3DL2 | KIR3DL2 |
| C1760 | NY-ESO-1 scFv | KIR3DL3 | KIR3DL3 | KIR3DL3 |
| C1762 | NY-ESO-1 scFv | PD1 | PD1 | PD1 |
| CT139 | MAGE-A3 pep1 TCR (both alpha and beta chains) | | | |

Figure 5:
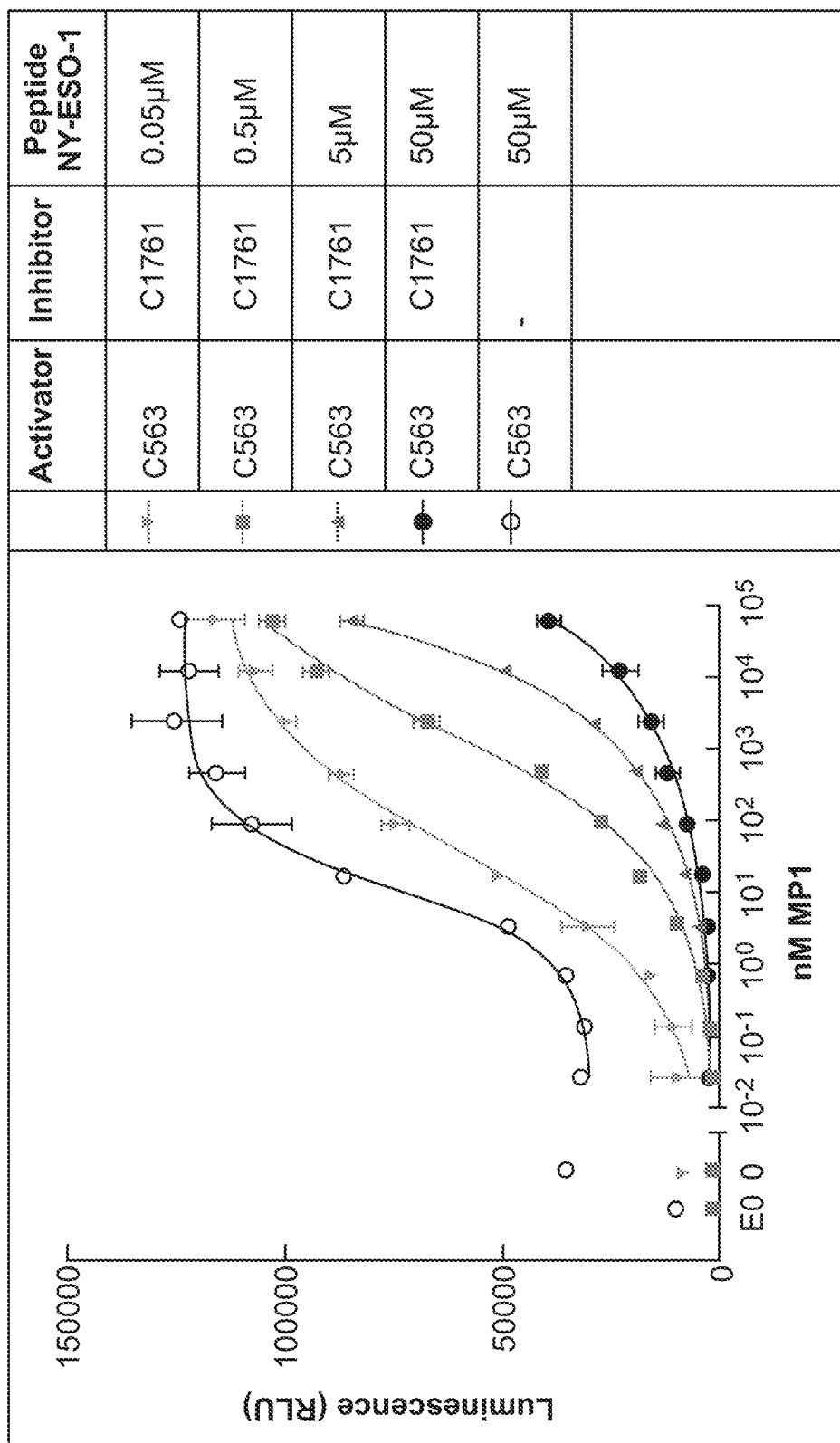
FIG. 5 shows a chart of luminescence in an NFAT-based reporter assay (RLU) at varying concentrations of MAGE-A3 peptide 1 (MP1, nM) for the indicated constructs in the presence of various concentrations (μM) of NY-ESO-1 peptide.

Inhibition by LILRB1-Based CAR Requires Antigen Recognition by its Ligand Binding Domain FIG. 5 shows testing of selected constructs from Table 1. The data show that LILRB1 inhibits signaling in trans in a dose-dependent fashion. At increasing concentrations of the inhibitory peptide NY-ESO-1 the response to activating peptide MAGE-A3 shifts downward. This shows that the inhibitory effect of the LILRB1-based CAR is dependent on engagement of the antigen to which the ligand binding domain is specific.

LILRB1 CAR Inhibits Signaling Through the T-Cell Receptor (ICR)

Figure 6:
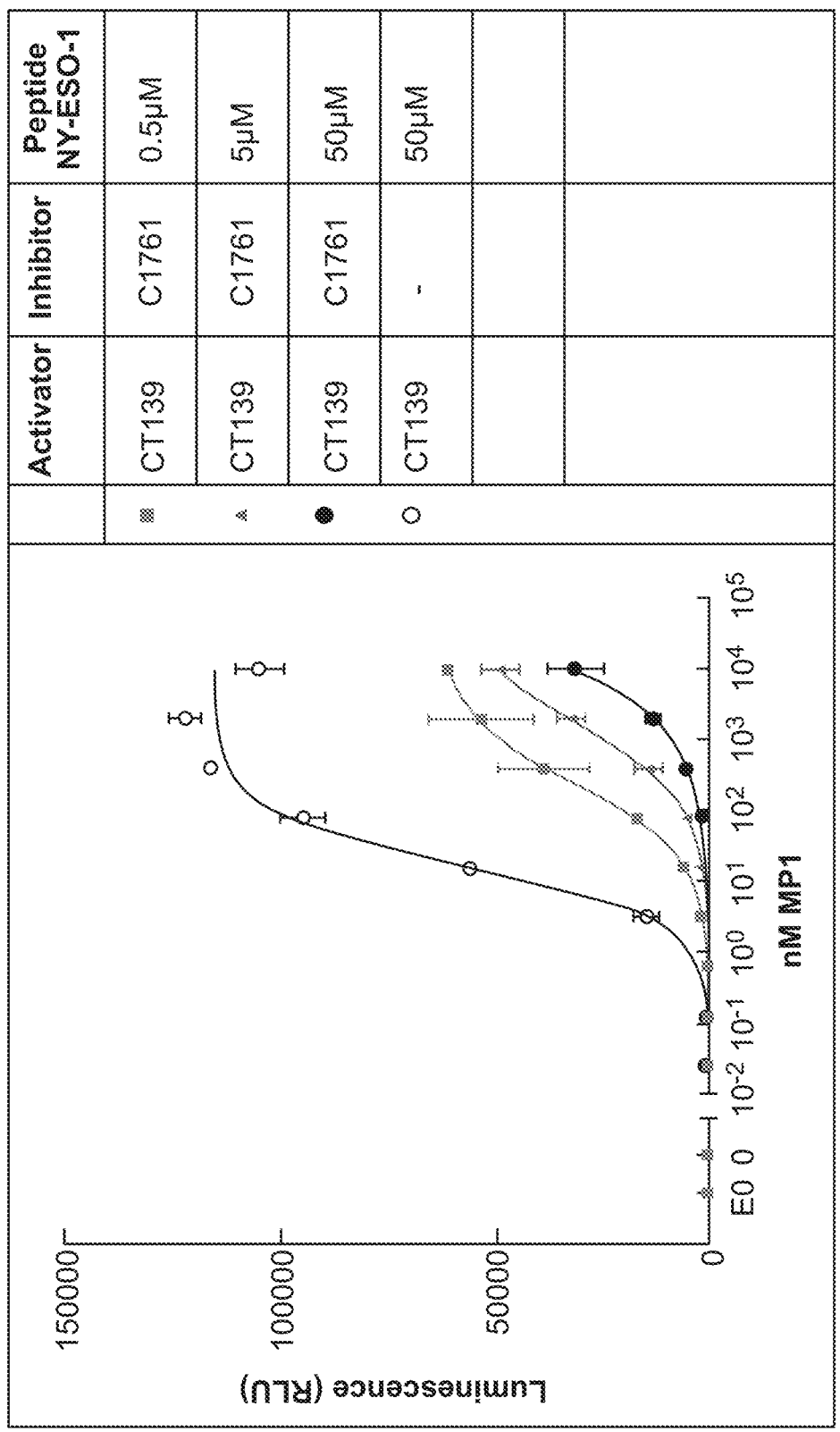
FIG. 6 shows a chart of luminescence in an NFAT-based reporter assay (RLU) at varying concentrations of MAGE-A3 peptide 1 (MP1, nM) for the indicated constructs in the presence of various concentrations (μM) of NY-ESO-1 peptide.

FIG. 6 shows testing of selected constructs from Table 1, in particular a TCR specific for activating peptide MAGE-A3 rather than the CARs used in previous experiments. The LILRB1-based inhibitory CAR inhibits TCR-mediated signaling in a dose-dependent fashion.

Figure 7:
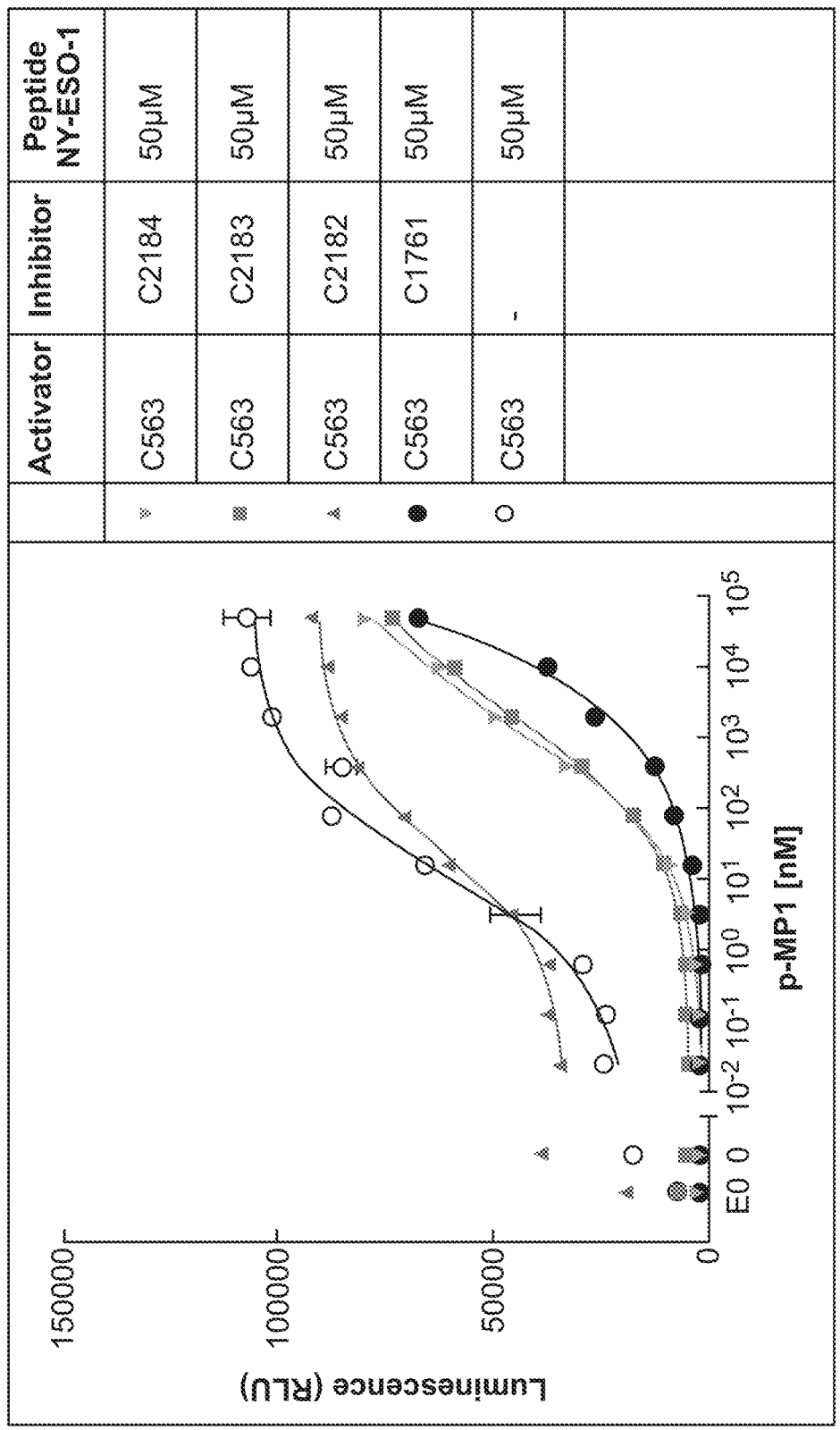
FIG. 7 shows a chart of luminescence in an NFAT-based reporter assay (RLU) at varying concentrations of MAGE-A3 peptide 1 (MP1, nM) for the indicated constructs in the presence of 50 μM NY-ESO-1 peptide.

LIRLB1 CAR Inhibition is Preserved when Two of the Four Native ITIMs are Present FIG. 7 show testing of LILRB1 intracellular domains having inactivating mutations in the ITIM motifs of LILRB1. Mutation of tyrosine to phenylalanine (Y→F) was used to inactivate the ITIMs indicated by a starred number in Table 2.

TABLE 2

|  | LBD | Hinge | TM | ICD |
|---|---|---|---|---|
| C563 | MAGE-A3 pep1 scFv | CD8[117-161] | CD28[135-161] | CD28[136-202] 41BB[197-238] CD3z[31-127] |
| C1761 | NY-ESO-1 scFv | LILRB1 | LILRB1 | LILRB1 (ITIMIs: 1, 2, 3, 4) |
| C2182 | NY-ESO-1 scFv | LILRB1 | LILRB1 | LILRB1 (ITIMs: 1*, 2*, 3*, 4*) |
| C2183 | NY-ESO-1 scFv | LILRB1 | LILRB1 | LILRB1 (ITIMs: 1*, 2*, 3, 4) |
| C2184 | NY-ESO-1 scFv | LILRB1 | LILRB1 | LILRB1 (ITIMs: 1, 2, 3*, 4*) |

Inactivation of all four ITIMs resulted in a non-functional inhibitory CAR (C2182). Inactivation of only two of the four ITIMs preserved the inhibitor function of the CAR at the concentrations tested (C1760 and C1762). Inactivation of all four ITIM (C1759) demonstrates that the ITIMs are necessary for inhibitory function. When all four ITIMs are mutated, the molecule loses inhibitory function. When only two of the four ITIMs are mutated, inhibitory activity is retained.

Figure 8:
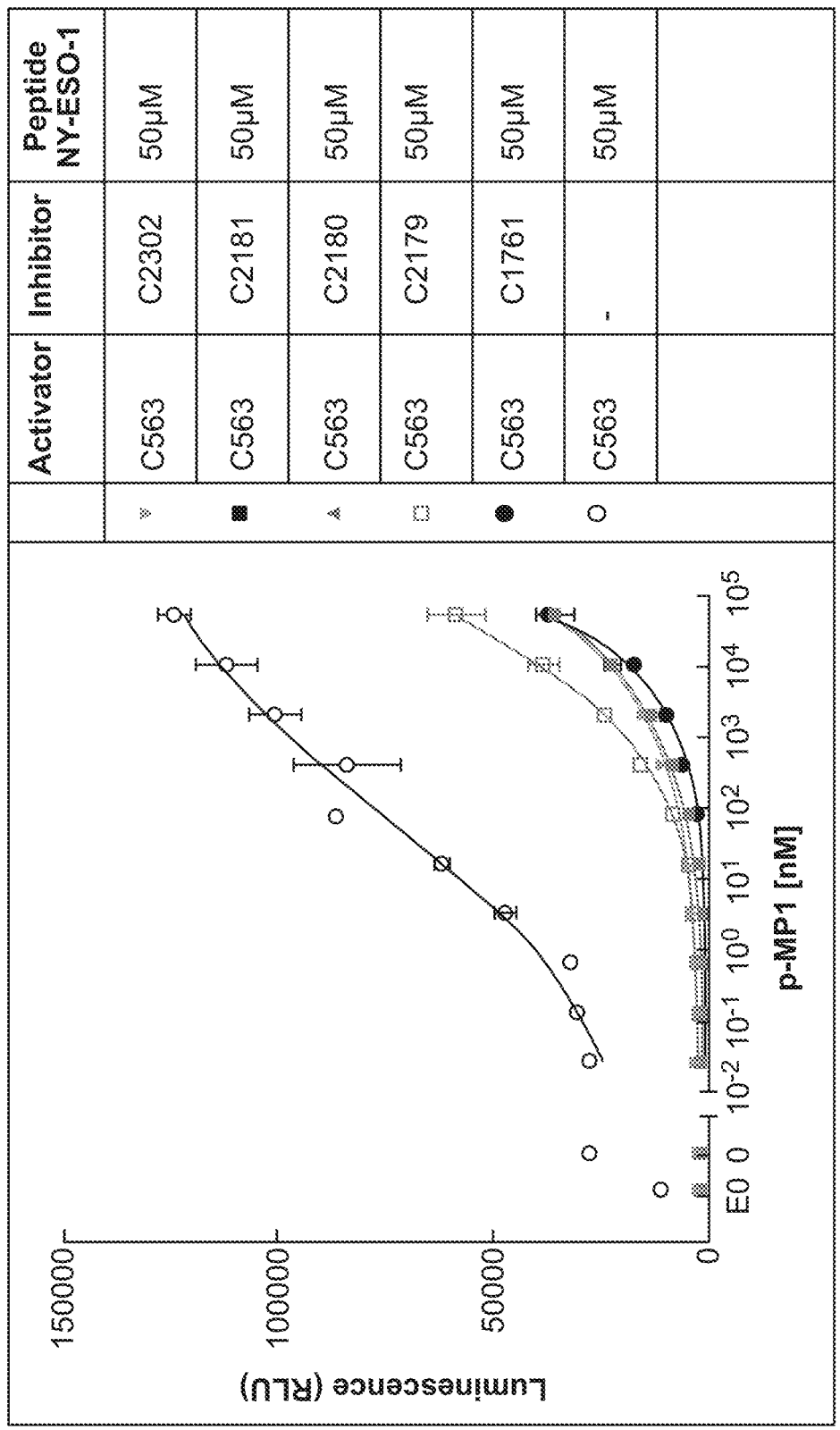
FIG. 8 shows a chart of luminescence in an NFAT-based reporter assay (RLU) at varying concentrations of MAGE-A3 peptide 1 (MP1, nM) for the indicated constructs in the presence of 50 μM NY-ESO-1 peptide.

FIG. 8 shows testing of LILRB1 ITIMs in combinations different from those of the native LILRB1 intracellular domain. As shown in Table 3, CARs having the third and fourth ITIMs of LILRB1 in four or six total copies achieve inhibitory activity comparable to the native LILRB1 intracellular domain. Inhibitory activity is also observed when only one copy each of the third and fourth ITIMs are used (C2179) or when two copies of each ITIM is used (C2180) or when multiple copies are used (C2302 or C2180).

TABLE 3

|  | LBD | Hinge | TM | ICD |
|---|---|---|---|---|
| C563 | MAGE-A3 pep1 scFv | CD8[117-161] | CD28[135-161] | CD28[136-202] 41BB[197-238] CD3z[31-127] |
| C1761 | NY-ESO-1 scFv | LILRB1 | LILRB1 | LILRB1 (ITIMs: 1, 2, 3, 4) |
| C2302 | NY-ESO-1 scFv | LILRB1 | LILRB1 | LILRB1 (ITIMs: 3, 4, 3, 4, 3, 4) |
| C2181 | NY-ESO-1 scFv | LILRB1 | LILRB1 | LILRB1 (ITIMs: 3, 4, 3, 4) |
| C2180 | NY-ESO-1 scFv | LILRB1 | LILRB1 | LILRB1 (ITIMs: 1, 2, 3, 4, 3, 4) |
| C2179 | NY-ESO-1 scFv | LILRB1 | LILRB1 | LILRB1 (ITIMs: 3, 4) |

Example 2: LILRB1 Hinge and Transmembrane Domains Enhance the Inhibitory Activity of BTLA-Based Inhibitory CARs BTLA-Based CAR and LILRB1/BTLA-Based CARs Inhibit Signaling Via NFAT B- and T-lymphocyte attenuator (BTLA), also known as CD272 (cluster of differentiation 272) interacts with B7 homology B7H4. Unlike CTLA-4 and PD-1, it is also a ligand for tumour necrosis factor (receptor) superfamily, member 14 (TNFRSF14). Inhibitory signaling through BTLA occurs in response to binding of B7H4 or TNFRSF14.

Figure 9:
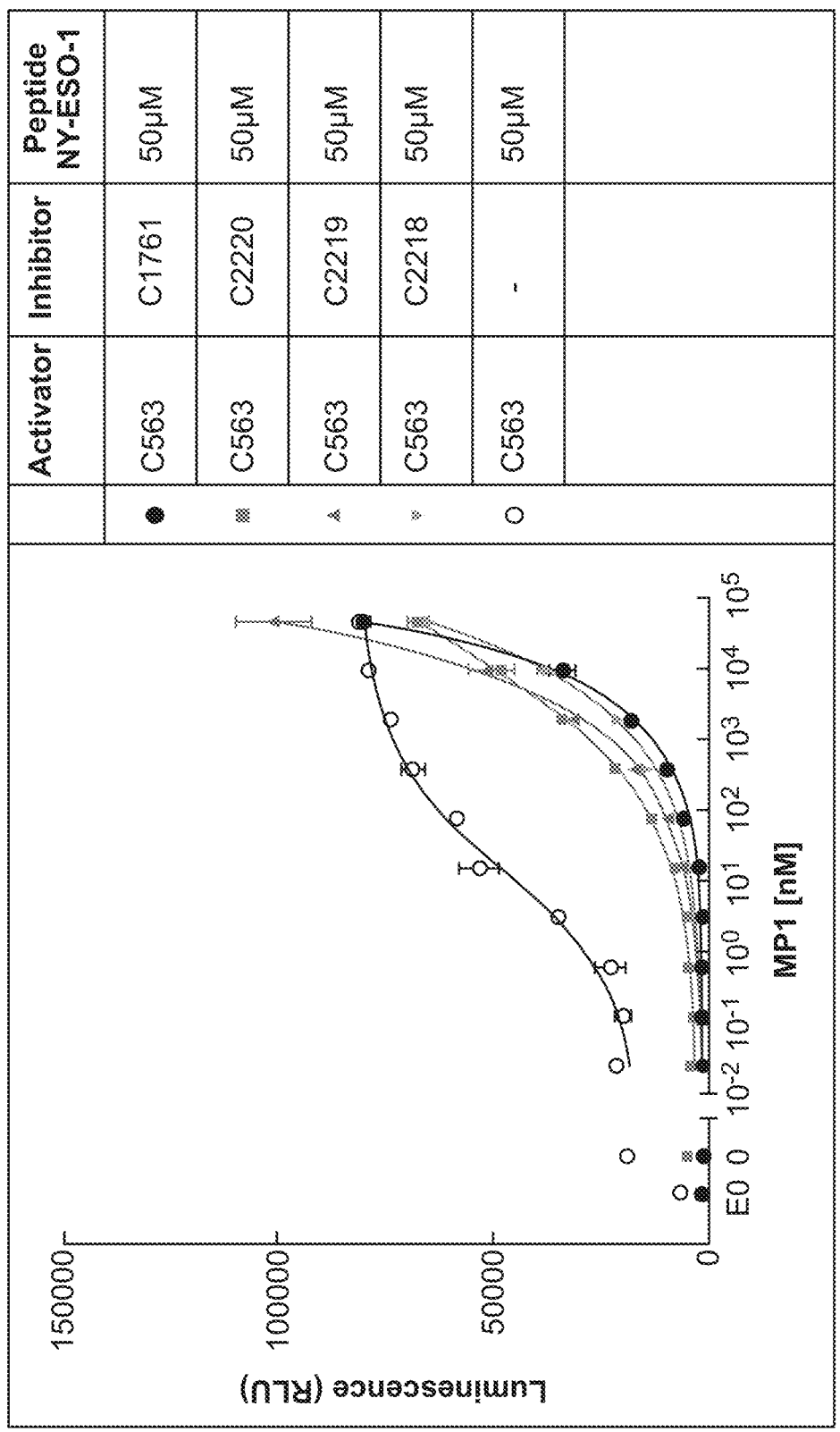
FIG. 9 shows a chart of luminescence in an NFAT-based reporter assay (RLU) at varying concentrations of MAGE-A3 peptide 1 (MP1, nM) for the indicated constructs in the presence of 5 μM NY-ESO-1 peptide.

The full length BTLA protein was cloned into a construct having an extracellular scFv domain (C2220), a construct replacing the extracellular domain of BTLA with that of LILRB1 (C2219), and a construct replacing the extracellular and transmembrane domains of BTLA with those of LILRB1 (C2218) were generated and tested, as shown in Table 4 and FIG. 9. The LILRB1-BTLA fusion exhibits inhibitory signaling comparable to the LILRB1-based CAR.

TABLE 4

|  | LBD | Hinge | TM | ICD |
|---|---|---|---|---|
| C563 | MAGE-A3 pep1 scFv | CD8[117-161] | CD28[135-161] | CD28[136-202] 41BB[197-238] CD3z[31-127] |
| C1761 | NY-ESO-1 scFv | LILRB1 | LILRB1 | LILRB1 |
| C2218 | NY-ESO-1 scFv | LILRB1 | LILRB1 | BTLA |
| C2219 | NY-ESO-1 scFv | LILRB1 | BTLA | BLTA |
| C2220 | NY-ESO-1 scFv | BTLA | BTLA | BTLA |

Example 3: LILRB1 Hinge and Transmembrane Compared to CD8 or CD28

Figure 10:
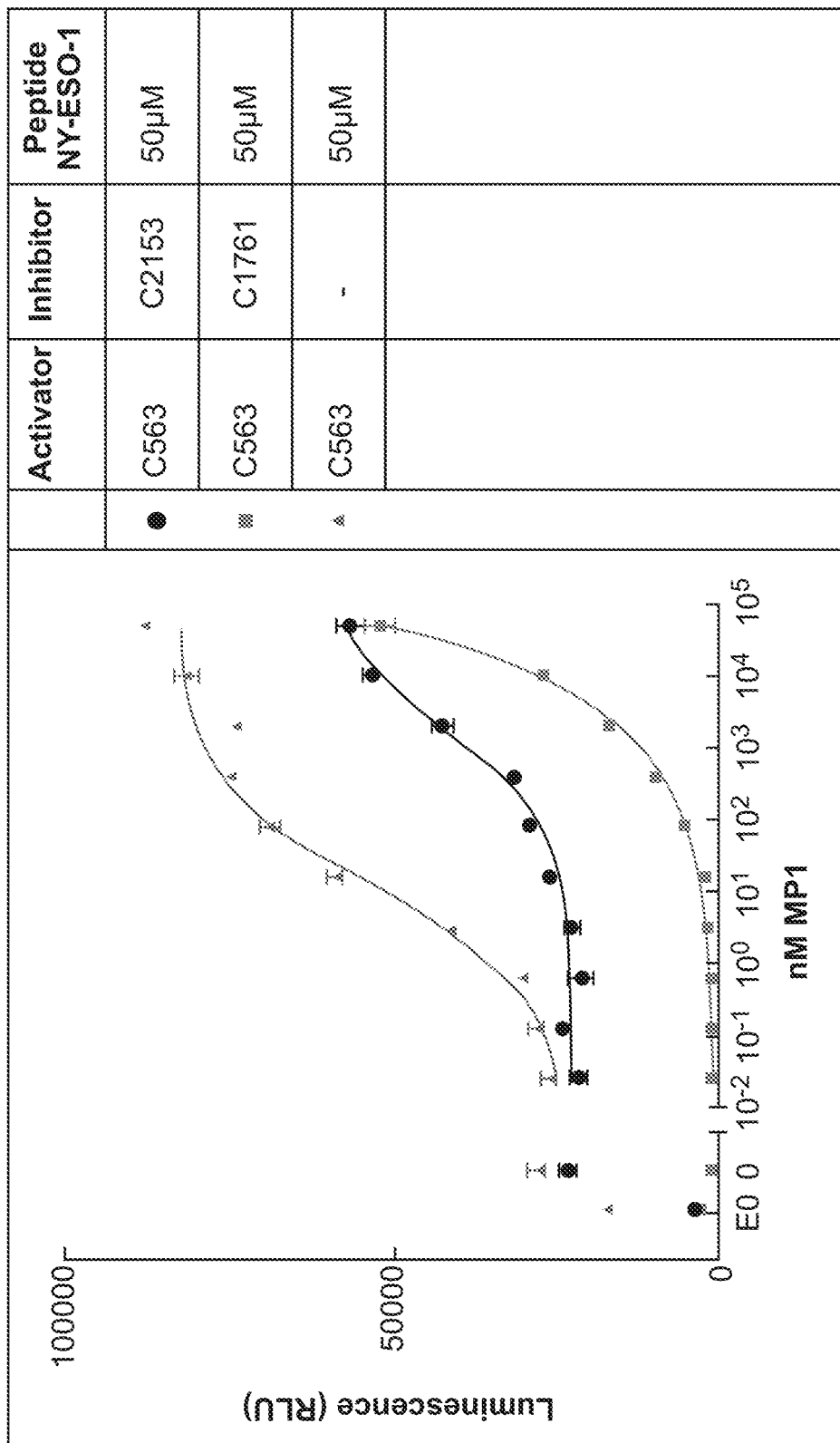
FIG. 10 shows a chart of luminescence in an NFAT-based reporter assay (RLU) at varying concentrations of MAGE-A3 peptide 1 (MP1, nM) for the indicated constructs in the presence of 50 µM NY-ESO-1 peptide.

LILRB1-Based CA1 with LILRB1 Hinge and Transmembrane is Superior to CD8 Hinge and CD28 Transmembrane Region The LILRB1-based CAR was compared to a CAR having the LILRB1 intracellular domain but CD8 hinge and CD28 transmembrane region, as shown in Table 5 and FIG. 10.

TABLE 5

|  | LBD | Hinge | TM | ICD |
|---|---|---|---|---|
| C563 | MAGE-A3 pep1 scFv | CD8[117-161] | CD28[135-161] | CD28[136-202] 41BB[197-238] CD3z[31-127] |
| C1761 | NY-ESO-1 scFv | LILRB1 | LILRB1 | LILRB1 |
| C2153 | NY-ESO-1 scFv | CD8 | C28 | LILRB1 |

The LILRB1 hinge and transmembrane region generate results surprisingly superior to a construct having the CD8 hinge and CD28 transmembrane regions. Emin is decreased. Overall dynamic range is increased. Inhibitory potency is increased.

TABLE 6

Summary of results shown in Examples 1-3.

| Inhibitor Construct | Activator Construct | uM Inhibitor peptide | $E_{min}$[RLU] | $EC_{50}$[nM] | $E_{max}$[RLU] |
|---|---|---|---|---|---|
| — | C563 | 50 | 30,000 | 10 | 100,000 |
| — | CT139 | 50 | 0 | 20 | 100,000 |
| C1761 | C563 | 50 | 1,000 | >10,000 | NA |
| C1761 | CT139 | 50 | 400 | >1,000 | NA |
| C1759 | C563 | 50 | 20,000 | 200 | 100,000 |
| C1760 | C563 | 50 | 5,000 | 60 | 100,000 |
| C1762 | C563 | 50 | 5,000 | 600 | 90,000 |
| C2184 | C563 | 50 | 1,000 | >1,000 | NA |
| C2183 | C563 | 50 | 4,000 | >1,000 | NA |
| C2182 | C563 | 50 | 30,000 | 30 | 90,000 |
| C2302 | C563 | 50 | 0 | >10,000 | NA |
| C2181 | C563 | 50 | 0 | >10,000 | NA |
| C2180 | C563 | 50 | 0 | >10,000 | NA |
| C2179 | C563 | 50 | 0 | >10,000 | NA |
| C2218 | C563 | 50 | 1,000 | >1,000 | NA |
| C2219 | C563 | 50 | 2,000 | >1,000 | NA |
| C2220 | C563 | 50 | 3,000 | >1,000 | NA |
| C2153 | C563 | 50 | 20,000 | 2,000 | 60,000 |
| C2107 | CT139 | 5 | 0 | 100 | 100,000 |
| C2106 | CT139 | 5 | 0 | 40 | 100,000 |

Example 4: TCR-Based Inhibitory Chimeric Antigen Receptors

Construct Design and Cloning

The NY-ESO-1-responsive inhibitory constructs were created using the high affinity anti-HLA-A*02:01/NY-ESO-1 1G4α95:LY T cell receptor (TCR) variant. The charged residues in the TM of TCRα (R253 and K258) and TCRβ (K288) were mutated to leucine. Then, the LILRB1 ITIM (residues 484-650) was appended to the mutated TCRα or TCRs. Anti-HLA-A*02:01/MAGE-A3 single chain variable fragment (scFv) was generated in-house. The anti-HLA-A2*02:01/MAGE-A3 chimeric antigen receptor (CAR) used in this study contains the anti-HLA-A*02:01/MAGE-A3 scFv, CD8 hinge, CD28 TM, and CD28, 41BB, and CD3ζ intracellular domains (ICDs). All fragments, including 5' and 3' BsmBI sites, were amplified using Q5 polymerase (New England Biolabs) and digested with DpnI (Thermo Scientific) at 37° C. for 60 min. The generated PCR fragments were purified using the Nucleospin gel and PCR cleanup kit (Macherey-Nagel). The plasmids were Golden Gate assembled in a reaction containing BsmBI (Thermo Scientific), T4 DNA ligase (Thermo Scientific), 10 mM ATP, and 1× FastDigest buffer (Thermo Scientific).

Jurkat NFAT Activation Assay

Jurkat T lymphocytes that contain firefly luciferase gene under the control of the nuclear factor of activator T cells (NFAT) transcription factor (BPS Bioscience) were co-transfected with plasmids encoding TCR and/or scFv-fusion constructs using the Neon transfection system (Thermo Fisher). The electroporated cells were incubated in RPMI media supplemented with 20% fetal bovine serum (FBS) heat-inactivated at 56° C. for 60 min (HIA-FBS) and 0.1% pencillin-streptomycin (P/S) (Gibco). TAP deficient T2 lymphoblasts (ATCC RL-1992) were loaded with varying amounts of a modified NY-ESO-1 peptide (SLLMWITQV) (SEQ ID NO: 107) alone, MAGE-A3 peptide (FLWGPRALV) (SEQ ID NO: 106) alone, or varying amounts of MAGE-A3 peptide in addition to 50 μM NY-ESO-1 peptide in RPMI supplemented with 1% BSA and 0.1% P/S (Gibco). Peptides used in the assay were synthesized to >95% purity assessed by mass spectrometry (Genscript). 18 hours post-transfection, Jurkats were resuspended at 0.8×10⁶ cells per mL in RPMI supplemented with 10% HIA-FBS and 1% P/S. In a 384 well plate, 12000 Jurkats were co-cultured with 12000 peptide-loaded T2s per well at 37° C., 5% $CO_2$ for 6 hours. NFAT-mediated luciferase production was measured by adding 15 uL of ONE-Step luciferase assay reagent (BPS Bioscience). After 20 minutes, luminescence was detected using a plate reader (Tecan).

TCR-Based Inhibitory CARs Using the LILRB1 Intracellular Domain

Figure 11:
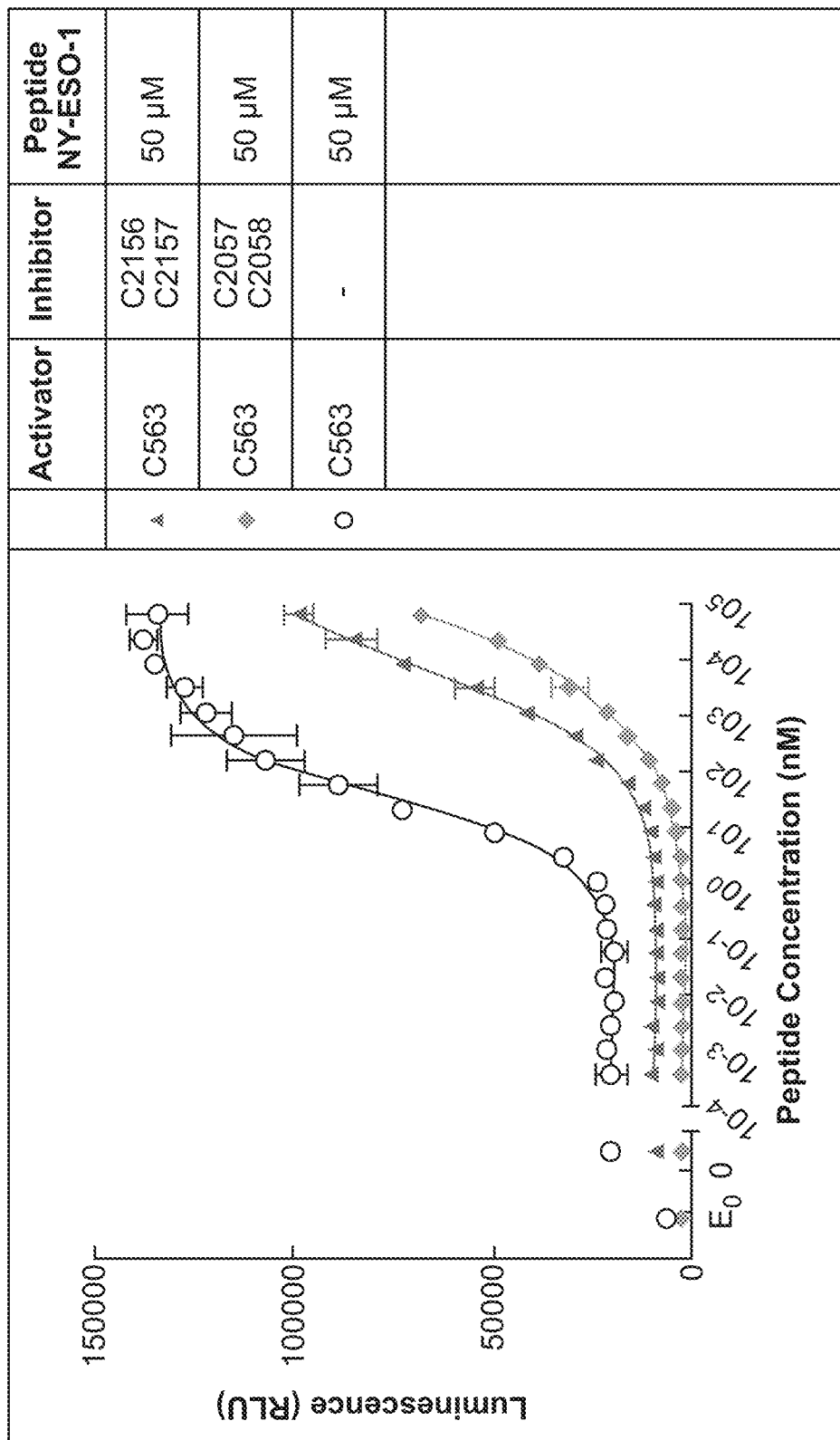
FIG. 11 shows a chart of luminescence in an NFAT-based report assay (RLU) at varying concentrations of MAGE-A3 peptide 1 (MP1, nM) for the indicated constructs in the presence of 50 µM NY-ESO-1 peptide.

As shown in Table 7 and FIG. 11, co-expression of TCR-based CARs having either only the extracellular domains of the TCR or also having the transmembrane regions of the TCRs with mutations to polar residues, yield functional inhibitory CARs.

TABLE 7

| | LBD | Hinge | TM | ICD |
|---|---|---|---|---|
| C563 | MAGE-A3 pep1 scFv | CD8[117-161] | CD28[135-161] | CD28[136-202] 41BB[197-238] CD3z[31-127] |
| C2057 | TCR 1G4:α95LY α | | LILRB1 | LILRB1 |
| C2058 | TCR 1G4:α95LY α | | LILRB1 | LILRB1 |

TABLE 7-continued

| | LBD | Hinge | TM | ICD |
|---|---|---|---|---|
| C2156 | TCR 1G4: α95LY α | | TCR 1G4: α95LY α (R253L/K258L) | LILRB1 |
| C2157 | TCR 1G4: α95LY α | | TCR 1G4: α95LY β (K288L) | LILRB1 |

TCR-base CARs inhibit the anti-HLA-A*02:01 MAGE-A3 CAR in trans. Jurkat-NFAT luciferase reporter cells were transfected with (1) anti-HLA-A*02:01/MAGE-A3 CAR alone (C563), (2) co-transfected with MAGE-A3 CAR (C563) and TCRα(R253L/K258L)-LILRB1 fusion and TCRβ(K288L)-LILRB1 ICD fusion TCR-inhibitory fusion construct (C2156+C2157) or (3) co-transfected with MAGE-A3 CAR and TCRαECD/TCRβECD-LIRT1(TM+ICD) fusion (C2057+C2058) TCR-inhibitory fusion construct. The effects of the two inhibitory variants on NFAT activation was measured by co-culturing transfected Jurkat cells with T2 cells loaded with 50 μM NY-ESO-1 peptide in combination with varying amounts of MAGE-A3 peptide. Data are summarized in Table 8.

TABLE 8

Trans effect of TCR-inhibitory fusion constructs on MAGE-A3 CAR

| Inhibitor Construct | Activator Construct | μM Inhibitor peptide | $E_{min}$[RLU] | $EC_{50}$[nM] | $E_{max}$[RLU] |
|---|---|---|---|---|---|
| — | C563 | 50 | 19949 | 24.52 | 134443 |
| C2057 + C2058 | C563 | 50 | 2072 | >10,000 | NA |
| C2156 + C2157 | C563 | 50 | 9198 | 7108 | NA |

Truncated TCR alpha or TCR beta extracellular domains (ECD)– with LILRB1 TM– ICD fusions inhibit CAR activation. TCR alpha or TCR beta extracellular domains (ECD)– with TCR TM– LILRB1 ICD fusions also acted as inhibitor CARs when the TCR transmembrane mutations abolish TCR-CD3 subunit interactions. The experiment demonstrates that the TCR α chain and β chains can be used to generate inhibitory chimeric antigen receptors by interfering with recruitment of stimulatory factors by CD3 subunits.

Example 5: Methods for Examples 6-14

Cell Culture

Jurkat cells encoding an NFAT luciferase reporter were obtained from BPS Bioscience. All other cell lines used in this study were obtained from ATCC. In culture, Jurkat cells were maintained in RPMI media supplemented with 10% FBS, 1% Pen/Strep and 0.4 mg/mL G418/Geneticin. T2, MCF7, Raji, K562 and HeLa cells were maintained as suggested by ATCC. "Normal" Raji cells were made by transducing Raji cells with HLA-A*02 lentivirus (custom lentivirus, Alstem) at a MOI of 5. HLA-A*02-positive Raji cells were sorted using a FACSMelody Cell Sorter (BD).

Plasmid Construction

The NY-ESO-1-responsive inhibitory construct was created by fusing the NY-ESO-1 scFv LBD to domains of receptors including hinge, transmembrane region, and/or intracellular domain of leukocyte immunoglobulin-like receptor subfamily B member 1, LILRB1 (LIR-1), programmed cell death protein 1, PDCD1 (PD-1), or cytotoxic T-lymphocyte protein 4, CTLA4 (CTLA-4). All activating CAR constructs contained an scFv fused to the CD8a hinge, CD28 TM, and CD28, 4-1BB and CD3zeta ICDs. The CD19-activating CAR scFv was derived from the FMC63 mouse hybridoma. MSLN-activating CAR scFvs were derived from human M5 (LBD1) as described and humanized SS1 (LBD2). Gene segments were combined using Golden Gate cloning and inserted downstream of a human EF1α promoter contained in a lentiviral expression plasmid.

Jurkat Cell Transfection

Jurkat cells were transiently transfected via 100 uL format Neon electroporation system (Thermo Fisher Scientific) according to manufacturer's protocol using the following settings: 3 pulses, 1500V, 10 msec. Cotransfection was performed with 1-3 ug of activator CAR or TCR construct and 1-3 ug of either scFv or TCR alpha/TCR beta LIR-1 blocker constructs or empty vector per 1e6 cells and recovered in RPMI media supplemented with 20% heat-inactivated FBS and 0.1% Pen/Strep. To confirm blocker surface expression, Jurkat cells were stained 18-24 hours post-transfection with 10 ug/mL streptavidin-PE-HLA-A*02-pMHC tetramer for 60 minutes at 4° C. in PBS with 1% BSA and characterized by flow cytometry (BD FACSCanto II).

Jurkat-NFAT-Luciferase Activation Studies

Peptides, MAGE-A3 (MP1; FLWGPRALV; SEQ ID NO: 106), MAGE-A3 (MP2; MPKVAELVHFL; SEQ ID NO: 108), HPV E6 (TIHDIILECV; SEQ ID NO: 109), HPV E7 (YMLDLQPET: SEQ ID NO: 110) and modified NY-ESO-1 ESO (ESO; SLLMWITQV; SEQ ID NO: 107), were synthesized by Genscript. Activating peptide was serially diluted starting at 50 uM. Blocker peptide, NY-ESO-1, was diluted to 50 uM (unless otherwise indicated) which was added to the activating peptide serial dilutions and subsequently loaded onto 1e4 T2 cells in 15 uL of RPMI supplemented with 1% BSA and 0.1% Pen/Strep and incubated in Corning® 384-well Low Flange White Flat Bottom Polystyrene TC-treated Microplates. The following day, 1e4 Jurkat cells were resuspended in 15 uL of RPMI supplemented with 10% heat-inactivated FBS and 0.1% Pen/Strep, added to the peptide-loaded T2 cells and co-cultured for 6 hours. ONE-Step Luciferase Assay System (BPS Bioscience) was used to evaluate Jurkat luminescence. For assays involving high density targets, Jurkat cells were similarly transfected and cocultured with tumor cells expressing target antigens at various Jurkat:tumor cell ratios. Assays were performed in technical duplicates.

Primary T Cell Transduction, Expansion, and Enrichment

Leukopaks were purchased from AllCells®. Collection protocols and donor informed consent were approved by an Institutional Review Board (IRB), with strict oversight. HIPAA compliance and approved protocols were also followed. Frozen PBMCs were thawed in 37° C. water bath and cultured at 1e6 cells/mL in LymphoONE (Takara) with 1% human serum and activated using 1:100 of T cell TransAct (Miltenyi) supplemented with IL-15 (10 ng/mL) and IL-21 (10 ng/mL). After 24 hours, lentivirus was added to PBMCs at MOI=5. Activator and blocker receptors were simultaneously co-transduced at a MOI=5 for each lentivirus. PBMCs were cultured for 2-3 additional days to allow cells to expand under TransAct stimulation. Post expansion, activator and blocker transduced primary T cells were enriched for blocker-positive T cells by positive selection using anti-PE microbeads (Miltenyi) according to manufacturer's instructions. Briefly, primary T cells were incubated with 10 ug/mL streptavidin-PE-HLA-A*02-pMHC tetramer for 60 minutes at 4° C. in MACS buffer (0.5% BSA+2 mM EDTA in PBS). Cells were washed 3 times in MACS buffer and passed through the LS column (Miltenyi) to separate blocker-positive cells (a mix of blocker-only and activator+blocker cells) from untransduced and activator-only cells.

Primary T Cell In Vitro Cytotoxicity Studies

For cytotoxicity studies with pMHC targets, enriched primary T cells were incubated with 2e3 MCF7 cells expressing *Renilla* luciferase (Biosettia) loaded with a titration of target peptide as described above at an effector:target ratio of 3:1 for 48 hours. Live luciferase-expressing MCF7 cells were quantified using a *Renilla* Luciferase Reporter Assay System (Promega). For cytotoxicity studies with non-pMHC targets, enriched primary T cells were incubated with 2e3 WT Raji cells ("tumor" cells) or HLA-A*02 transduced Raji cells ("normal" cells) at an effector:target ratio of 3:1 for up to 6 days. WT "tumor" Raji cells stably expressing GFP and *Renilla* luciferase (Biosettia) or HLA-A*02 transduced "normal" Raji cells stably expressing RFP and firefly luciferase (Biosettia) were imaged together with unlabeled primary T cells using an IncuCyte live cell imager. Fluorescence intensity of live Raji cells over time was quantified using IncuCyte imaging software. For reversibility studies, enriched primary T cells were similarly cocultured with "normal" or "tumor" Raji cells for 3 days and imaged. After 3 days, T cells were separated from remaining Raji cells using CD19 negative selection and reseeded with fresh "normal" or "tumor" Raji cells as described. In separate wells, live luciferase-expressing Raji cells were quantified using a Dual-Luciferase Reporter Assay System (Promega) at 72 hours. For studies in which IFNγ secretion was assessed, supernatants collected after 48 hours of co-culture were tested for IFNγ using a BD Human IFNγ flex kit following manufacturer's exact instructions.

Mouse Xenograft Study

Frozen PBMCs were thawed in 37° C. water bath and rested overnight in serum-free TexMACS Medium (Miltenyi) prior to activation. PBMCs were activated in 1.5e6 cells/mL using T cell TransAct (Miltenyi) and TexMACS Medium supplemented with IL-15 (20 ng/mL) and IL-21 (20 ng/mL). After 24 hours, lentivirus was added to PBMCs at a MOI of 5. PBMCs were cultured for 8-9 additional days to allow cells to expand under TransAct stimulation. Post expansion, T cells were enriched on A2-LIR-1 using anti-PE microbeads (Miltenyi) against streptavidin-PE-HLA-A*02-pMHC for 2-5 additional days prior to in vivo injection. Enriched T cells were also validated by flow cytometry (BD FACSCanto II) for expression of CD19 scFv activator and HLA-A*02 LIR-1 blocker by sequential staining with CD19-Fc (1:100; R&D Systems) and goat anti-human IgG-FITC (1:200; Invitrogen) for activator and 10 ug/mL streptavidin-APC-HLA-A*02-pMHC for blocker.

In vivo experiments were conducted by Explora BioLabs under Institutional Animal Care and Use Committee (IACUC)-approved protocols. 5-6 week old female NOD.Cg-Prkdcscid Il2rgtm1Wjl Tg(HLA-A/H2-D/B2M)1Dvs/SzJ (NSG-HLA-A2/HHD) mice were purchased from The Jackson Labs. Animals were acclimated to the housing environment for at least 3 days prior to the initiation of the study. Animals were injected with 2e6 WT Raji cells or HLA-A*02 transduced Raji cells in 100 uL volume subcutaneously in the right flank. When tumors reached an average of 70 mm3 (V=L×W×W/2), animals were randomized into 5 groups (n=7) and 2e6 or 1e7 T cells were administered via the tail vein. Post T cell injection, tumor measurements were performed 3 times per week and blood was collected 10 days and 17 days after for flow analysis. One animal from the WT Raji group receiving 1e7 CD19-CAR+A2-LIR-1 T cells was excluded from the study due to a failed tail vein injection, followed by flow cytometry confirmation of the absence of human T cells in the blood. At each time point, human T cells in the blood were quantified by flow cytometry (BD FACSCanto II) post RBC lysis. Cells were stained with anti-mouse CD45-FITC (clone 30-F11), anti-human CD3-PE (clone SK7), anti-human CD4-APC (clone OKT4), and anti-human CD8-PerCP-Cy5.5 (clone RPA-T8). All antibodies were obtained from Biolegend and used at a 1:100 dilution. DAPI (Invitrogen) was used to exclude dead cells from analysis. For histopathological analysis, tumor samples were fixed, sectioned and stained for huCD3 (clone EP449E). Image quantification was done using ImageJ software.

Statistical Analysis

Statistical analyses were performed using GraphPad Prism software. All peptide and cell titration studies are shown as mean±standard deviation (SD), while in vitro and in vivo studies using primary T cells are shown as mean±standard error of the mean (SEM), unless otherwise noted. Peptide and cell titration curves were fit using a four-parameter non-linear regression analysis. EC50 values were calculated directly from the curves. All other groups of data were analyzed using an ordinary two-way ANOVA followed by a Tukey's multiple-comparisons test, unless otherwise noted.

Example 6: Assaying the Effect of the LIR-1 Hinge on Blocking Activity

Figure 12A:
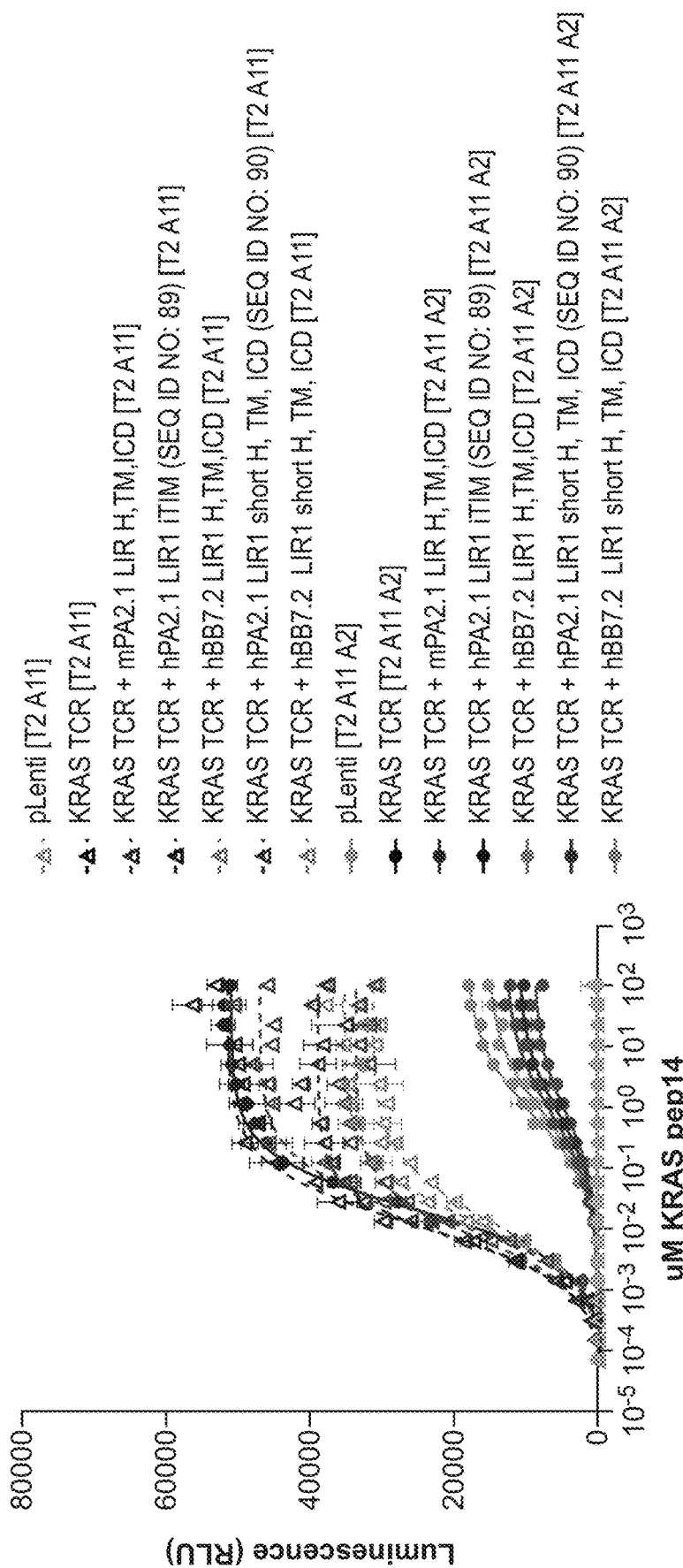
FIG. 12A is a plot showing the effect of LIR-1 hinge on the ability of an HLA-A*02 scFv inhibitory receptor to block activation of Jurkat cells by a KRAS TCR. H: hinge, T: transmembrane domain, ICD: intracellular domain, s: short. LIR-1 constructs are described in more detail in FIG. 12B. Humanized PA2.1 and humanized BB7.2 with shorter LIR-1 hinge block similarly to original, longer hinge.
Figure 12B:
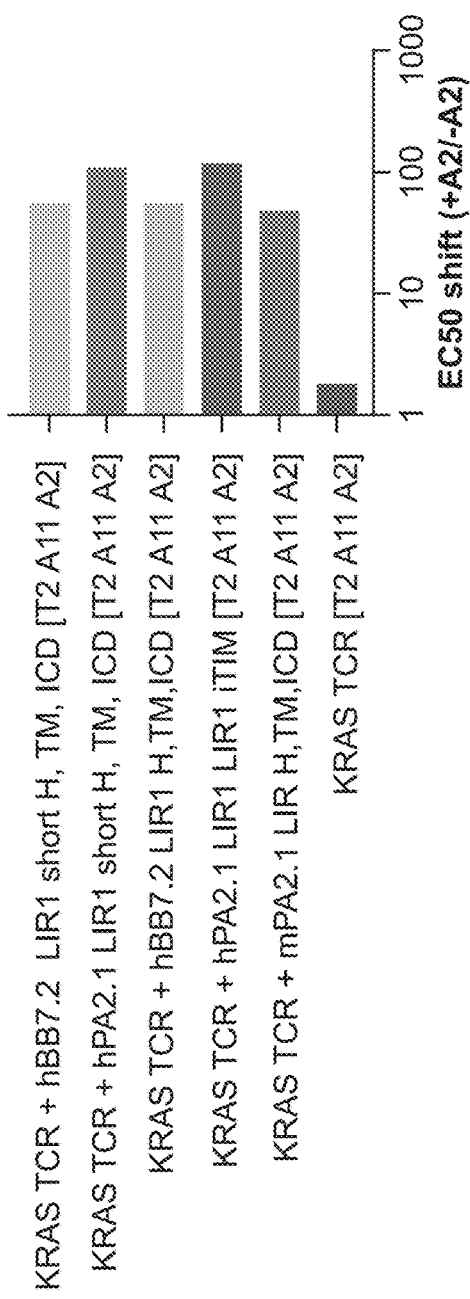
FIG. 12B is a plot and a table showing EC50 shift (+/−HLA-A*02 target cells) for Jurkat cells expressing a KRAS TCR activator and the HLA-A*02 scFv LIR-1 inhibitory receptor shown in the table at bottom.
Figure 13A:
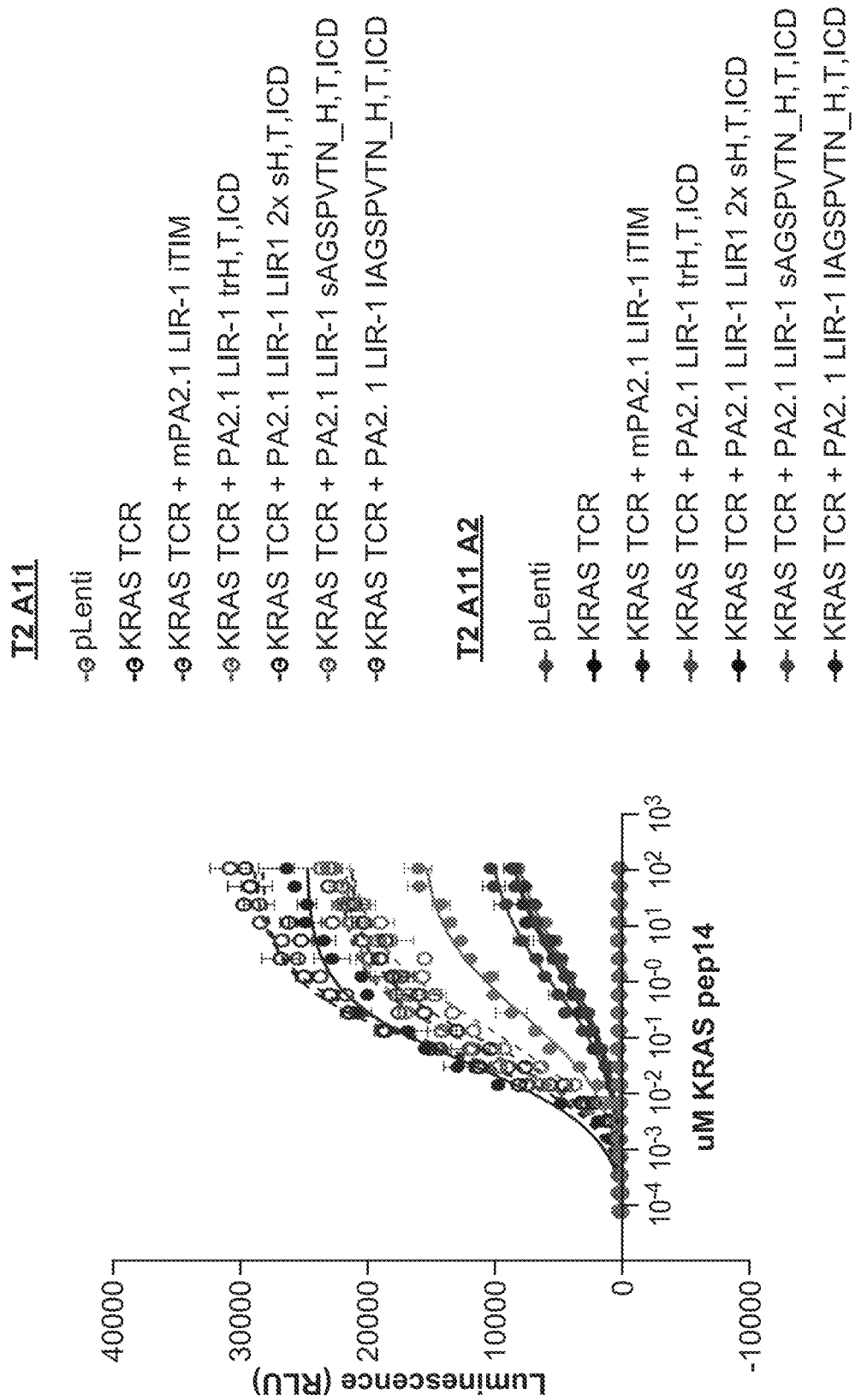
FIG. 13A is a plot showing the effect of LIR-1 hinge on the ability of an HLA-A*02 inhibitory receptor to block activation of Jurkat cells by a KRAS TCR. H: hinge, TM: transmembrane domain, ICD: intracellular domain, s: short; tr: truncated. LIR-1 constructs are described in more detail in FIG. 13B. Mouse PA2.1 with slightly longer hinges function similarly to original LIR-1 hinge in T2-Jurkat assay.
Figure 13B:
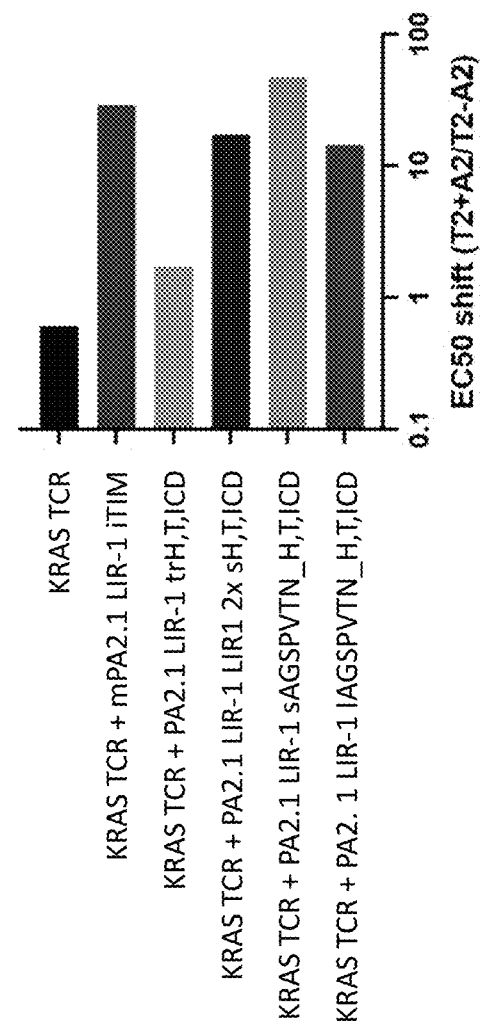
FIG. 13B is a plot and a pair of tables showing EC50 shift (+/−HLA-A*02 target cells) for Jurkat cells expressing a KRAS TCR activator and the HLA-A*02 scFv LIR-1 inhibitory receptors shown in the table at bottom, with hinge lengths shown in the table at left.

The effects of different LIR-1 hinges on the ability of HLA-A*02 scFv LIR-1 inhibitory receptors to block killing by Jurkat cells expressing a KRAS TCR activator was assayed using the Jurkat NFat Luciferase assays described supra. A humanized PA2.1 scFv LIR-1 receptor and humanized BB7.2 scFv LIR-1 with a shorter LIR-1 hinge were assayed in Jurkat cells as previously described, and the results are shown in FIGS. 12A-12B. Jurkat cells were transfected with a KRAS TCR activator receptor and/or HLA-A*02 scFv LIR-1 inhibitory receptor (humanized PA2.1 or humanized BB7.2) with a variety of LIR-1 derived hinges, and co-cultured with T2 target cells that were either HLA:A11 positive, or HA:A11 and HLA:A02 positive. Inhibitory receptors with both the shorter and longer hinge behaved similarly (FIG. 12A-12B). An inhibitory receptor with a mouse PA2.1 scFv and slightly longer hinges was also assayed functioned similarly to shorter LIR-1 hinges in the T2-Jurkat assay (FIG. 13A-13B). Hinge sequences are shown in black in FIG. 12B and FIG. 13B, with the gray SS in the sequences in FIG. 13B representing a linker between the antigen-binding domain and the hinge, and the gray VIGIL the start of the LLR-1 transmembrane domain. Hinge, transmembrane domain and intracellular domain of the inhibitory receptors were all derived from LIR-1. FIGS. 12A-12B and 13A-13B show that LIR-1 hinge length can be varied without negatively effecting the LIR-1 inhibitory receptor. Shorter hinges can provide an advantage when packaging nucleic acid sequences encoding LIR-1 inhibitory receptors in lentiviral vectors for delivery.

TABLE 9

Sequences of constructs

| Name | Amino Acid Sequence | Nucleotide Sequence |
|---|---|---|
| PA2.1.14 (VL:VH) scFv LIR1 sHTICD | TEFTLTISSLQPD DFATYYCFQGSHV PRTFGQGTKVEVK GGGGSGGGGSGG GSGGGQVQLVQSGA EVKKPGSSVKVSC KASGYTFTSYHIH WVRQAPGQGLEWI GWIYPGNVNTEYN EKFKGKATITADE STNTAYMELSSLR SEDTAVYYCAREE ITYAMDYWGQGTL VTVSSVVSGPSGG PSSPTTGPTSTSG PEDQPLTPTGSDP QSGLGRHLGVVIG ILVAVILLLLLLL LLFLILRHRRQGK HWTSTQRKADFQH PAGAVGPEPTDRG LQWRSSPAADAQE ENLYAAVKHTQPE DGVEMDTRSPHDE DPOAVTYAEVKHS RPRREMASPPSPL SGEFLDTKDRQAE EDRQMDTEAAASE APQDVTYAQLHSL TLRREATEPPPSQ EGPSPAVPSIYAT LAIH (SEQ ID NO: 92) | GACATTCAAATGACC CAGAGCCCATCCACC CTGAGCGCATCTGTA GGTGACCGGGTCACC ATCACTTGTAGATCC AGTCAGAGTATTGTA CACAGTAATGGGAAC ACCTATTTGGAATGG TATCAGCAGAAACCA GGTAAAGCCCCAAAA TTGCTCATCTACAAA GTCTCTAACAGATTT AGTGGTGTACCAGCC AGGTTCAGCGGTTCC GGAAGTGGTACTGAA TTCACCCTCACGATC TCCTCTCTCCAGCCA GATGATTTCGCCACT TATTACTGTTTTCAA GGTTCACATGTGCCG CGCACATTCGGTCAG GGTACTAAAGTAGAA GTCAAAGGCGGAGGT GGAAGCGGAGGGGGA GGATCTGGCGGCGGA GGAAGCGGAGGGCAG GTGCAGCTGGTGCAG TCTGGGGCTGAGGTG AAGAAGCCTGGGTCC TCAGTGAAGGTTTCC TGCAAGGCTTCTGGA TACACCTTCACTAGC TATCATATACATTGG GTGCGCCAGGCCCCC GGACAAGGGCTTGAG TGGATCGGATGGATC TACCCTGGCAATGTT AACACAGAATATAAT GAGAAGTTCAAGGGC AAAGCCACCATTACC GCGGACGAATCCACG AACACAGCCTACATG GAGCTGAGCAGCCTG AGATCTGAAGACACG GCTGTGTATTACTGT GCGAGGGAGGAAATT ACCTACGCTATGGAC TACTGGGGCCAGGGA ACCCTGGTCACCGTG TCCTCAGTGGTCTCT GGAGCGTCTGGGGGC CCCAGCTCCCCGACA ACAGGCCCCACCTCC ACATCTGGCCCTGAG GACCAGCCCCTCACC |

TABLE 9-continued

Sequences of constructs

| Name | Amino Acid Sequence | Nucleotide Sequence |
|---|---|---|
| | | CCCACCGGGTCGGAT CCCCAGAGTGGTCTG GGAAGGCACCTGGGG GTTGTGATCGGCATC TTGGTGGCCGTCATC CTACTGCTCCTCCTC CTCCTCCTCCTCTTC CTCATCCTCCGAGAT CGACGTCAGGGCAAA CACTGGACATCGACC CAGAGAAAGGCTGAT TTCCAACATCCTGCA GGGGCTGTGGGGCCA GAGCCCACAGACAGA GGCCTGCAGTGGAGG TCCAGCCCAGCTGCC GATGCCCAGGAAGAA AACCTCTATGCTGCC GTGAAGCACACACAG CCTGAGGATGGGGTG GAGATGGACACTCGG AGCCCACACGATGAA GACCCCAGGCAGTG ACGTATGCCGAGGTG AAACACTCCAGACCT AGGAGAGAAATGGCC TCTCCTCCTTCCCCA CTGTCTGGGGAATTC CTGGACACAAAGGAC AGACAGGCGGAAGAG GACAGGCAGATGGAC ACTGAGGCTGCTGCA TCTGAAGCCCCCCAG GATGTGACCTACGCC CAGCTGCACAGCTTG ACCCTCAGACGGGAG GCAACTGAGCCTCCT CCATCCCAGGAAGGG CCCTCTCCAGCTGTG CCCAGCATCTACGCC ACTCTGGCCATCCAC TAG (SEQ ID NO: 114) |
| PA2.1.14 (VL:VH) scFv LIR1 HTICD | DIQMTQSPSTLSA SVGDRVTITCRSS QSIVHSNGNTYLE WYQQKPGKAPKLL IYKVSWRFSGVPA RFSGSGSGTEFTL TISSLQPDDFATY YCFQGSHVPRTFG QGTKVEVKGGGGS GGGGSGGGGSGGQ VQLVQSGAEVKKP GSSVKVSCKASGY TFTSYHIHWVRQA PGQGLEWIGWIYP GNVNTEYNEKFKG KATITADESTNTA YMELSSLRSEDTA VYYCAREEITYAM DYWGQGTLVTVSS YGSQSSKPYLLTH PSDPLELVVSGPS GGPSSPTTGPTST SGPEDQPLTPTGS DPQSGLGRHLGVV IGILVAVILLL1L LLLLHLILRHRRQ GKHWTSTQRKADF QHPAGAVGPEPTD RGLQWRSSPAADA QEENLYAAVKHTQ PEDGVEMDTRSPH | GACATTCAAATGACC CAGAGCCCATCCACC CTGAGCGCATCTGTA GGTGACCGGGTCACC ATCACTTGTAGATCC AGTCAGAGTATTGTA CACAGTAATGGGAAC ACCTATTTGGAATGG TATCAGCAGAAACCA GGTAAAGCCCCAAAA TTGCTCATCTACAAA GTCTCTAACAGATTT AGTGGTGTACCAGCC AGGTTCAGCGGTTCC GGAAGTGGTACTGAA TTCACCCTCACGATC TCCTCTCTCCAGCCA GATGATTTCGCCACT TATTACTGTTTTCAA GGTTCACATGTGCCG CGCACATTCGGTCAG GGTACTAAAGTAGAA GTCAAAGGCGGAGGT GGAAGCGGAGGGGGA GGATCTGGCGGCGGA GGAAGCGGAGGCCAG GTGCAGCTGGTGCAG TCTGGGGCTGAGGTG AAGAAGCCTGGGTCC TCAGTGAAGGTTTCC TGCAAGGCTTCTGGA |

TABLE 9-continued

Sequences of constructs

| Name | Amino Acid Sequence | Nucleotide Sequence |
|---|---|---|
| | DEDPQAVTYAEVK HSRPRREMASPPS PLSGEFLDTKDRQ AEEDRQMDTEAAA SEAPQDVTYAQLH SLTLRRSATEPPP SQEGPSPAVPSIY ATLAIH (SEQ ID NO: 91) | TACACCTTCACTAGC TATCATATACATTGG GTGCGCCAGGCCCCC GGACAAGGGCTTGAG TGGATCGGATGGATC TACCCTGGCAATGTT AACACAGAATATAAT GAGAAGTTCAAGGGC AAAGCCACCATTACC GCGGACGAATCCACG AACACAGCCTACATG GAGCTGAGCAGCCTG AGATCTGAAGACACG GCTGTGTATTACTGT GCGAGGGAGGAAATT ACCTACGCTATGGAC TACTGGGGCCAGGGA ACCCTGGTCACCGTG TCCTCATACGGCTCA CAGAGCTCCAAACCC TACCTGCTGACTCAC CCCAGTGACCCCCTG GAGCTCGTGGTCTCA GGACCGTCTGGGGGC CCCAGCTCCCCGACA ACAGGCCCCACCTCC ACATCGGCCCTGAG GACCAGCCCCTCACC CCCACCGGGTCGGAT CCCCAGAGTGGTCTG GGAAGGCACCTGGGG GTTGTGATCGGCATC TTGGTGGCCGTCATC CTACTGCTCCTCCTC CTCCTCCTCCTCTTC CTCATCCTCCGACAT CGACGTCAGGGCAAA CACTGGACATCGACC CAGAGAAAGGCTGAT TTCCAACATCCTGCA GGGGCTGTGGGGCCA GAGCCCACAGACAGA GGCCTGCAGTGGAGG TCCAGCCCAGCTGCC GATGCCCAGGAAGAA AACCTCTATGCTGCC GTGAAGCACACACAG CCTGAGGATGGGGTG GAGATGGACACTCGG AGCCCACACGATGAA GACCCCCAGGCAGTG ACGTATGCCGAGGTG AAACACTCCAGACCT AGGAGAGAAATGGCC TCTCCTCCTTCCCCA CTGTCTGGGGAATTC CTGGACACAAAGGAC AGACAGGCGGAAGAG GACAGGCAGATGGAC ACTGAGGCTGCTGCA TCTGAAGCCCCCCAG GATGTGACCTACGCC CAGCTGCACAGCTTG ACCCTCAGACGGGAG GCAACTGAGCCTCCT CCATCCCAGGAAGGG CCCTCTCCAGCTGTG CCCAGCATCTACGCC ACTCTGGCCATCCAC TAG (SEQ ID NO: 113) |
| PA2.1.14 scFv LIR1 | QVQLVQSGAEVKK PGSSVKVSCKASG YTFTSYHIHWVRQ | CAGGTGCAGCTGGTG CAGTCTGGGGCTGAG GTGAAGAAGCCTGGG |
| sHTICD | APGQGLEWIGWIY PGNVNTEYNEKFK GKATITADESTNT AYMELSSLRSEDT AVYYCAREEITYA MDYWGQGTLVTVS SGGGGSGGGGSGG GGSGGDIQMTQSP STLSASVGDRVTI TCRSSQSIVHSNG NTYLEWYQQKPGK APKLLIYKVSNRF SGVPARFSGSGSG TEFTLTISSLQPD DFATYYCFQGSHV PRTFGQGTKVEVK VVSGPSGGPSSPT TGPTSTSGPEDQP LTPTGSDPQSGLG RHLGVVIGILVAV ILLLLLLLLLFLI LRHRRQGKHWTST QRKADFQHPAGAV GPEPTDRGLQWRS SPAADAQEENLYA AVKHTQPEDGVEM DTRSPHDEDPQAV TYAEVKHSRPRRE MASPPSPLSGEFL DTKDRQAEEDRQM DTEAAASEAPQDV TYAQLHSLTLRRE ATEPPPSQEGPSP AVPSIYATLAIH (SEQ ID NO: 90) | TCCTCAGTGAAGGTT TCCTGCAAGGCTTCT GGATACACCTTCACT AGCTATCATATACAT TGGGTGCGCCAGGCC CCCGGACAAGGGCTT GAGTGGATCGGATGG ATCTACCCTGGCAAT GTTAACACAGAATAT AATGAGAAGTTCAAG GGCAAAGCCACCATT ACCGCGGACGAATCC ACGAACACAGCCTAC ATGGAGCTGAGCAGC CTGAGATCTGAAGAC ACGGCTGTGTATTAC TGTGCGAGGGAGGAA ATTACCTACGCTATG GACTACTGGGGCCAG GGAACCCTGGTCACC GTGTCCTCAGGCGGA GGTGGAAGCGGAGGG GGAGGAAGCGGAGGC GACATTCAAATGACC CAGAGCCCATCCACC CTGAGCGCATCTGTA GGTGACCGGGTCACC ATCACTTGTAGATCC AGTCAGAGTATTGTA CACAGTAATGGGAAC ACCTATTTGGAATGG TATCAGCAGAAACCA GGTAAAGCCCCCAAA TTGCTCATCTACAAA GTCTCTAACAGATTT AGTGGTGTACCAGCC AGGTTCAGCGGTTCC GGAAGTGGTACTGAA TTCACCCTCACGATC TCCTCTCTCCAGCCA GATGATTTCGCCACT TATTACTGTTTTCAA GGTTCACATGTGCCG CGCACATTCGGTCAG GGTACTAAAGTAGAA GTCAAAGTGGTCTCA GGACCGTCTGGGGGC CCCAGCTCCCCGACA ACAGGCCCCACCTCC ACATCGGCCCTGAG GACCAGCCCCTCACC CCCACCGGGTCGGAT CCCCAGAGTGGTCTG GGAAGGCACCTGGGG GTTGTGATCGGCATC TTGGTGGCCGTCATC CTACTGCTCCTCCTC CTCCTCCTCCTCTTC CTCATCCTCCGACAT CGACGTCAGGGCAAA CACTGGACATCGACC CAGAGAAAGGCTGAT TTCCAACATCCTGCA GGGGCTGTGGGGCCA GAGCCCACAGACAGA GGCCTGCAGTGGAGG TCCAGCCCAGCTGCC GATGCCCAGGAAGAA AACCTCTATGCTGCC GTGAAGCACACACAG CCTGAGGATGGGGTG GAGATGGACACTCGG AGCCCACACGATGAA GACCCCCAGGCAGTG |

TABLE 9-continued

Sequences of constructs

| Name | Amino Acid Sequence | Nucleotide Sequence |
|---|---|---|
| | | ACGTATGCCGAGGTG<br>AAACACTCCAGACCT<br>AGGAGAGAAATGGCC<br>TCTCCTCCTTCCCCA<br>CTGTCTGGGGAATTC<br>CTGGACACAAAGGAC<br>AGACAGGCGGAAGAG<br>GACAGGCAGATGGAC<br>ACTGAGGCTGCTGCA<br>TCTGAAGCCCCCAG<br>GATGTGACCTACGCC<br>CAGCTGCACAGCTTG<br>ACCCTCAGACGGGAG<br>GCAACTGAGCCTCCT<br>CCATCCCAGGAAGGG<br>CCCTCTCCAGCTGTG<br>CCCAGCATCTACGCC<br>ACTCTGGCCATCCAC<br>TAG<br>(SEQ ID NO: 112) |
| PA2.1.14<br>scFv<br>LIR1<br>HTICD | QVQLVQSGAEVKK<br>PGSSVKVSCKASG<br>YTFTSYHIHWVRQ<br>APGQGLSWIGWIY<br>PGNVNTEYNEKFK<br>GKATITADESTNT<br>AYMELSSLRSEDT<br>AVYYCAREEITYA<br>MDYWGQGTLVTVS<br>SGGGGSGGGGSGG<br>GGSGGDIQMTQSP<br>STLSASVGDRVTI<br>TCRSSQSIVHSNG<br>NTYLEWYQQKPGK<br>APKLLIYKVSNRF<br>SGVFARFSGSGSG<br>TEFTLTISSLQPD<br>DFATYYCFQGSHV<br>PRTFGQGTKVEVK<br>YGSQSSKPYLLTH<br>PSDPLELVVSGPS<br>GGPSSPTTGPTST<br>SGPEDQPLTPTGS<br>DPQSGLGRHLGVV<br>IGILVAVILLLLL<br>LLLLFLILRHRRQ<br>GKHWTSTQRKADF<br>QHPAGAVGPEPTD<br>RGLQWRSSPAADA<br>QEENLYAAVKHTQ<br>PEDGVEMDTRSPH<br>DEDPQAVTYAEVK<br>HSRPRREMASPPS<br>PLSGEFLDTKDRQ<br>AEEDRQMDTEAAA<br>SEAPQDVTYAQLH<br>SLTLRREATEPPP<br>SQEGPSPAVPSIY<br>ATLAIH (SEQ ID NO: 89) | CAGGTGCAGCTGGTG<br>CAGTCTGGGGCTGAG<br>GTGAAGAAGCCTGGG<br>TCCTCAGTGAAGGTT<br>TCCTGCAAGGCTTCT<br>GGATACACCTTCACT<br>AGCTATCATATACAT<br>TGGGTGCGCCAGGCC<br>CCCGGACAAGGGCTT<br>GAGTGGATCGGATGG<br>ATCTACCCTGGCAAT<br>GTTAACACAGAATAT<br>AATGAGAAGTTCAAG<br>GGCAAAGCCACCATT<br>ACCGCGGACGAATCC<br>ACGAACACAGCCTAC<br>ATGGAGCTGAGCAGC<br>CTGAGATCTGAAGAC<br>ACGGCTGTGTATTAC<br>TGTGCGAGGGAGGAA<br>ATTACCTACGCTATG<br>GACTACTGGGGCCAG<br>GGAACCCTGGTCACC<br>GTGTCCTCAGGCGGA<br>GGTGGAAGCGGAGGG<br>GGAGGATCTGGCGGC<br>GGAGGAAGCGGAGGC<br>GACATTCAAATGACC<br>CAGAGCCCATCCACC<br>CTGAGCGCATCTGTA<br>GGTGACCGGGTCACC<br>ATCACTTGTAGATCC<br>AGTCAGAGTATTGTA<br>CACAGTAATGGGAAG<br>ACCTATTTGGAATGG<br>TATCAGCAGAAACCA<br>GGTAAAGCCCCAAAA<br>TTGCTCATCTACAAA<br>GTCTCTAACAGATTT<br>AGTGGTGTACCAGCC<br>AGGTTCAGCGGTTCC<br>GGAAGTGGTACTGAA<br>TTCACCCTCACGATC<br>TCCTCTCTCCAGCCA<br>GATGATTTCGCCACT<br>TATTACTGTTTTCAA<br>GGTTCACATGTGCCG<br>CGCACATTCGGTCAG<br>GGTACTAAAGTAGAA<br>GTCAAATACGGCTCA<br>CAGAGCTCCAAACCC<br>TACCTGCTGACTCAC<br>CCCAGTGACCCCCTG<br>GAGCTCGTGGTCTCA |

| Name | Amino Acid Sequence | Nucleotide Sequence |
|---|---|---|
| | | GGACCGTCTGGGGGC<br>CCCAGCTCCCCGACA<br>ACAGGCCCCACCTCC<br>ACATCTGGCCCTGAG<br>GACCAGCCCCTCACC<br>CCCACCGGGTCGGAT<br>CCCCAGAGTGGTCTG<br>GGAAGGCACCTGGGG<br>GTTGTGATCGGCATC<br>TTGGTGGCCGTCATC<br>CTACTGCTCCTCCTC<br>CTCCTCCTCCTCTTC<br>CTCATCCTCCGACAT<br>CGACGTCAGGGCAAA<br>CACTGGACATCGACC<br>CAGAGAAAGGCTGAT<br>TTCCAACATCCTGCA<br>GGGGCTGTGGGGCCA<br>GAGCCCACAGACAGA<br>GGCCTGCAGTGGAGG<br>TCCAGCCCAGCTGCC<br>GATGCCCAGGAAGAA<br>AACCTCTATGCTGCC<br>GTGAAGCACACACAG<br>CCTGAGGATGGGGTG<br>GAGATGGACACTCGG<br>AGCCCACACGATGAA<br>GACCCCCAGGCAGTG<br>ACGTATGCCGAGGTG<br>AAACACTCCAGACCT<br>AGGAGAGAAATGGCC<br>TCTCCTCCTTCCCCA<br>CTGTCTGGGGAATTC<br>CTGGACACAAAG<br>GACAGACAGGCGGAA<br>GAGGACAGGCAGATG<br>GACACTGAGGCTGCT<br>GCATCTGAAGCCCCC<br>CAGGATGTGACCTAC<br>GCCCAGCTGCACAGC<br>TTGACCCTCAGACGG<br>GAGGCAACTGAGCCT<br>CCTCCATCCCAGGAA<br>GGGCCCTCTCCAGCT<br>GTGCCCAGCATCTAC<br>GCCACTCTGGCCATC<br>CACTAG<br>(SEQ ID NO: 111) |

Example 7: Comparison of LIR-1, CTLA-4 and PD-1 Inhibitory Receptors

An NY-ESO-1-responsive inhibitory construct was created by fusing the NY-ESO-1 scFv LBD to domains of receptors including hinge, transmembrane region, and/or intracellular domain of leukocyte immunoglobulin-like receptor subfamily B member 1, LILRB1 (LIR-1), programmed cell death protein 1, PDCD1 (PD-1), or cytotoxic T-lymphocyte protein 4, CTLA4 (CTLA-4). MAGE-A3 activating CAR constructs contained an scFv fused to the CD8a hinge, CD28 TM, and CD28, 4-1BB and CD 3zeta intracellular domains (ICDs). Gene segments were combined using Golden Gate cloning and inserted downstream of a human EF1α promoter contained in a lentiviral expression plasmid.

Figures 14A, 14B:
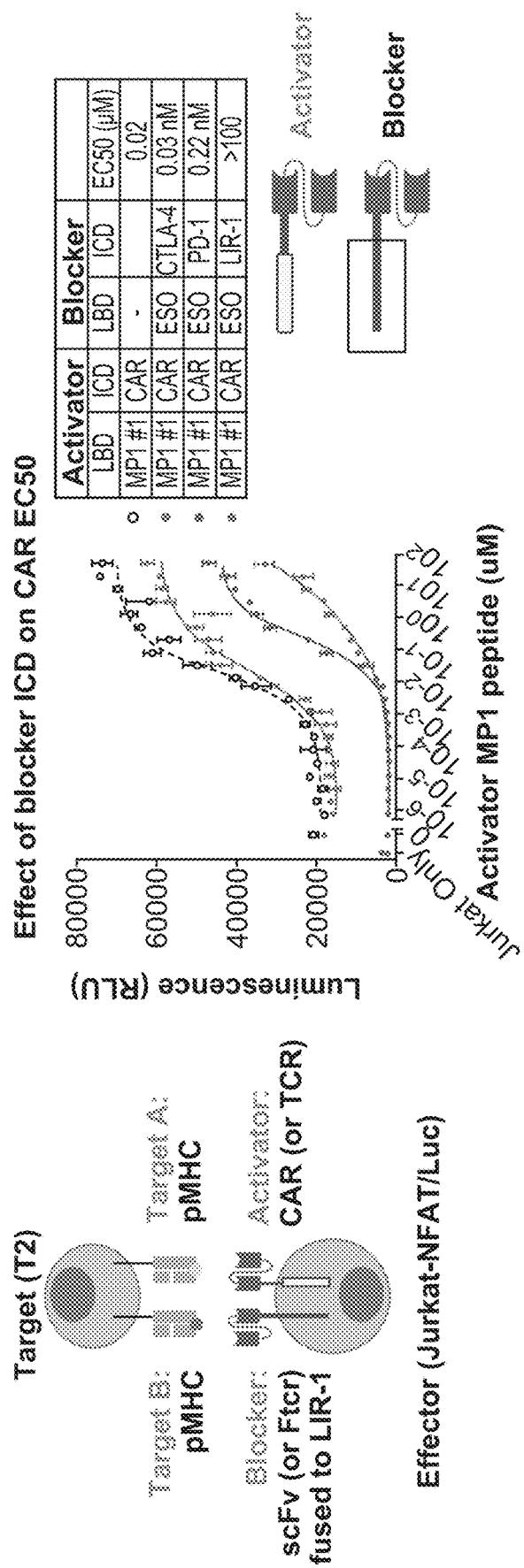
FIG. 14A is a diagram showing a schematic of T2-Jurkat experiments to evaluate blocker constructs.
FIG. 14B is a plot, table and diagram showing the effect of various NY-ESO-1 scFv LBD blocker modules (PD-1, CTLA-4, LIR-1) on EC50 of MAGE-A3 CAR activator (MP1-LBD 1-CAR), measured by MAGE peptide titration of cells loaded with a fixed (50 µM) NY-ESO-1 blocker peptide concentration. In each of FIGS. 14B-14F, NFAT-luciferase signal of Jurkat cells transfected with either activator CAR alone or in combination with each blocker receptor after 6 hours of co-culture with activator and blocker peptide-loaded T2 cells was assayed. The baseline (Jurkat only) varies with different activator alone constructs and can be especially high with CARs; in most cases expression of the blocker receptor absent its ligand suppresses the baseline. Activator peptide concentrations range from 0 then $10^{-6}$ to $10^2$ µM and luminescence measurements ranged from 0 to 80000 RLU.

Initially, peptide-MHC (pMHC) targets for both the activator and blocker receptors were used, because pMHCs allow convenient quantification of the pharmacology of the system (FIG. 14A). Specifically, a single-chain fragment variable (scFv) that binds HLA-A*02-NY-ESO-1$_{(SLL-MWITQC/V)}$ was used as the inhibitor receptor ligand-binding domain (LBD), and a second scFv against HLA-A*02-MAGE-A3$_{(FLWGPRALV)}$ pMHC (Gallo, unpublished) was as part of an activator receptor third-generation CAR. Jurkat effector cells that express luciferase upon NFAT activation were used to readout activator sensitivity, with EC50 values reporting the half-maximum activator peptide concentration required for a response. Both PD-1 and CTLA-4 intracellular domains (ICD) mediated a shift in EC50 of activation in Jurkat cells of less than ~10×, measured by titration of peptides loaded on T2 cells as stimulus (FIG. 14B).

Figure 15:
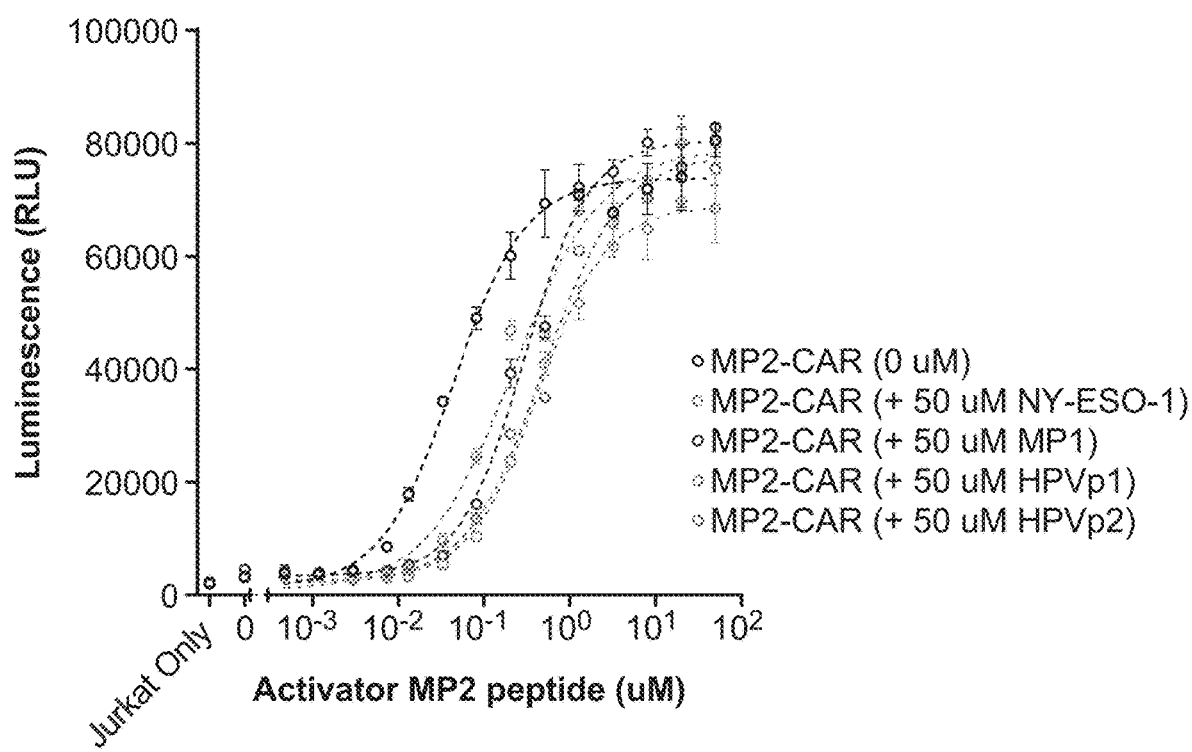
FIG. 15 is a plot showing the effect of blocker peptide loading (50 µM each of NY-ESO-1, MAGE-A3, HPV E6, and HPV E7) on activating MAGE-A3 CAR. MP2-CAR [0 µM], EC50=44 nM; MP2-CAR [50 µM HPVp2], EC50=495 nM. RLU=relative light units; error bars indicate ±SD (n=2).
Figure 16A:
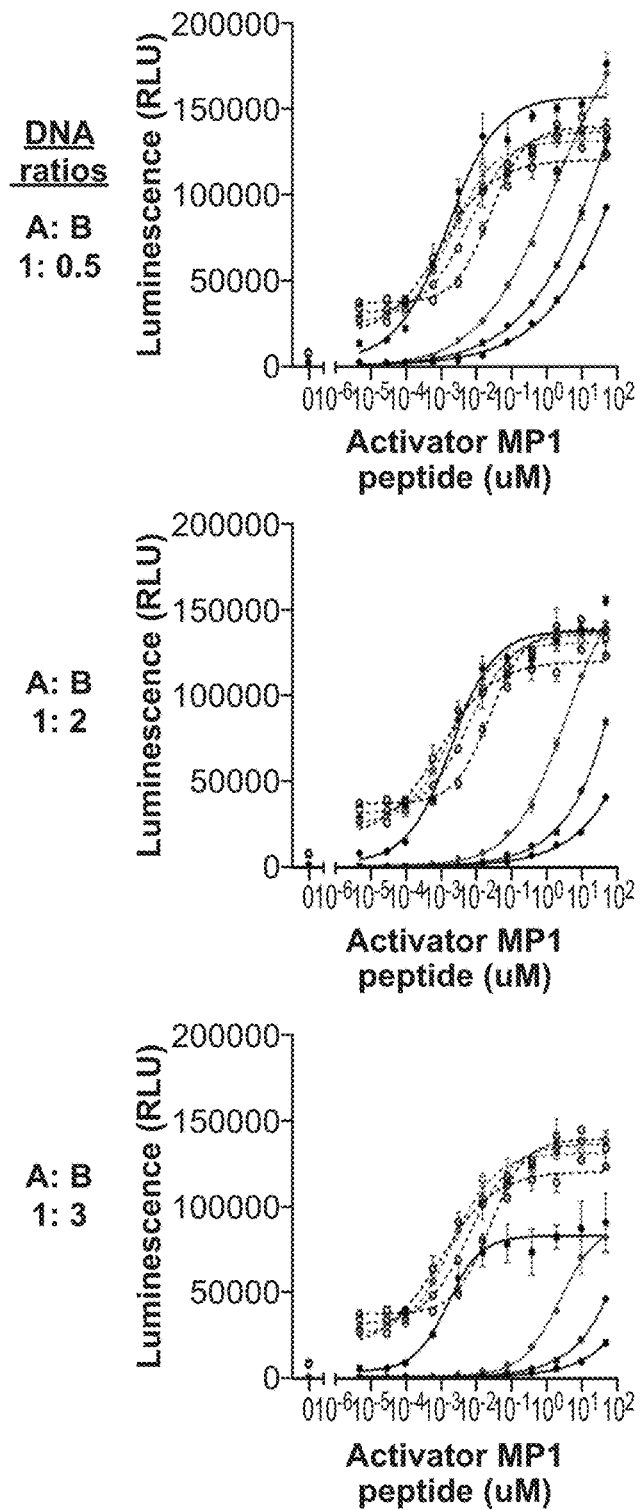
FIG. 16A is a series of plots showing NFAT-luciferase signal of Jurkat cells transfected with either activator MAGE-A3 CAR alone or in combination with various amounts of NY-ESO-1 scFv LBD blocker (DNA ratios of activator and blocker receptors components shown on left as A:B, activator receptor:blocker receptor after 6 h of co-culture with activator and blocker peptide-loaded T2 cells. T2 cells were loaded with titrated amounts of activator MAGE-A3 peptide and a fixed amount of blocker NY-ESO-1 peptide concentration. Activator and/or blocker peptide concentrations range from 0 then $10^{-6}$ to $10^2$ µM and luminescence measurements ranged from 0 to 200000 RLU.
Figure 16B:
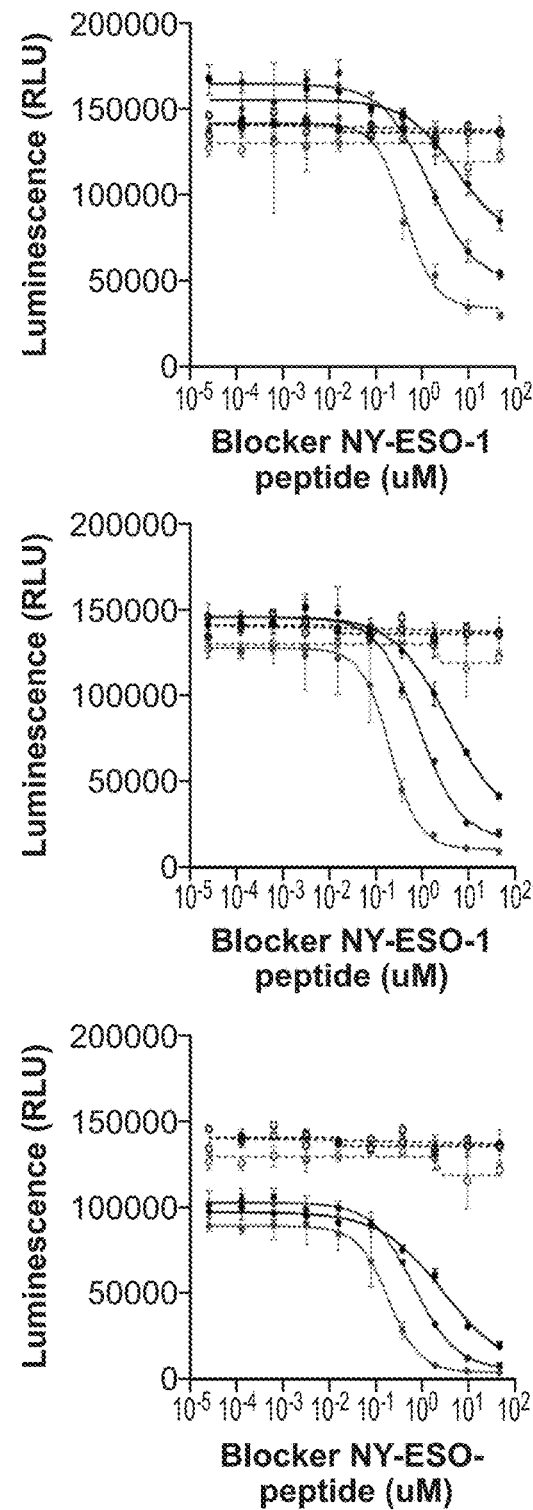
FIG. 16B is a series of plots showing NFAT-luciferase signal of Jurkat cells transfected with either activator MAGE-A3 CAR alone or in combination with various amounts of NY-ESO-1 scFv LBD blocker. T2 cells were loaded with titrated amounts of blocker NY-ESO-1 peptide and a fixed amount of activator MAGE-A3 peptide concentration above the Emax concentration (~0.1 mM). Activator and/or blocker peptide concentrations range from $10^{-5}$ to $10^2$ µM and luminescence measurements ranged from 0 to 200000 RLU.
Figure 16C:
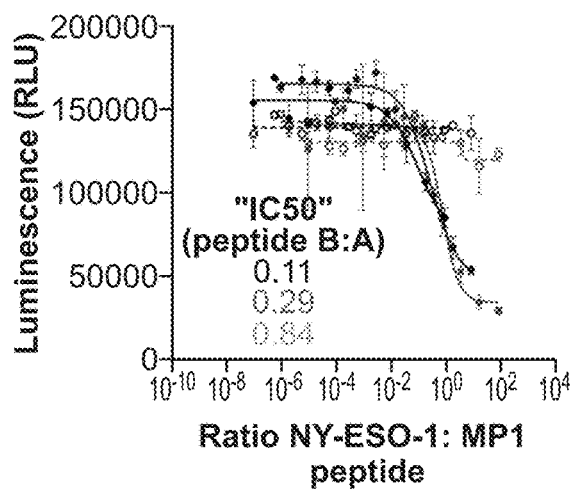
FIG. 16C is a series of plots and two tables showing NFAT-luciferase signal of Jurkat cells transfected with either activator MAGE-A3 CAR alone or in combination with various amounts of NY-ESO-1 scFv LBD blocker. The x-value blocker NY-ESO-1 peptide concentrations from FIG. 16B were normalized to the constant activator MAGE peptide concentrations used for each curve and plotted on the x-axis. The ratio of blocker peptide to activator peptide required for 50% blocking (IC50) are indicated for each curve. For all DNA ratios, the B:A peptide ratio required is less than 1 indicating that, for this pair of activator CAR and blocker, similar (or fewer) blocker pMHC antigens are required on target cells to block activator pMHC antigens. Activator and/or blocker peptide concentrations range from $10^{-10}$ to $10^4$ µM and luminescence measurements ranged from 0 to 200000 RLU.
Figure 16C:
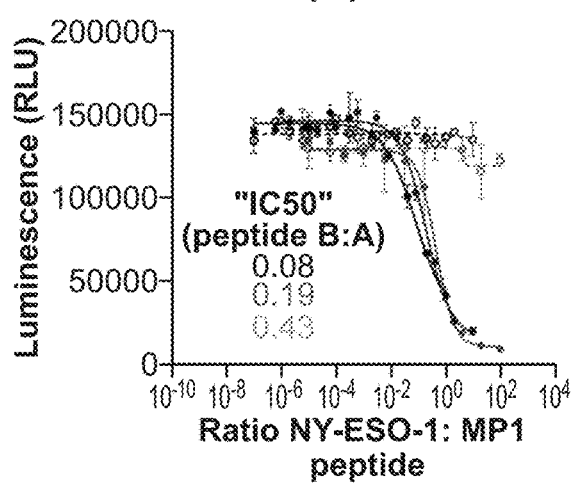
Figure 16C:
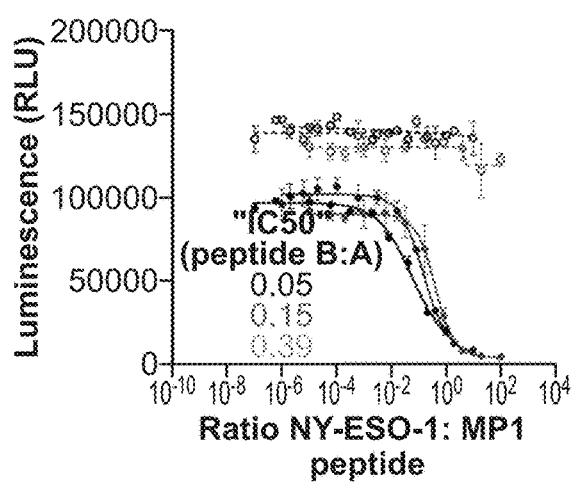
Figure 16D:
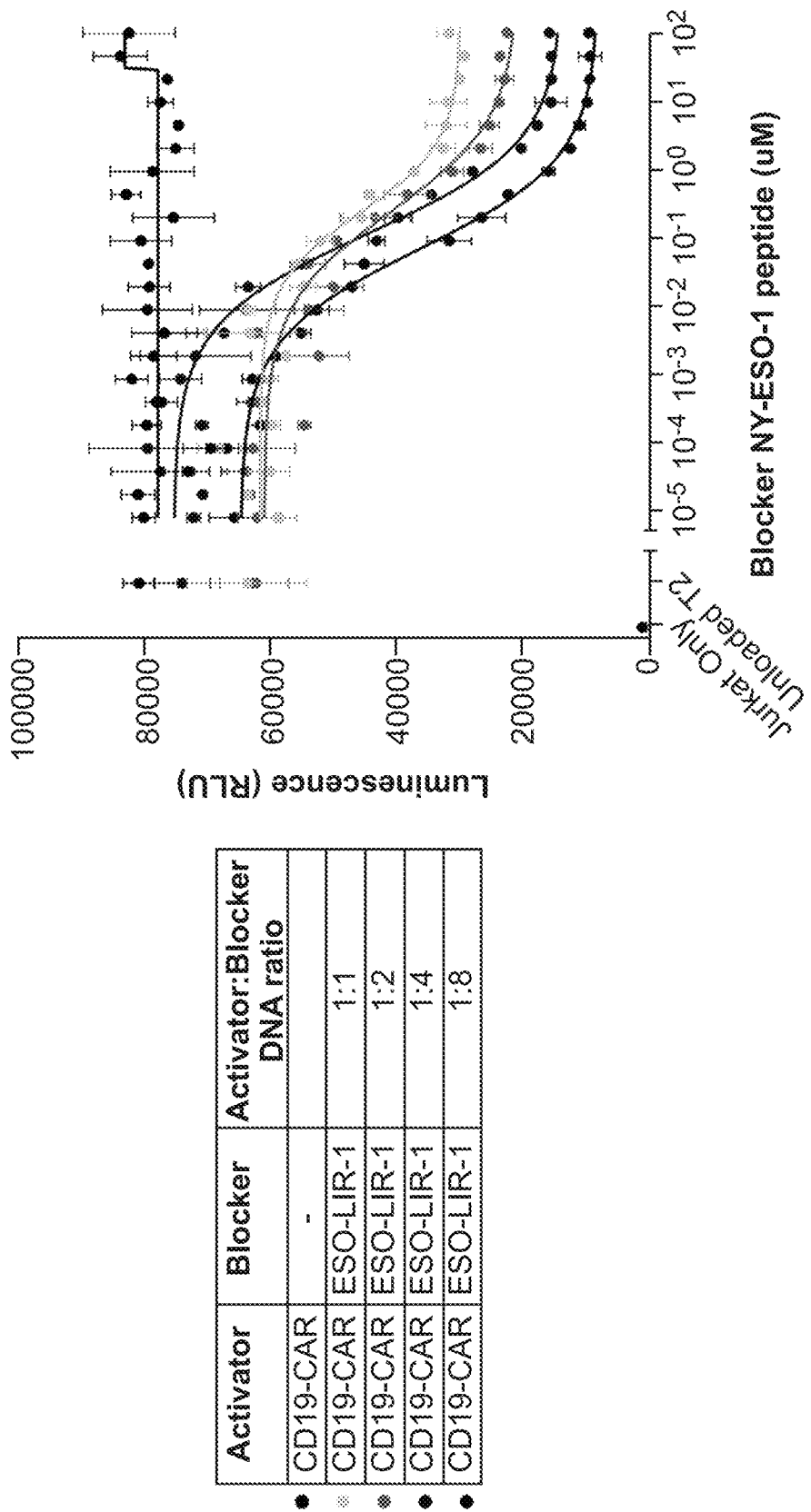
FIG. 16D is a table and a plot showing that blocking CD19-CAR activator is possible with pMHC blockers at blocker pMHC antigen densities similar to those required to activate pMHC CARs. NFAT-luciferase signal of Jurkat cells transfected with either activator CD19 CAR alone or in combination with various amounts of NY-ESO-1 blocker (DNA ratios shown) after 6 h of co-culture with blocker peptide-loaded T2 cells which express endogenous levels of CD19 antigen. The IC50 is estimated from the inhibition curves to range from 0.1-1.0 mM, corresponding to ~1,500-3,500 pMHCs/cell. RLU=relative light units; error bars indicate ±SD (n=2).

A variety of potential inhibitor (blocker) receptor constructs were screened, and the LIR-1 blocker constructed was discovered to have stronger blocking properties than PD-1 and CTLA-4. This blocker receptor includes the intracellular, transmembrane (TM) and hinge domains of the LIR-1 (LILRB1) receptor, one of several LIR-family molecules encoded by the human genome. The LIR-1 blocker (henceforth referred to as LIR-1) fused to the NY-ESO-1 LBD mediated an EC50 shift of >5,000× (FIG. 14B, FIGS. 17A-17D). A control, titration of unrelated HLA-A*02-binding peptides provided an estimate of the shift caused by competition of loaded peptides on T2 cells for available HLA molecules, a contribution to the total shift typically less than ~10× (FIG. 15). For the EC50 shift values reported here, comparisons were typically to EC50s of activator-only constructs. Further, for a given pair of activator/blocker receptors, the mid-point of titration for inhibition was approximately constant and depended on the ratio of activating to blocking peptide, presumably directly correlated with the target-antigen ratio (FIGS. 16A-16D). The target concentration explored in the majority of these experiments is estimated to have ranged from ~1,000-10,000 copies/cell.

Example 8: LIR-1 Inhibitory Receptors with Multiple scFv Ligand Binding Domains

Figure 14C:
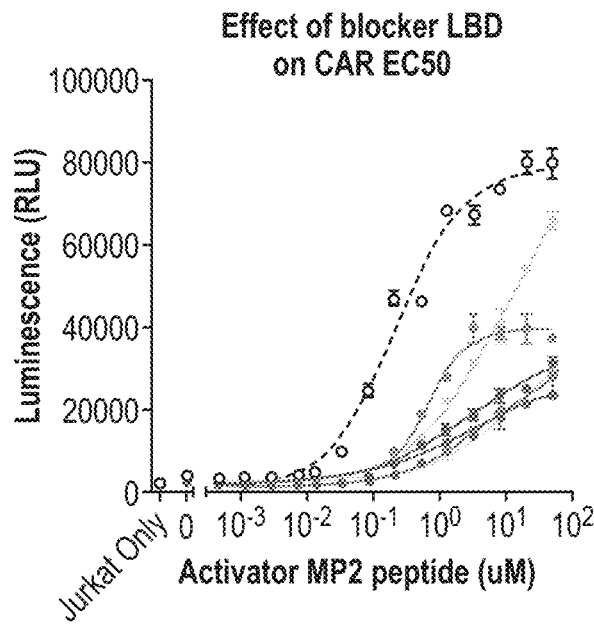
FIG. 14C is a plot, table and diagram showing the effect of LIR-1 blocker receptor with various scFv LBDs (ESO, MP1 LBD 1, MP1 LBD 2, HPV E6 LBD 1, HPV E6 LBD 2, HPV E7) on EC50 of MAGE-A3 CAR activator (MP1-CAR) when loaded with corresponding blocker peptide at fixed (50 µM) peptide concentration, as in FIG. 14B. RLU=relative light units; error bars indicate ±SD (n=2). Activator peptide concentrations range from 0 then $10^{-3}$ to $10^2$ µM and luminescence measurements ranged from 0 to 100000 RLU.
Figure 14C:
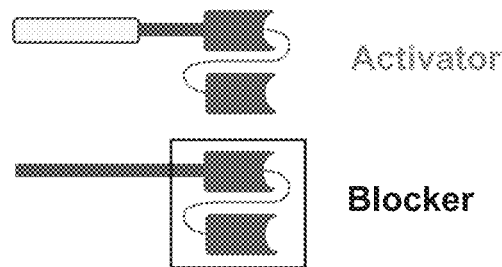
Figure 14D:
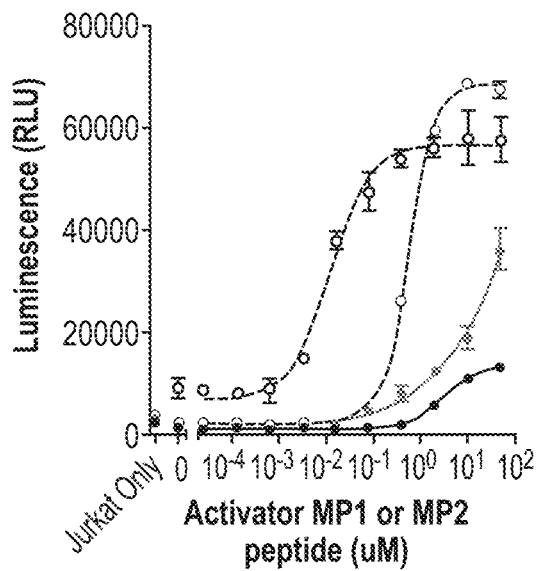
FIG. 14D is a plot, table and diagram showing the effect of LIR-1 blocker receptor with NY-ESO-1 scFv LBD on EC50 of different MAGE-A3 CAR activators (MP1-LBD 1-CAR or MP2-CAR) when loaded with 50 uM NY-ESO-1 blocker peptide. Activator peptide concentrations range from 0 then $10^{-4}$ to $10^2$ µM and luminescence measurements ranged from 0 to 80000 RLU.
Figure 14D:
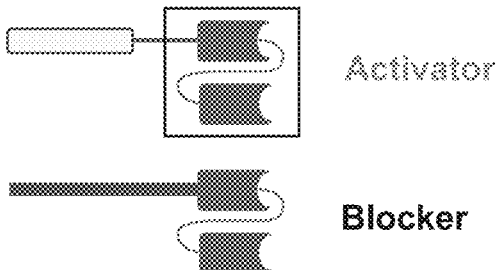
Figure 14E:
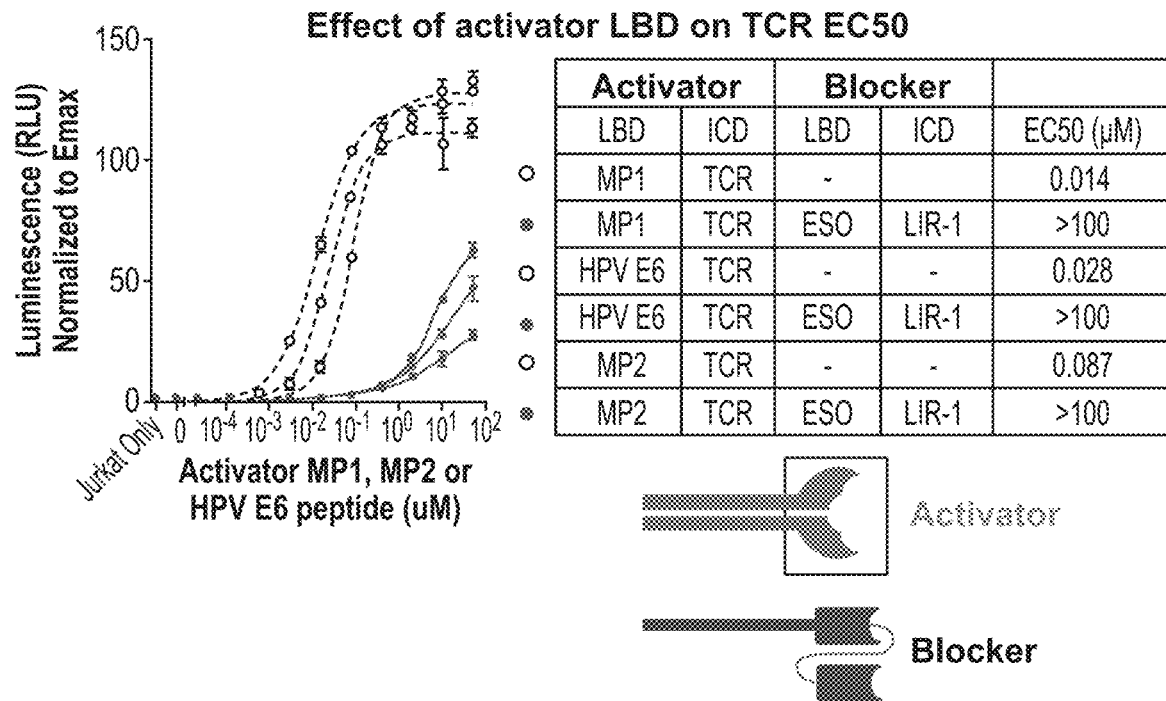
FIG. 14E is a plot, table and diagram showing the effect of LIR-1 blocker receptor with NY-ESO-1 scFv LBD on EC50 of different TCR activators (MP1-TCR, MP2-TCR, HPV E6-TCR) when loaded with 50 uM NY-ESO-1 blocker peptide. Activator peptide concentrations range from 0 then $10^{-4}$ to $10^2$ µM and normalized luminescence measurements ranged from 0 to 150 RLU.
Figure 14F:
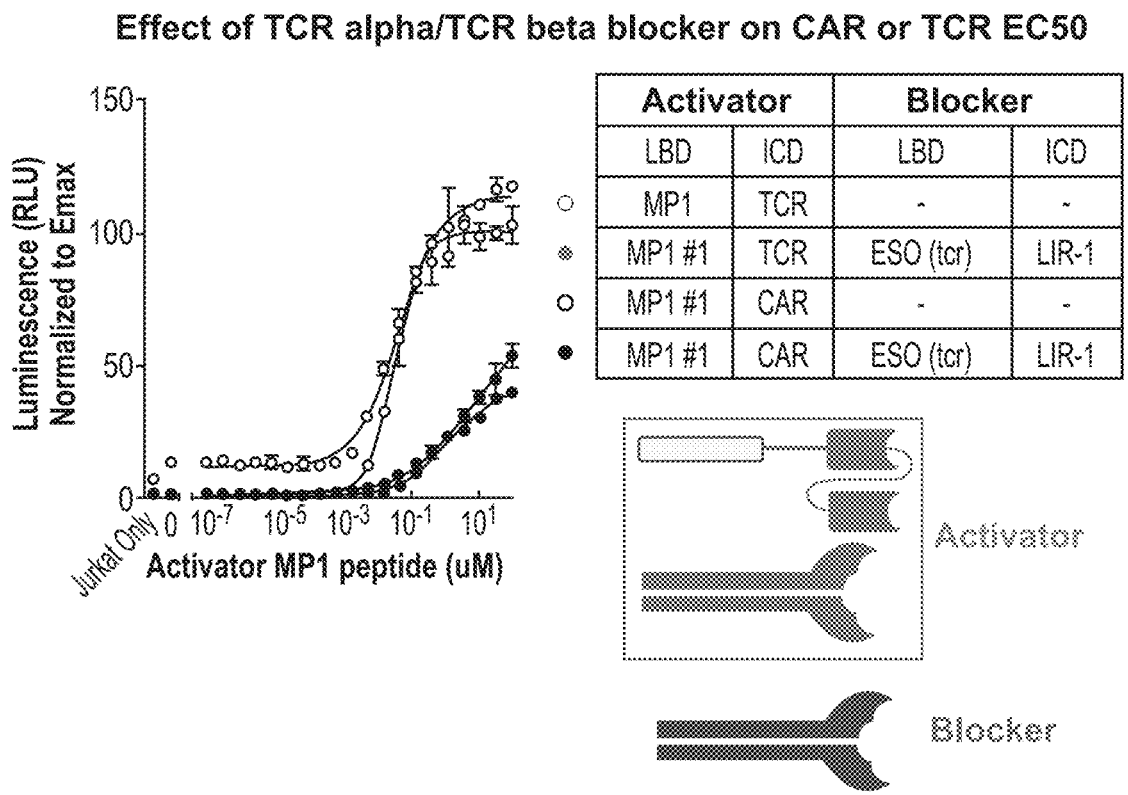
FIG. 14F is a plot, table and diagram showing the effect of LIR-1 blocker receptor with NY-ESO-1 TCR LBDs on EC50 of MAGE-A3 CAR and TCR activators (MP1-LBD 1-CAR, MP1-TCR) when loaded with 50 uM NY-ESO-1 blocker peptide. RLU=relative light units; error bars indicate ±SD (n=2). Activator peptide concentrations range from 0 then $10^{-7}$ to $10^1$ µM and normalized luminescence measurements ranged from 0 to 150 RLU.
Figure 17A:
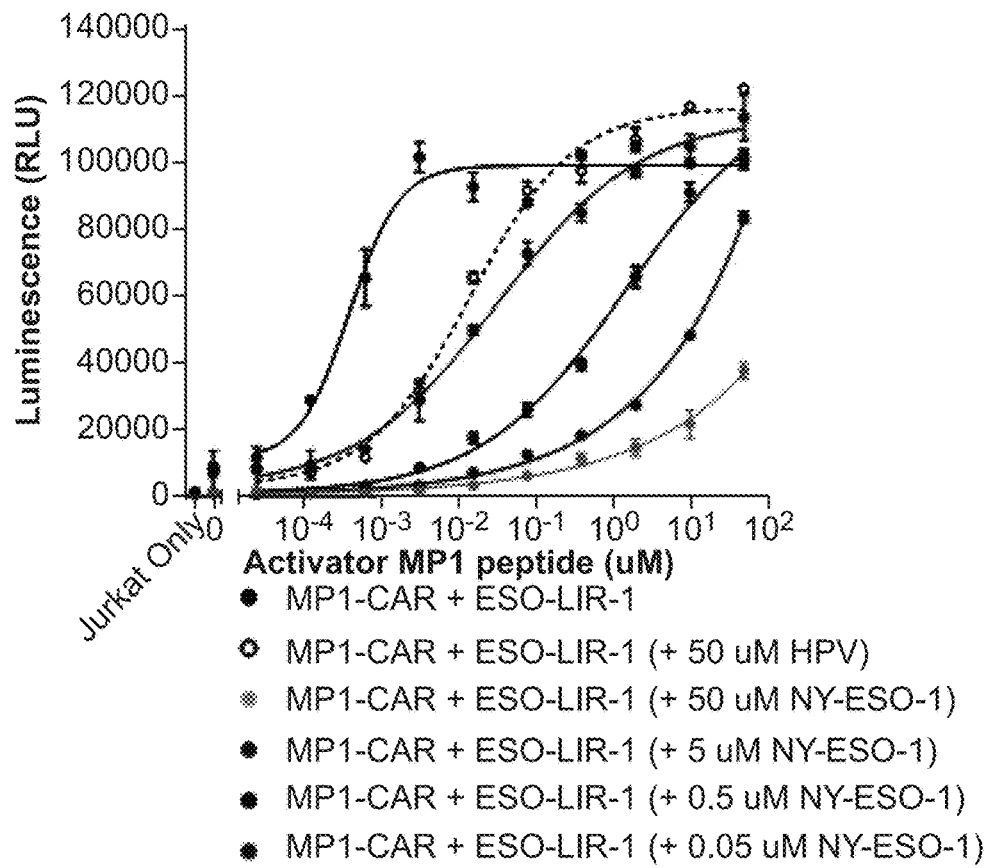
FIG. 17A is a plot showing the effect of NY-ESO-1-LIR-1 blocker on EC50 of activating MAGE-A3 CAR (MP1-CAR) when loaded with various concentrations of NY-ESO-1 blocker peptide. The EC50 shifts are greater as the concentration of blocker peptide (NY-ESO-1) increases. The shift in the presence of a negative-control HPV peptide (binds HLA-A*02 but not NY-ESO-1 blocker scFv) is routinely seen and believed to be caused by competition of the control peptide for binding sites on the T2 HLA-A*02 molecules, reducing the number of activator targets. Activator concentrations range from 0 then $10^4$ to $10^2$ μM and luminescence measurements ranged from 0 to 140000 RLU.
Figure 17B:
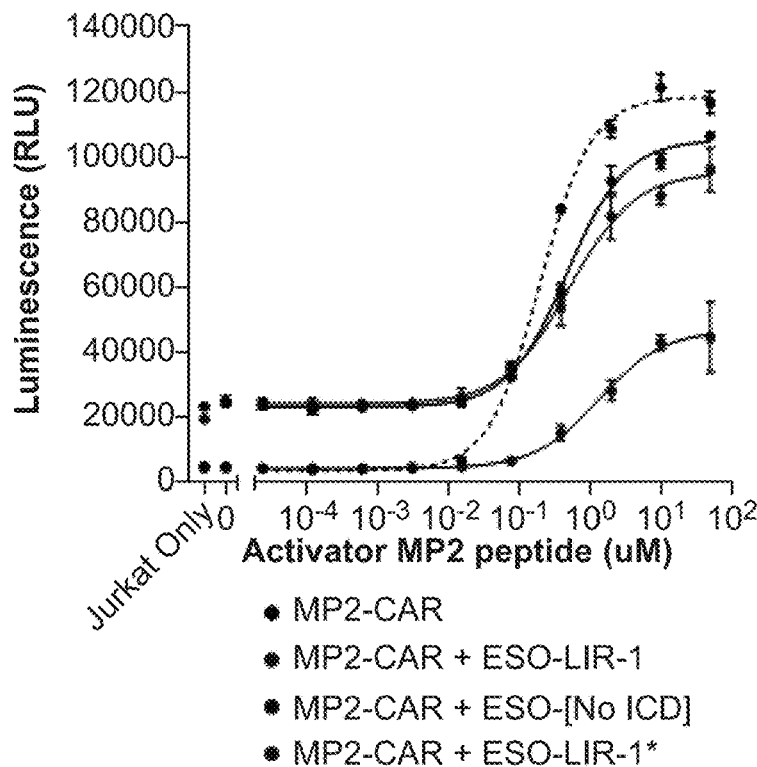
FIG. 17B is a plot showing the effect of modified LIR-1 blocker receptors containing no ICD or a mutated ICD with NY-ESO-1 scFv LBD on EC50 of MAGE-A3 CAR activator (MP2-CAR) when loaded with 10 μM of NY-ESO-1 blocker peptide. Activator concentrations range from 0 then $10^1$ to $10^2$ μM and luminescence measurements ranged from 0 to 140000 RLU.
Figures 17C, 17D:
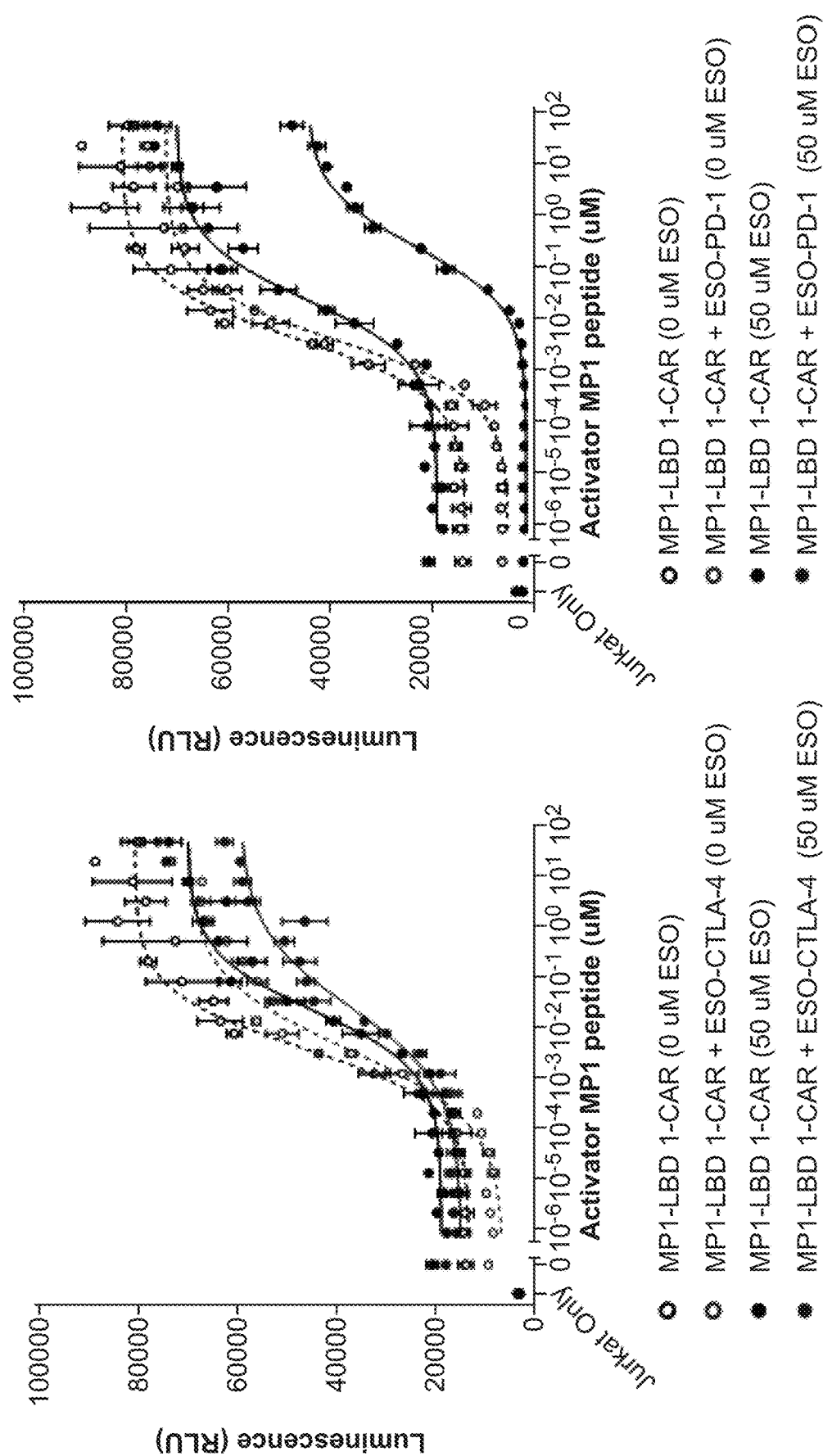
FIGS. 17C-17E are a series of plots showing the effect of various NY-ESO-1 scFv LBD blocker receptors (CTLA-4 (FIG. 17C), PD-1 (FIG. 17D) and LIR-1 (FIG. 17E)) on EC50 of MAGE-A3 CAR activator (MP1-LBD 1-CAR) when blockers are stimulated or unstimulated. NFAT-luciferase signal of Jurkat cells transfected with either activator CAR alone or in combination with each blocker after 6 h of co-culture with peptide-loaded T2 cells. T2 cells were loaded with titrated amounts of activating MAGE peptide and tested with and without loading additional constant amount (50 μM) of NY-ESO-1 blocker peptide. RLU=relative light units; error bars indicate ±SD (n=2). Activator concentrations range from 0 then $10^{-6}$ to $10^2$ μM and luminescence measurements ranged from 0 to 100000 RLU.
Figure 17E:
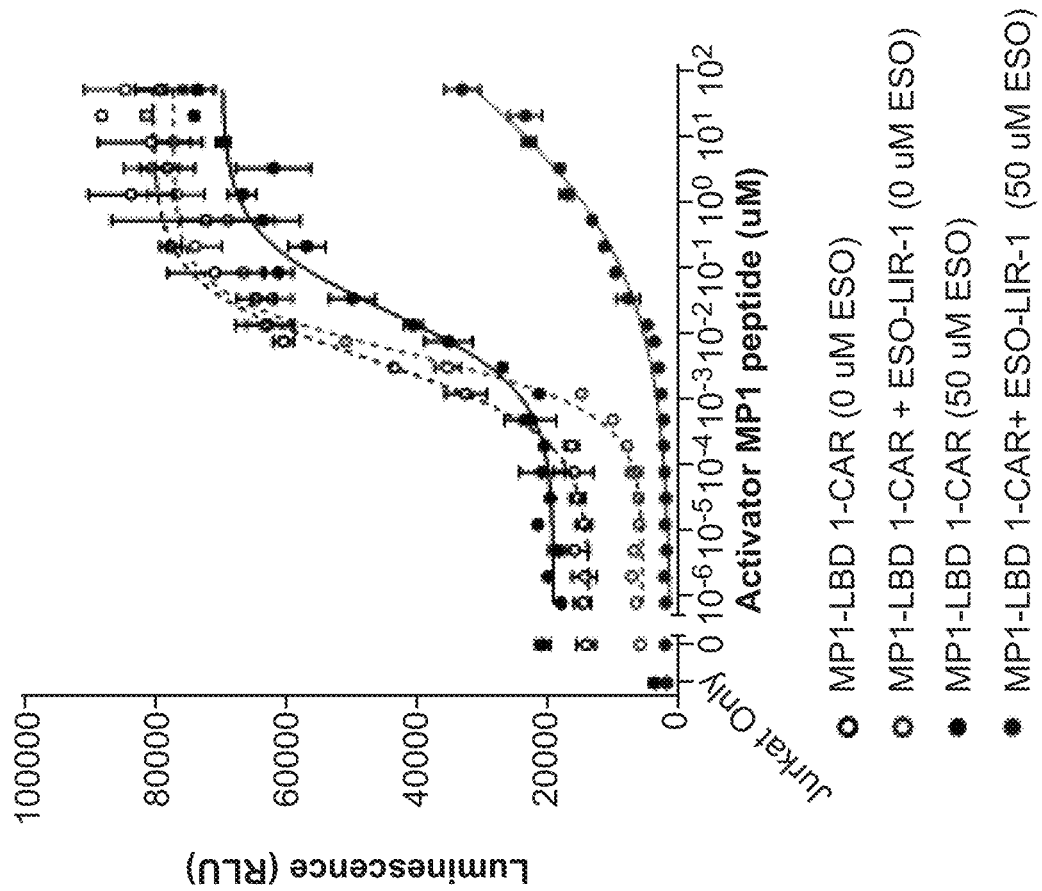

The activity of the LIR-1 inhibitory receptor was tested with a variety of antigen-binding domains specific to other pMHC targets. For four different pMHC targets, a total of six different scFvs grafted onto the LIR-1 mediated dramatic shifts in EC50, ranging from 10 to 1,000× (FIG. 14C). With respect to its interaction with activator receptors, the LIR-1 receptor was also robust; its blocking behavior was applicable to multiple targets and scFvs (FIG. 14D). The blockade was ligand-dependent (FIG. 17A), although many LIR-1 constructs produced lower basal/tonic signaling when paired with specific activator receptors. The EC50 shifts depended on the presence of a fused ICD, as LIR-1 constructs completely lacking ICD, or containing mutations in key elements of the ICD, had no effect (FIG. 17B). The ligand-independent blocker activity, however, had little effect on the activation EC50 absent ligand (FIG. 16A-16D). LIR-1 inhibitory receptors are a modular, adaptable, ligand-gated system that functions across multiple targets and antigen-binding domains.

Example 9: LIR-1 Inhibitory Domains Fused to TCR Alpha and TCR Beta

The LIR-1 inhibitory receptor was tested when fused to TCRalpha and TCR beta subunits, or when in combination with a TCR activator receptor. TCRs directed against 3 different pMHC targets, 2 from MAGE-A3 and one from HPV (see Methods, supra). In every case, LIR-1 shifted the activation EC50 by large amounts, estimated to range >1,000× (FIG. 14E; FIG. 19A). Furthermore, an NY-ESO-1 TCR LBD, when fused to LIR-1, also produced substantial EC50 shifts (FIG. 14F; FIG. 19B). Indeed, all combinations of a MAGE-A3$_{(FLWGPRALV)}$ CAR or TCR with an NY-ESO-1$_{(SLLMWITQV)}$ scFv or TCR displayed large shifts. Thus, the LIR-1 inhibitory receptor exhibited modularity that encompassed both CARs and TCRs.

Example 10: LIR-1 Inhibitory Receptors Respond to Target Antigen Present in Cis to Activator Receptor Target Antigen The ability of the LIR-1 blocker receptor to inhibit activation by an activator receptor when activator and inhibitor targets were presented in cis was assayed. In a first assay, a simplified stimulus consisting of target-loaded beads roughly the size of cells (d~2.8 um) was used. Jurkat cells expressing activator and blocker receptors were activated only by beads that contained the A (activator) target, not by beads with dual A/B (activator/blocker) targets (FIG. 18A). Interestingly, the effector cells were activated by a mixture of A+ and B+ beads, even when the A+ beads comprised only 20% of the total. This demonstrated that the cells expressing the activator and blocker receptors are: (i) blocked from activation by the blocker receptor when the targets are present in cis on the same surface; and, (ii) activated by individual A+ beads among an excess of B+ beads.

Example 11: LIR-1 Inhibitory Receptors and Cell Surface Antigens

The ability of the LIR-1 inhibitor receptor to block activation in response to non-pMHC targets, representing surface antigens that can extend into the realm of 100,000 epitopes/cell, was assayed. scFvs that bind either the B-cell marker CD19, the solid-tumor antigen mesothelin (MSLN), or HLA-A*02 in a peptide-independent fashion were tested. In these cases, the target antigen concentration was not controlled, as with exogenous peptide as with pMHCs. Instead, the ratio of activator to blocker expression was varied using different DNA concentrations in transient transfection assays. Though assay sensitivity prevented exploration of the full range of EC50 shifts, shifts in Emax over 10× were observed. These experiments showed that the properties of the LIR-1 receptor in a dual receptor system were generally the same for high-density targets (FIG. 18B; FIGS. 16-16D, FIG. 21A) and that the blocker receptor blocked activation of the A receptor to an extent reflected by its relative surface level on the effector cells (FIG. 18C). The LIR-1 receptor also behaved in a modular manner in this high-antigen-density setting. An scFv against HLA-A*02 acted either as activator (FIG. 18D) or blocker when fused to either an activator or blocker receptor, respectively. The LIR-1 receptor is flexible enough to accommodate low and high target densities, in principle allowing optimization for pMHC targets as well as non-pMHC surface antigens.

Example 12: LIR-1 Inhibitory Receptors in Primary T Cells

The ability of the LIR-1 receptor to block activation of primary T cells was assayed. pMHC targets were used initially. After enrichment for transduced T cells via physical selection, engineered T cells expressing activator and blocker receptors were assayed using target cells engineered to express luciferase as the readout for viable cells. With an

Figure 20B:
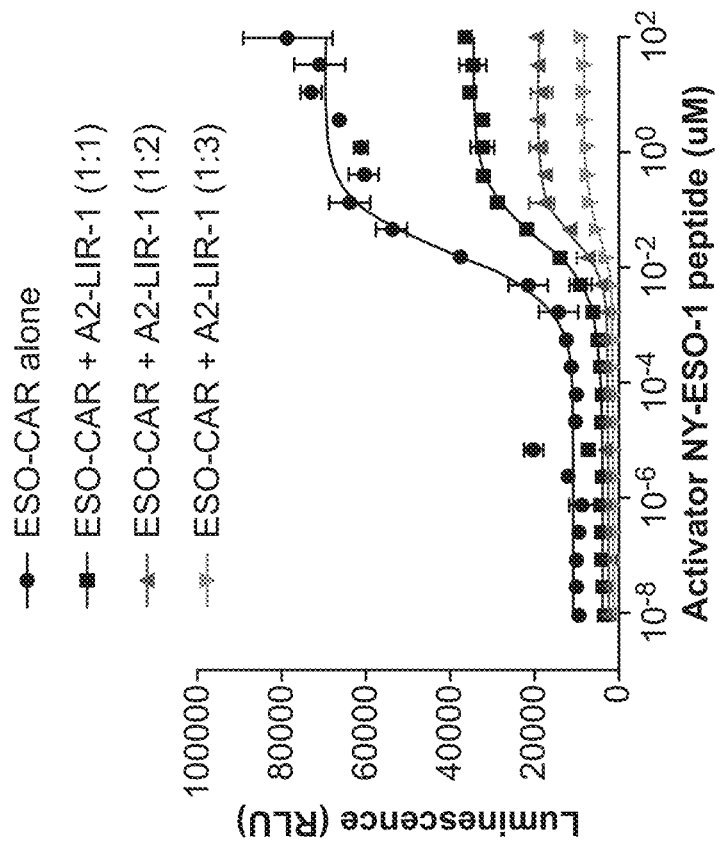
FIG. 20B is a plot showing that HLA-A*02-LIR-1 blocks NY-ESO-1 CAR activator at various activator:blocker DNA ratios in Jurkat cells using NY-ESO-1 peptide-loaded T2 target cells. RLU=relative light units; error bars indicate ±SD (n=2).
Figure 20A:
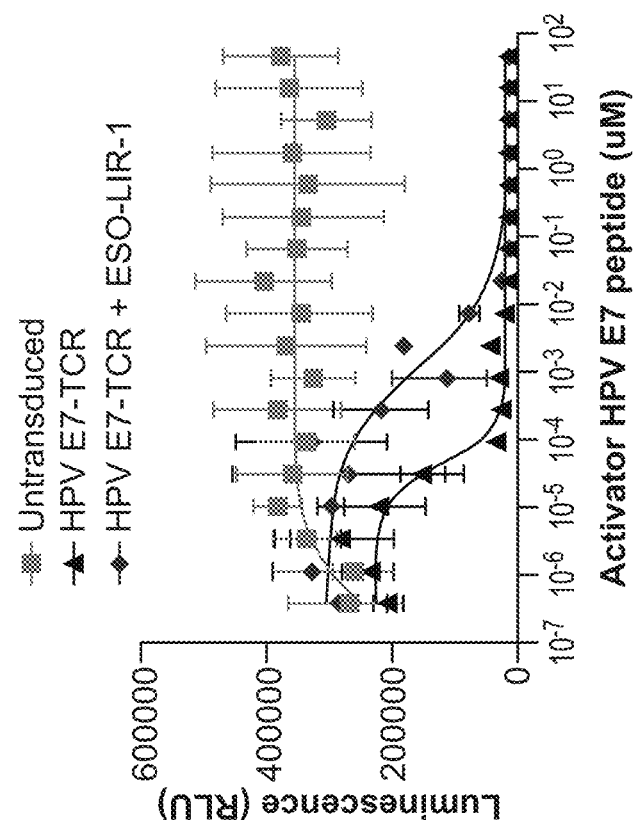
FIG. 20A is a plot showing primary T cells (donor 1) transduced with HPV E7-TCR activator and ESO-LIR-1 blocker shifts EC50~25× in primary T cell killing assay (HPV E7 TCR EC50=0.044 nM; HPV E7 TCR+ESO-LIR-1, EC50=1.1 nM). The assay was performed using peptide-loaded MCF7 target cells at a 3:1 E:T. Luciferase measurement represents live target cells at 48 hours.
Figure 21A:
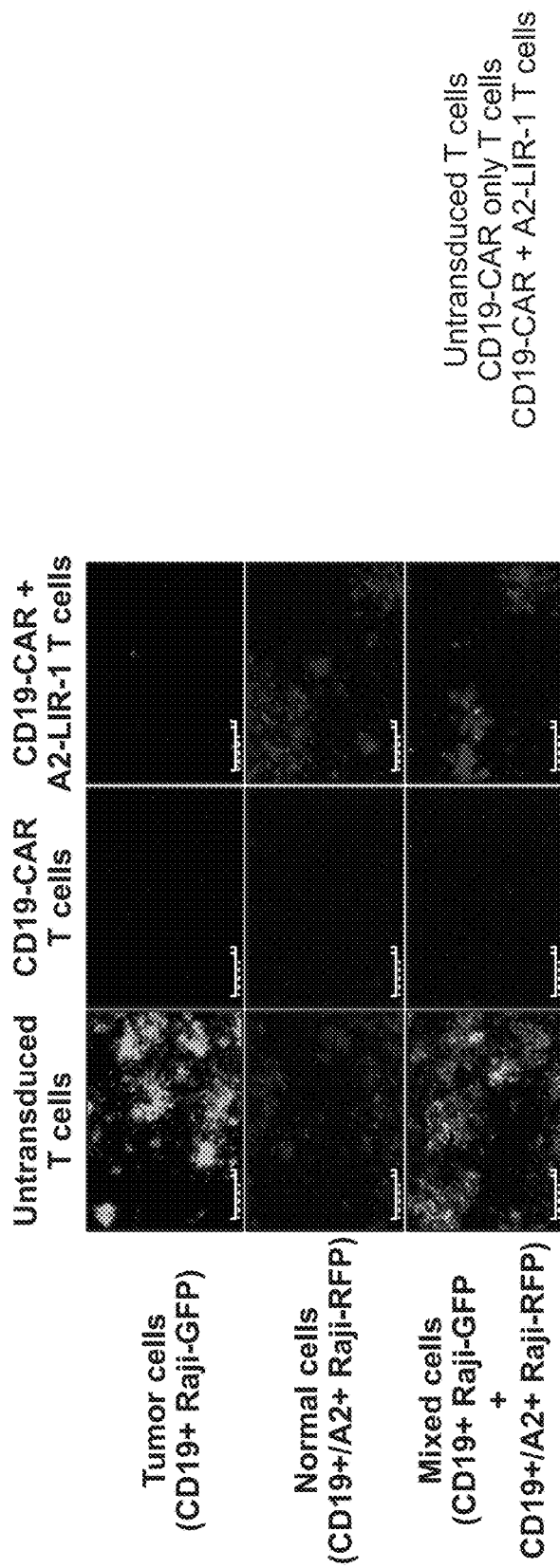
FIG. 21A is a series of images and plots showing that primary T cells (donor 1) transduced with CD19 CAR activator and HLA-A*02 blocker distinguish "tumor" cells from "normal" cells in in vitro cytotoxicity assay and demonstrate selective killing of "tumor" cells in mixed target cell assay at 3:1 E:T. Images shown were captured at 72 hours. Shown are Untransduced, CD19-CAR T cells, and CD19-CAR T+A2-LIR-1. Measurements were taken between 0 and 150 hours and normalized fluorescent protein intensity (GFP or RFP) ranged from 0 to 10.
Figure 21A:
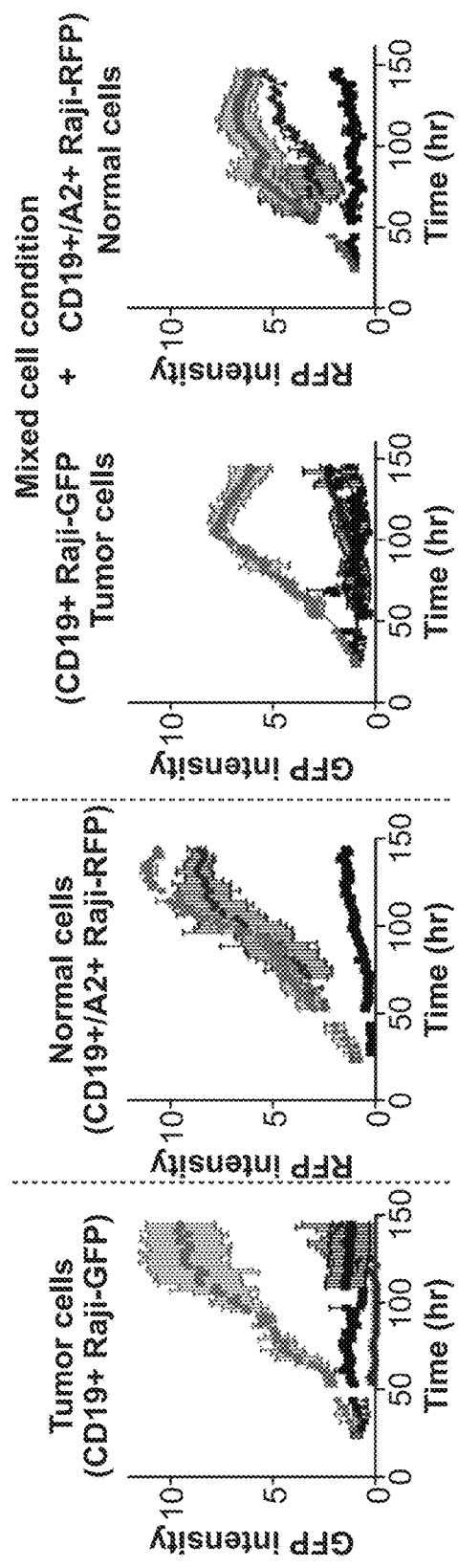
Figure 21B:
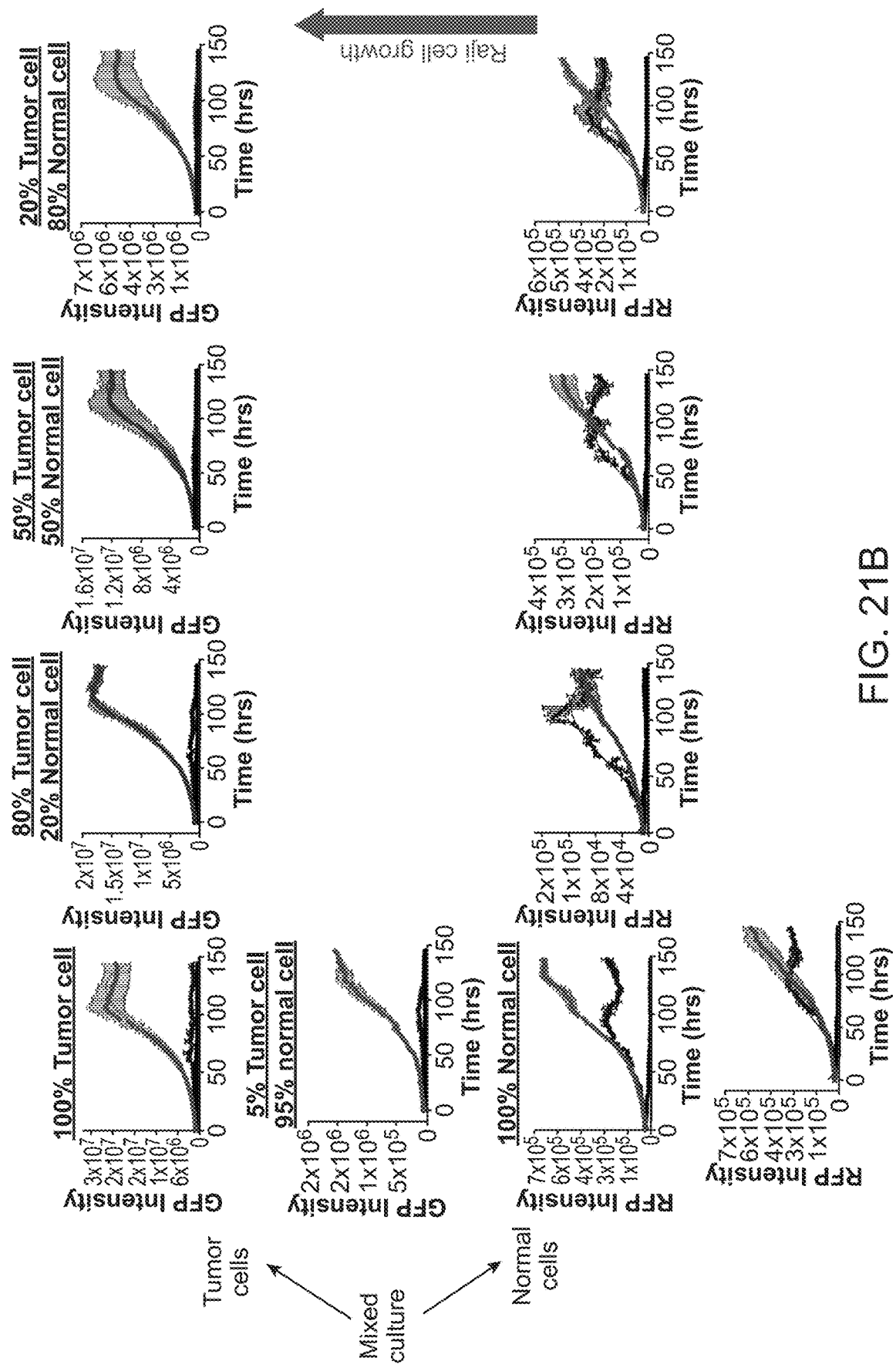
FIG. 21B is a series of plots showing that primary T cells (donor 1) selectively kill tumor cells similarly at various tumor to "normal" cell ratios at 3:1 E:T ratios in Incucyte imaging assay. RLU values were normalized against target cell mixtures grown in the absence of primary T cells. Shown are Untransduced, CD19-CAR T cells, and CD19-CAR T+A2-LIR-1. Measurements were taken between 0 and 150 hours and normalized fluorescent protein intensity (GFP or RFP) ranged from, on the top row, from left to right: 0 to $3\times10^7$, 0 to $2\times10^7$, 0 to $1.6\times10^7$, 0 to $7\times10^6$, 0 to $2\times10^6$; bottom row, from left to right: 0 to $7\times10^5$, 0 to $2\times10^5$, 0 to $4\times10^5$, 0 to $6\times10^5$, 0 to $7\times10^5$.
Figure 21C:
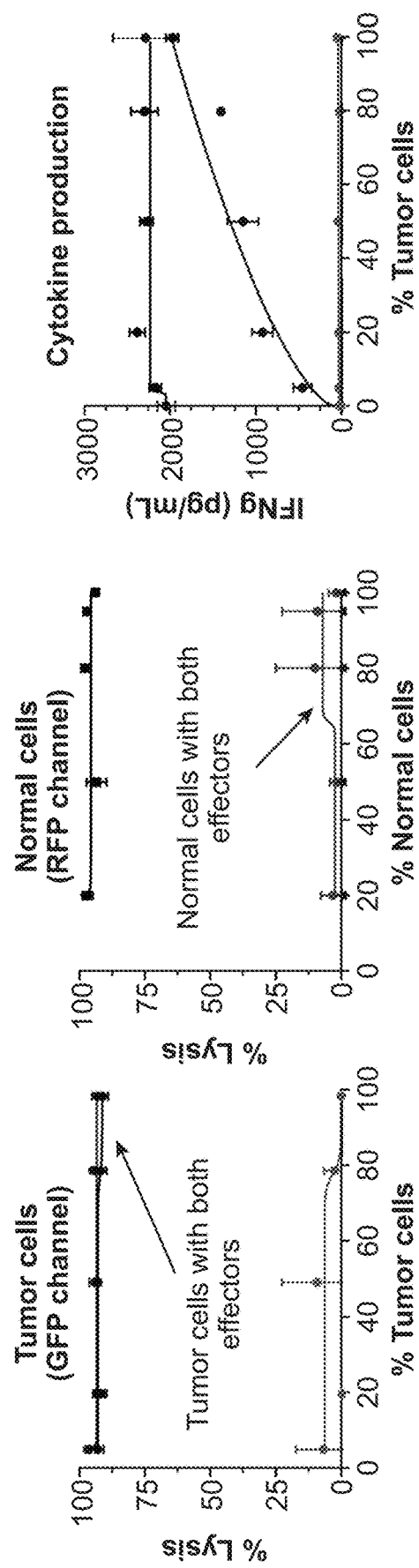
FIG. 21C is a series of plots showing that primary T cells (donor 1) selectively kill tumor cells similarly at various tumor to "normal" cell ratios at 3:1 E:T ratios in quantitative target cell lysis and IFNγ secretion. Shown are Untransduced, CD19-CAR T cells, and CD19-CAR T+A2-LIR-1.
Figure 23:
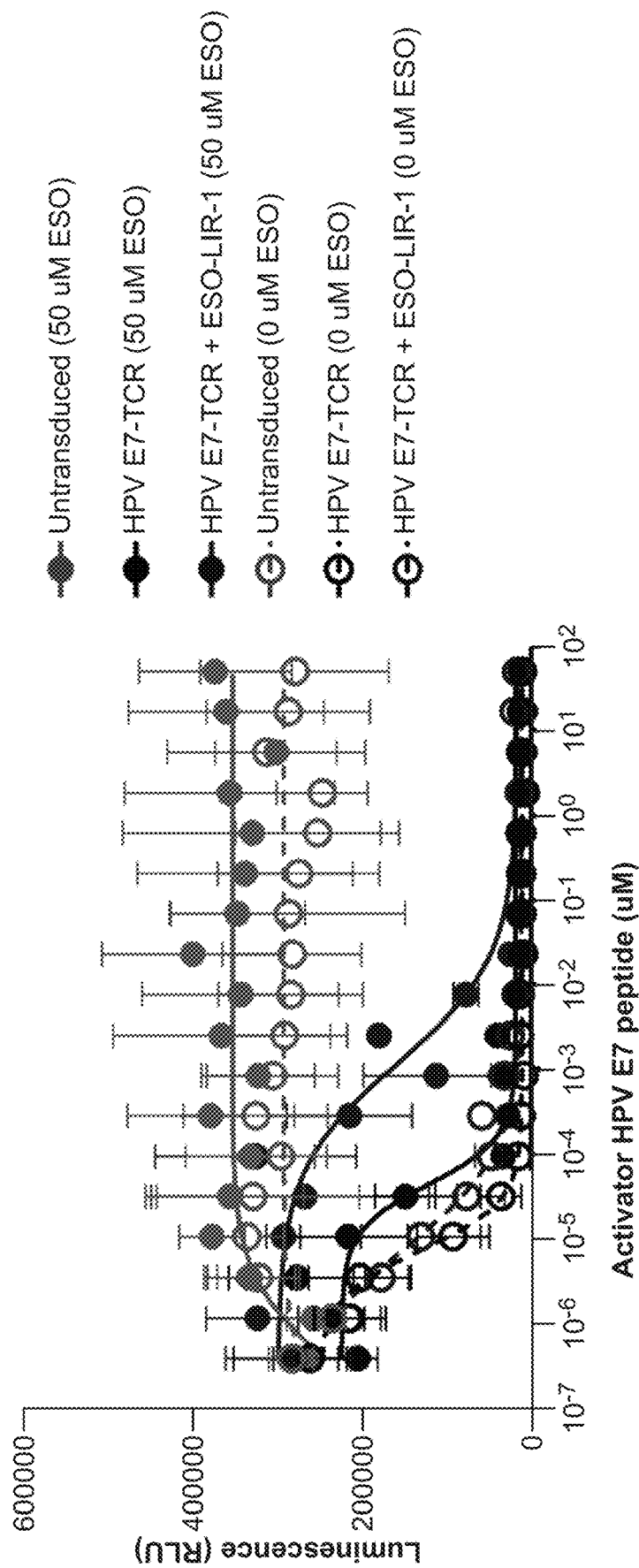
FIG. 23 is a plot showing that LIR-1 blocker receptors have little effect on killing efficacy of activator in absence of blocker antigen. In the absence of NY-ESO-1 blocker antigen, primary T cells (donor 1) transduced with HPV E7-TCR activator and ESO-LIR-1 blocker display similar killing efficacy to primary T cells transduced with only the HPV E7-TCR activator. Luciferase measurement represents live target cells. RLU=relative light units; error bars indicate ±SD (n=2).
Figures 25A, 25B:
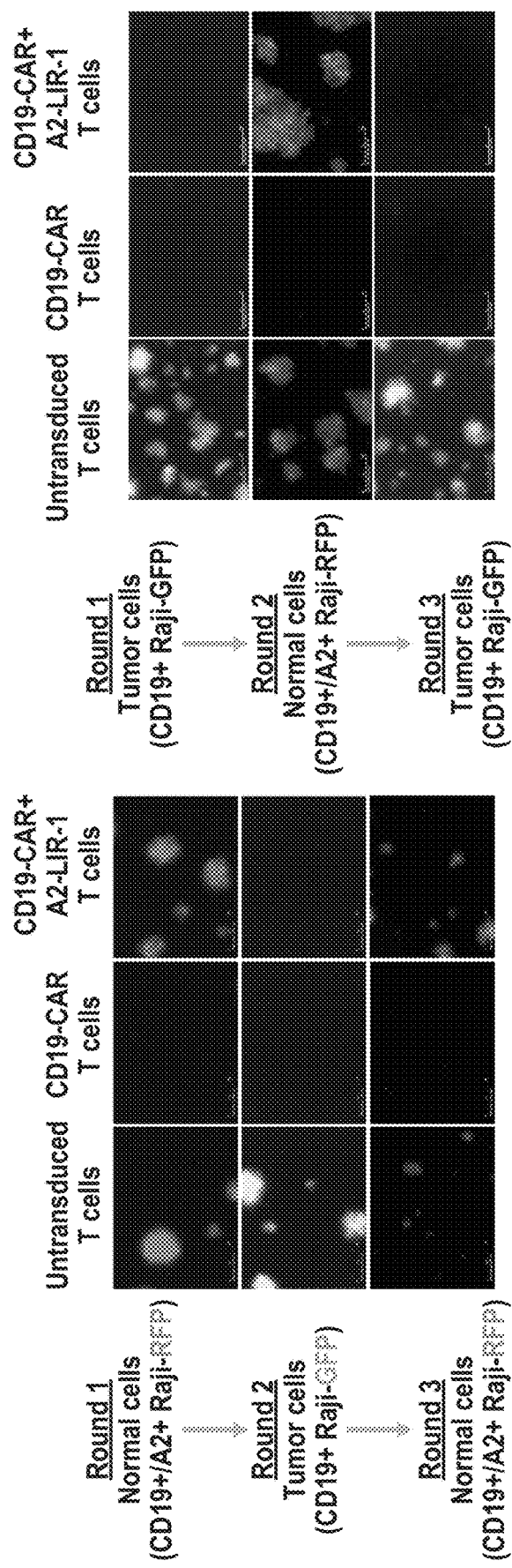
FIGS. 25A-25B are each a series of images showing the reversibility of blockade by LIR-1 inhibitory receptors. Primary T cells (donor 2) transduced with CD19 CAR activator and HLA-A*02 blocker demonstrate reversible blockade (FIG. 25A) and activation (FIG. 25B) after 3 rounds of antigen exposure (AB-A-AB and A-AB-A) in in vitro cytotoxicity assay at 3:1 E:T. Primary T cell cytotoxicity assay was reproduced with three HLA-A*02-negative donors. Images shown were captured at 72 hours.
Figure 25C:
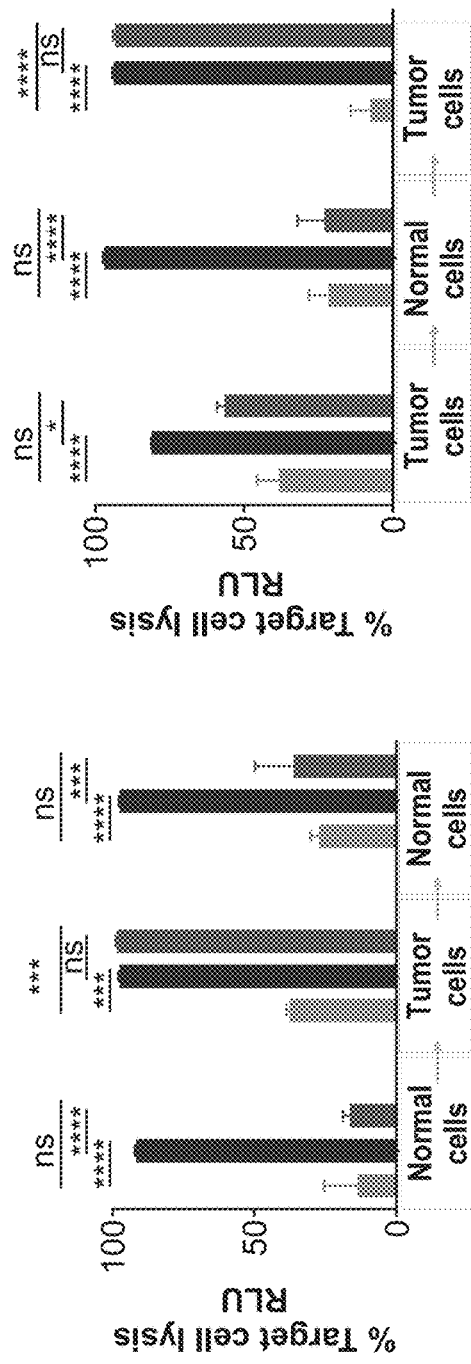
FIGS. 25C-25D are each a pair of plots showing quantification of target cell lysis (FIG. 25C) and IFNγ (FIG. 25D) in response to repeated exposure to multiple rounds of normal and target cells, 3:1 E:T (T cells from donor 2). Shown conditions are Untransduced, CD19-CAR T cells, and CD19-CAR T+A2-LIR-1. Error bars indicate ±SEM (n=2). $*p<0.05$, $p<0.01$, $*p<0.001$, $****p<0.0001$, determined using a two-way ANOVA followed by Tukey's multiple-comparisons test. In this experiment, IFNγ response diminished over time, while cytotoxicity remained robust.
Figure 25D:
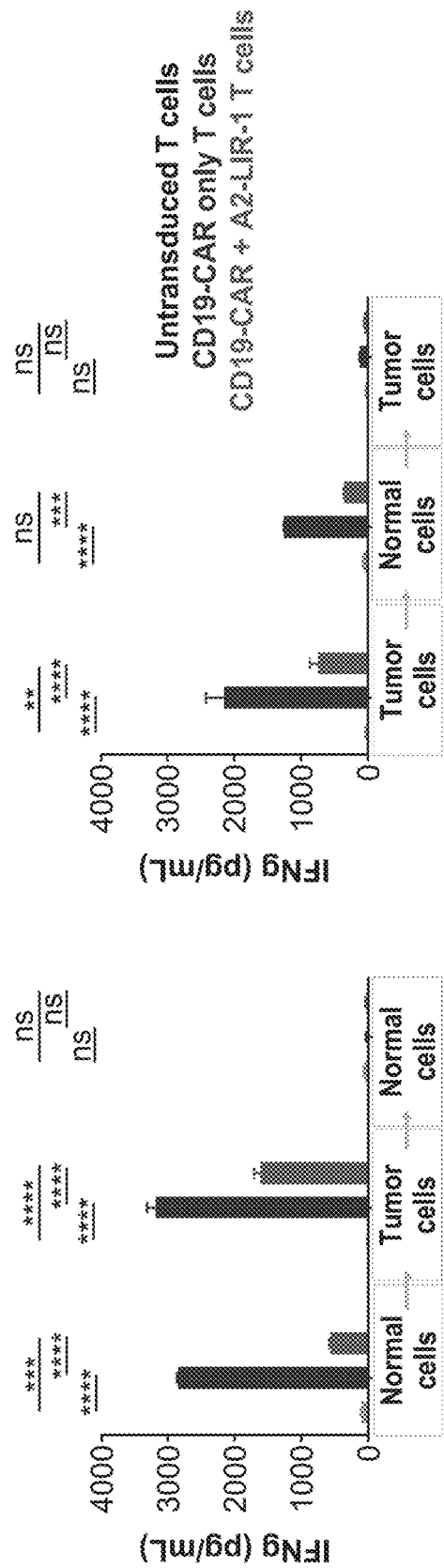

HPV TCR as activator, the NY-ESO-1 scFv fused to LIR-1 shifted the cell-count vs. peptide-concentration curve in peptide-loaded MCF7 tumor cells by ~25× (FIG. 20A; FIG. 23). Thus, the behavior of LIR-1 receptor demonstrated in Jurkat cell activation assays was extended to primary T cell functions, including cytotoxicity.

Figure 18A:
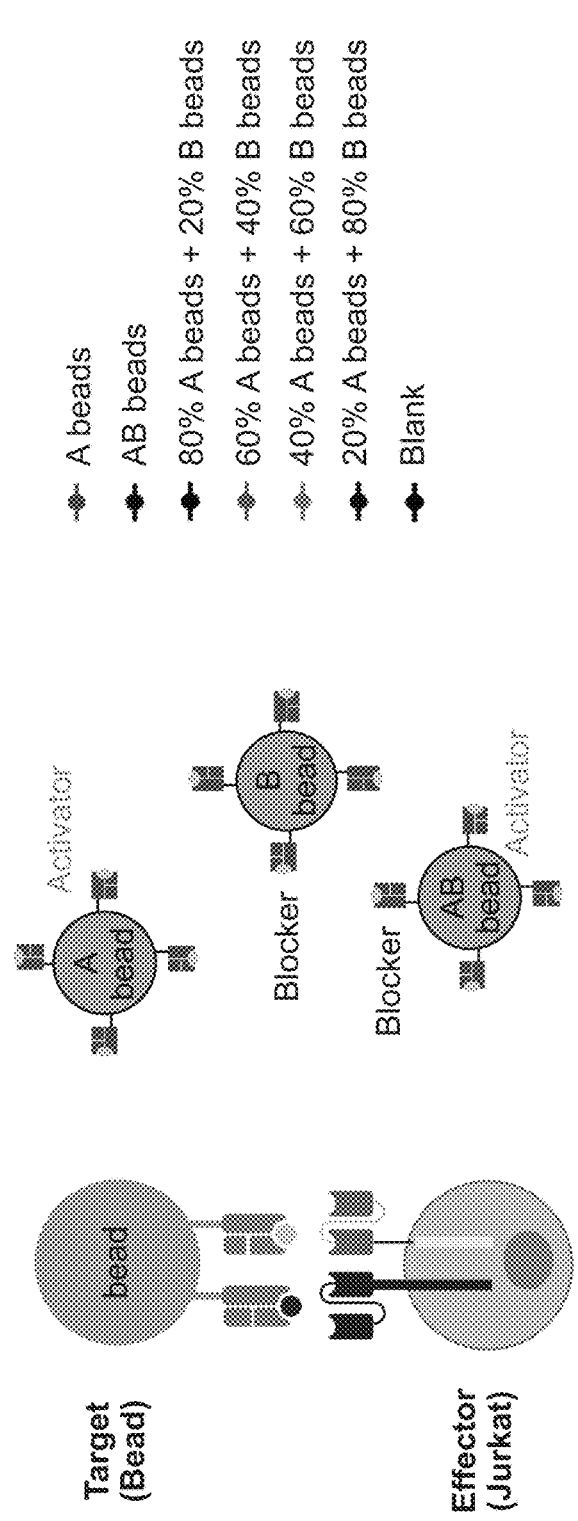
FIG. 18A is a diagram and a pair of plots showing that Jurkat cells transfected with either HPV E7-CAR or HPV E7-CAR & A2-LIR-1 co-cultured with beads displaying various ratios of activator (HPV E7) and blocker (NY-ESO-1) antigen demonstrates blocking in cis but not trans.
Figure 18A:
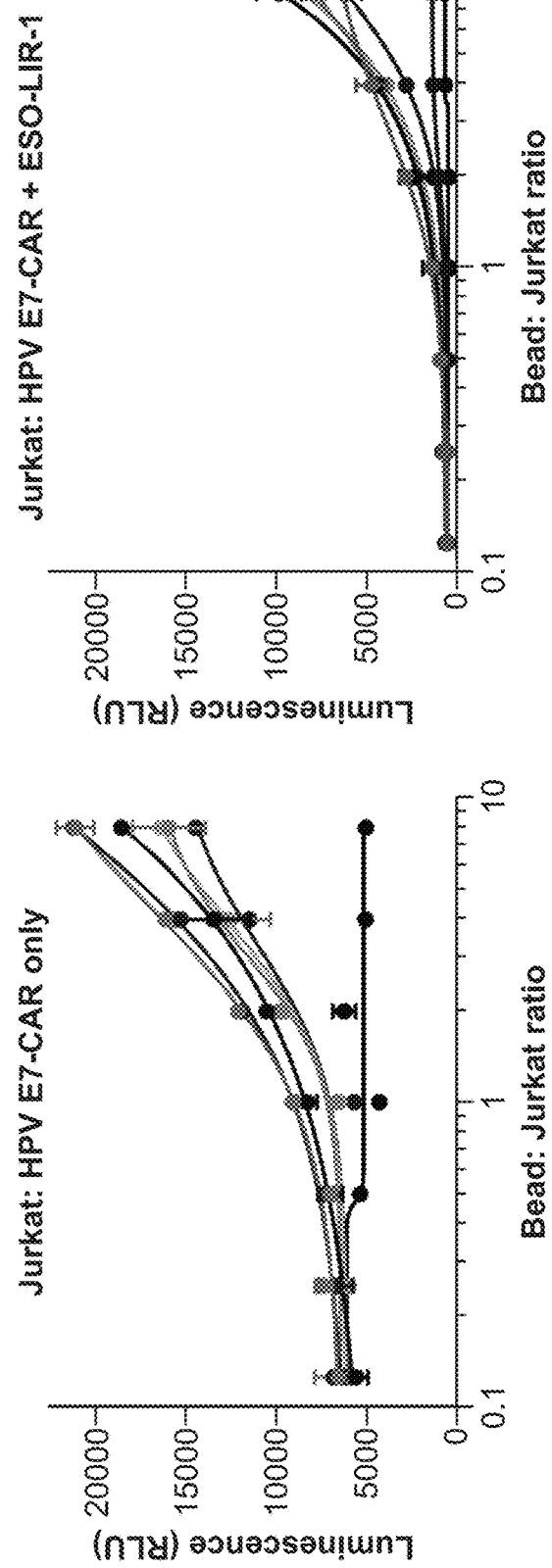
Figures 18B, 18C:
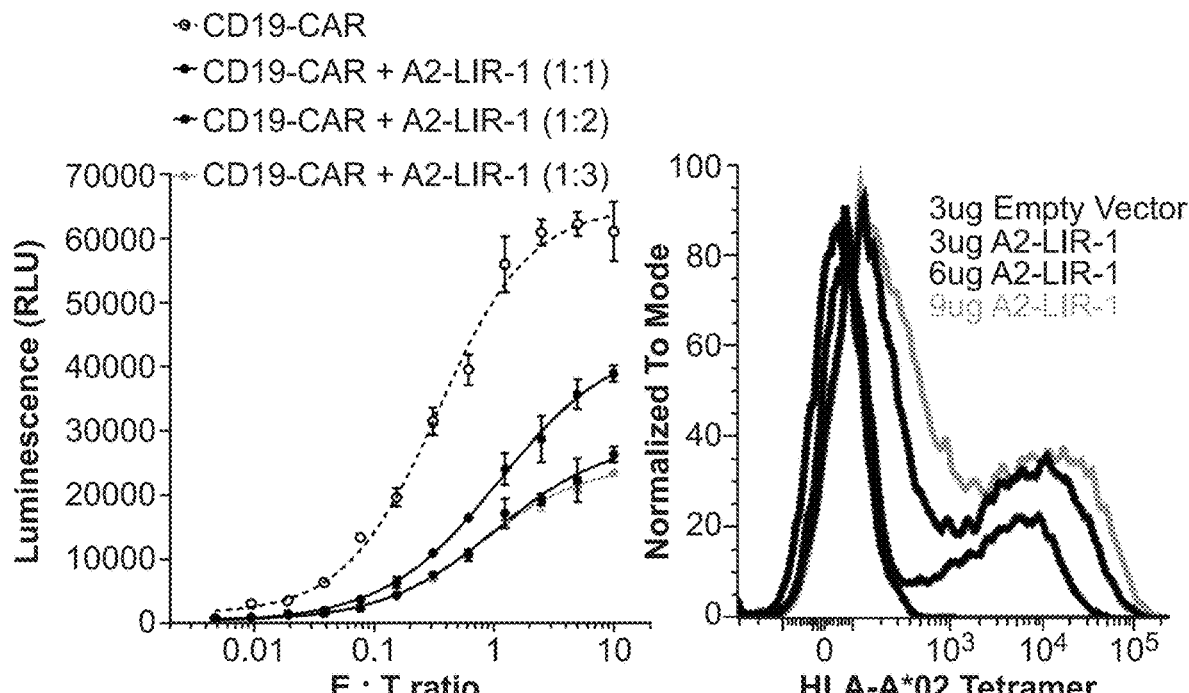
FIG. 18B is a plot showing that HLA-A*02-LIR-1 blocker receptor blocks CD19-CAR activator at various activator to blocker ratios. Ratios ranged from 0 to 10 and luminescence (RLU) ranged from 0 to 70000.
FIG. 18C is a plot showing surface expression of titrated HLA-A*02 (A2) LIR-1 blocker receptor.
Figure 18D:
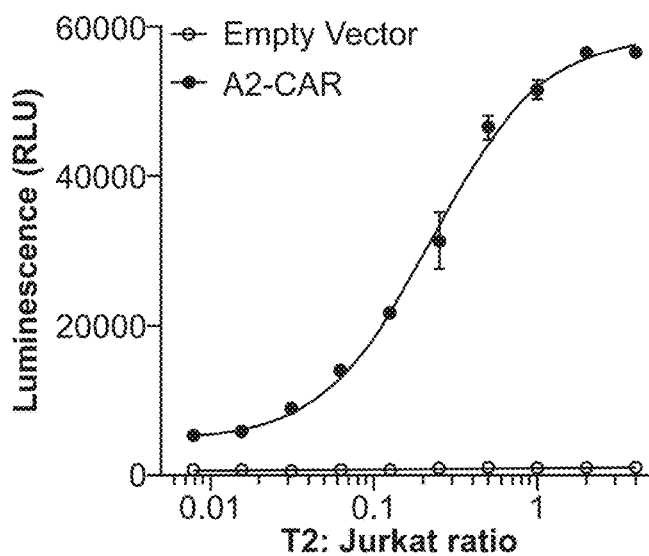
FIG. 18D is a plot showing that an scFv against HLA-A*02 can also serve as an activator when fused to activator CAR. T2 cells expressing endogenous HLA-A*02 serve as the target. RLU=relative light units; error bars indicate f SD (n=2).
Figures 19A, 19B:
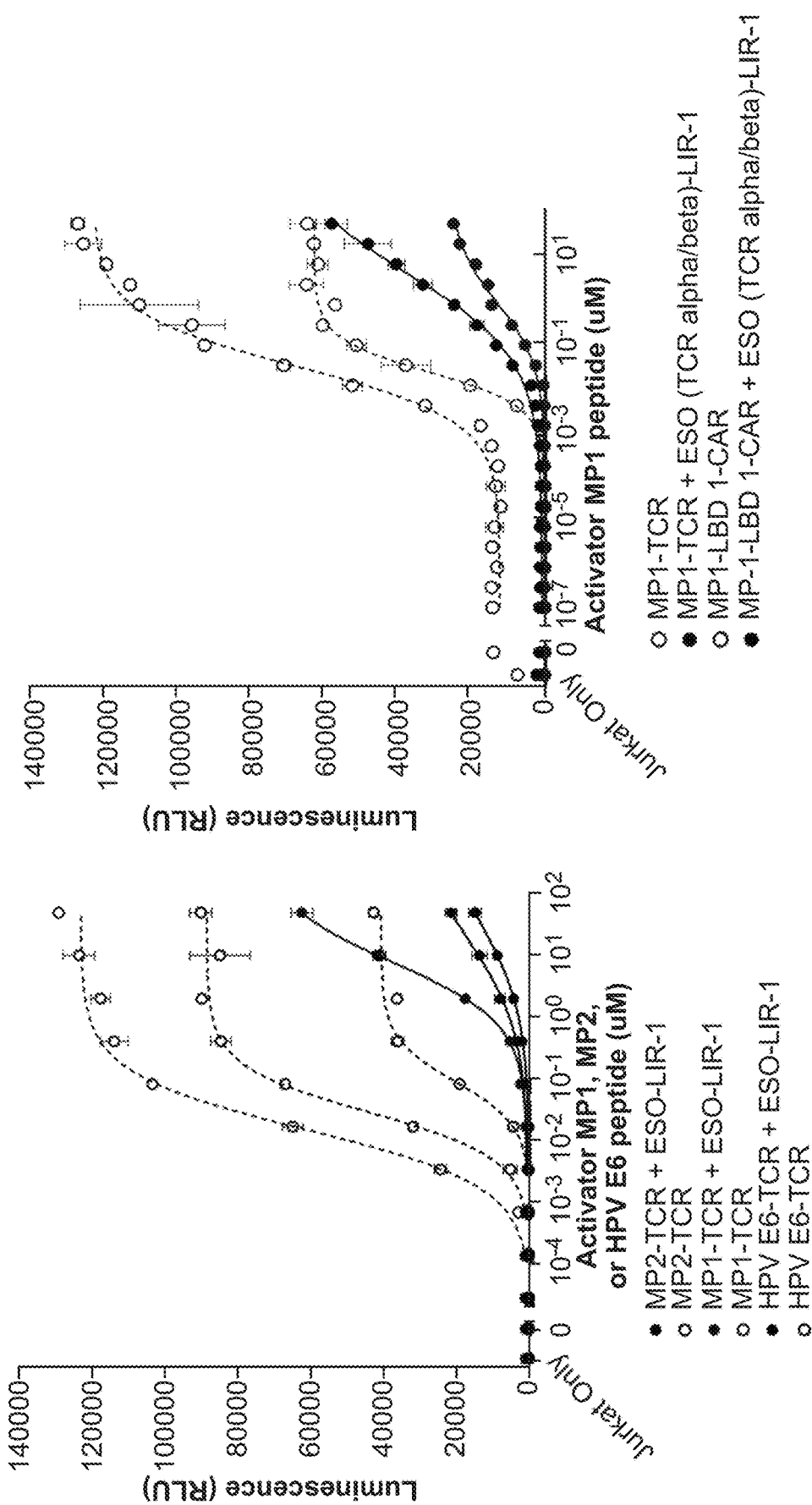
FIG. 19A is a plot showing the effect of LIR-1 blocker receptor with NY-ESO-1 scFv LBD on EC50 of different TCR activators (MP1-TCR, MP2-TCR, HPV E6-TCR) when loaded with NY-ESO-1 blocker peptide. For FIG. 14E each set was normalized to the Emax of the curve showing response of the activator only. Activator concentrations range from 0 then $10^{-4}$ to $10^2$ μM and luminescence measurements ranged from 0 to 140000 RLU.
FIG. 19B is a plot showing the effect of LIR-1 blocker receptor with NY-ESO-1 TCR LBDs on EC50 of MAGE-A3 CAR and TCR activators (MP1-LBD 1-CAR, MP1-TCR). Each set was normalized to the Emax of the curve showing response of the activator only. RLU=relative light units; error bars indicate ±SD (n=2). Activator concentrations range from 0 then $10^{-7}$ to $10^1$ μM and luminescence measurements ranged from 0 to 140000 RLU.

To establish proof of concept, the HLA-A*02 LIR-1 construct was shown to function as a blocker in the presence of pMHC-dependent activators in Jurkat cells with T2 target cells (FIG. 20B). For the activator, a CD19 scFv was used as a CAR. This activator/blocker pair was shown to function together as robustly as other pairs previously tested in Jurkat cells (FIG. 18B). T model tumor cells that differentially express the LIR-1 receptor ligand, CD19-positive, HLA-A*02-negative Raji cells were used. To model the corresponding normal cells, the same cell line stably expressing the HLA-A*02 gene was used (FIG. 24A). The cell lines activated Jurkat cells if the target cells expressed CD19 only, but not if they expressed both CD19 and HLA-A*02: i.e., the HLA-A*02 blocker receptor blocked activation by CD19-CAR in a ligand-dependent way (FIG. 24B).

Figure 22C:
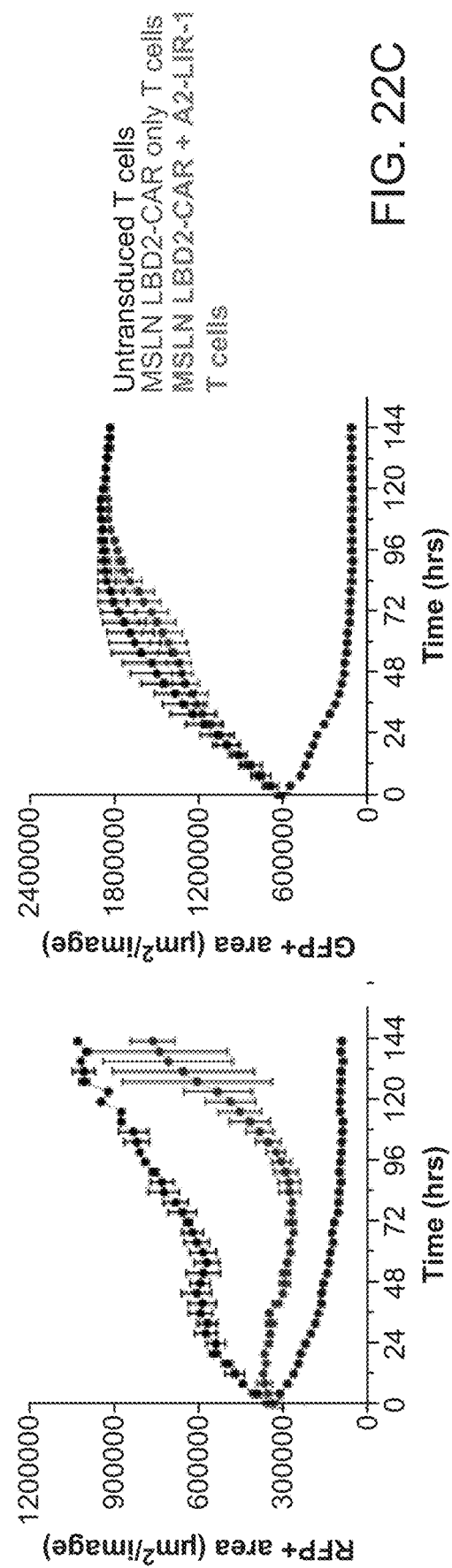
FIG. 22C is a pair of plots showing killing of endogenous MSLN+ HeLa cells by MLSN LBD2-CAR T cells. The effect of A2-LIR-1 blocker on T cell killing is in part controlled by the activator LBD.

The CD19/HLA-A*02 receptor pair also worked in primary T cells (FIG. 21). Engineered T cells killed CD19-expressing Raji cells in the absence of HLA-A*02 expression. Raji cells that expressed both CD19 and HLA-A*02 were blocked from cytotoxicity. Importantly, primary T cells bearing the receptor pairs distinguished CD19+ "tumor" from CD19+/HLA-A*02+ "normal" cells in a mixed culture. These findings mirrored results from the above-mentioned bead experiment, but in a more complex cellular setting where the effector cells' cytotoxicity focused on "tumor" targets, even when surrounded by "normal" cells. The degree of selectivity was impressive given that neither receptor had been subjected to deliberate optimization for maximal selectivity. This behavior was confirmed with a second antigen, MSLN (FIG. 22B).

Example 13: Reversibility of Inhibition by LIR-1 Inhibitory Receptors

Figures 26A, 26B:
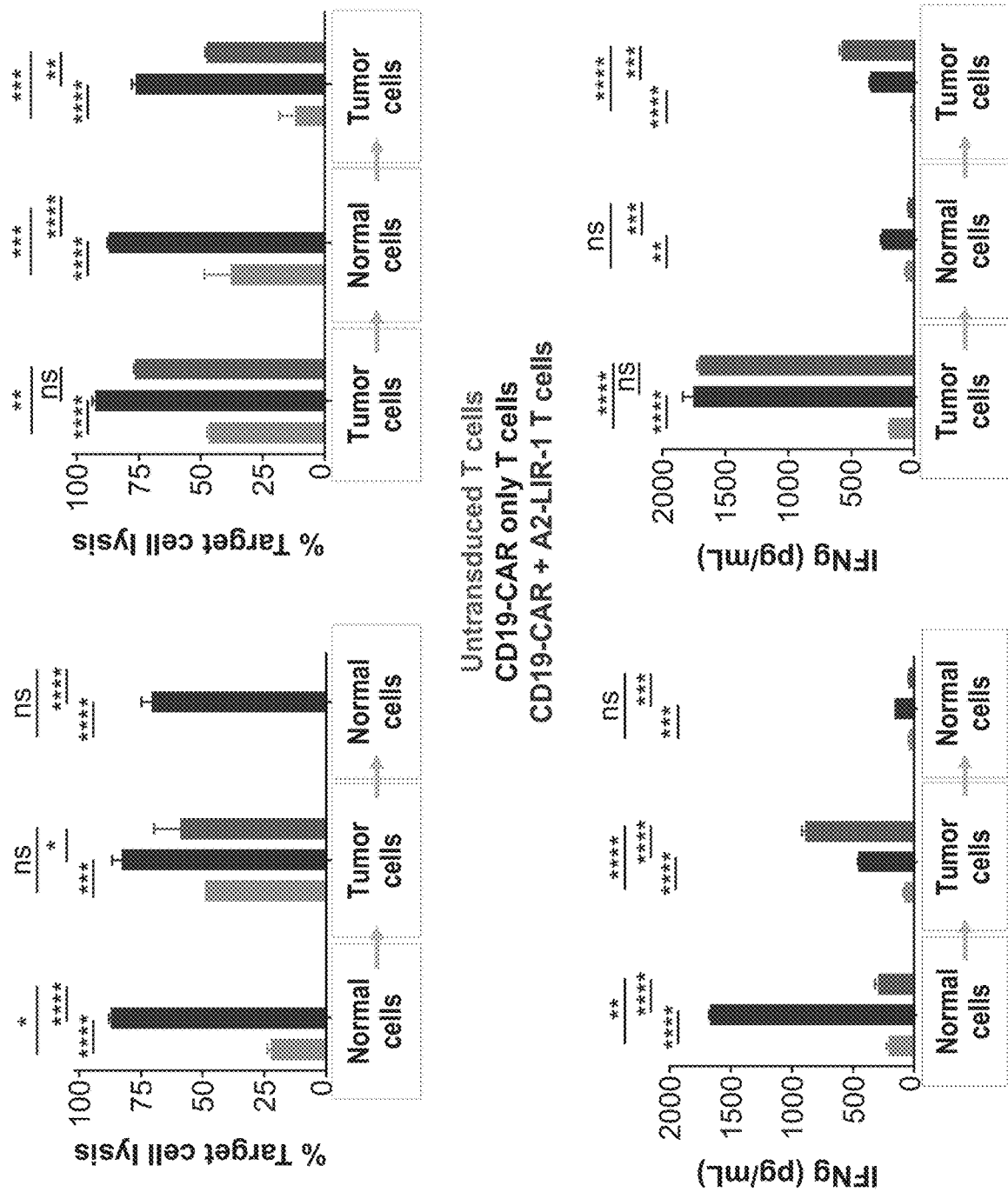
FIGS. 26A-26B are each a pair of plots showing cytotoxic T cell killing and secretion of IFNγ in co-culture with a separate donor (donor 3). Cytotoxic CD19 CAR activator and HLA-A*02 blocker transduced T cells demonstrate reversible blocking after multiple rounds of antigen exposure in cytotoxic assays and IFNγ at 9:1 E:T. We noted that this donor's T cells survival and activity tailed off overtime in culture. Shown conditions are Untransduced, CD19-CAR T cells, and CD19-CAR T+A2-LIR-1. Cytotoxicity (FIG. 26A) and IFNγ (FIG. 26B) results correspond to FIGS. 25C-25D. Error bars indicate SEM (n=2). $*p<0.05$, $p<0.01$, $*p<0.001$, $****p<0.0001$, determined using a two-way ANOVA followed by Tukey's multiple-comparisons test.

The LIR-1 inhibitory receptor was tested for its ability to function reversibly; that is, to cycle from a state of blockade to activation and back to blockade. Effector T cells expressing the LIR-1 receptor and activator receptor were tested to see if they could function reversibly and iteratively. The effector cells were co-cultured with Raji cells, either to mimic tumor (CD19+) or normal (CD19+/HLA-A*02+) cell encounter. After each round of exposure to target cells, the Raji cells were removed from the culture and a new population of target cells was introduced. Cytotoxicity and gamma-interferon (IFNγ) were measured at the end of each round. In both permutations, block-kill-block and kill-block-kill, the T cells functioned as required by a cell therapeutic of this type (FIGS. 25A-25D). They reversibly cycled from a state of block to cytotoxicity and back, depending on the target cells to which they were exposed. This result demonstrates that a T cell expressing an activator receptor and the LIR-1 inhibitory receptor do not get stuck in one state (blockade or activation), but rather can switch back and forth as it integrates signals from normal and tumor cells. Additionally, these experiments were reproduced in primary T cells from multiple donors (FIGS. 21A-D, FIGS. 25A-25D; FIGS. 26A-26B), despite their complexity, heterogeneity and donor-to-donor variability, demonstrating the robust functions of the LIR-1 inhibitory receptor.

Example 14: Human T Cells Expressing an Activator Receptor and LIR-1 Blocker Receptor Selectively Target Cancer Cells in a Mouse Model The ability of the CD19/HLA-A*02 activator/blocker pair engineered in primary T cells to allow expansion of the T cells in vitro to large numbers using standard CD3/CD28 stimulation was assayed (FIG. 27A; FIG. 28A). Thus, T cells expressing the activator and LIR-1 receptors c can be scaled up to sufficient numbers for animal experiments and ultimately for patients.

Figure 27D:
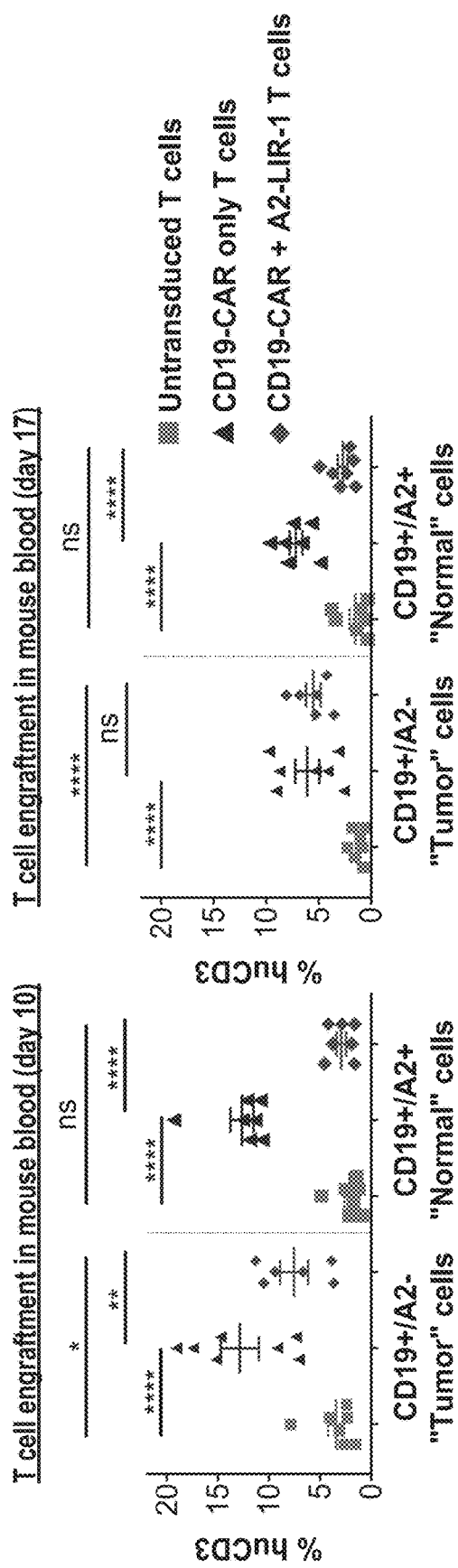
Figure 27E:
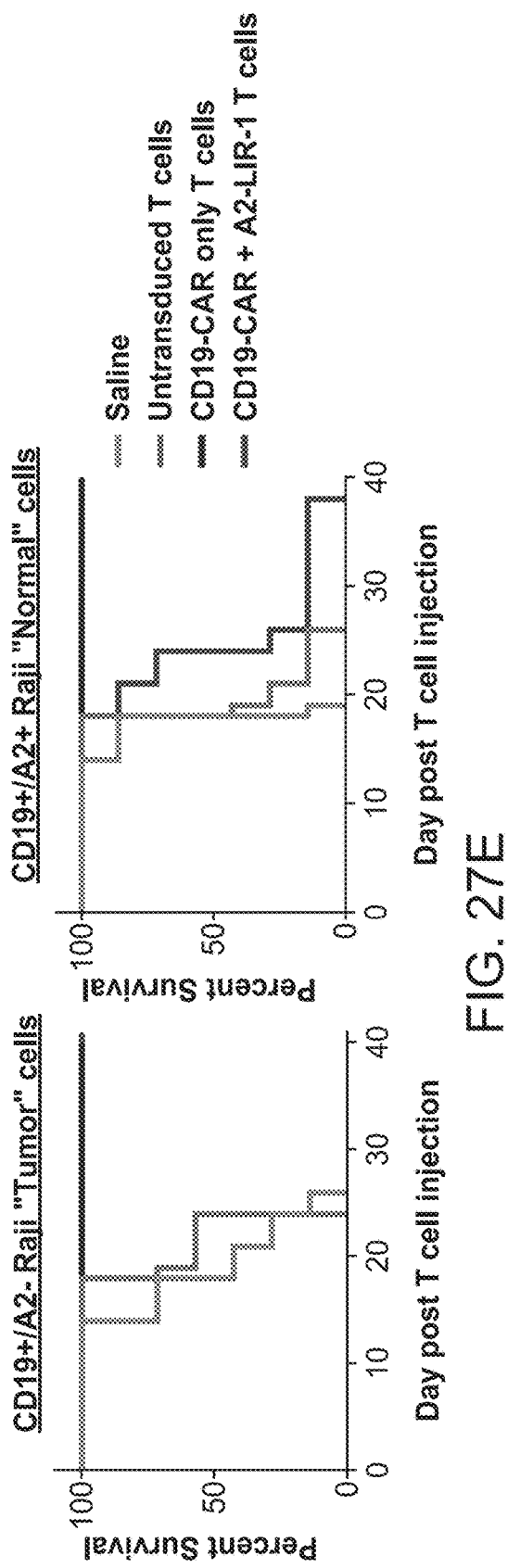
Figure 28A:
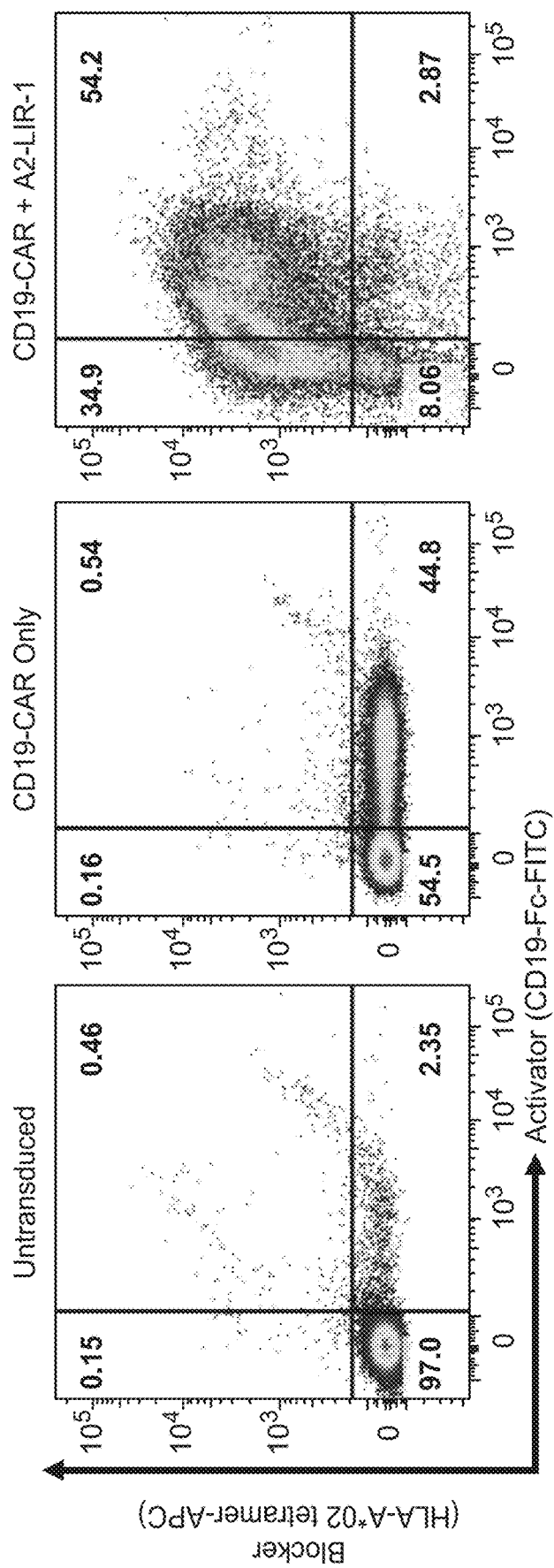
FIG. 28A is a series of plots showing flow cytometry analysis of primary T cell post-enrichment and expansion prepared for mouse tail vein injection. Tumor volume was measured at the number of days from T cell injection, starting 10 days prior to T cell injection (-10) to 40 days following T cell injection (40). Tumor volumes ranged from 0 to 2500 mm³.
Figure 28B:
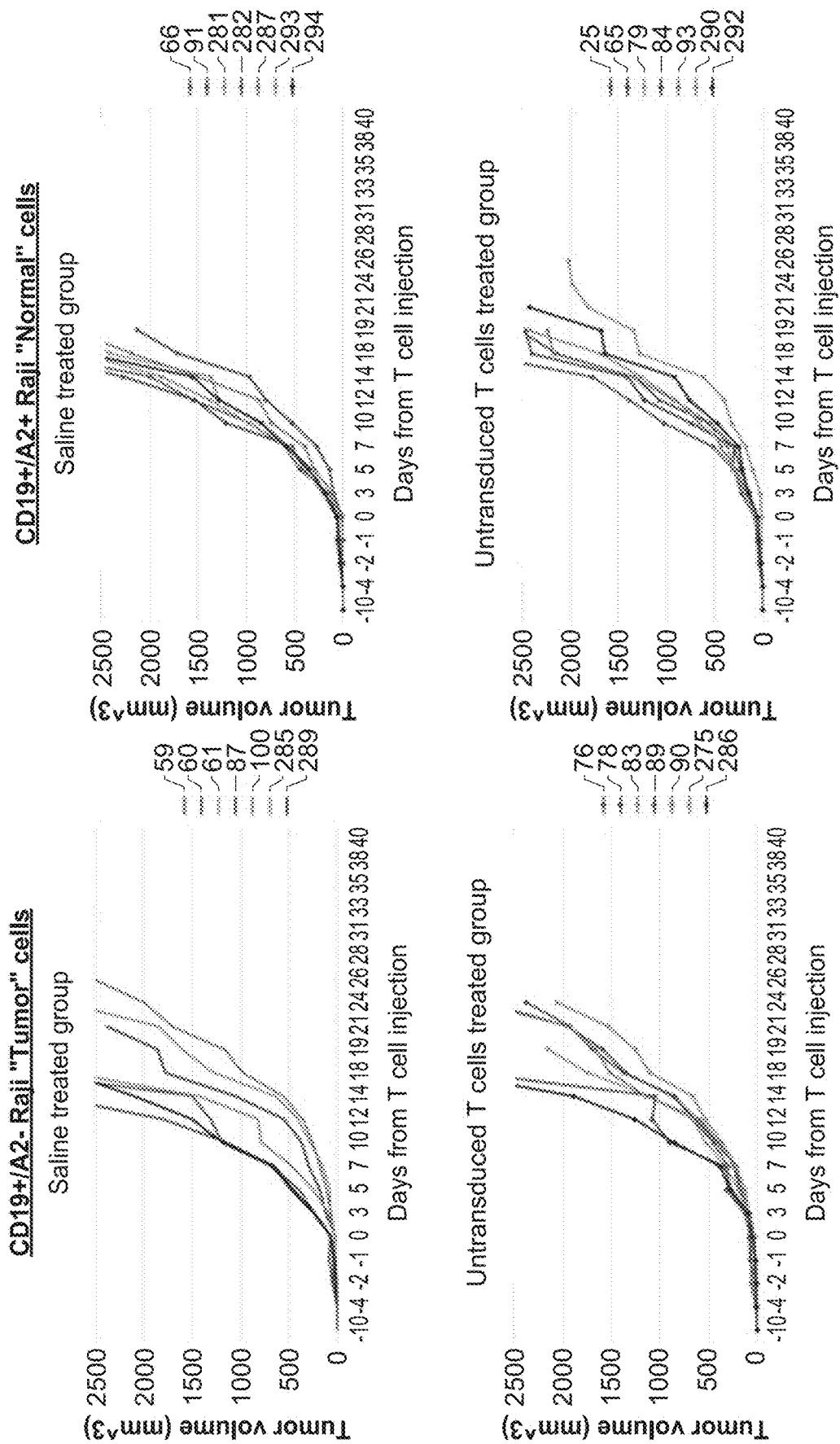
FIG. 28B is a series of plots showing tumor measurement by caliper plotted for individual mice in each group.
Figure 28B:
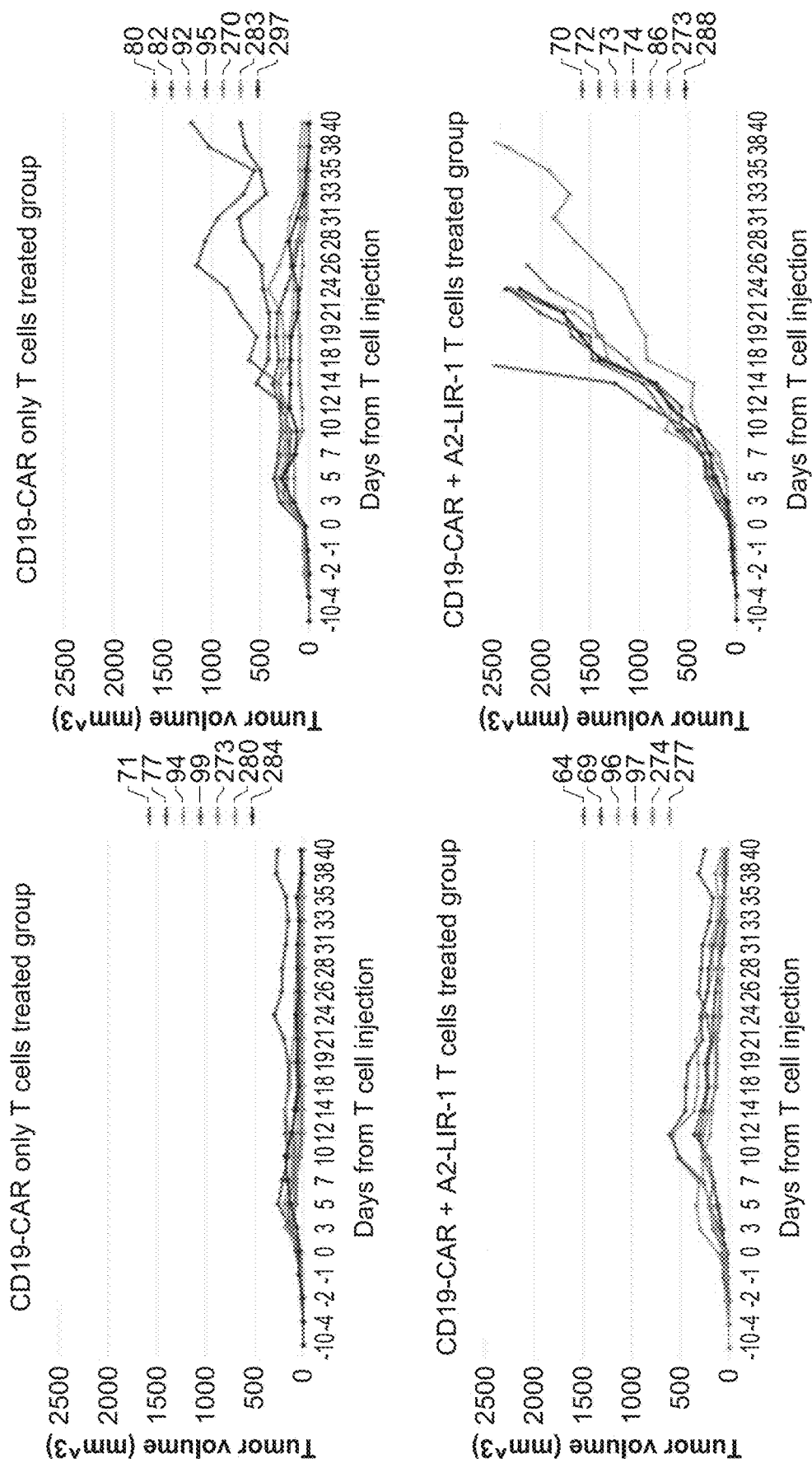
Figure 28C:
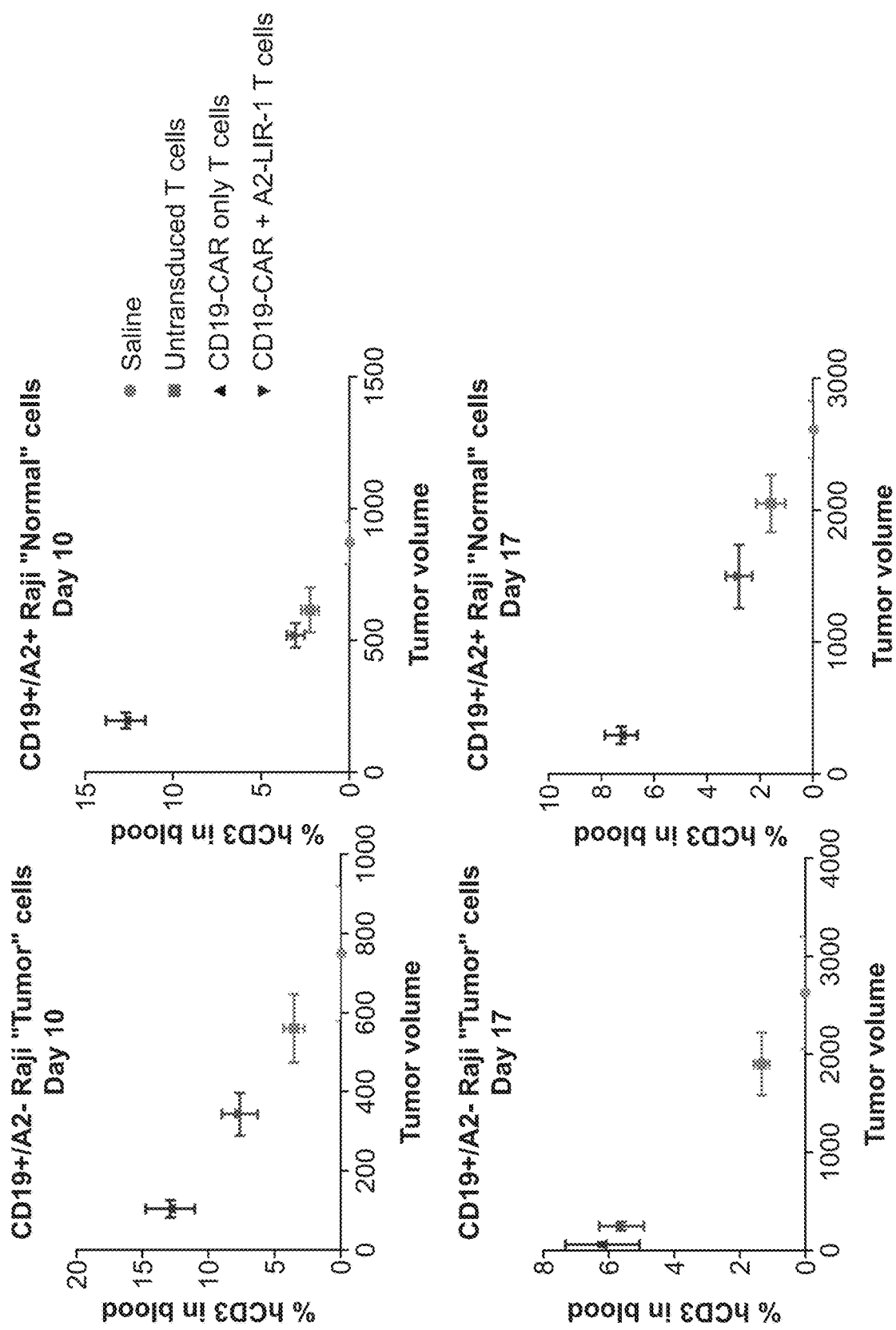
FIG. 28C is a series of plots showing correlation of huCD3+ T cells in mouse blood to tumor growth. Graph of huCD3+ T cells compared to tumor volume 10 days and 17 days after T cell injection.
Figure 28D:
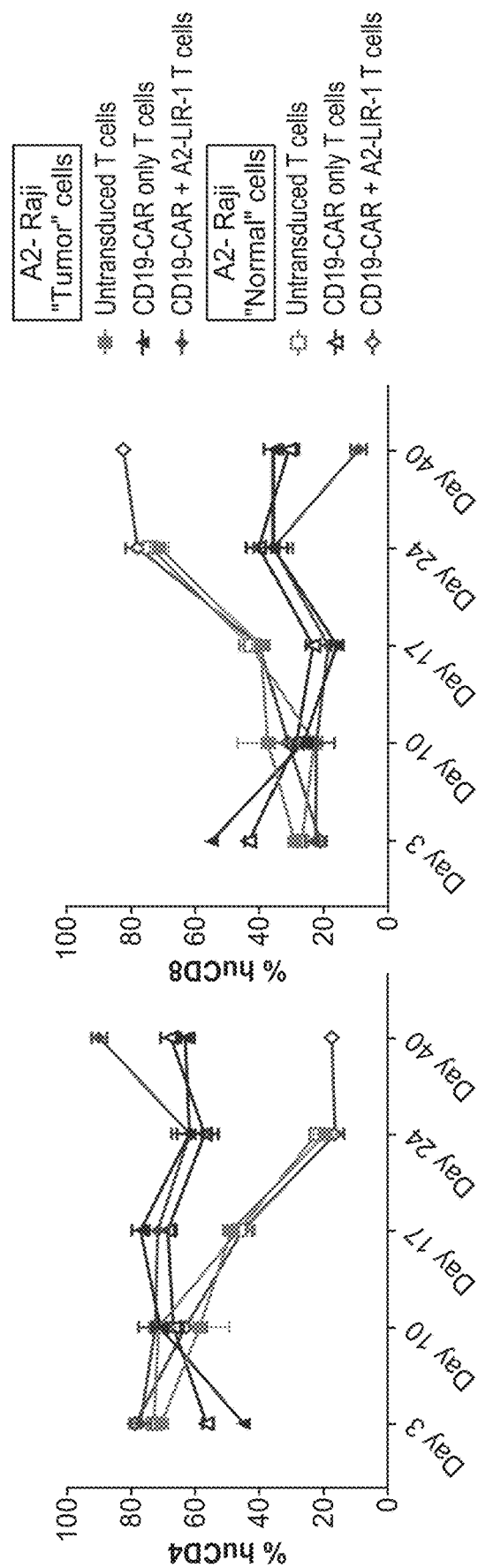
FIG. 28D is a pair of plots showing huCD4+ and huCD8+ T cell counts in peripheral blood by flow cytometry. Open circles, mice grafted with "normal" cells; closed circle, mice grafted with tumor cells. Samples with fewer than 100 cells were excluded from the analysis. Error bars indicate f SEM (n=7 in all groups except n=6 in CD19+/A2- Raji group treated with CD19-CAR+A2-LIR-1 T cells).
Figure 29A:
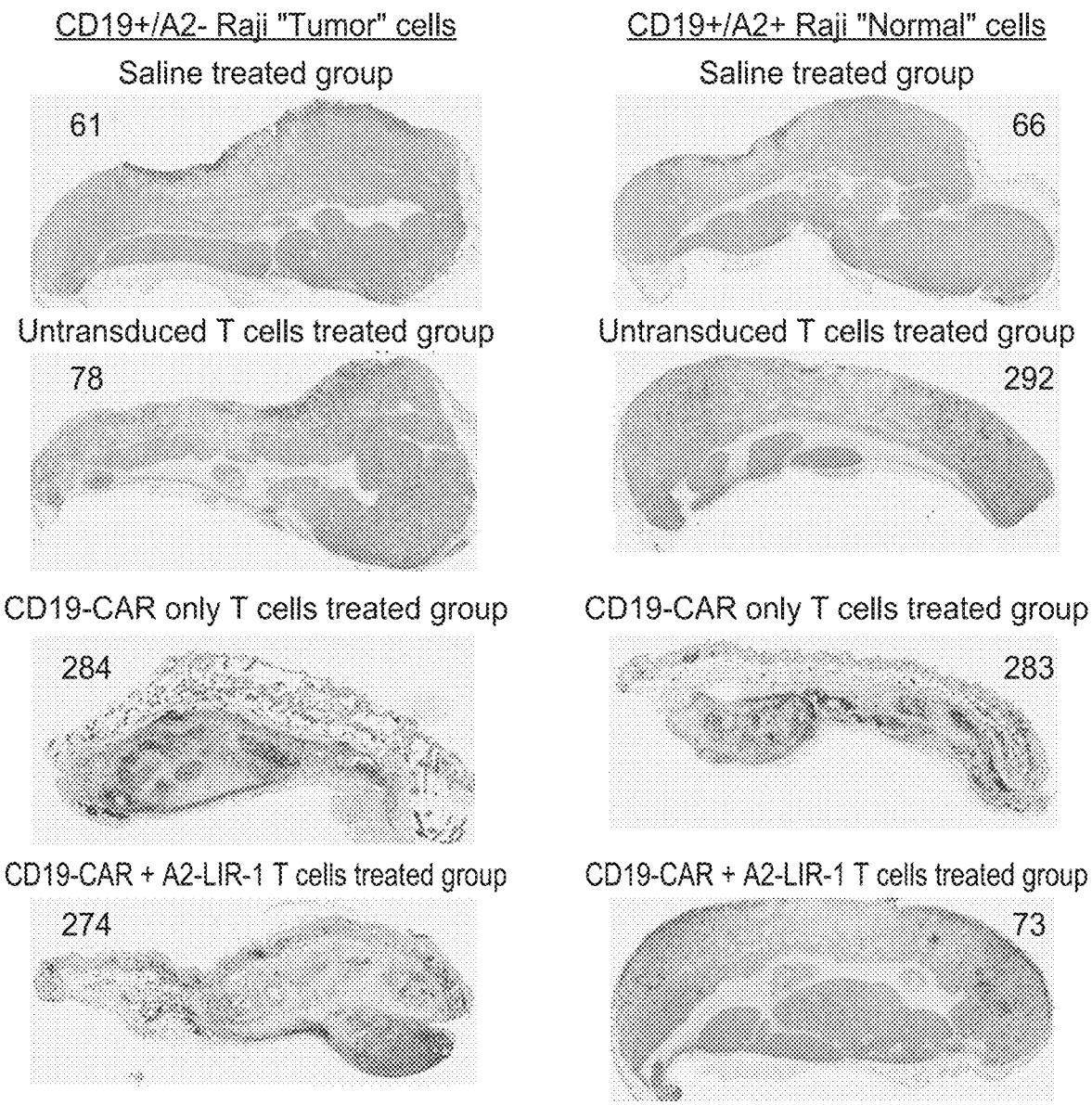
FIG. 29A is a series of images showing histological analysis of T cell infiltration in tumors. Representative images of tumor samples collected at study termination, sectioned and stained for huCD3 are shown.
Figure 29B:
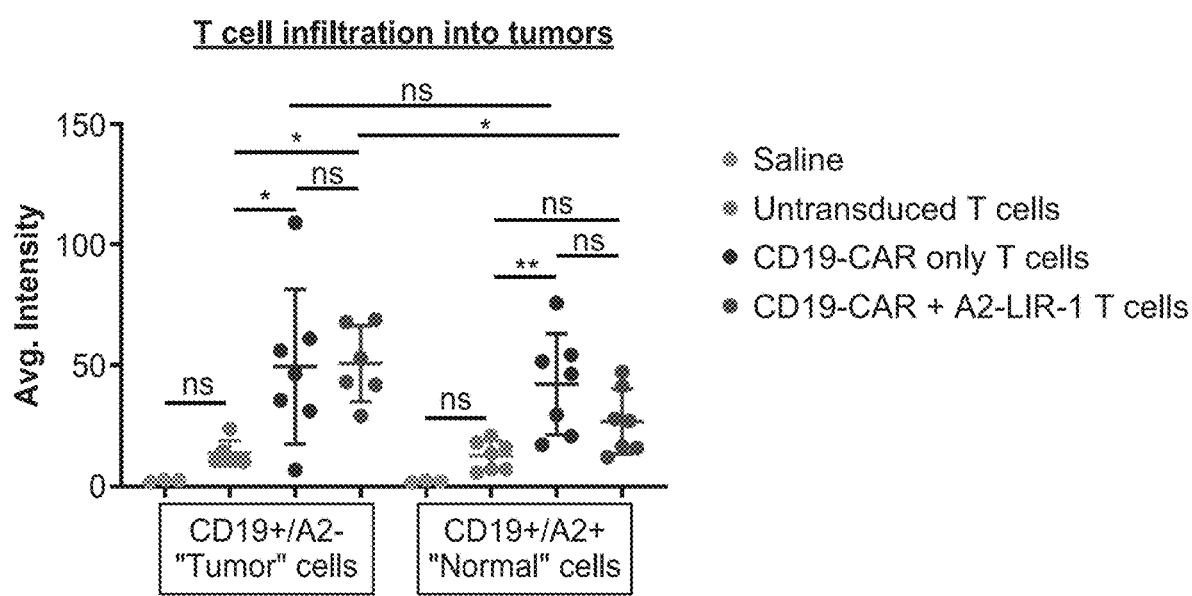
FIG. 29B is a plot showing quantification of T cell infiltration using ImageJ. T cell infiltration was significantly higher for T cells with CD19-CAR or CD19-CAR+A2-LIR-1 in CD19+/A2- tumors compared to untransduced cells. However, in CD19+/A2+ tumors, CD19-CAR+A2-LIR-1 T cells were not significantly different compared to untransduced cells. There was also a significant drop in infiltration of CD19-CAR+A2-LIR-1 T cells between CD19+/A2- and CD19+/A2+ tumors. Qualitatively, CD19-CAR+A2-LIR-1 T cells were less prevalent in CD19+/A2+ tumors compared to CD19-CAR only T cells; however, this difference was not statistically significant. Saline samples were similarly quantified to show background staining levels. Groups of data were analyzed using an ordinary one-way ANOVA, while individual pairs between "tumor" and "normal" were analyzed using an unpaired t test. ns=not significant, $*p<0.05$, $**p<0.01$.

The CD19/HLA-A*02 activator/blocker combination was tested in vitro to demonstrate selective killing of CD19+ tumor cells, while sparing CD19+/HLA-A*02+ cells in a mouse xenograft cancer model (FIG. 27B). The same two Raji cell lines described above, one CD19+ and the other CD19+/HLA-A*02+, were injected into the flanks of immunocompromised (NGS-HLA-A2.1) mice. T cells engineered with the test constructs were injected at two doses, 2e6 (not shown) or 1e7 T cells. The growth of the tumor, as well as the persistence of the implanted T cells, were analyzed overtime. Only the CD19+ tumor cells were killed in the mouse and the tumor control tracked with transferred T cell numbers, promoting survival of the host mice (FIGS. 27C-27E, FIGS. 28B-28C). The CD19+/HLA-A*02+ cells designed to model normal cells were unaffected. Human CD4+/CD8+ cell ratios in the blood of mice bearing engineered cells tracked with their control counterpart; i.e., in "tumor"-grafted mice, CD4+>CD8+ cells, as in the CD19 CAR positive control mice; and, in "normal"-grafted mice, CD4+<CD8+ cells, similar to mice harboring untransduced T cells (FIG. 28D). Moreover, huCD3+ cells in the tumor (FIGS. 29A-29B) correlated inversely with tumor volume, and engineered T cells expressing the two receptors behaved like untransduced T cells in "normal" grafts (low infiltrate), and like the CD19 CAR in "tumor" grafts (high infiltrate). Finally, the mice appeared normal with regard to typical clinical observations (Table 10). Together, these results demonstrated that the LIR-1 inhibitory receptor can function hi vivo to inhibit an activator receptor, in a simplified setting devised to mimic the different normal and tumor cell types that will be encountered in patients.

TABLE 10

Clinical observations of mice during in vivo experiment

| Group | Animal ID | 6 CO | 8 CO | 10 CO | 13 CO | 15 CO | 17 CO | 20 CO | 22 CO | 24 CO | 28 CO | 29 CO |
|---|---|---|---|---|---|---|---|---|---|---|---|---|
| Tumor | 59 | N | N | N | N | N | N | N | N | N | N | N, EUT |
| Untreated | 100 | N | N | N | N | N | N | N | N | N | N | N |
|  | 61 | N | N | N | N | N | N | N | N | N | 19AN(1) | 19AN(1) |
|  | 285 | N | N | N | N | N | N | N | N | N | N | N, EUT |
|  | 289 | N | N | N | N | N | N | N | N | 19AN(1) | N | N, EUT |

TABLE 10-continued

Clinical observations of mice during in vivo experiment

| Group | Animal ID | 6 CO | 8 CO | 10 CO | 13 CO | 15 CO | 17 CO | 20 CO | 22 CO | 24 CO | 28 CO | 29 CO |
|---|---|---|---|---|---|---|---|---|---|---|---|---|
| | 87 | N | N | N | N | N | N | N | N | N | N | N, EUT |
| | 60 | N | N | N | N | N | N | N | N | N | N | N |
| Tumor | 286 | N | N | N | N | N | N | N | N | N | 19AN(1) | 19AN(1), EUT |
| Untransduced | 78 | N | N | N | N | N | N | N | N | N | N | N |
| | 76 | N | N | N | N | N | N | N | N | N | N | N |
| | 89 | N | N | N | N | N | N | N | N | N | N | N, EUT |
| | 90 | N | N | N | N | N | N | N | N | N | N | N |
| | 275 | N | N | N | N | N | N | N | N | N | N | N |
| | 83 | N | N | N | N | N | N | N | N | N | 19AN(1) | 19AN(1), EUT |
| Tumor | 280 | N | N | N | N | N | 19AN(1) | 19AN(1) | 19AN(1) | 19AN(1) | N | N |
| CD19-CAR | 99 | N | N | N | N | N | N | N | N | N | N | N |
| only | 284 | N | N | N | N | N | N | N | N | N | N | N |
| | 71 | N | N | N | N | N | N | N | N | N | N | N |
| | 279 | N | N | N | N | N | N | N | N | N | N | N |
| | 77 | N | N | N | N | N | N | N | N | N | N | N |
| | 94 | N | N | N | N | N | N | N | N | N | N | N |
| Tumor | 64 | N | N | N | N | N | N | N | N | N | N | N |
| CD19-CAR + | 69 | N | N | N | N | N | N | N | N | N | N | N |
| A2-LIR1 | 274 | N | N | N | N | N | N | N | N | N | N | N |
| | 96 | N | N | N | N | N | N | N | N | 19AN(1) | 19AN(1) | 19AN(1) |
| | 277 | N | N | N | N | N | N | N | N | 19AN(1) | 19AN(1) | 19AN(1) |
| | 97 | N | N | N | N | N | N | N | N | N | N | N |
| "Normal" | 66 | N | N | N | N | N | N | N | N | 19AN(1) | 19AN(2) | 19AN(2), EUT |
| Untreated | 294 | N | N | N | N | N | N | 19AN(1) | 19AN(1) | 19AN(2) | 19AN(2), EUT | |
| | 293 | N | N | N | N | N | N | 19AN(1) | 19AN(1) | 19AN(2) | 19AN(2), EUT | |
| | 91 | N | N | N | N | N | N | 19AN(1) | 19AN(1) | 19AN(2) | 19AN(2), EUT | |
| | 287 | N | N | N | N | N | N | N | 19AN(1) | 19AN(1) | 19AN(2), EUT | |
| | 281 | N | N | N | N | N | N | 19AN(1) | 19AN(1) | 19AN(2) | 19AN(2), EUT | |
| | 282 | N | N | N | N | N | N | N | 19AN(1) | 19AN(1) | 19AN(1), EUT | |
| "Normal" | 290 | N | N | N | N | N | N | N | N | 19AN(1) | 19AN(1), EUT | |
| Untransduced | 25 | N | N | N | N | N | N | N | 19AN(1) | 19AN(1) | 19AN(1), EUT | |
| | 93 | N | N | N | N | N | N | N | N | N | N | N, EUT |
| | 84 | N | N | N | N | N | N | N | N | N | N | N, EUT |
| | 292 | N | N | N | N | N | N | N | 19AN(1) | 19AN(1) | 19AN(1) | |
| | 65 | N | N | N | N | N | N | N | N | 19AN(1) | 19AN(1), EUT | |
| | 79 | N | N | N | N | N | N | N | N | N | N | N |
| "Normal" | 270 | N | N | N | N | N | N | N | N | N | N | N |
| CD19-CAR | 283 | N | N | N | N | N | N | N | N | N | N | N |
| only | 82 | N | N | N | N | N | N | N | N | N | N | N |
| | 92 | N | N | N | N | N | 19AN(1) | 19AN(1) | 19AN(1) | 19AN(1) | 19AN(1) | 19AN(1) |
| | 95 | N | N | N | N | N | N | N | 19AN(1) | 19AN(1) | 19AN(1) | 19AN(1) |
| | 80 | N | N | N | N | N | N | N | N | N | N | N |
| | 297 | N | N | N | N | N | N | 19AN(1) | 19AN(1) | N | 19AN(1) | 19AN(1) |
| "Normal" | 86 | N | N | N | N | N | N | N | N | N | N | N |
| CD19-CAR + | 74 | N | N | N | N | N | N | N | N | N | N | N |
| A2-LIR1 | 288 | N | N | N | N | N | N | N | N | N | N | N |
| | 273 | N | N | N | N | N | N | N | N | N | N | N |
| | 70 | N | N | N | N | N | N | N | N | 19AN(1) | 19AN(1) | 19AN(1) |
| | 73 | N | N | N | N | N | N | N | N | 19AN(1) | 19AN(1) | 19AN(1) |
| | 72 | N | N | N | N | N | N | N | N | 19AN(1) | 19AN(1) | 19AN(1), EUT |

Tumor and "normal" cells were injected on study day 0 and treatment started on study day 10. Clinical observation (CO) were performed 3×/week focusing on poor health, stress and pain. Per IACUC guidelines, mice were euthanized if tumors reached >2000 mm$^3$. Codes: N=normal; 19A=Abnormal Tumor [N=Necrotic, O=Open], EUT=Euthanized. Severity codes: 0=Not present, 1=Moderate, 2=Severe.

What is claimed is:

1. A method of treating a subject with a disease or a disorder, comprising administering to the subject an immune cell comprising an inhibitory receptor comprising:
   a) an antigen binding domain comprising a single chain variable fragment (scFv);
   b) an LILRB1 hinge domain;
   c) a transmembrane domain; and
   d) an LILRB1 intracellular domain comprising at least one immunoreceptor tyrosine-based inhibitory motif (ITIM) selected from the group consisting of NLYAAV (SEQ ID NO: 8), VTYAEV (SEQ ID NO: 9), VTYAQL (SEQ ID NO: 10), and SIYATL (SEQ ID NO: 11),
   wherein the LILRB1 hinge domain, transmembrane domain, and LILRB1 intracellular domain comprises a sequence at least 95% identical to SEQ ID NO: 2 or 3.

2. The method of claim 1, wherein the immune cell comprises an activator receptor.

3. The method of claim 2, wherein the activator receptor is a chimeric antigen receptor or a T cell receptor.

4. The method of claim 3, wherein the chimeric antigen receptor or T cell receptor specifically binds to a target antigen expressed on cancer cells.

5. The method of claim 1, wherein the intracellular domain comprises a sequence at least 95% identical to SEQ ID NO: 7.

6. The method of claim 1, wherein the transmembrane domain comprises a LILRB1 transmembrane domain.

7. The method of claim 6, wherein the LILRB1 transmembrane domain comprises a sequence at least 95% identical to SEQ ID NO: 5.

8. The method of claim 1, wherein the LILRB1 hinge domain comprises a sequence at least 95% identical to any one of SEQ ID NO 4, SEQ ID NO: 18, SEQ ID NO: 19, SEQ ID NO: 80 or SEQ ID NO: 81.

9. The method of claim 1, wherein the LILRB1 hinge and transmembrane domains comprises a sequence at least 95% identical to SEQ ID NO: 20.

10. The method of claim 1, wherein the transmembrane and LILRB1 intracellular domain comprises a sequence at least 95% identical to SEQ ID NO: 21.

11. The method of claim 1, wherein the LILRB1 hinge, transmembrane and LILRB1 intracellular domains comprises SEQ ID NO: 2.

12. The method of claim 1, wherein the antigen binding domain is specific to a major histocompatibility class I allele.

13. The method of claim 12, wherein the major histocompatibility class I allele comprises HLA-A allele, HLA-B allele, HLA-C allele or HLA-E allele.

14. The method of claim 13, wherein the HLA-A allele is HLA-A*02.

15. The method of claim 1, wherein the scFv comprises complementarity determined regions (CDRs) comprising SEQ ID NOS: 22-27 or SEQ ID NOS: 28-33.

16. The method of claim 15, wherein the scFv comprises a sequence at least 95% identical to any one of SEQ ID NOS: 35, 37, 45 or 125.

17. The method of claim 1, wherein the inhibitory receptor comprises an amino acid sequence of any one of SEQ ID NOS: 50, 64, 89, 120, or 122.

18. The method of claim 1, wherein the immune cell is a T cell.

* * * * *